(12) United States Patent
Meitav et al.

(10) Patent No.: US 11,846,778 B2
(45) Date of Patent: Dec. 19, 2023

(54) SYSTEM FOR PROVIDING ILLUMINATION OF THE EYE

(71) Applicant: Magic Leap, Inc., Plantation, FL (US)

(72) Inventors: Nizan Meitav, Kiryat Ata (IL); Fahri Yaras, Cedar Park, TX (US); David Carl Jurbergs, Austin, TX (US)

(73) Assignee: Magic Leap, Inc., Plantation, FL (US)

( * ) Notice: Subject to any disclaimer, the term of this patent is extended or adjusted under 35 U.S.C. 154(b) by 81 days.

(21) Appl. No.: 17/439,594

(22) PCT Filed: Mar. 19, 2020

(86) PCT No.: PCT/US2020/023581
§ 371 (c)(1),
(2) Date: Sep. 15, 2021

(87) PCT Pub. No.: WO2020/191170
PCT Pub. Date: Sep. 24, 2020

(65) Prior Publication Data
US 2022/0099977 A1    Mar. 31, 2022

Related U.S. Application Data

(60) Provisional application No. 62/821,121, filed on Mar. 20, 2019.

(51) Int. Cl.
*G02B 27/01* (2006.01)
*F21V 8/00* (2006.01)
*G06F 3/01* (2006.01)
*A61B 3/113* (2006.01)
(Continued)

(52) U.S. Cl.
CPC ....... *G02B 27/0172* (2013.01); *G02B 6/0026* (2013.01); *G02B 6/0031* (2013.01); *G02B 6/0066* (2013.01); *G02B 2027/014* (2013.01); *G02B 2027/0138* (2013.01)

(58) Field of Classification Search
USPC ............................................. 345/8
See application file for complete search history.

(56) References Cited

U.S. PATENT DOCUMENTS 6,850,221 B1   2/2005  Tickle
9,213,178 B1   12/2015 Giri et al.
(Continued)

FOREIGN PATENT DOCUMENTS

WO    2019060741 A1    3/2019
WO    WO 2020/191170   9/2020

OTHER PUBLICATIONS

Extended European Search Report in European Appln. No. 20773905.3, dated Nov. 18, 2022, 15 pages.
(Continued)

*Primary Examiner* — Chineyere D Wills-Burns
(74) *Attorney, Agent, or Firm* — Fish & Richardson P.C.

(57) ABSTRACT

A thin transparent layer can be integrated in a head mounted display device and disposed in front of the eye of a wearer. The thin transparent layer may be configured to output light such that light is directed onto the eye to create reflections therefrom that can be used, for example, for glint based tracking. The thin transparent layer can be configured to reduced obstructions in the field of the view of the user.

18 Claims, 65 Drawing Sheets

(51) Int. Cl.
*A61B 3/12* (2006.01)
*G02B 27/00* (2006.01)

(56) References Cited

U.S. PATENT DOCUMENTS

| | | | | |
|---|---|---|---|---|
| 2005/0057941 | A1* | 3/2005 | Pederson | F21S 10/06 |
| | | | | 362/542 |
| 2006/0028436 | A1 | 2/2006 | Armstrong | |
| 2007/0081123 | A1 | 4/2007 | Lewis | |
| 2009/0261848 | A1* | 10/2009 | Araki | G01N 21/67 |
| | | | | 324/705 |
| 2011/0213664 | A1* | 9/2011 | Osterhout | G06F 3/013 |
| | | | | 705/14.58 |
| 2012/0127062 | A1 | 5/2012 | Bar-Zeev et al. | |
| 2012/0162549 | A1 | 6/2012 | Gao et al. | |
| 2013/0082922 | A1 | 4/2013 | Miller | |
| 2013/0117377 | A1 | 5/2013 | Miller | |
| 2013/0125027 | A1 | 5/2013 | Abovitz | |
| 2013/0208234 | A1 | 8/2013 | Lewis | |
| 2013/0242262 | A1 | 9/2013 | Lewis | |
| 2014/0071539 | A1 | 3/2014 | Gao | |
| 2014/0177023 | A1 | 6/2014 | Gao et al. | |
| 2014/0218468 | A1 | 8/2014 | Gao et al. | |
| 2014/0267420 | A1 | 9/2014 | Schowengerdt | |
| 2015/0016777 | A1* | 1/2015 | Abovitz | G02B 27/0093 |
| | | | | 385/37 |
| 2015/0103306 | A1 | 4/2015 | Kaji et al. | |
| 2015/0178939 | A1 | 6/2015 | Bradski et al. | |
| 2015/0205126 | A1* | 7/2015 | Schowengerdt | G02B 5/1814 |
| | | | | 345/633 |
| 2015/0309263 | A2 | 10/2015 | Abovitz et al. | |
| 2015/0326570 | A1 | 11/2015 | Publicover et al. | |
| 2015/0346495 | A1 | 12/2015 | Welch et al. | |
| 2016/0011419 | A1* | 1/2016 | Gao | G02B 3/12 |
| | | | | 359/471 |
| 2016/0026253 | A1 | 1/2016 | Bradski et al. | |
| 2016/0334574 | A1* | 11/2016 | Czornomaz | H01L 27/14 |
| 2017/0045741 | A1 | 2/2017 | Raffle et al. | |
| 2017/0205875 | A1 | 7/2017 | Kaehler | |
| 2018/0035101 | A1* | 2/2018 | Osterhout | G02B 27/0172 |
| 2018/0143438 | A1 | 5/2018 | Oh | |
| 2018/0143485 | A1 | 5/2018 | Oh | |
| 2018/0143509 | A1 | 5/2018 | Oh | |
| 2018/0164627 | A1 | 6/2018 | Oh | |
| 2018/0239147 | A1 | 8/2018 | Schowengerdt et al. | |
| 2018/0239177 | A1 | 8/2018 | Oh | |
| 2018/0275409 | A1 | 9/2018 | Gao et al. | |
| 2019/0072703 | A1* | 3/2019 | Ostlie | G02B 6/001 |
| 2019/0086674 | A1* | 3/2019 | Sinay | G06T 19/006 |
| 2019/0146165 | A1* | 5/2019 | Lee | G02B 6/4214 |
| | | | | 438/27 |

OTHER PUBLICATIONS

International Search Report and Written Opinion for PCT Application No. PCT/US 20/23581, dated Jun. 19, 2020.
ARToolKit: https://web.archive.org/web/20051013062315/http://www.hitl.washington.edu:80/artoolkit/documentation/hardware.htm, archived Oct. 13, 2005.
Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.
Azuma, "Predictive Tracking for Augmented Realty," TR95-007, Department of Computer Science, UNC—Chapel Hill, NC, Feb. 1995.
Bimber, et al., "Spatial Augmented Reality—Merging Real and Virtual Worlds," 2005 https://web.media.mit.edu/~raskar/book/BimberRaskarAugmentedRealityBook.pdf.
Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).
Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).
International Preliminary Report on Patentability for PCT Application No. PCT/US 20/23581, dated Sep. 16, 2021.

* cited by examiner

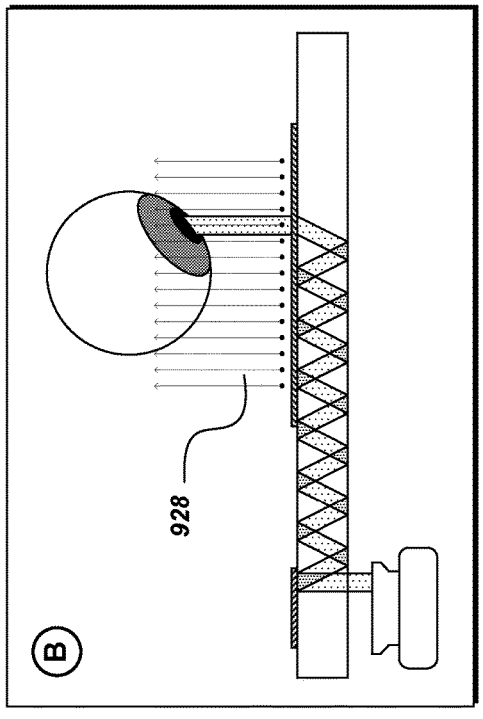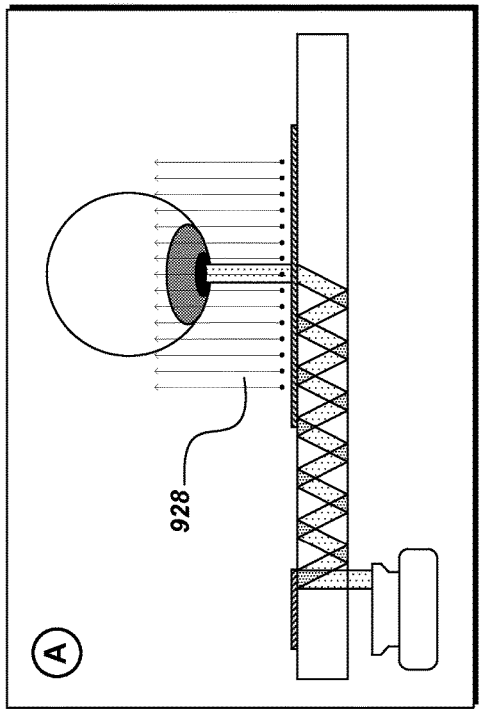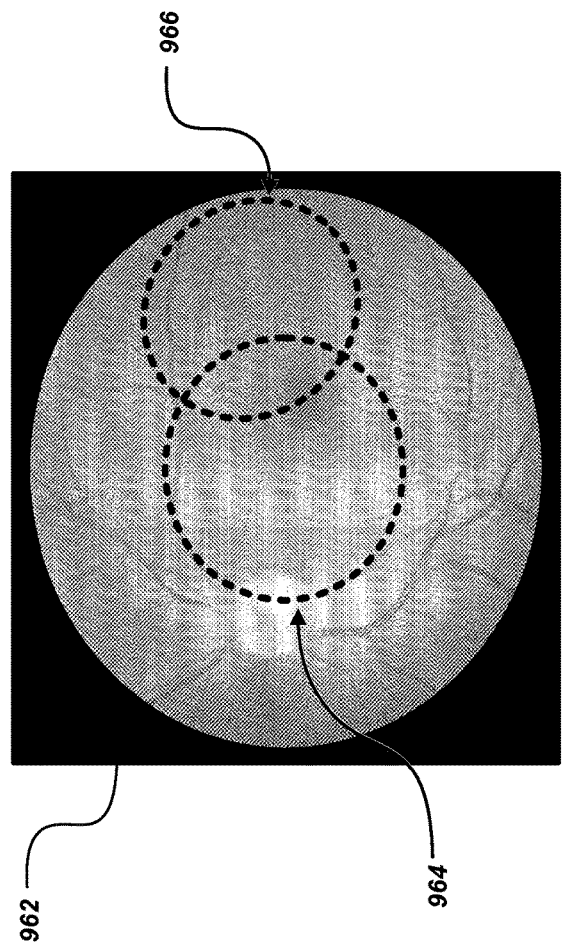
FIG. 13A

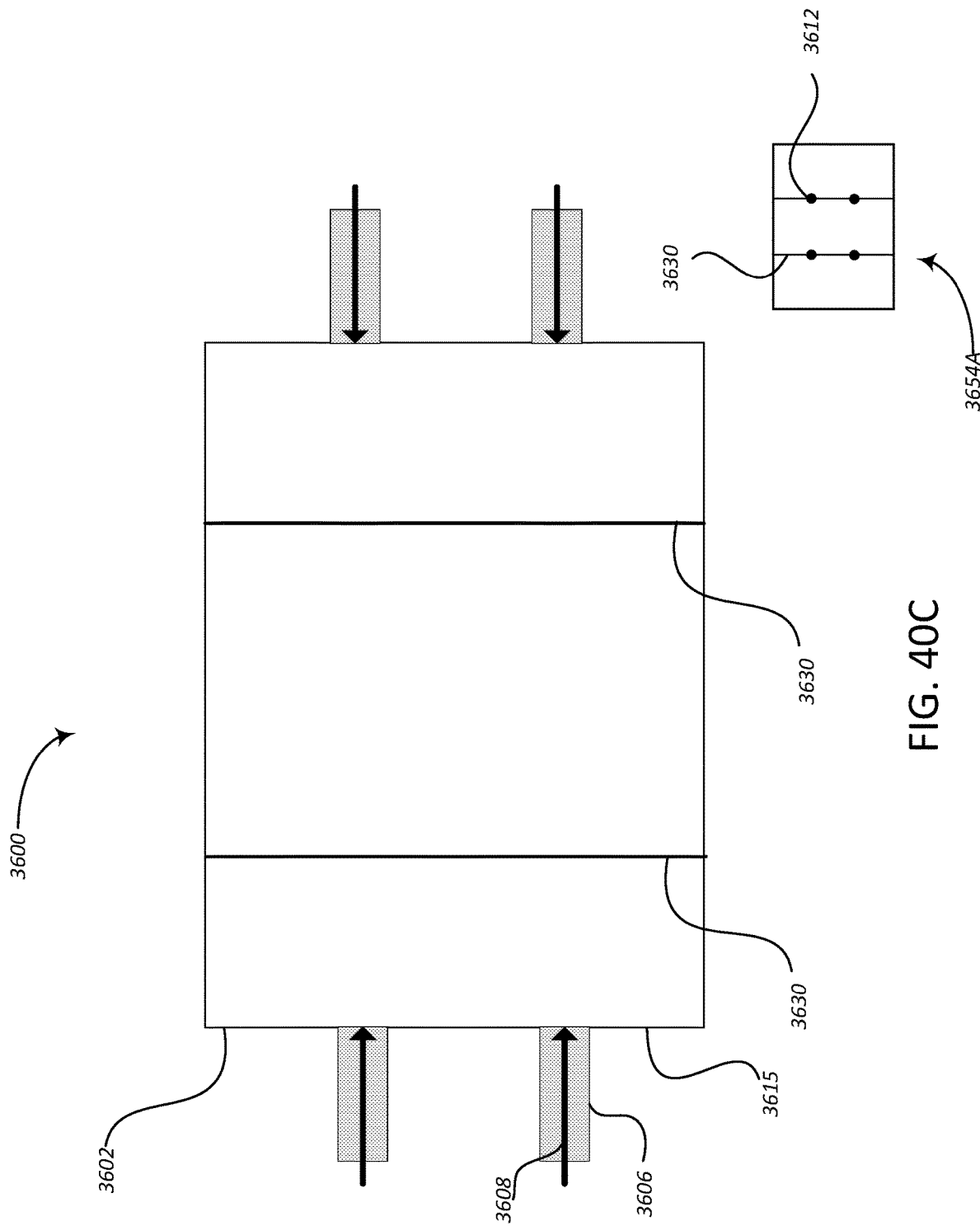

SYSTEM FOR PROVIDING ILLUMINATION OF THE EYE

CROSS-REFERENCE TO RELATED APPLICATIONS

This application claims the benefit of priority to U.S. Provisional Patent Application No. 62/821,121 filed Mar. 20, 2019, entitled "SYSTEM FOR PROVIDING ILLUMINATION OF THE EYE", the disclosure of which is hereby incorporated by reference herein in its entirety.

BACKGROUND

Field

The present disclosure relates to optical devices, including augmented reality imaging and visualization systems.

Description of the Related Art

Modern computing and display technologies have facilitated the development of systems for so called "virtual reality" or "augmented reality" experiences, in which digitally reproduced images or portions thereof are presented to a user in a manner wherein they seem to be, or may be perceived as, real. A virtual reality, or "VR", scenario typically involves the presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, an MR scenario may include AR image content that appears to be blocked by or is otherwise perceived to interact with objects in the real world.

Referring to FIG. 1, an augmented reality scene 10 is depicted. The user of an AR technology sees a real-world park-like setting 20 featuring people, trees, buildings in the background, and a concrete platform 30. The user also perceives that he/she "sees" "virtual content" such as a robot statue 40 standing upon the real-world platform 30, and a flying cartoon-like avatar character 50 which seems to be a personification of a bumble bee. These elements 50, 40 are "virtual" in that they do not exist in the real world. Because the human visual perception system is complex, it is challenging to produce AR technology that facilitates a comfortable, natural-feeling, rich presentation of virtual image elements amongst other virtual or real-world imagery elements.

Systems and methods disclosed herein address various challenges related to AR and VR technology.

Polarizing beam splitters may be used in display systems to direct polarized light to light modulators and then to direct this light to a viewer. There is a continuing demand to reduce the sizes of display systems generally and, as a result, there is also a demand to reduce the sizes of the constituent parts of the display systems, including constituent parts utilizing polarizing beam splitters.

SUMMARY

Various implementations described herein include display systems configured to provide illumination and/or image projection to the eye. Additionally or alternatively, the display systems can image the eye and/or the environment.

In some embodiments, a head mounted display system is configured to project light to an eye of a user to display augmented reality image content in a vision field of said user. The head-mounted display system can include a frame that is configured to be supported on a head of the user. The display system can also include an image projector that is configured to project images into the user's eye to display image content in the vision field of the user. The display system can include a camera, at least one waveguide, at least one coupling optical element that is configured such that light is coupled into said waveguide and guided therein, and at least one out-coupling element. The at least one out-coupling element can be configured to couple light that is guided within said waveguide out of said waveguide and direct said light to said camera. The camera can be disposed in an optical path with respect to said at least one out-coupling optical element to receive at least a portion of the light that is coupled into said waveguide via the coupling element and guided therein and that is coupled out from said waveguide by said out-coupling coupling element such that images may be captured by said camera.

BRIEF DESCRIPTION OF THE DRAWINGS

FIG. 13A schematically illustrates how the imaging system can image various portions of the eye, for example, of the retina, which can enable the orientation of the eye to be determined and the eye position tracked.

FIGS. 40A-40C are side, perspective, and top views, respectively, of an example transparent layer that includes a pair of tilted surfaces that reflect light guided through the transparent layer towards the eye.

The drawings are provided to illustrate example embodiments and are not intended to limit the scope of the disclosure. Like reference numerals refer to like parts throughout.

DETAILED DESCRIPTION

Figure 1:
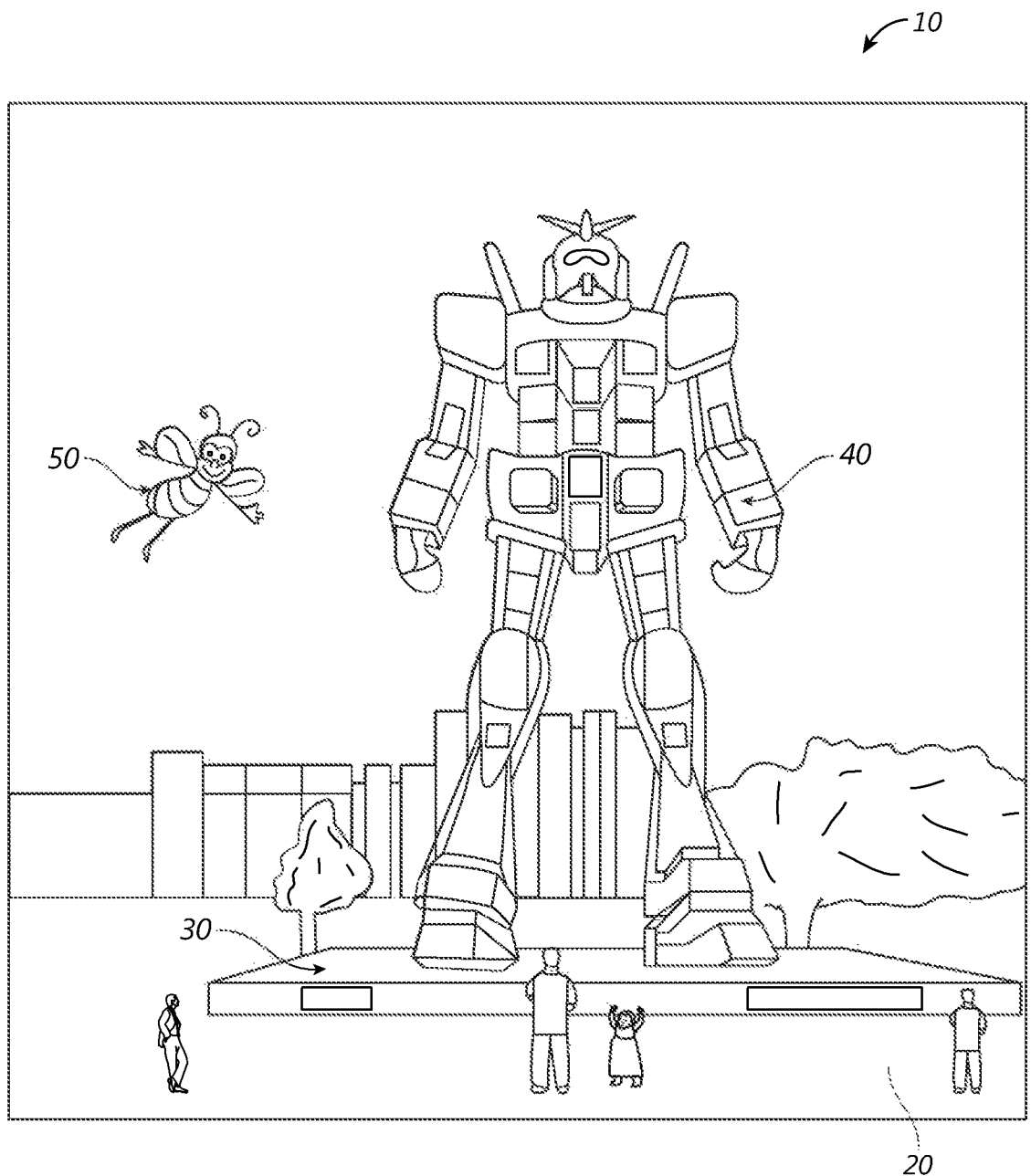
FIG. 1 illustrates a user's view of augmented reality (AR) through an AR device.

Reference will now be made to the figures, in which like reference numerals refer to like parts throughout.

Figure 2:
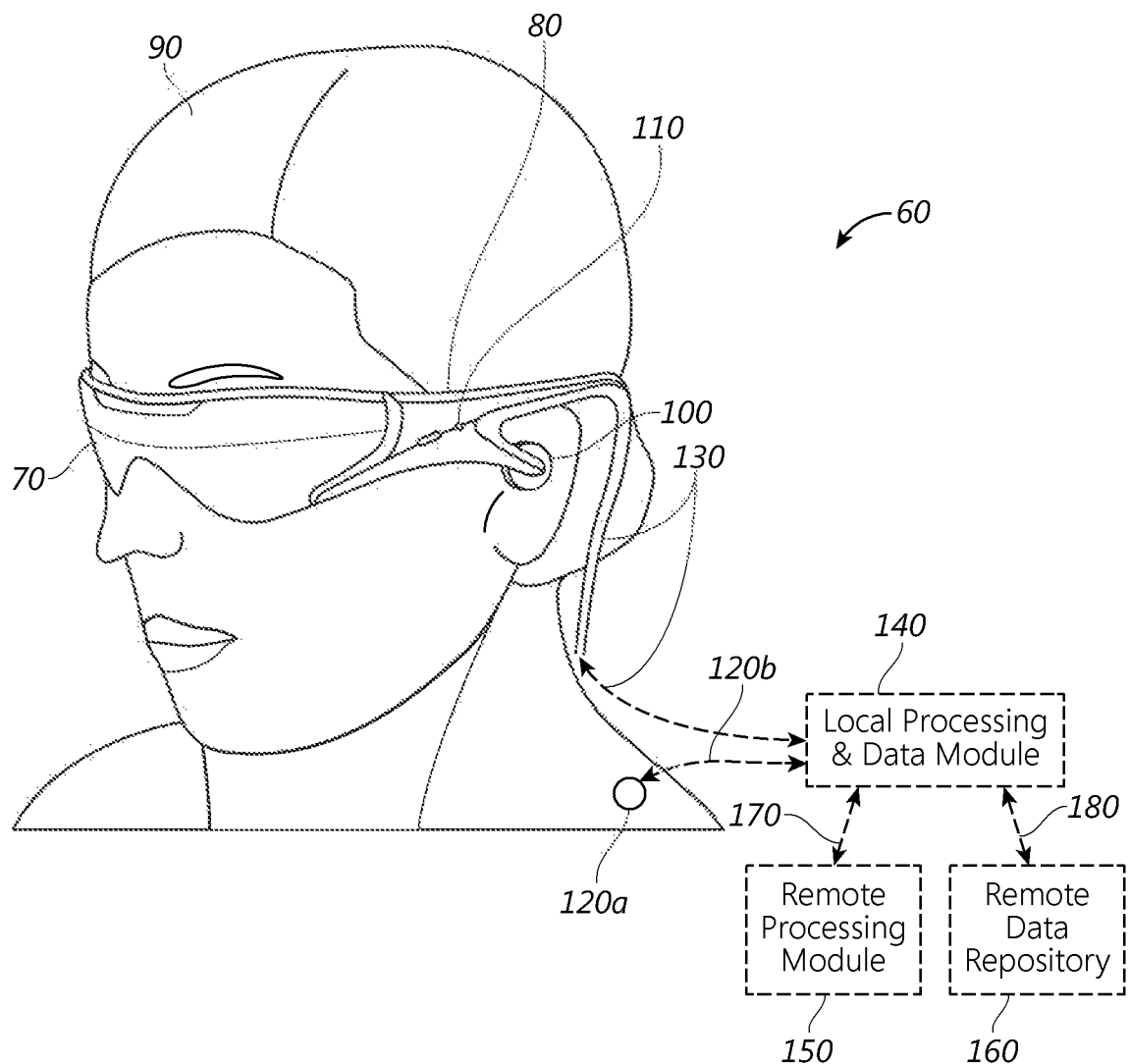
FIG. 2 illustrates an example of wearable display system.

FIG. 2 illustrates an example of wearable display system 60. The display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system may also include a peripheral sensor 120a, which may be separate from the frame 80 and attached to the body of the user 90 (e.g., on the head, torso, an extremity, etc. of the user 90). The peripheral sensor 120a may be configured to acquire data characterizing a physiological state of the user 90 in some embodiments. For example, the sensor 120a may be an electrode.

With continued reference to FIG. 2, the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120a may be operatively coupled by communications link 120b, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. The data include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 2, in some embodiments, the remote processing module 150 may comprise one or more processors configured to analyze and process data and/or image information. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating augmented reality content, to the local processing and data module 140 and/or the remote processing module 150. In some embodiments, all data is stored and all computations are performed in the local processing and data module, allowing fully autonomous use from a remote module.

Figure 3:
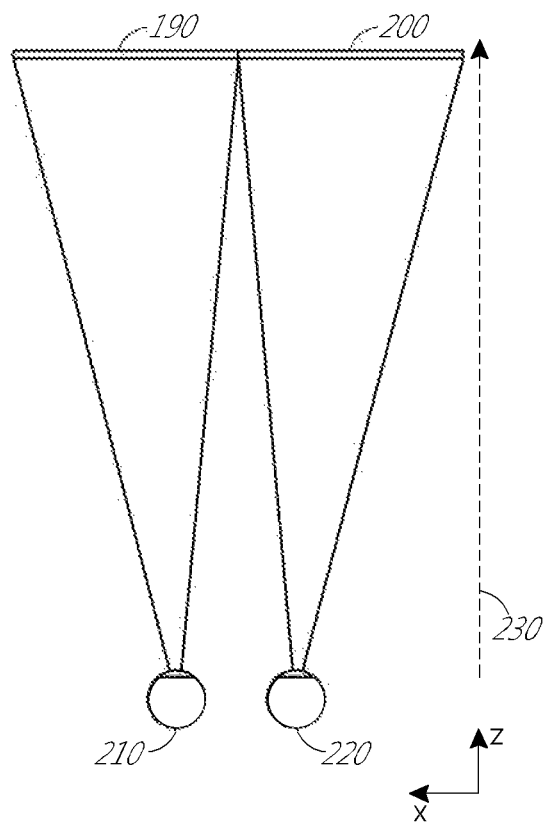
FIG. 3 illustrates a conventional display system for simulating three-dimensional imagery for a user.

With reference now to FIG. 3, the perception of an image as being "three-dimensional" or "3-D" may be achieved by providing slightly different presentations of the image to each eye of the viewer. FIG. 3 illustrates a conventional display system for simulating three-dimensional imagery for a user. Two distinct images 190, 200—one for each eye 210, 220—are outputted to the user. The images 190, 200 are spaced from the eyes 210, 220 by a distance 230 along an optical or z-axis that is parallel to the line of sight of the viewer. The images 190, 200 are flat and the eyes 210, 220 may focus on the images by assuming a single accommodated state. Such 3-D display systems rely on the human visual system to combine the images 190, 200 to provide a perception of depth and/or scale for the combined image.

It will be appreciated, however, that the human visual system is more complicated and providing a realistic perception of depth is more challenging. For example, many viewers of conventional "3-D" display systems find such systems to be uncomfortable or may not perceive a sense of depth at all. Without being limited by theory, it is believed that viewers of an object may perceive the object as being "three-dimensional" due to a combination of vergence and accommodation. Vergence movements (i.e., rotation of the eyes so that the pupils move toward or away from each other to converge the lines of sight of the eyes to fixate upon an object) of the two eyes relative to each other are closely associated with focusing (or "accommodation") of the lenses and pupils of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex," as well as pupil dilation or constriction. Likewise, a change in vergence will trigger a matching change in accommodation of lens shape and pupil size, under normal conditions. As noted herein, many stereoscopic or "3-D" display systems display a scene using slightly different presentations (and, so, slightly different images) to each eye such that a three-dimensional perspective is perceived by the human visual system. Such systems are uncomfortable for many viewers, however, since they, among other things, simply provide different presentations of a scene, but with the eyes viewing all the image information at a single accommodated state, and work against the "accommodation-vergence reflex." Display systems that provide a better match between accommodation and vergence may form more realistic and comfortable simulations of three-dimensional imagery.

Figure 4:
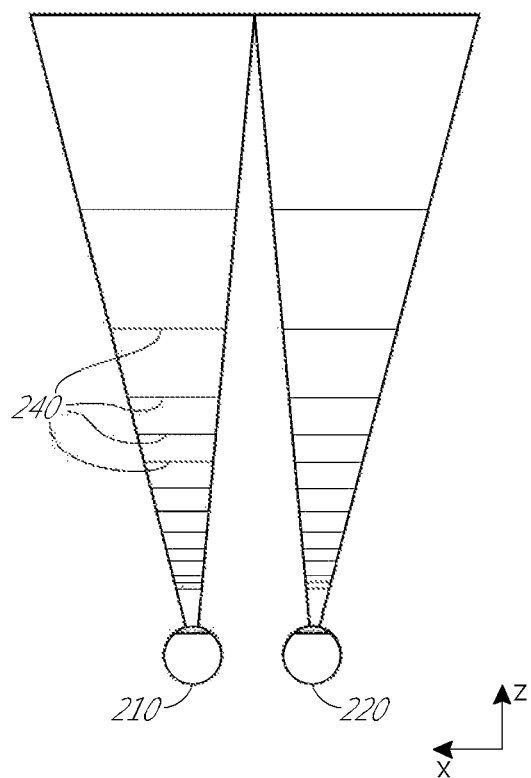
FIG. 4 illustrates aspects of an approach for simulating three-dimensional imagery using multiple depth planes.

FIG. 4 illustrates aspects of an approach for simulating three-dimensional imagery using multiple depth planes. With reference to FIG. 4, objects at various distances from eyes 210, 220 on the z-axis are accommodated by the eyes 210, 220 so that those objects are in focus. The eyes 210, 220 assume particular accommodated states to bring into focus objects at different distances along the z-axis. Consequently, a particular accommodated state may be said to be associated with a particular one of depth planes 240, with has an associated focal distance, such that objects or parts of objects in a particular depth plane are in focus when the eye is in the accommodated state for that depth plane. In some embodiments, three-dimensional imagery may be simulated by providing different presentations of an image for each of the eyes 210, 220, and also by providing different presentations of the image corresponding to each of the depth planes. While shown as being separate for clarity of illustration, it will be appreciated that the fields of view of the eyes 210, 220 may overlap, for example, as distance along the z-axis increases. In addition, while shown as flat for ease of illustration, it will be appreciated that the contours of a depth plane may be curved in physical space, such that all features in a depth plane are in focus with the eye in a particular accommodated state.

Figure 5A:
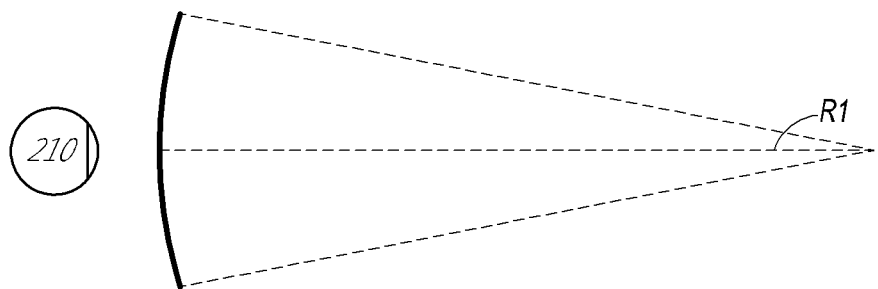
FIGS. 5A-5C illustrate relationships between radius of curvature and focal radius.
Figure 5B:
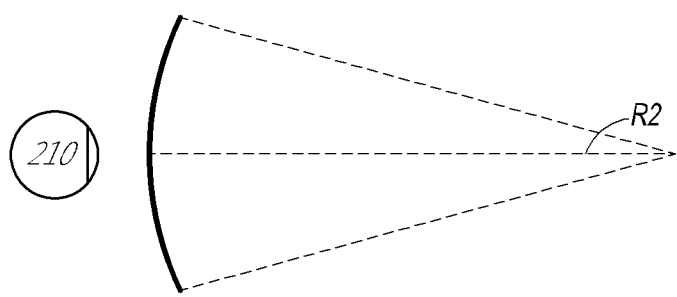
Figure 5C:
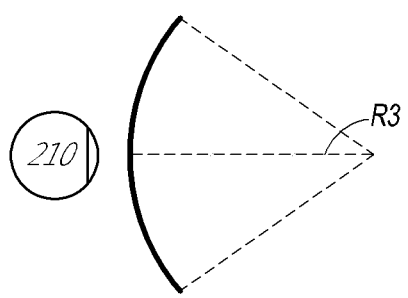

The distance between an object and the eye 210 or 220 may also change the amount of divergence of light from that object, as viewed by that eye. FIGS. 5A-5C illustrate relationships between distance and the divergence of light rays. The distance between the object and the eye 210 is represented by, in order of decreasing distance, R1, R2, and R3. As shown in FIGS. 5A-5C, the light rays become more divergent as distance to the object decreases. As distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. Consequently, at different depth planes, the degree of divergence of light rays is also different, with the degree of divergence increasing with decreasing distance between depth planes and the viewer's eye 210. While only a single eye 210 is illustrated for clarity of illustration in FIGS. 5A-5C and other figures herein, it will be appreciated that the discussions regarding eye 210 may be applied to both eyes 210 and 220 of a viewer.

Without being limited by theory, it is believed that the human eye typically can interpret a finite number of depth planes to provide depth perception. Consequently, a highly believable simulation of perceived depth may be achieved by providing, to the eye, different presentations of an image corresponding to each of these limited number of depth planes. The different presentations may be separately focused by the viewer's eyes, thereby helping to provide the user with depth cues based on the accommodation of the eye required to bring into focus different image features for the scene located on different depth plane and/or based on observing different image features on different depth planes being out of focus.

Figure 6:
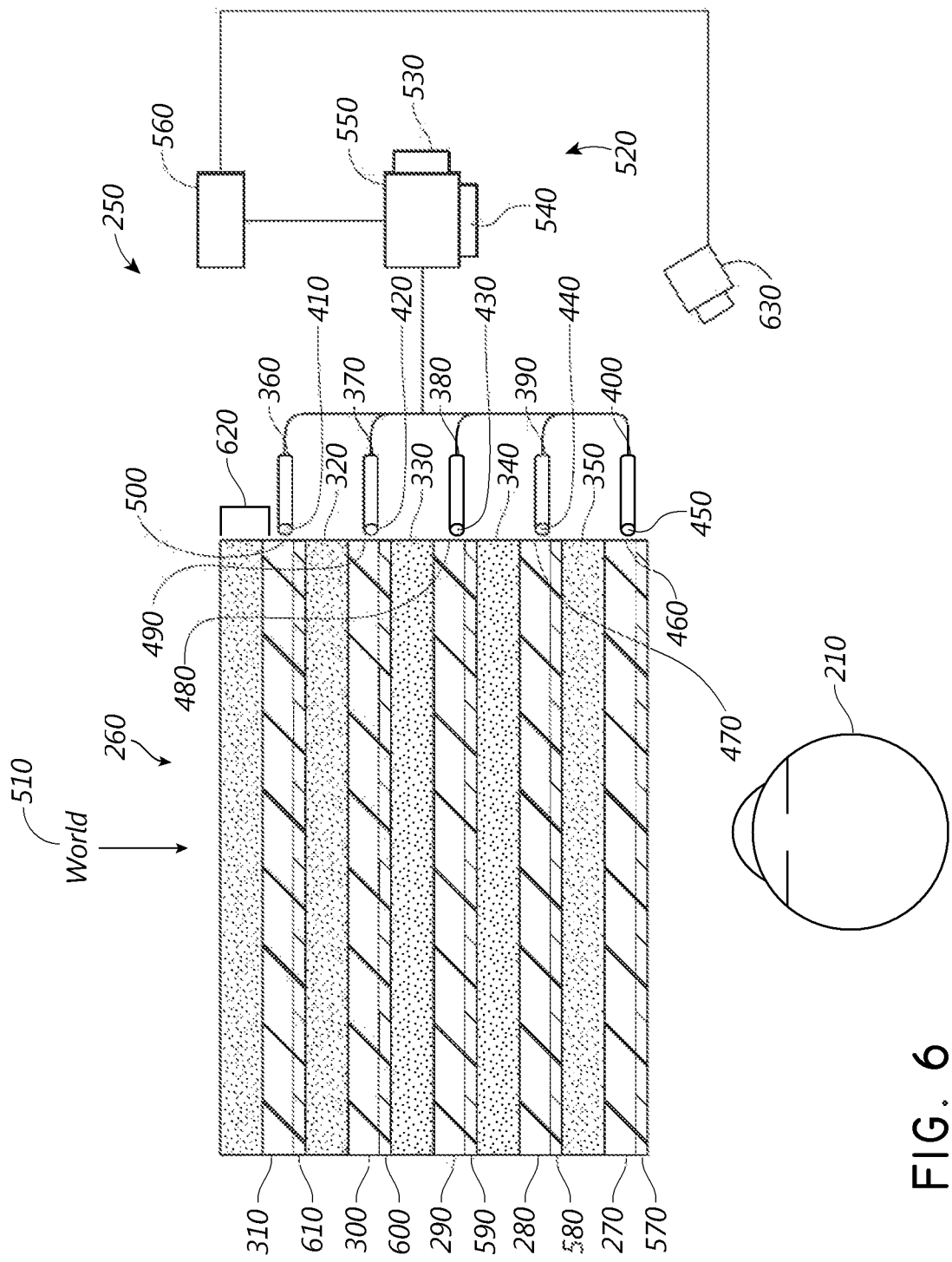
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. In some embodiments, the display system 250 is the system 60 of FIG. 2, with FIG. 6 schematically showing some parts of that system 60 in greater detail. For example, the waveguide assembly 260 may be part of the display 70 of FIG. 2. It will be appreciated that the display system 250 may be considered a light field display in some embodiments. In addition, the waveguide assembly 260 may also be referred to as an eyepiece.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, the each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projector system 520, which comprises a light module 540, which may include a light emitter, such as a light emitting diode (LED). The light from the light module 540 may be directed to and modified by a light modulator 530, e.g., a spatial light modulator, via a beam splitter 550. The light modulator 530 may be configured to change the perceived intensity of the light injected into the waveguides 270, 280, 290, 300, 310. Examples of spatial light modulators include liquid crystal displays (LCD) including a liquid crystal on silicon (LCOS) displays. It will be appreciated that the image injection devices 360, 370, 380, 390, 400 are illustrated schematically and, in some embodiments, these image injection devices may represent different light paths and locations in a common projection system configured to output light into associated ones of the waveguides 270, 280, 290, 300, 310.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 540 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 540, and the light modulator 530. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 2) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it can reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This can provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame 80 (FIG. 2) and may be in electrical communication with the processing modules 140 and/or 150, which may process image information from the camera assembly 630. In some embodiments, one camera assembly 630 may be utilized for each eye, to separately monitor each eye.

Figure 7:
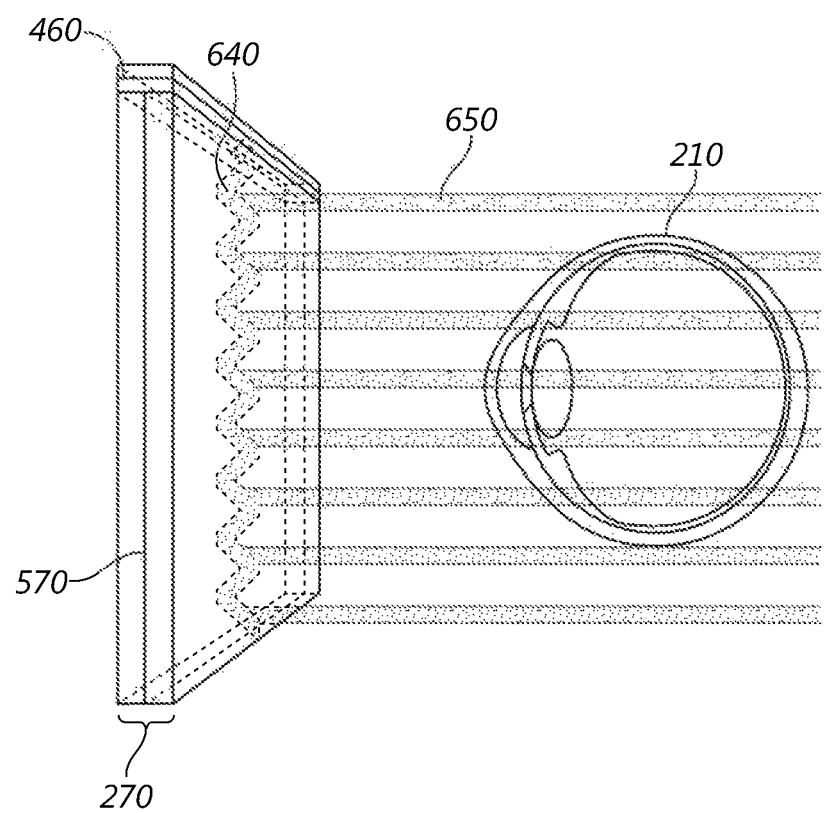
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

Figure 8:
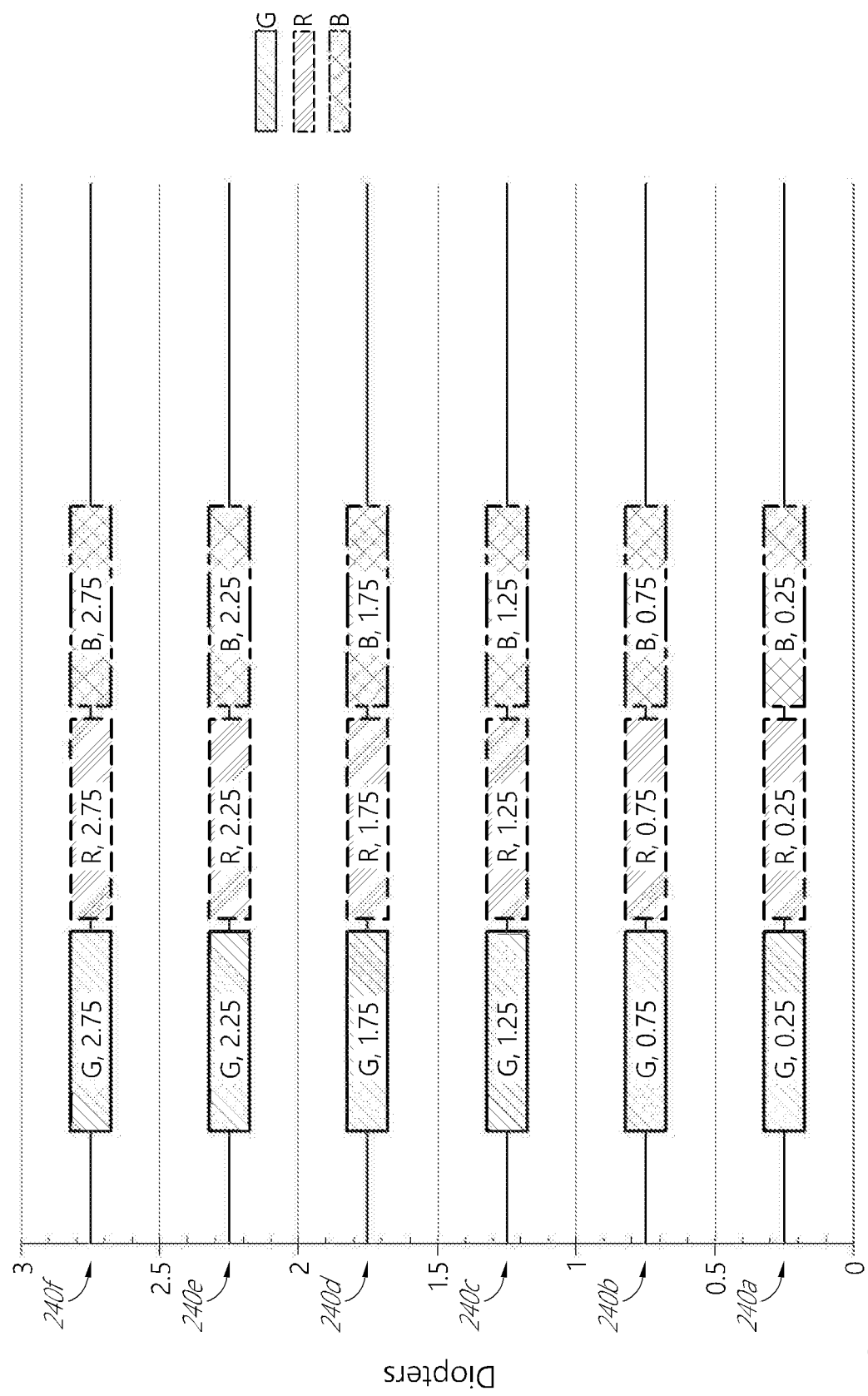
FIG. 8 illustrates an example of a stacked waveguide assembly in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 540 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
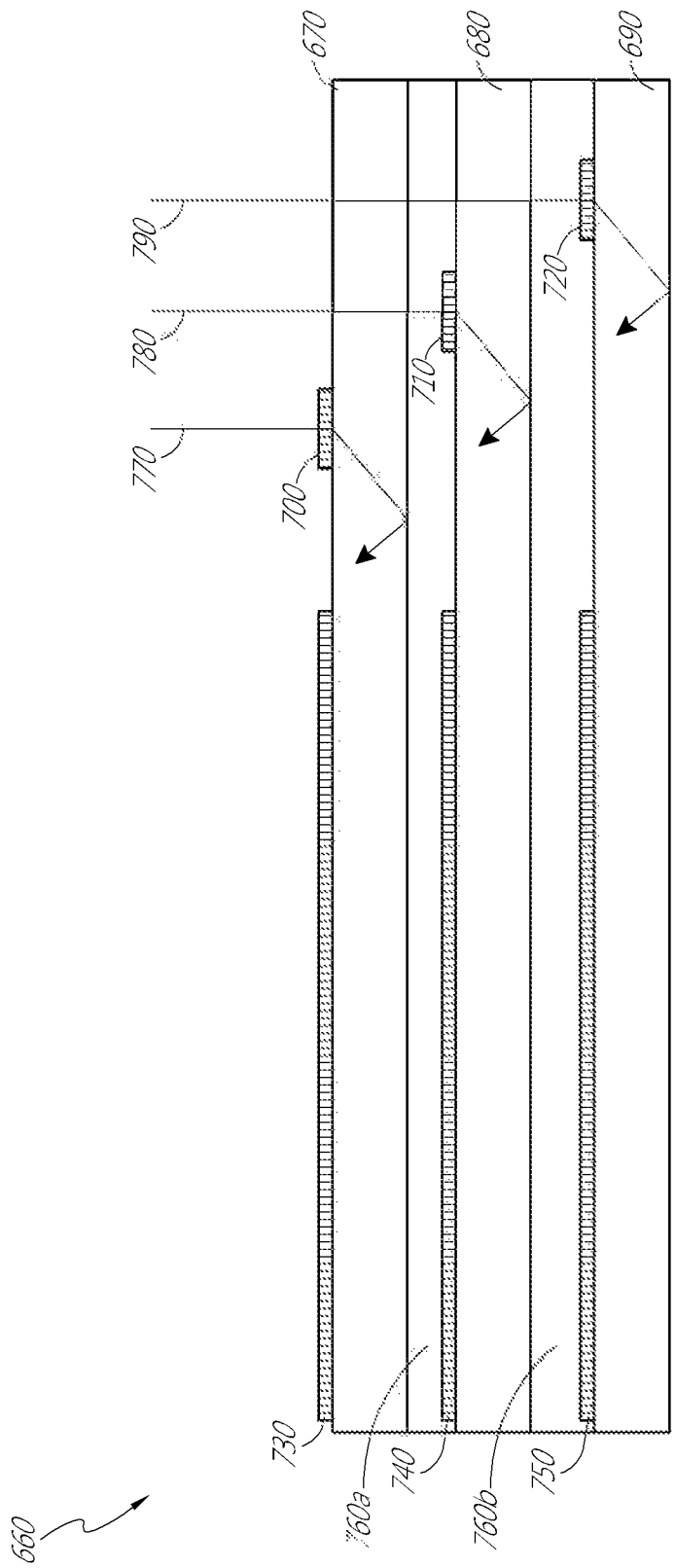
FIG. 9A illustrates a cross-sectional side view of an example of a set of stacked waveguides that each includes an incoupling optical element. As discuss herein, the stack of waveguide may comprise an eyepiece.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material. For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760a, 760b is 0.05 or more, or 0.10 or less than the refractive index of the material forming the waveguides 670, 680, 690. Advantageously, the lower refractive index layers 760a, 760b may function as cladding layers that facilitate total internal reflection (TIR) of light through the waveguides 670, 680, 690 (e.g., TIR between the top and bottom major surfaces of each waveguide). In some embodiments, the layers 760a, 760b are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760a, 760b are similar or the same. In some embodiments, the material forming the waveguides 670, 680, 690 may be different between one or more waveguides, and/or the material forming the layers 760a, 760b may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TIR. In some embodiments, the incoupling optical elements 700, 710, 720 each selectively deflect one or more particular wavelengths of light, while transmitting other wavelengths to an underlying waveguide and associated incoupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by TIR until impinging on the waveguide's corresponding light distributing elements 730, 740, 750.

Figure 9B:
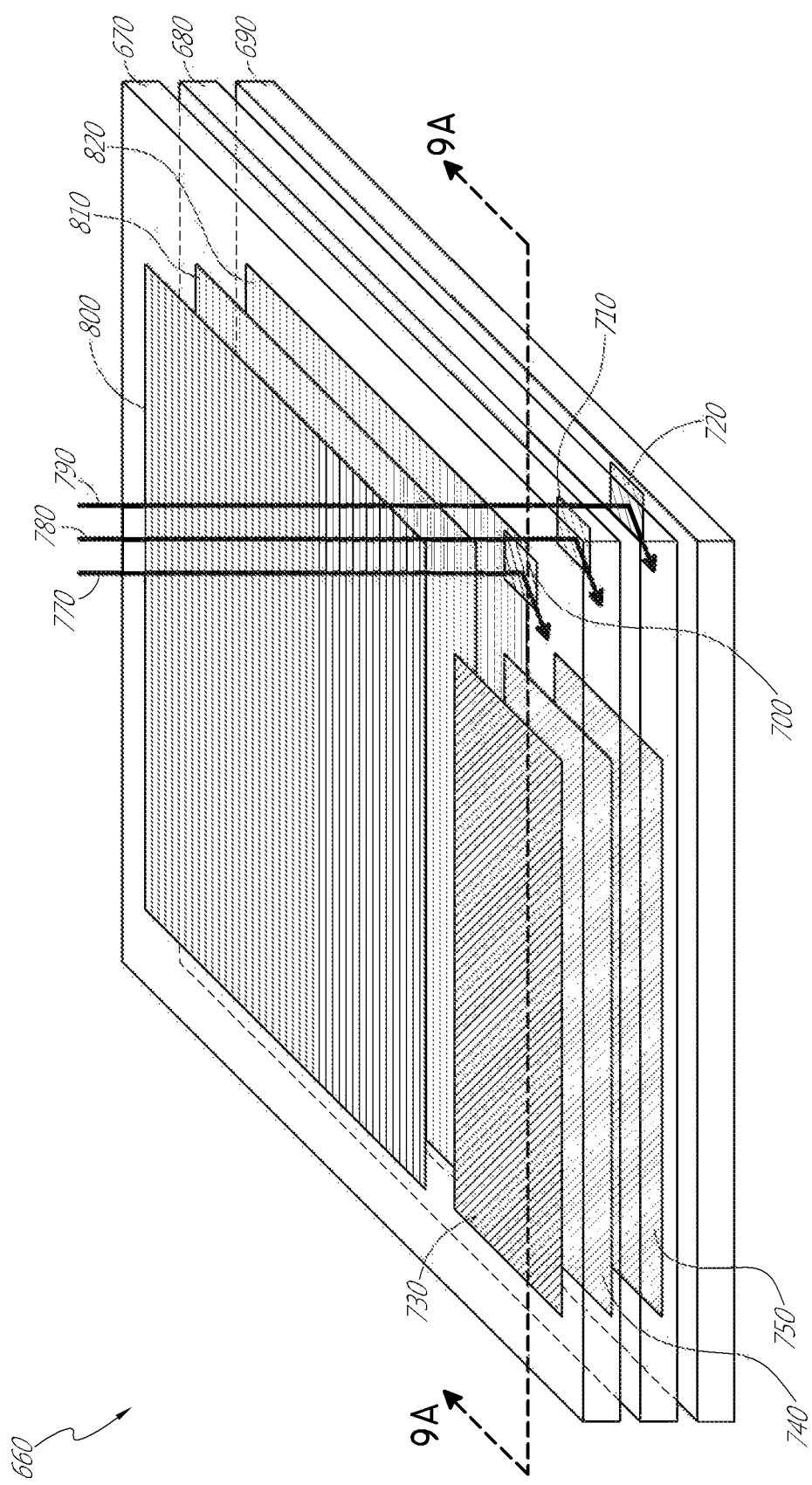
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of incoupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810.

Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
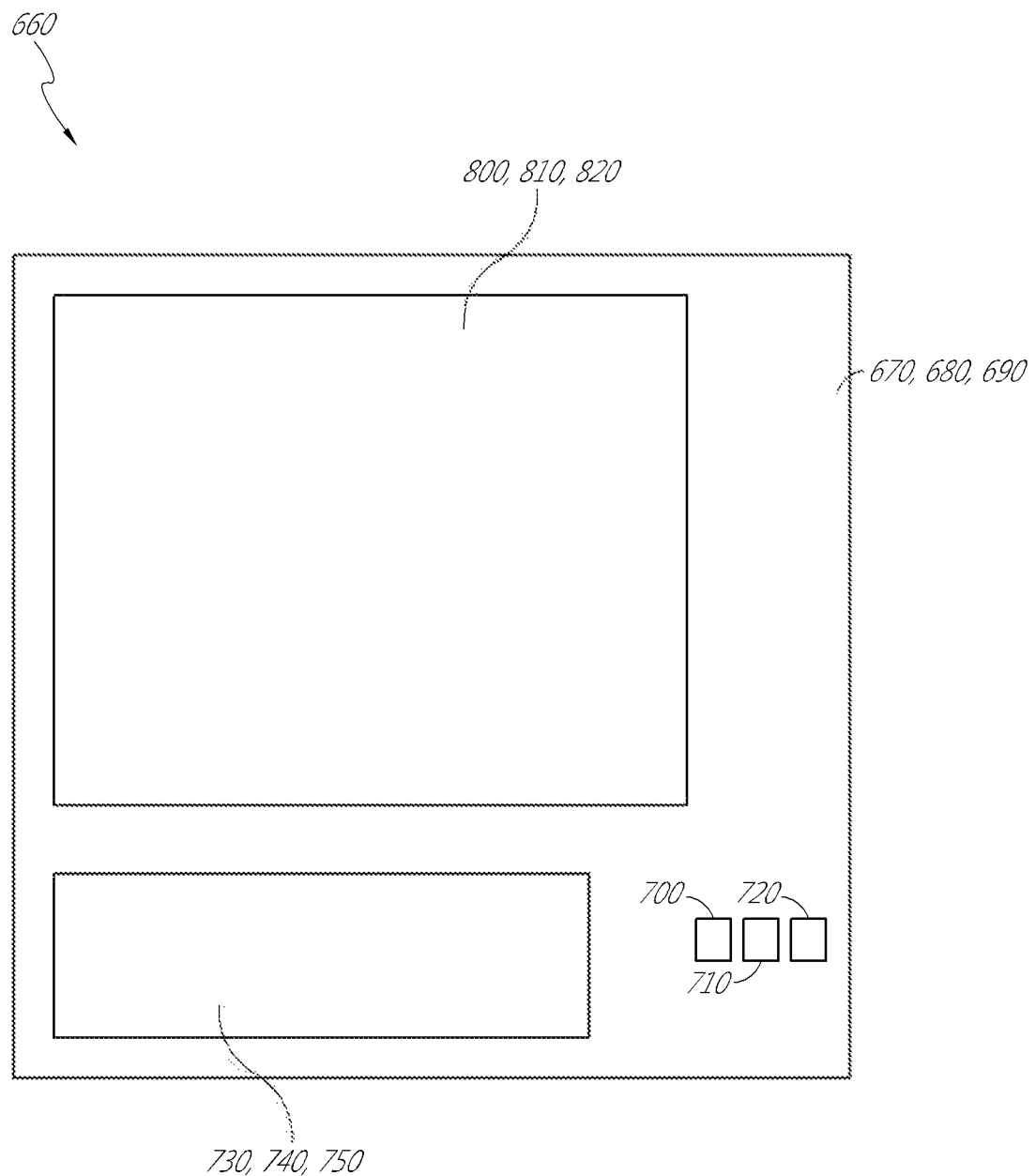
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub pupils.

Eye Imaging and Environment Imaging

As discussed above, head mounted displays can be used to provide image content to a user integrated with, in conjunction with, and/or superimposed over the view of the world in front of the wearer. Such head mounted display systems can be configured to project light into an eye of a user to form augmented reality image content as well as to transmit light from an environment in front of the user to the user. A head mounted display system may include one or more cameras for imaging the environment and/or the user's eye. Outward facing cameras may be used for directly imaging the environment, for example, to determine where to place augmented reality image content with respect to objects in the environment. For example, imaging the environment may provide the location of a table such that the head mounted display may render an image of person standing next to the table instead of on the table or in the table. Inward-facing cameras may be used for directly imaging the eye such as for eye tracking. Disclosed herein are examples of head-mounted display systems and/or imaging systems that can be configured also to image the eye and/or the environment. In some designs, the systems do not require inward and/or outward facing cameras to directly image the eye and/or environment, respectively. Such systems may employ one or more cameras that are configured to receive light from the eye/environment via the eyepiece such as one or more waveguides in the eyepiece that are in optical communication with the one or more cameras. With the light collected by the waveguide(s), the one or more cameras can generate images of the eye and/or the environment in front of the user. Using the waveguide to collect the light for imaging the eye and/or environment may potentially reduce the form factor of the head mounted display, making the head mounted display possibly more compact and/or aesthetically desirable.

Figure 10:
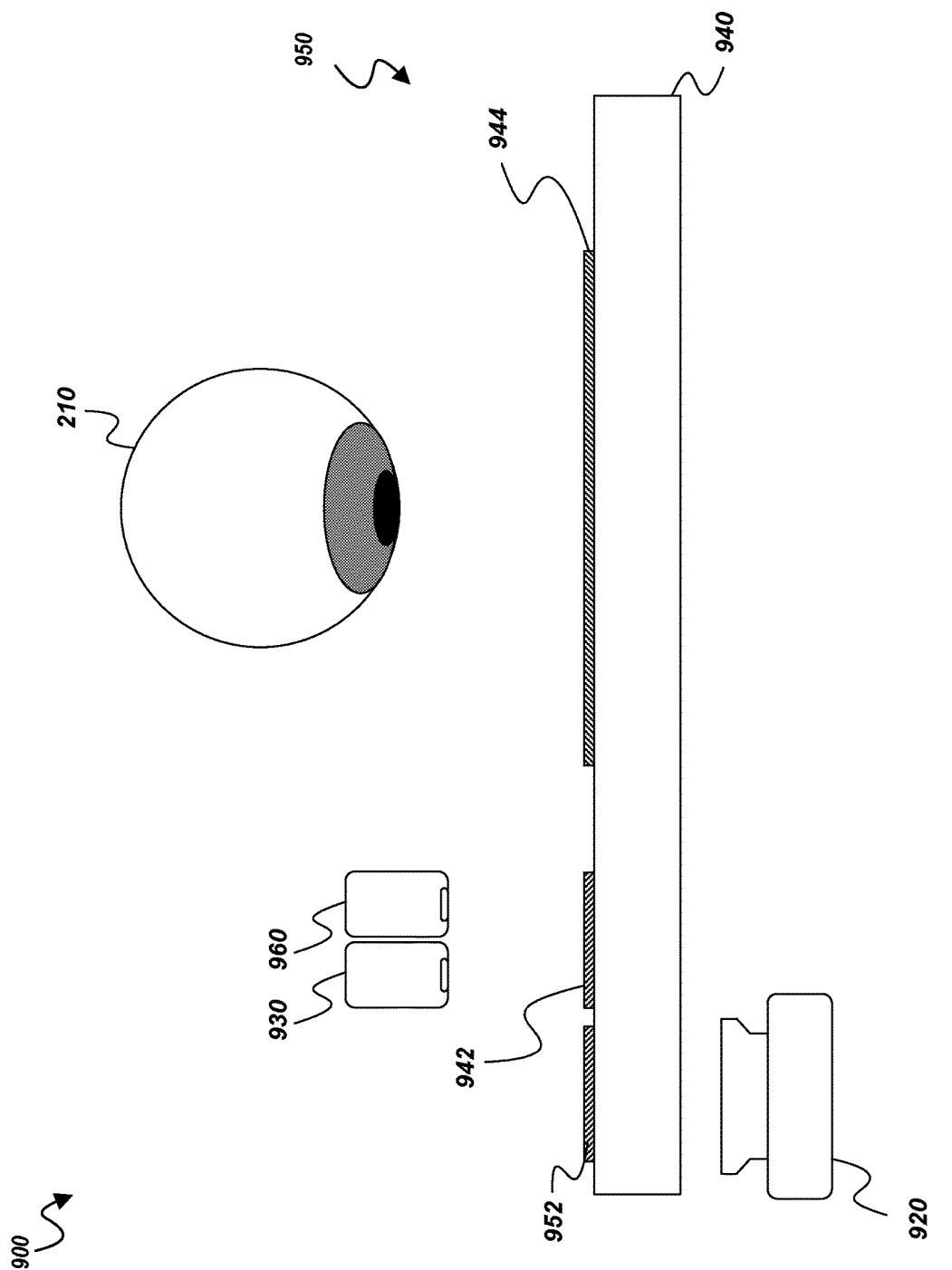
FIG. 10 schematically illustrates a cross-sectional side view of an example imaging system comprising an eyepiece, an image projector, a light source for illuminating the eye, and a camera for capturing an image of the eye.

FIG. 10 illustrates an example imaging system 900 configured to image the eye that is integrated with an eyepiece 950 that can be used on in head mounted display. The eyepiece 950, which can be disposed in front of the user's eye 210 can be used to both inject image content into the eye as well as image the eye. FIG. 10 shows one eyepiece 950 in front of one eye 210. Various head mounted display systems such as shown in FIG. 2, may include a pair of eyepieces 950 and associated components disposed in front of respective left and right eyes 210. A single waveguide 940 is shown in FIG. 10, but the waveguide 940 may include one, two, three, four, six, seven, eight, or more waveguides (e.g., one or more stacks of waveguides).

The imaging system 900 can include a light source or illumination source 960 illuminating the eye to facilitate image capture, the eyepiece 950 comprising a waveguide 940 configured to propagate light therein, and/or an imaging device 920 such as a camera for image capture. An image projector 930 for producing an image that can be injected into the eye via the eyepiece 950 is also shown. The eyepiece 950 may include one or more waveguides 940 configured to transport light from the illumination source 960 and/or image projector 930 to the eye and to transport light from the eye to the camera 920. The eyepiece 950 may further comprise one or more coupling optical elements 944 for coupling light out of the waveguide 940 and to the eye for illuminating the eye and for image injection and/or from the eye and into the waveguide for image capture. The eyepiece 950 may additionally comprise one or more incoupling optical elements 942 for coupling light from the illumination source 960 and/or image projector 930 into the waveguides 940 as well as one or more outcoupling optical elements 952 for coupling light from the waveguide out to the camera 920.

The eyepiece 950 may be disposed on a frame wearable on the head. The eyepiece 950 may be disposed in front of the eye 210. The eyepiece 950 may have a medial or nasal side closer to the nose of the wearer and an opposite lateral or temporal side closer to the temples and farther from the nose of the wearer. In FIG. 10, the coupling optical element 944 is medial or nasal with respect to the incoupling 942 and outcoupling 952 optical elements (which are lateral or temporal to the coupling optical elements 944). The illumination source 960 is also more medial or nasal with respect to the image projector 930 (or the image projector is more lateral or temporal than the illumination source.) The relative positions can be different, however. For example, the illumination source 960 may be more lateral or temporal than the image projector 930 in some designs.

The waveguide 940 may comprise a sheet or layer having two major surfaces (a forward and a rearward surface), having the largest surface areas, disposed opposite one another. The forward surface may be farther from the user's eye 210 (closer to the environment in front of the wearer) and the rearward closer to the user's eye (and farther from the environment in front of the wearer) when the user wears the head mounted display. The waveguide 940 may comprise a transparent material with an index of refraction greater than 1.0 (e.g., glass, plastic) such that light may be guided therein by total internal reflection between the major surfaces. Elements with the same numbers may have the same functionality for one or more of the embodiments described herein.

A coupling optical element 944 for coupling light to the eye 210 from waveguide 940 and/or from the waveguide to the eye may be disposed on or in the waveguide 940. As shown in FIG. 10, the coupling optical element 944 may be disposed in an optical path between the user's eye 210 and the waveguide 940 such that light coupled from the waveguide 940 via the coupling optical element 944 may be incident on the user's eye 210 (for example to illuminate the eye and/or for image injection). The coupling optical element 944 may comprise a plurality of turning features configured to turn light guided within the waveguide out of the waveguide or turn light incident on the coupling optical element 944 at an angle into the waveguide to be guided therein by total internal reflection. The coupling optical element 944 and turning features may be in physical engagement with the waveguide 940. For example, the coupling optical element 944 may comprise a holographic or diffractive optical element (e.g., surface relief grating) patterned (e.g., etched) in or on the waveguide 940. The coupling optical element 944 may comprise a layer disposed on the waveguide 940 or may be formed in the waveguide 940. For example, a volume holographic or other diffractive optical element may be formed by changing the index of refraction of material comprising the waveguide or a layer disposed thereon. Accordingly, the coupling optical element 944 may be disposed in the volume of the waveguide 940 or as a layer disposed thereon.

Depending on the design, the coupling optical element 944 may be transmissive or reflective and may operate in transmission or reflection. For example, the coupling optical element 944 may include a transmissive or reflective diffractive optical element (e.g., grating) or holographical optical element that operates in transmission or reflection respectively, e.g., turning light via that is transmitted therethrough or that is reflected therefrom. The coupling optical element 944 can include a polarization optical element, such as a polarization selective turning element (e.g., polarizer). The polarization selective turning element may include one or more polarization gratings, diffractive optical elements, and/or holographic optical elements and may comprise liquid crystal structures such as liquid crystal polarization gratings. The coupling optical element 944 may be configured to direct light from the image projector 930 and/or light source 960 guided within the waveguide 940 by total internal reflection (TIR) to the user's eye 210 at an angle less than (e.g., more normal) than the critical angle so as to be ejected out of the waveguide to the eye. Additionally or in the alternative, the coupling optical element 944 may be configured to couple light from the eye 210 into the waveguide 940 at an angle greater (e.g., less normal) than the critical angle so as to be guided therein by total internal reflection to the camera 920.

As shown in FIG. 10, an incoupling optical element 942 for coupling light from the illumination source 960 and/or the image projector 930 into the waveguide 940 may be disposed on or in the waveguide 940. The incoupling optical element 942 may be disposed in an optical path between the light source 960 and the waveguide 940 such that light coupled from the light source 960 via the incoupling optical element 942 is guided within the waveguide 940. The incoupling optical element 942 may comprise, for example, a plurality of turning features configured to turn light incident thereon at an angle into the waveguide to be guided therein by total internal reflection. The incoupling optical element 942 may comprise liquid crystal structures such as liquid crystal polarization gratings. Additionally or alternatively, the incoupling optical element 942 may include a blazed grating. The incoupling optical element 942 may comprise a layer disposed on the waveguide 940 or may be formed on or in the waveguide 940 (e.g., patterned) or may be otherwise manufactured therein. For example, a surface holographic or diffractive optical element (e.g., surface relief grating) may be fabricated by patterning (e.g., etching) a surface of the waveguide or a layer thereon. A volume holographic or diffractive optical element may also be formed by changing the index of refraction of material comprising the waveguide or a layer disposed thereon. Accordingly, the incoupling optical element 942 may be disposed in the volume of the waveguide 940 or a layer disposed thereon. Depending on the design, the incoupling optical element 942 may be transmissive or reflective and may operate in transmission or reflection. For example, the incoupling optical element 942 may include a transmissive or reflective diffractive optical element (e.g., grating) or holographical optical element that operates in transmission or reflection, respectively, e.g., turning light that is transmitted therethrough or that is reflected therefrom.

The incoupling optical element 942 may comprise a reflective optical element (e.g., mirror). For example, the incoupling optical element 942 may comprise an off-axis reflector. Additionally or alternatively, the incoupling optical element 942 and/or coupling optical element 944 can include a polarization optical element, such as a polarization selective turning element (e.g., polarizer). The polarization selective turning element may include one or more polarization gratings, diffractive optical elements, and/or holographic optical elements and may comprise liquid crystal structures such as liquid crystal polarization gratings. For example, one or both of the incoupling optical element 942 and/or the coupling optical element 944 can include liquid crystal polarization gratings (LCPGs). LCPGs can provide high efficiency diffraction potentially at broad wavelengths. Accordingly, LCPGs may be useful for incoupling optical elements 942 and/or the coupling optical element 944. The LCPG may be polarization dependent. The LCPG or other type of liquid crystal grating, diffractive optical element, or optical element may include a pattern or arrangement of molecules of liquid crystal configured to provide one or more functions such as turn light into a waveguide or out of a waveguide. Accordingly, incoupling optical element 942 and/or the coupling optical element 944 may comprise polarization gratings. Additionally or alternatively, incoupling optical element 942 and/or the coupling optical element 944 can comprises liquid crystal and thus in some implementations one or both may be liquid crystal gratings or liquid crystal diffractive optical elements. Additionally or alternatively, one or both of the incoupling optical element 942 and/or the coupling optical element 944 can include a blazed grating. In some designs, the incoupling optical element 942 comprises a liquid crystal reflector, such as a cholesteric liquid crystal reflective lens (e.g., reflective liquid crystal diffraction lens, Bragg-reflective structure, reflective liquid crystal diffraction grating, etc.). Some non-limiting examples of liquid crystal gratings, liquid crystal polarization gratings and other liquid crystal optical elements are discussed in the following published applications, each of which is hereby incorporated by reference herein in its entirety and for all purposes: U.S. Publication No. 2018/0143438, titled "MULTILAYER LIQUID CRYSTAL DIFFRACTIVE GRATINGS FOR REDIRECTING LIGHT OF WIDE INCIDENT ANGLE RANGES," filed on Nov. 16, 2017; U.S. Publication No. 2018/0143485, titled "SPATIALLY VARIABLE LIQUID CRYSTAL DIFFRACTION GRATINGS," filed on Nov. 16, 2017; U.S. Publication No. 2018/0143509, titled "WAVEGUIDE LIGHT MULTIPLEXER USING CROSSED GRATINGS," filed on Nov. 16, 2017; U.S. Publication No. 2018/0239147, titled "DISPLAY SYSTEM WITH VARIABLE POWER REFLECTOR," filed on Feb. 22, 2018; U.S. Publication No. 2018/0239177, titled "VARIABLE-FOCUS VIRTUAL IMAGE DEVICES BASED ON POLARIZATION CONVERSION," filed on Feb. 22, 2018; and U.S. Publication No. 2018/0164627, titled "DIFFRACTIVE DEVICES BASED ON CHOLESTERIC LIQUID CRYSTAL," filed on Dec. 7, 2017. The designs of the incoupling optical element 942 and/or the coupling optical element 944, however, are not limited to these and may include other types of optical elements, diffractive optical element, liquid crystal optical element, liquid crystal gratings and liquid crystal polarization gratings. Further information on examples of cholesteric liquid crystal structures such as reflectors may also be found below in in the section titled "Cholesteric Liquid Crystal Mirror." As discussed above, other liquid crystal optical elements as well as other non-liquid crystal optical elements may be used. Accordingly, many types of coupling optical elements (e.g. incoupling optical element 942 and/or the coupling optical element 944), diffractive optical element, gratings, polarization gratings, etc., may be used, both those described herein as well as other types of gratings, diffractive optical elements, liquid crystal elements, and optical elements generally. In various implementations, the incoupling optical element 942 may be configured to couple light from the image projector 930 and/or the light source 960 into the waveguide at an angle greater than the critical angle so as to be guided within the waveguide 940 by total internal reflection to the eye to the user's eye 210.

The waveguide 940 may comprise one or more waveguides. In some implementations, the one or more waveguides 940 comprises a stack of waveguides. In some designs, for example, different waveguides of the stack of waveguides are configured to output light with different wavefront divergence as if projected from different distances from the user's eye. For example, a first waveguide or group of waveguides may be configured to output light that is collimated or has a first divergence as if projected from a first depth, and a second waveguide or group of waveguides may be configured to output light that is diverging (not collimated) or is at a second divergence (greater than the first divergence) as if projected from a second depth closer than the first depth. In some designs, the different waveguides may be configured to output light having different associated colors. For example, a first waveguide may be configured to output red light, a second waveguide may be configured to output green light, and a third waveguide may be configured to output blue light. A fourth waveguide may be configured to output and/or input infrared light.

The outcoupling optical element 952 for coupling light from the waveguide 940 to the camera 920 such as shown in FIG. 10 may comprise, for example, a plurality of turning features configured to turn light incident thereon at an angle such that light is not guided within the waveguide and is turned out of the waveguide to the camera. The outcoupling optical element 952 may be disposed within an interior of the waveguide 940 or may be patterned (e.g., etched) in or on a surface (e.g., major surface) of the waveguide 940. For example, a surface holographic or diffractive optical element (e.g., surface relief grating) may be fabricated by patterning (e.g., etching) a surface of the waveguide or a layer thereon. A volume holographic or diffractive optical element may also be formed by changing the index of refraction of material comprising the waveguide or a layer disposed thereon. Depending on the design, the outcoupling optical element 952 may be transmissive or reflective and may operate in transmission or reflection. For example, the outcoupling optical element 952 may include a transmissive or reflective diffractive optical element (e.g., grating) or holographical optical element that operates in transmission or reflection, respectively, e.g., turning light that is transmitted therethrough or that is reflected therefrom.

The outcoupling optical element 942 may comprise a reflective optical element (e.g., mirror). For example, the outcoupling optical element 952 may comprise an off-axis reflector. In some designs, the outcoupling optical element 952 can include a polarization optical element, such as a polarization selective turning element (e.g., polarizer). Accordingly, the polarization selective turning element may include one or more polarization gratings, diffractive optical elements, and/or holographic optical elements and may comprise liquid crystal structures such as liquid crystal polarization gratings. In some implementations, for example, the outcoupling optical element 952 can include liquid crystal polarization gratings (LCPGs). LCPGs can provide high efficiency diffraction potentially at broad wavelengths. Likewise, LCPGs may be useful for outcoupling optical element 952. The LCPG may be polarization dependent. The LCPG or other types of liquid crystal gratings may include a pattern or arrangement of molecules of liquid crystal configured to provide one or more functions such as turn light into a waveguide or out of a waveguide. Accordingly, outcoupling optical element 952 may comprise polarization gratings. Additionally or alternatively, outcoupling optical element 952 can comprises liquid crystal and thus in some implementations may be liquid crystal gratings or other liquid crystal optical element such as liquid crystal diffractive optical elements. Additionally or alternatively, the outcoupling optical element 952 can include a blazed grating. In some designs, the outcoupling optical element 952 comprises a liquid crystal reflector, such as a cholesteric liquid crystal reflective lens (e.g., reflective liquid crystal diffraction lens, Bragg-reflective structure, reflective liquid crystal diffraction grating, etc.). Some nonlimiting examples of liquid crystal gratings, liquid crystal polarization gratings and other liquid crystal optical elements are discussed in the following published applications, each of which is hereby incorporated by reference herein in its entirety and for all purposes: U.S. Publication No. 2018/0143438, titled "MULTILAYER LIQUID CRYSTAL DIFFRACTIVE GRATINGS FOR REDIRECTING LIGHT OF WIDE INCIDENT ANGLE RANGES," filed on Nov. 16, 2017; U.S. Publication No. 2018/0143485, titled "SPATIALLY VARIABLE LIQUID CRYSTAL DIFFRACTION GRATINGS," filed on Nov. 16, 2017; U.S. Publication No. 2018/0143509, titled "WAVEGUIDE LIGHT MULTIPLEXER USING CROSSED GRATINGS," filed on Nov. 16, 2017; U.S. Publication No. 2018/0239147, titled "DISPLAY SYSTEM WITH VARIABLE POWER REFLECTOR," filed on Feb. 22, 2018; U.S. Publication No. 2018/0239177, titled "VARIABLE-FOCUS VIRTUAL IMAGE DEVICES BASED ON POLARIZATION CONVERSION," filed on Feb. 22, 2018; and U.S. Publication No. 2018/0164627, titled "DIFFRACTIVE DEVICES BASED ON CHOLESTERIC LIQUID CRYSTAL," filed on Dec. 7, 2017. The designs of the outcoupling optical element 952, however, are not limited to these and may include other types of optical elements, diffractive optical element, liquid crystal optical element, liquid crystal gratings and liquid crystal polarization gratings. Further information on examples of cholesteric liquid crystal structures such as reflectors may also be found below in the section titled "Cholesteric Liquid Crystal Mirror." As discussed above, other liquid crystal optical elements as well as other non-liquid crystal optical elements may be used. Accordingly, many types of coupling optical elements (e.g. outcoupling optical element 952), diffractive optical element, gratings, polarization gratings, etc., may be used, both those described herein as well as other types of gratings, diffractive optical elements, liquid crystal elements, or optical elements generally. As referred to above, the outcoupling optical element 952 may be configured to redirected light guided within the waveguide 940 at an angle less than the critical angle so as not to be guided within the waveguide by total internal reflection but to be ejected out to the camera 920.

In various designs, the coupling optical element 944 may be transparent in the visible spectrum such that the user can see through the coupling optical element 944 and the eyepiece 950 to the environment in front of the user. The incoupling optical element 942 may also turn light in the visible spectrum, for example, if the incoupling optical element is used to receive light from the image projector 930 and/or if the illumination source 960 is configured to output visible light to illuminate the eye 210 with visible light. In some embodiments, the incoupling optical element 942 is configured to turn infrared light, for example, if the illumination source 960 is configured to output infrared light to illuminate the eye 210 with infrared light. In some designs such as shown in FIG. 10, the incoupling optical element 942 may be more medial or nasal than the outcoupling optical element 952. However, in other designs the incoupling optical element 942 may be more lateral or temporal than the outcoupling optical element 952. In certain implementations such as shown in FIG. 10, the outcoupling optical element 952 may be adjacent the incoupling optical element 942 although non-adjacent positioning is possible.

The illumination source 960 may be disposed on the same side of the eyepiece 950 as the eye 210 (e.g., rearward or proximal side), as shown in FIG. 10. (Proximal may refer to the side closest to the eye 210.) Alternatively, the illumination source 960 may be disposed on the side opposite the eye 210 (e.g., forward or distal side). The illumination source 960 may be configured to direct light into at least one of the major surfaces of the waveguide 940 via the incoupling optical element 942. The light source 960 may be configured to emit invisible light (e.g., infrared). The light source 960 may include one or more LEDs. The LEDs may comprise infrared LEDs. The light source 960 may be configured to emit coherent light. In some designs, the light source 960 comprises a laser (e.g., infrared laser). In some designs, the light source 960 emits pulsed light. For example, the camera 920 can be configured to capture an image periodically. Accordingly, the illumination source 960 can be pulsed to coincide with the period during which the camera obtains images. The intensity output from the illumination source 960 can be reduced when the camera is not obtaining an image. By concentrating the total energy of the illumination on a short time increased signal to noise can be obtained while not exposing the eye 210 to unsafe intensity levels. In some cases, for example, the camera 920 captures one image every 30 milliseconds and the exposure time of the camera is few milliseconds. The illumination source 960 can be configured to output pulses having similar period and duration to match that of the camera 920.

In some implementations, different light sources having different wavelengths are alternately pulsed to provide different wavelength illumination at different times as discussed below.

The incoupling optical element 942 may be in direct optical communication with the illumination source 960 and/or image projector 930, for example, so as to guide light from said image projector 930 and/or light source 960 therein. For example, light emitted by the light source 960 may be incident on the incoupling optical element 942 before optically interacting with either the coupling optical element 944 and/or outcoupling optical element 952.

As shown in FIGS. 11A-11E, light 902 projected from the image projector 930 may form an image on the retina. The image projector 930 may include a light source, a modulator, and/or projection optics. The light source for the image projector 930 may comprise one or more LEDs, lasers or other light sources and may comprises one or more visible light sources. The modulator may comprise a spatial light modulator such as a liquid crystal spatial light modulator. Such a spatial light modulator may be configured, for example, to modulate the intensity of light at different spatial locations. The projection optics may comprise one or more lenses. Other types of image projectors 930 capable of projecting and/or forming images may be employed. For example, the image projector 930 may comprise a scanning optical fiber.

The image projector 930 and the incoupling optical element 942 may be in direct optical communication with each other. The image projector 930 may, for example, be aligned with the incoupling optical element 942 into which light from the image projector 930 is directed. In some cases, image projector 930 is disposed adjacent the corresponding incoupling optical element 942 and/or the waveguide 940. The image projector 930 may also be disposed in an optical path that includes the incoupling optical element 942, the coupling optical element 944, and the eye 210.

The image projector 930 may be a separate element than the illumination source 960, as shown in FIG. 10 as well as in FIGS. 11A-11E. However, in some cases the image projector 930 may be used as the illumination source. For example, in addition to injecting images into the eye 210, the image projector 930 may be used to direct visible and/or infrared light into the eye to illuminate the eye for image capture. Alternatively, however, one or more separate light sources 960 may be used to illuminate the eye 210 for image capture.

The light emitted by the illumination source 960 may comprise a particular wavelength range of light such as, for example, invisible light. The illumination source 960 may be configured to project invisible (e.g., infrared) light onto/into the eye 210 for imaging one or more parts (e.g., cornea, retina) of the eye 210. In certain example implementations, the light source 960 may be configured to emit light in the range of between about 850 nm and 940 nm. The light source 960 may be configured to emit light extending over a wavelength range of at least about 20 nm. Other ranges are also possible. The wavelength range emitted may be 5 nm, 10 nm, 15 nm, 50 nm, 75 nm, 100 nm, 150 nm, 200 nm, or any range between any of these values. The light source 960 may be configured to emit light across a broad band of wavelengths, such as any range within the infrared spectrum.

The imaging device 920, which may comprise a camera, may comprise a detector array and possibly imaging optics. The detector array may comprise, for example, a CCD or CMOS detector array and the imaging optics may comprise one or more lenses. The one or more lenses may have positive optical power and an associated focal length. In certain designs, the camera 920 is focused at infinity. For example, the optics may have a focal length, f, and detector array may be disposed a distance away from the optics corresponding to the focal length such that objects at a large distance are imaged onto the detector array. Similarly, light from the eye or objects in the environment that is collimated will be focus on the detector array to form an image of the eye or object thereon.

The imaging device 920 may be disposed on the opposite side of the waveguide 940 as the illumination source 960 and/or the eye 210. In some designs, the imaging device 920 may be disposed on the same side of the waveguide 940 as the light source 960 and/or eye 210. As shown in FIG. 10, the imaging device 920 may be disposed near a lateral or temporal edge of the eyepiece 950 although other locations are possible.

Figure 11A:
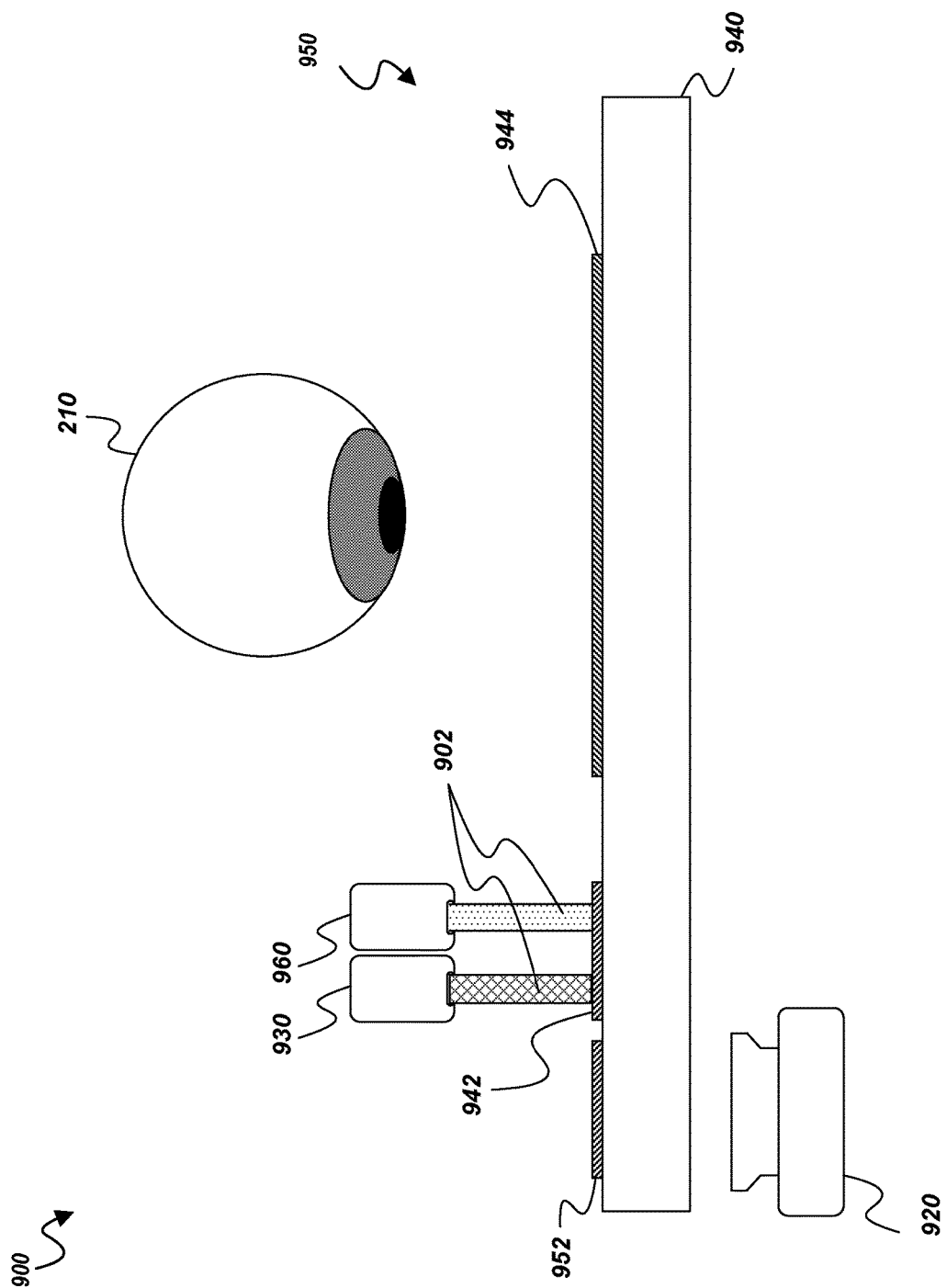
FIG. 11A schematically illustrates the light source for illuminating the eye and the image projector for injecting images in the eye both emitting light toward an incoupling optical element on a waveguide of the eyepiece.
Figure 11B:
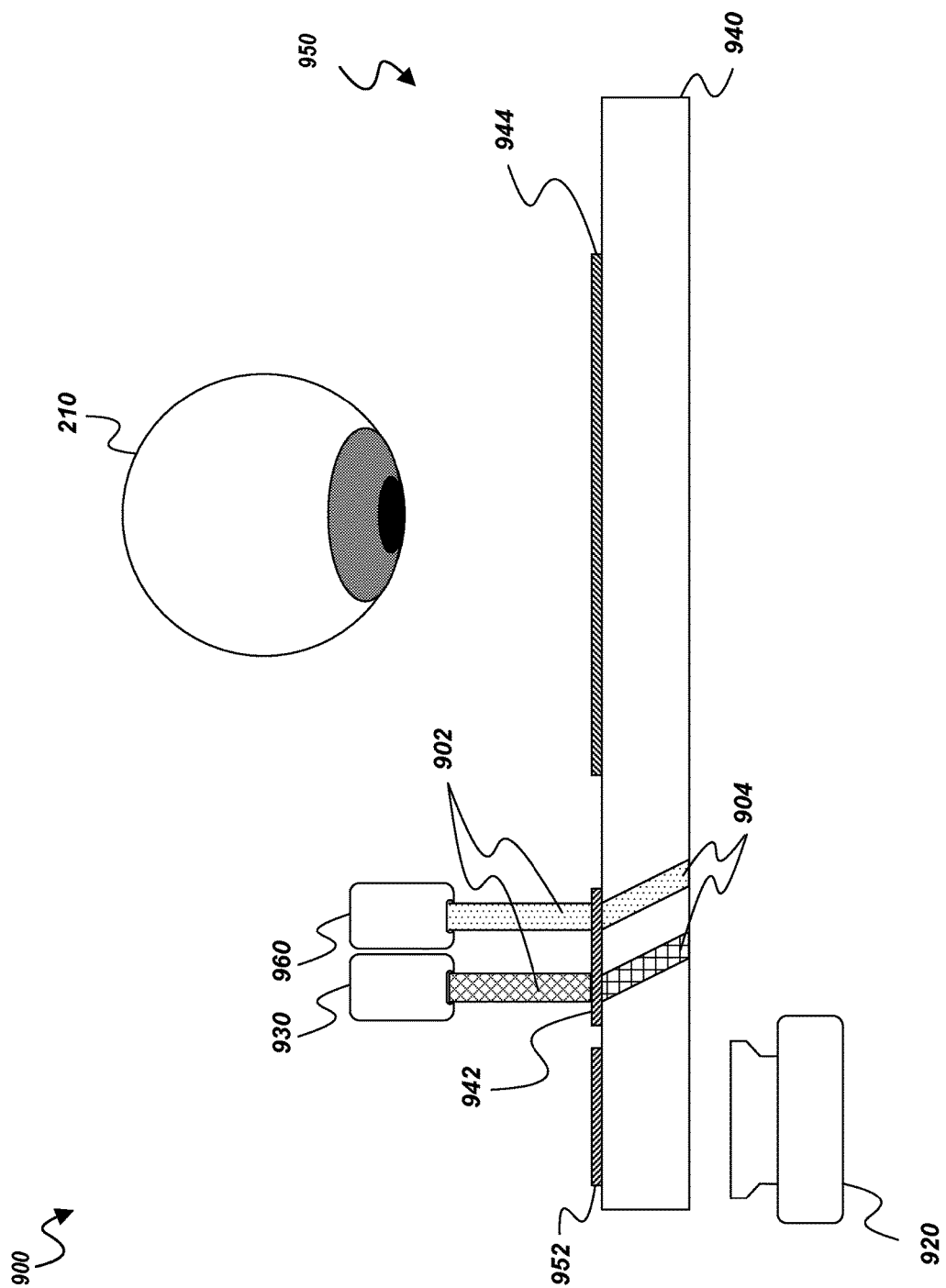
FIG. 11B schematically illustrates projected light from the light source and from the image projector coupled into the waveguide.
Figure 11C:
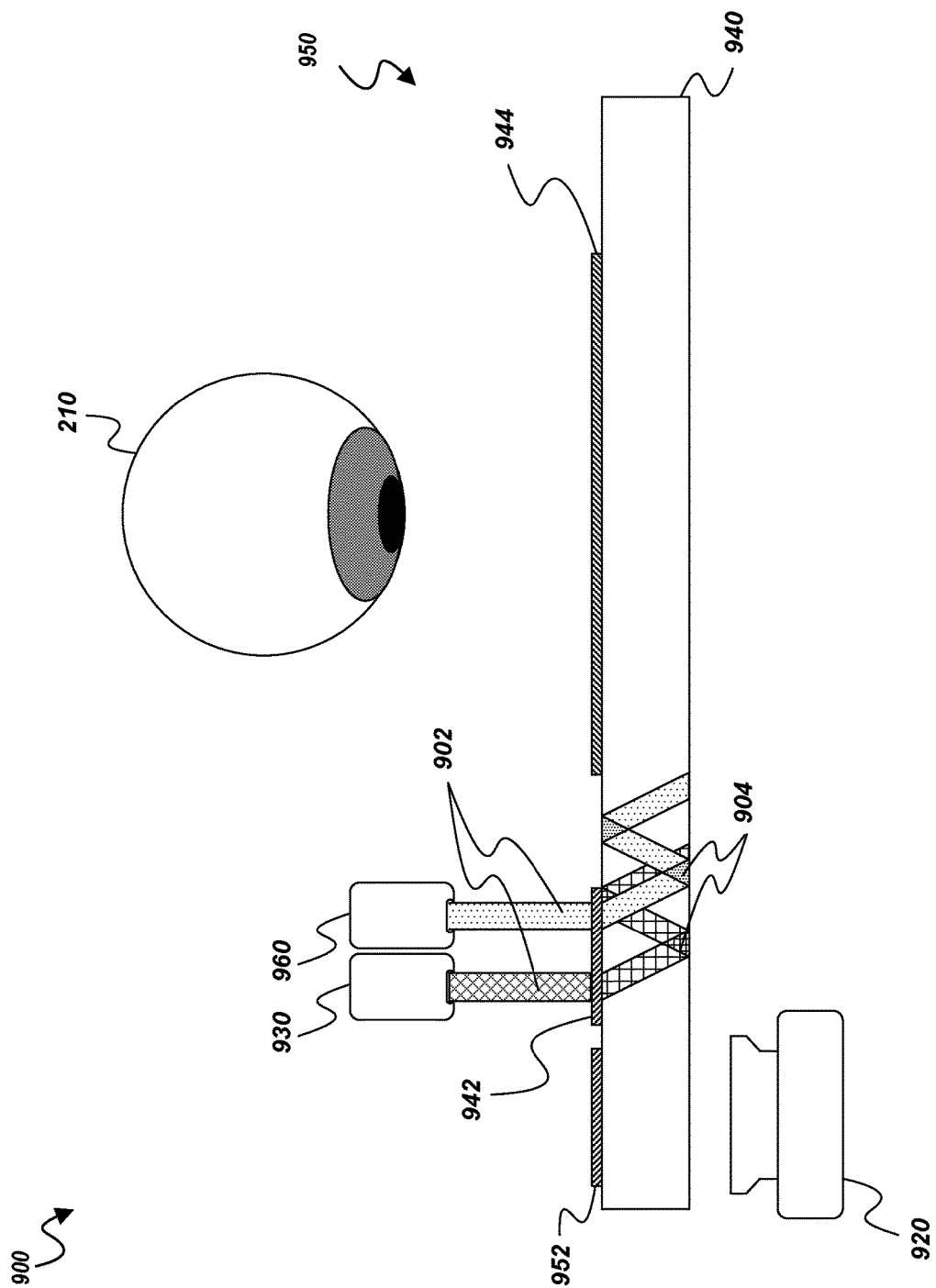
FIG. 11C schematically illustrates how incoupled light may propagate through a waveguide by total internal reflection.

FIGS. 11A-11E illustrate the operation of the example imaging system 900 of FIG. 10. FIG. 11A shows the illumination source 960 emitting light 902 toward the incoupling optical element 942 on the waveguide 940. As shown, the light 902 can be directed generally at normal incidence to the eyepiece 950 although other angles are possible. In some designs, the light source 960 is configured to emit collimated light into the eyepiece 950. As shown in FIG. 11B, the illumination light 902 can be coupled into the waveguide 940 via the incoupling optical element 942. In some designs where the incoupling optical element 942 comprises a diffractive optical element (e.g., grating, holographic element) the light incident thereon is diffracted at an angle greater than the critical angle of the waveguide to cause the incoupled light 904 to be guided within the eyepiece 950 by total internal reflection (TIR). In some designs, the incoupling optical element 942 may be configured to direct light toward the coupling optical element 944. The incoupling optical element 942 may be polarization selective. For example, the incoupling optical element 942 can include a polarization selective turning element such a polarization grating like a liquid crystal polarization grating. FIG. 11C shows how the incoupled light 904 propagating through the waveguide 940 by TIR.

Figure 11D:
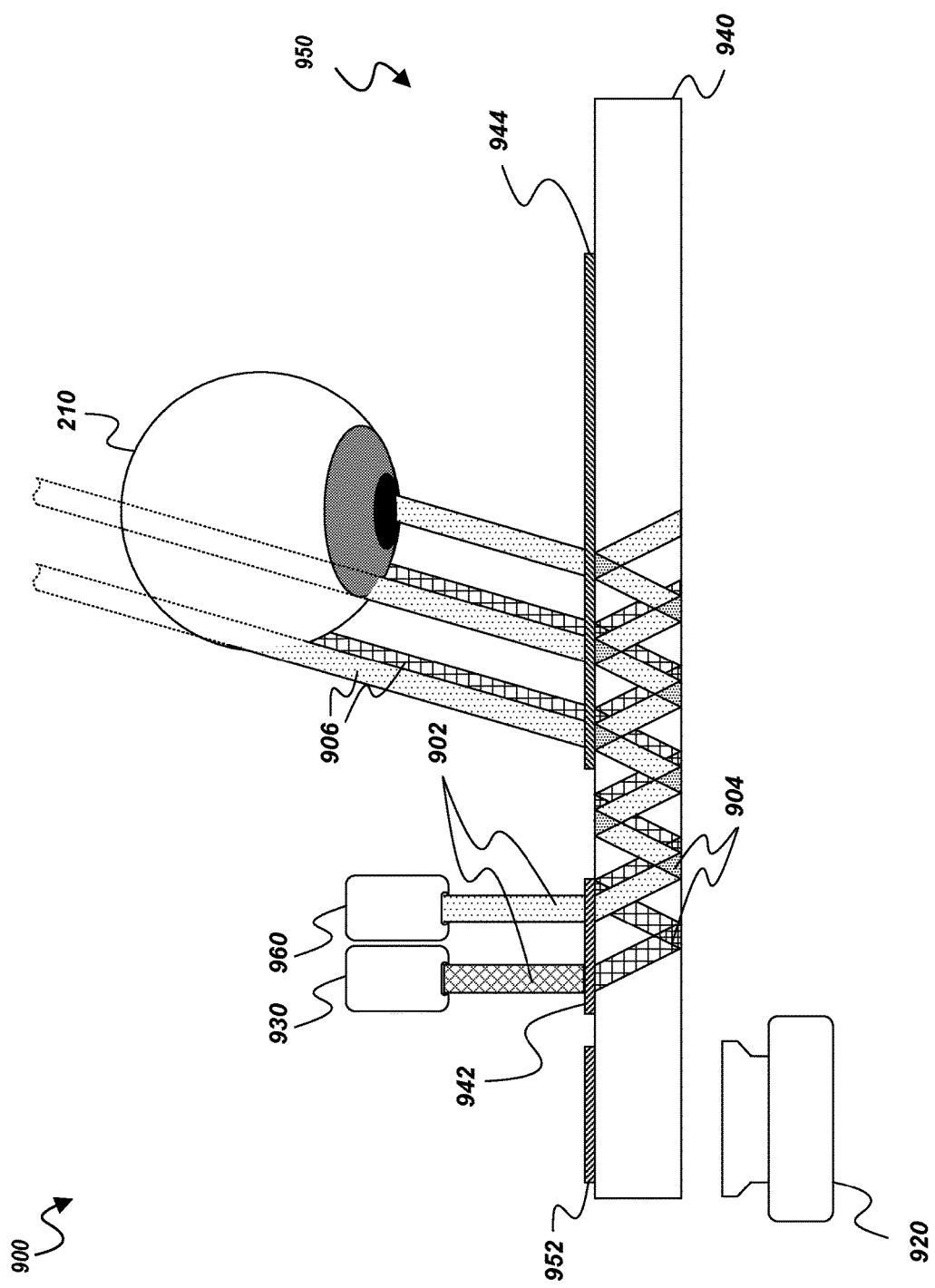
FIG. 11D schematically illustrates light from the light source and from the image projector coupled out of the eyepiece.

FIG. 11D illustrates an example imaging system 900 coupling light out of the eyepiece 950. As the incoupled light 904 propagates through the waveguide 940, some of the light may be incident on the coupling optical element 944. The coupling optical element 944 can be configured to couple the incoupled light 904 out of the eyepiece 950 and toward the user's eye 210. The coupling optical element 944 may be configured to couple the light as collimated light toward the eye 210. The coupling optical element 944 may be tuned to light of a particular wavelength range. For example, the coupling optical element 944 may be configured to couple infrared light (e.g., between about 700 nm and 15000 nm) out of the waveguide 940. In some designs, the coupling optical element 944 can be configured to couple multiple wavelengths of light out of the eyepiece 950. For example, the coupling optical element 944 may be tuned for both infrared and visible light. The coupling optical element 944 can also be configured to couple light into the waveguide 940, as described more fully below.

The coupling optical element 944 can be configured to increase one or more dimensions of an eyebox for a user. For example, the one or more dimensions may be measured along a first axis (e.g., x axis). The eyepiece 950 may further include an orthogonal pupil expander (OPE). The OPE may have at least one light redirecting element disposed on or in the waveguide (e.g., on one of the major surfaces) or the OPE may be disposed within the waveguide 940. The OPE may include features similar or identical to those described above for light distributing elements 730, 740, 750 above. In some implementations, the light redirecting element may comprise a diffractive optical element. The OPE may be configured to increase a dimension of the eyebox along a second axis (e.g., y axis) orthogonal to the first axis.

FIG. 11D shows some of the light exiting the eyepiece 950 toward the user's eye 210. In some designs, the coupling optical element 944 is configured such that incoupled light 904 that is incident on the coupling optical element 944 at various portions of the coupling optical element 944 along the first axis (e.g., parallel to the x-axis) exits the eyepiece 950 at each portion of the coupling optical element 944 along the first axis. This may provide a user with a light for projecting images or illuminating the eye for different eye positions or locations.

Figure 11E:
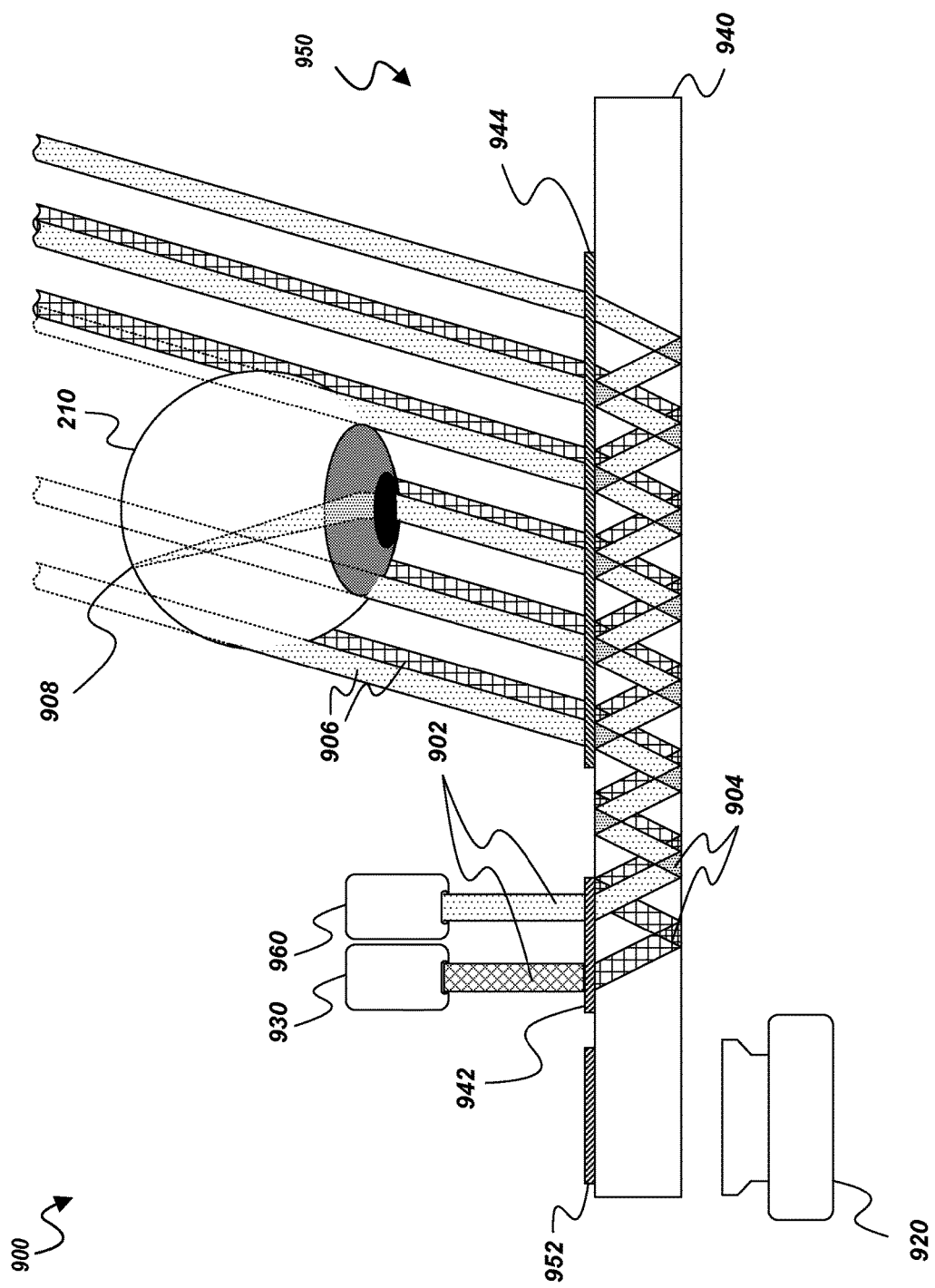
FIG. 11E schematically illustrates the waveguide and coupling optical element configured to propagate incoupled light at least along a full dimension (e.g., along the x-direction) of the coupling optical element. Light entering the eye is shown from an extended source (e.g., the imaging light will capture a region of the retina).

As shown in FIGS. 11D-11E, the coupling optical element 944 may be configured to couple the incoupled light 904 out of the eyepiece 950 as collimated light. This light may also be directed in general near normal relative to a major surface of the eyepiece 950 and/or waveguide 940. The collimated light may be directed into the eye and focus by the eye (e.g., the cornea and natural lens of the eye) onto the retina. This light 908 incident on the retina may be provide illumination for imaging the retina and/or providing image content to the eye. Some of this light 908, for example, may be reflected or scatter off the retina, exiting the eye and providing for images of the retina to be captured. The light source 960 may be an extended light source such that the light will illuminate a region of the retina.

Figure 12A:
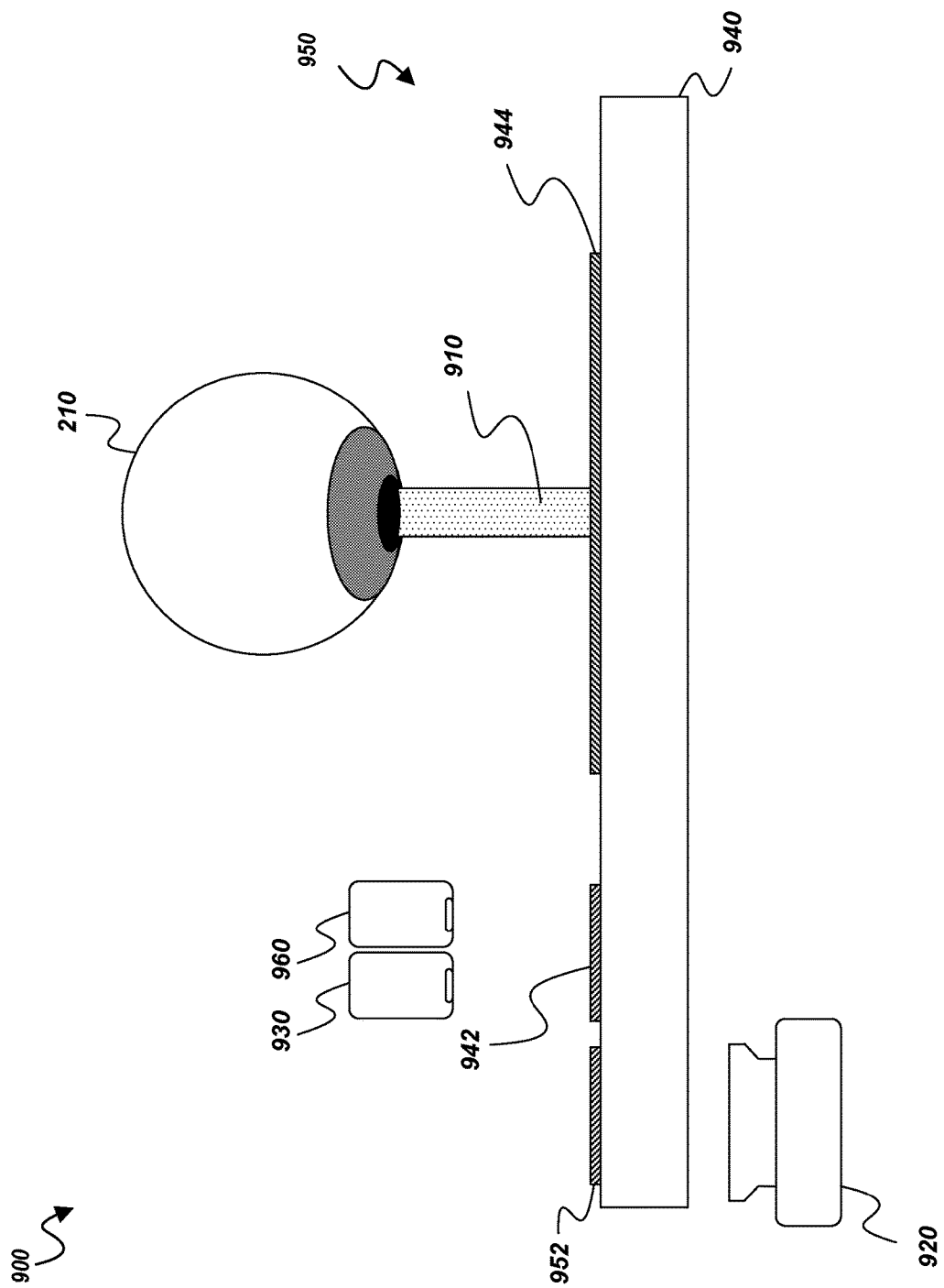
FIG. 12A is a cross-sectional view that schematically shows light reflected from the retina exiting the eye and incident on the eyepiece.

FIGS. 12A-12E illustrate how the imaging system 900 of FIGS. 11A-11E may additionally or alternatively be used for image collection of the eye 210. FIG. 12A shows light 910 reflected from the retina exiting the eye 210. As shown, the light 910 scattered or reflected from the retina that passes through the natural lens of the eye, the pupil in the eye and the cornea from may be collimated. This light may also be incident on the eyepiece 950 at normal incidence (e.g., at a right angle to a major surface of the waveguide 940 and/or coupling optical element 944). The coupling optical element 944 may be configured to couple the light 910 reflected from the retina into the waveguide 940.

Figure 12B:
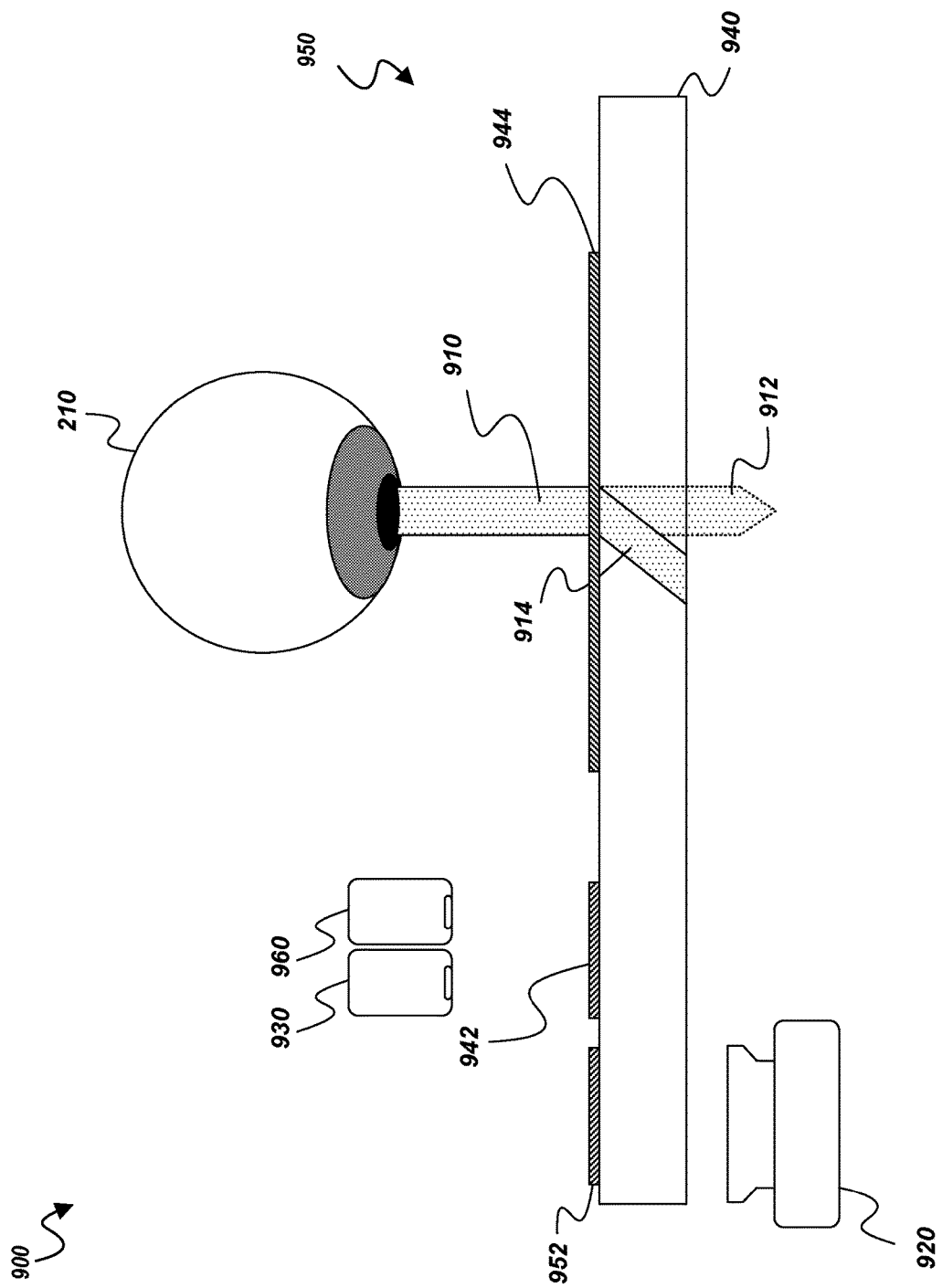
FIG. 12B schematically illustrates the example light coupled into the waveguide of the eyepiece.

FIG. 12B illustrates an example imaging system 900 as it couples light into the eyepiece 950. The coupling optical element 944 may include a turning feature such as a diffractive optical element, or other structures that redirect the light at an angle greater than the critical angle so as to be guided within the waveguide 940. The coupling optical element 944 may be configured to direct the incoupled light 914 generally toward the light source 960 and/or the imaging device 920. The coupling optical element 944 can be configured to couple less than a fraction of this light propagating toward the camera 920 back out of the waveguide 940. For example, a partially reflective element (e.g., semi-transparent mirror) may be disposed on or in the waveguide 940 such that a portion of the incoupled light 914 continues to propagate within the waveguide 940 by total internal reflection while reducing leakage of the incoupled light 914 out of the waveguide 940 along portions of the waveguide 940 where the coupling optical element 944 is disposed. The portion of light that does not leak out may be any fraction between 0 and 1. For example, the portion may be 0.90, where 90% of the light rays propagating through the waveguide 940 along the coupling optical element 944 are maintained within the waveguide 940 at each reflection of the light rays. Other portions are possible (e.g., 0.10, 0.20, 0.30, 0.40, 0.50, 0.60, 0.70, 0.80, or any range between any of these values). Such partially reflective element(s) can similarly be used in implementations described below.

Figure 12C:
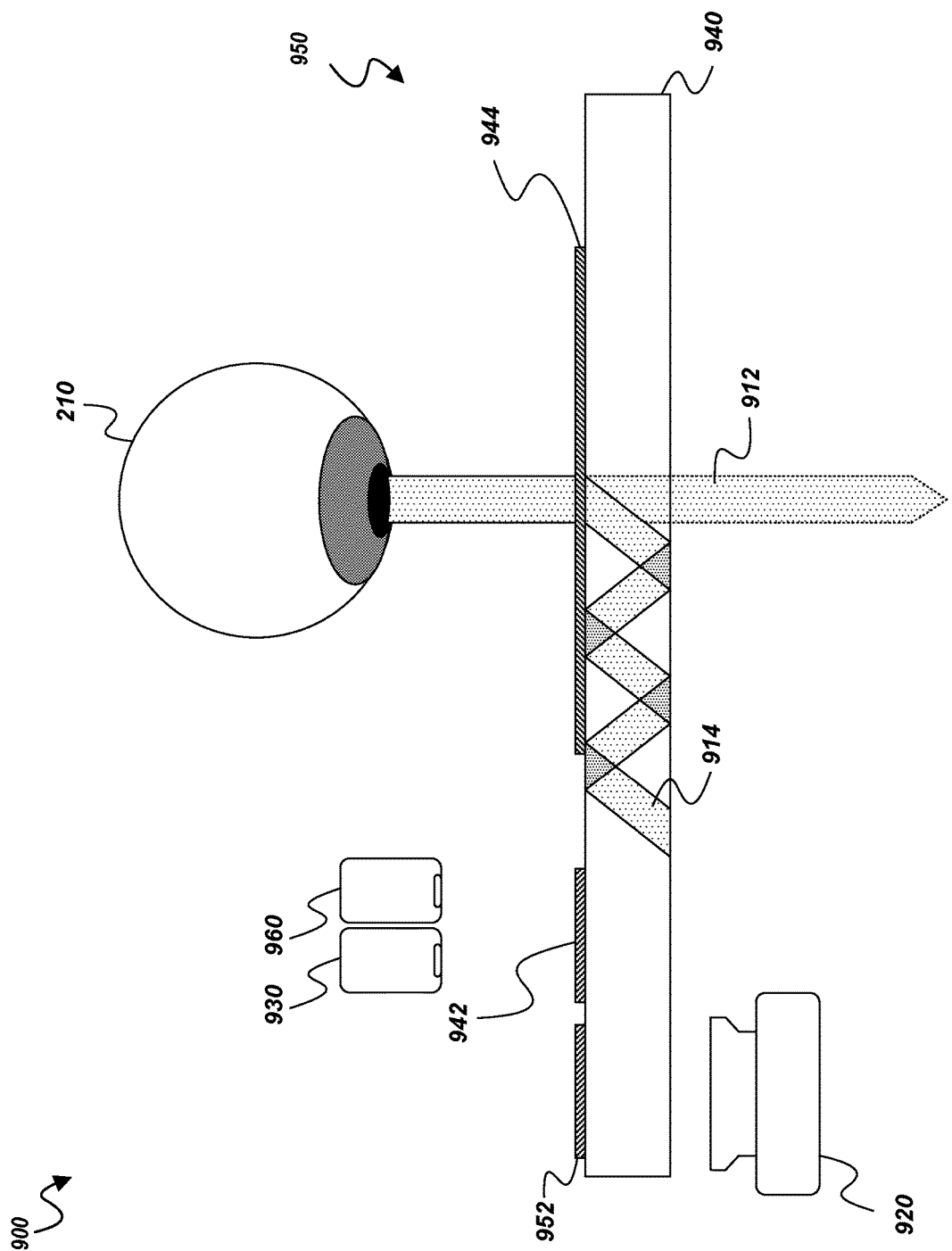
FIG. 12C schematically illustrates collimated incoupled light from the eye propagating through a waveguide toward an imaging device.
Figure 12D:
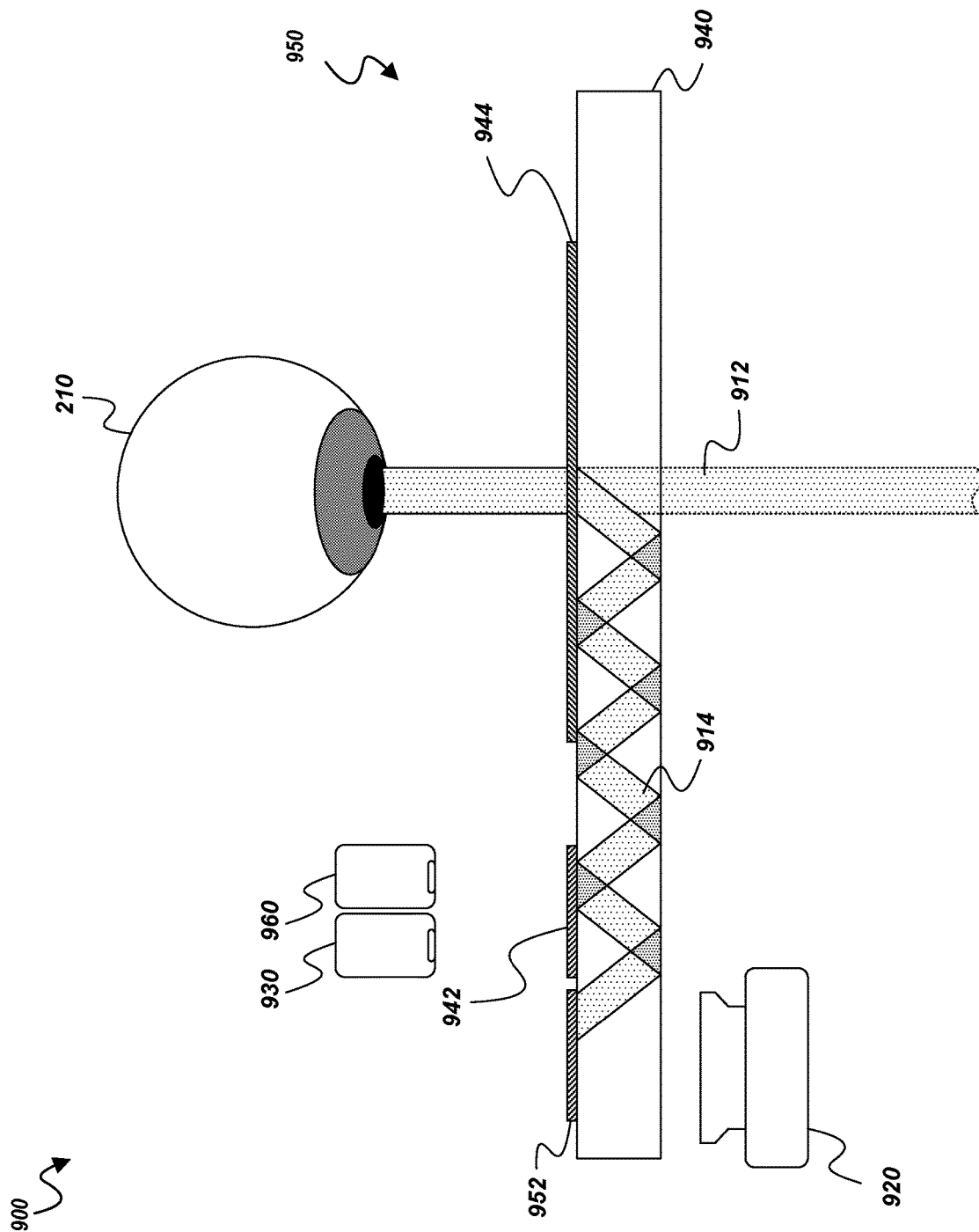
FIG. 12D schematically shows incoupled light from the eye propagating to the one or more outcoupling optical elements.

As shown in FIG. 12C, collimated incoupled light 914 may continue to propagate through the waveguide 940 toward the imaging device 920. FIG. 12D shows how some of the incoupled light 914 can continue to propagate until it is incident on one or more outcoupling optical elements 952. In order to reduce the amount of leakage of incoupled light 914 out of the incoupling optical element 942, the incoupling optical element 942 can be configured to couple little of this light propagating toward the camera 920 back out of the waveguide. For example, a partially reflective element (e.g., semi-transparent mirror) may be disposed on or in the waveguide 940 such that the a portion of the incoupled light 914 continues to propagate within the waveguide 940 by total internal reflection while reducing leakage of the incoupled light 914 out of the waveguide 940 along portions of the waveguide 940 where the incoupling optical element 942 is disposed. The portion of light that does not leak out may be any fraction between 0 and 1. For example, the portion may be 0.90, where 90% of the light rays propagating through the waveguide 940 along the coupling optical element 944 are maintained within the waveguide 940 at each reflection of the light rays. Other portion may be possible (e.g., 0.10, 0.20, 0.30, 0.40, 0.50, 0.60, 0.70, 0.80, or any range between any of these values). Such partially reflective element(s) can similarly be used in implementations described below.

Figure 12E:
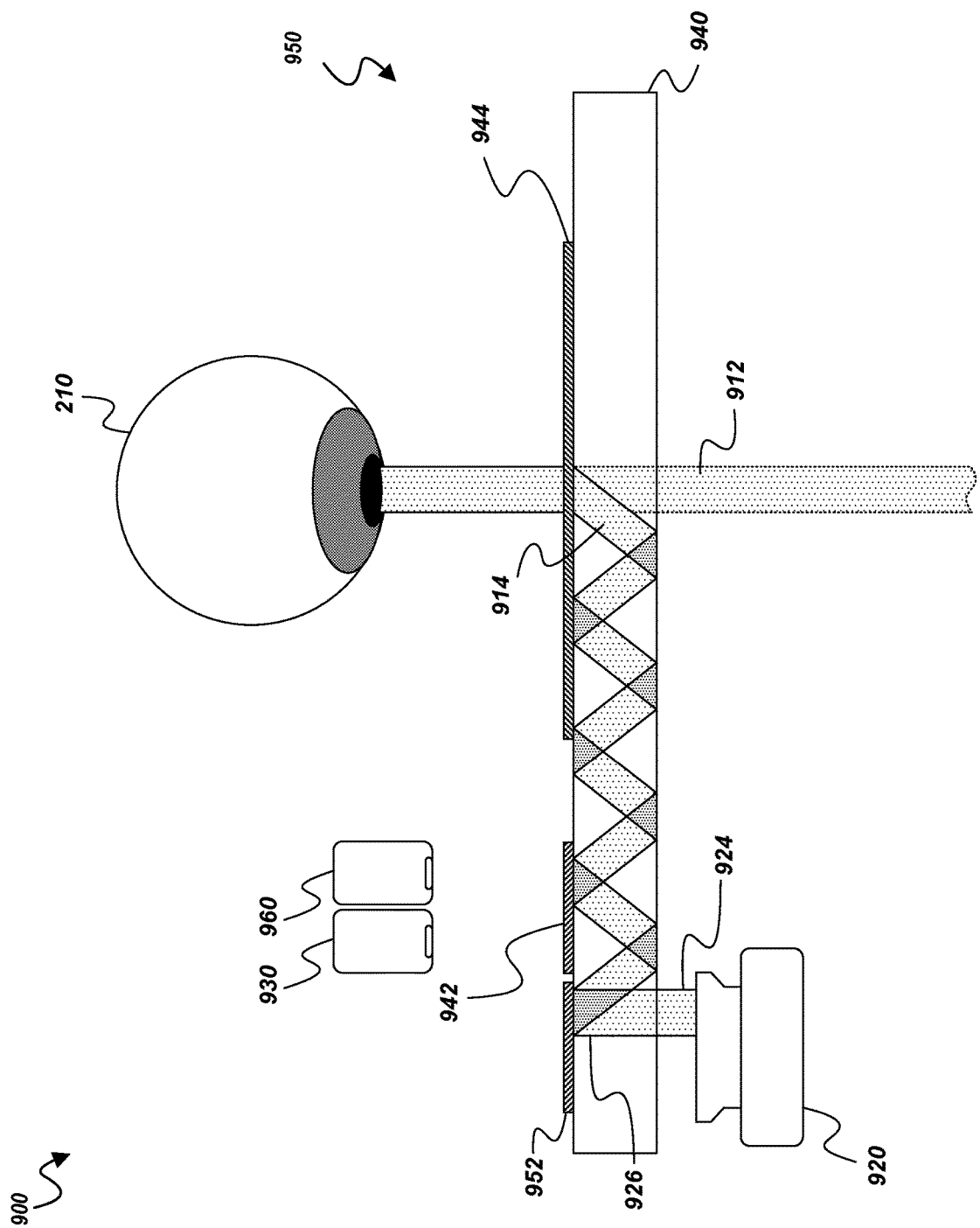
FIG. 12E schematically illustrates light from the eye coupled out of the waveguide by the outcoupling optical element and directed to the camera so that an image of the eye (e.g., the retina) can be captured by the camera.

As shown in FIG. 12E, the outcoupling optical element 952 can be configured to couple light guided within the waveguide 940 out of the waveguide 940 and to the imaging device 920. As a result, light propagating in the waveguide 940 that is incident on the outcoupling element 952 may be redirected so as to be ejected out of the waveguide 940, for example, out of a major surface of the waveguide 940 (e.g., the forward or rearward side of the waveguide 940) and directed on the imaging device 920. The outcoupling optical element 952 may be configured to direct the light 926 to exit the waveguide 940 perpendicular (e.g., normal) to the major surface of waveguide 940. In some designs, the outcoupling optical element 952 is configured to direct collimated light 924 onto the imaging device 920 at normal incidence to a light sensitive portion of the imaging device 920. As discussed above, the camera 920 may be infinity focused, for example, the imaging optics may be configured to focus collimated light onto the detector array.

Accordingly, the waveguide 940 may be configured to guide light coupled from the user's eye 210 into the waveguide 940 to be received by the imaging device 920 (e.g., camera) so as to capture an image of at least a portion of the eye 210 of the user. The same waveguide 940 may be configured to guide light coupled from the image projector 930 such that light from the image projector 930 can be directed to the user's eye 210 such that the image from the image projector 930 is in the vision field of the user. In some implementations, the same waveguide is configured to guide light coupled from the illumination source 960 such that light from the illumination source can be directed to the user's eye 210 to illuminate the eye such that an image of the eye can be captured by the camera 920.

In some implementations, the same coupling optical element 944 can be configured to (i) couple light from the user's eye 210 into the waveguide 940 to be received by the imaging device 920 and (ii) couple light from the image projector 930 out from the waveguide 940 to the user's eye 210 to project image content into the user's vision field. In some implementations, the same coupling optical element 944 can be configured to couple light from the illumination source 960 out of the waveguide to the user's eye 210 such that light from the illumination source can illuminate the eye.

In other designs, different waveguides can be used and/or different coupling optical elements 944 can be used. In some designs for example, a first waveguide 940 may be configured to guide light coupled from the user's eye 210 to be received by the camera 920 so as to capture an image of at least a portion of the eye 210 of the user and a second waveguide may be configured to guide light coupled from the image projector 930 such that light from the image projector 930 can be directed to the user's eye 210. The first and second waveguides may be stacked on top of one another. Another waveguide may in addition or in the alternative be configured to guide light coupled from the illumination source 960 such that light from the illumination source can be directed to the user's eye 210 to illuminate the eye.

Also, in some implementations, a first coupling optical element 944 can be configured to (i) couple light from the user's eye 210 into the waveguide 940 to be received by the imaging device 920 and (ii) couple light from the image projector 930 out from the waveguide 940 to the user's eye 210 to project image content into the user's vision field. Another coupling optical element may in addition or in the alternative be configured to coupled light from the illumination source 960 out of the waveguide to the user's eye 210 such that light from the illumination source can illuminate the eye.

In some designs, the coupling optical element 944 can include a plurality of diffractive optical elements (DOEs). For example, a first DOE can be configured to couple light from the user's eye 210 into the waveguide 940 to be received by the imaging device 920. A second DOE can be configured to couple light from the image projector 930 out of the waveguide 940 to the user's eye 210 to project image content into the user's vision field. Optionally, a third DOE can be configured to couple light from the light source 960 out of the waveguide 940 to the user's eye 210 to illuminate the eye. The first and second (and possibly third) DOEs can be stacked, e.g., in some implementations such that light from the environment in front of the user passes through the first DOE and is then incident on the second DOE and then incident on the third DOE and incident on the user's eye. The order, however, may be different.

In some designs, the first and second DOEs are integrated in a single element or volume of the waveguide 940. In some implementations, for example, both the first and second DOEs are superimposed on each other (e.g., occupy the same or approximately the same volume) within the waveguide 2102. For example, the first and second DOE may be recorded in the same medium.

As described above, image capture of the eye, e.g., of the retina, can facilitate eye tracking. FIG. 13A, for example, illustrates the imaging system 900 configured to image various portions of the eye 210 (e.g., retina), for example, at different times when the eye is in different positions. Stages A and B may refer to images of the eye 210 during different orientations of the eye. FIG. 13A shows imaging of the eye 210 and the results thereof during both stage A and stage B imaging.

In some implementations, the light emission 928 (e.g., from an illumination source 960 such as described above or from one or more illuminations sources configured and/or located differently) can be used to obtain one or more images of the retina 962, as shown by FIG. 13A. The image of the retina 962 may comprise one or more regions 964, 966 that are imaged during different orientations of the eye 210. FIG. 13A shows two regions 964, 966 of the image of the retina 962. For example, the region 964 of retina imaged in stage A may be imaged while the eye 210 is directed at an angle normal to the waveguide 940. The image data for the region 966 of retina imaged in stage B may be obtained while the eye 210 is oriented at an acute angle with the waveguide 940. Using one or more orientations of the eye 210 during one or more stages of imaging, a composite image or map of the retina 962 may be obtained. Processing electronics or a processor, such as data module 140 (see FIG. 2), may be used to find overlapping image data between two neighboring regions. Using the overlapping regional image data, a composite image or of the retina 962 can be determined. A larger size (e.g., full-size) composite image or map of the user's retina can be stored.

As described herein, the head mounted display can be used to map a user's eye retina based on the direction that user's eye is directed. To provide a realistic and intuitive interaction with objects in the user's environment using eye gaze and/or to identify a wearer of the head mounted display device, the head mounted display system can use retinal mapping to incorporate a uniqueness of a user's eye features and other conditions that may have some effect on eye measurements. For example, the images may be identified based on positions of blood vessels in the corresponding retinal image.

Retinal mapping can involve a process for enabling a computing device to learn how to associate a user's eye gaze (e.g., as identified in retinal images) with gaze points in a 2D or 3D space. An eye gaze may be associated with a single point in the 2D or 3D space. An eye gaze can also be associated with multiple points in the space, which can describe a movement of a virtual object (e.g., a series of points, a location of a moving image).

The head mounted display system can determine a user's eye gaze based on retinal images. The head mounted display system can obtain retinal images using sensors (e.g., eye cameras such as the imaging device 920). The head mounted display system can image one or both eyes of the user while the user changes his or her eye gazes (such as, e.g., when the user is looking around to follow a moving or shifting calibration target or fixation target). To map a user's retina, the head mounted display system can present a virtual target, e.g., a fixation target, for the user to look at. The virtual target may be associated with one or more known points of gaze in the 2D or 3D space. While the user is looking at the target, the head mounted display system can acquire retinal image(s) and associate the image(s) with gaze point(s). The head mounted display system can calculate and/or generate a mapping matrix based on the associations of respective retinal images and points of gaze associated with the target.

The retinal mapping result can reflect uniqueness in each person's eyes. For example, the head mounted display system can generate a mapping matrix customized to one or both eyes of a specific individual. For example, the users may have different amounts of eye movements or eye gazes in response to a specific target. Additionally or alternatively, the user may have a different position, size, shape, and/or orientation of blood vessels in the retina. As a result, by generating a calibration result specific to an individual user, the head mounted display system may allow more accurate user interactions with eye gazes and/or may allow for identification a particular user.

Accordingly, when a user puts on the head mounted display device, the system can detect whether the user is a previous user or a new user. A confusion matrix can be calculated where a score for a particular eye gaze image stored in the system memory is compared to a corresponding image of the current user. The confusion matrix can include a comparison score for a plurality of eye gazes and associated retinal images. Based on the comparison scores, the system may be able to make a determination with regard to an identity of the user (e.g., whether the user is the same as the individual for which the stored retinal images or composite map are associated) and/or a confidence level for the determination. The confidence level may, for example, include an identity coefficient. Stored images, for example, a composite image or map, may be compared with later obtained images referred to as instantaneous or real-time images obtained for a current user. The system may provide an alert if the system detects that the user is a new user or may take other action.

The system may apply filtering such as digital filtering or image processing to the images of the retina captured by the camera. Such filtering or imaging processing, may for example, enhance features that may be used for identification, stitching, assembling a composite images, eye tracking, etc. Such filtering or image processing may comprise edge enhancement. Such a filter may comprise, for example, a Frangi filter although other types of filters may be used. Such a filter or processing (e.g., edge enhancement or a Frangi filter) can be used to enhance and/or detect images features such as vessels or tubular structures or fibers in retinal images.

Figure 13B:
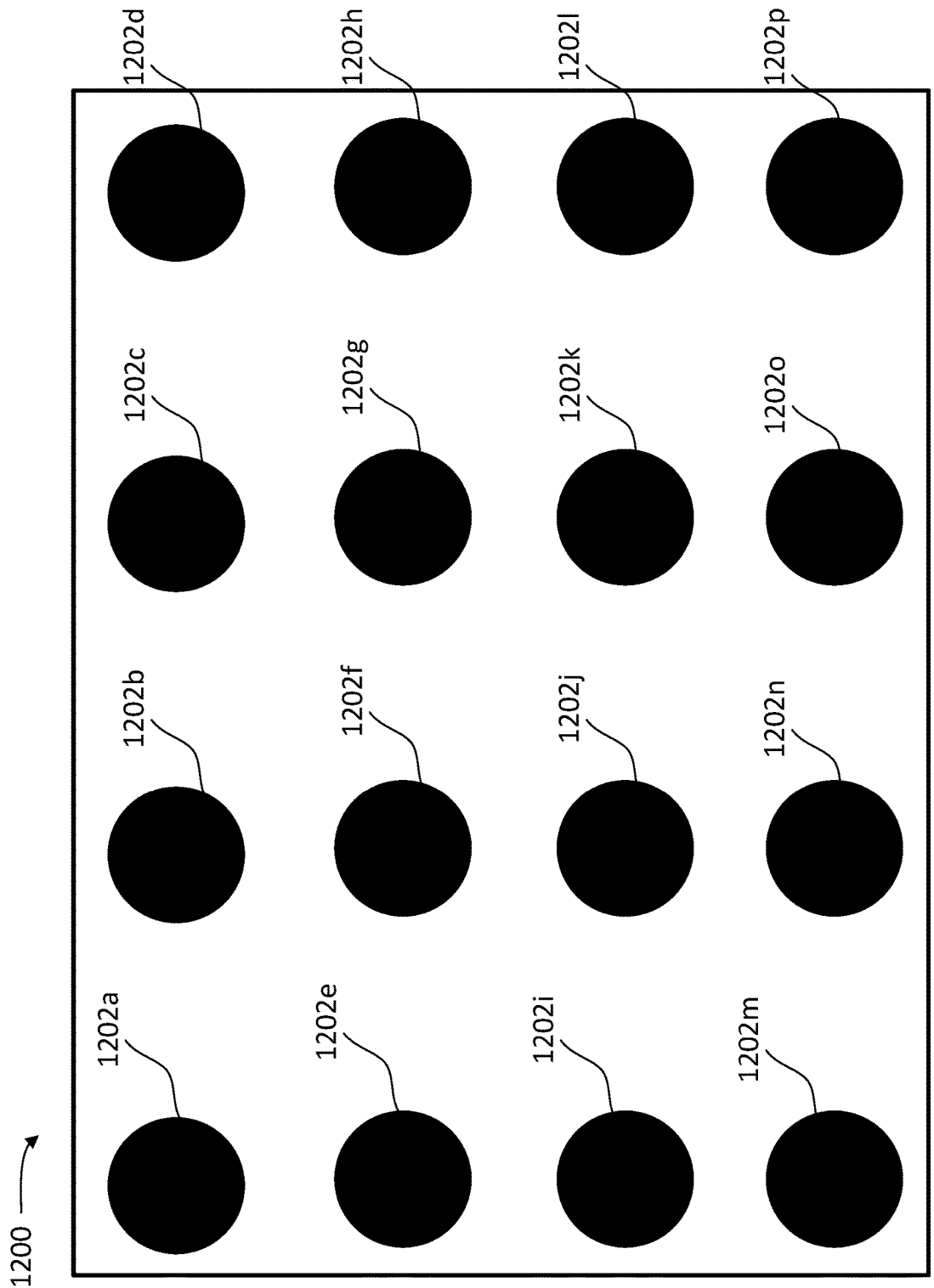
FIG. 13B illustrates a pattern of sequentially displayed fixation targets used to cause the eye to be directed in a variety of different directions during which the retina is imaged. The resultant images correspond to non-identical portions of the retina. For example, when the eye is directed in various directions to view differently located fixation targets on the display, images captured by the camera include different portions of the retina. These images can be assembled to form a larger map or composite image of the retina.

FIG. 13B illustrates a pattern of sequentially displayed fixation targets that can be used in the retinal mapping process. These virtual targets on which a user's eye will direct their gaze can cause the eye's gaze to be redirected to a variety of different directions during which the retina can be imaged. The resultant images associated with the different gaze directions correspond to non-identical portions of the retina. As discussed above, when the eye is gazing in different directions to view differently located fixation targets on the display, images captured by the camera include different portions of the retina. These images can be assembled to form a larger map or composite image of the retina.

FIG. 13B shows a virtual target at sixteen different location in a user's field of view (FOV) 1200. In various implementations, the virtual target would be presented at a given location at a given time. One or more retinal images would be obtained during a time when the virtual target is presented at that particular location to a user. This image or these images may be associated with that target position and/or a corresponding gaze direction. Greater or fewer target locations may be used. In the example shown in FIG. 13B, the sixteen targets locations 1202a-1202p are shown. More or less target locations may be used. The target locations may also be different. The order at which the targets are presented at the different locations may vary. For example, the target may move in a raster pattern from the left to the right side of the field of view of the user, back to from the right to the left, and again from the left to the right, lowering the position of the target in the field of view with each lateral pass across the field of view. However, other patterns and approaches are possible. Likewise, the target can be rendered identically or differently at the different locations. For example, the target rendered may be different sizes, shapes, colors, etc. The targets can be rendered sequentially to a user during the eye tracking calibration process. For example, as discussed above the head mounted display system may render target in a serpentine pattern. For example, the target 1202a may be followed by 1202b, then 1202c, then 1202d, then 1202h, then 1202g, and so forth. Other patterns are possible. For example, the target could be displayed in more random or non-sequential patterns. In some embodiments, a single target is displayed to the user, and the target moves around the user's field of view (for example, passing or temporarily stopping at the positions 1202a-1202p during the target's movement). The head mounted display system can acquire an image of the user's retina(s) while the user is looking at these targets. For example, the head mounted display system can acquire a first image when the user is looking at the target at the first location 1202a while acquiring a second image when the user is looking at the target at a second location 1202b, and a third image when the user is looking at the target at a third location 1202c, and so forth. The wearable system can associate the first image to the first position 1202a and associate the second image with the second position 1202b, and the third image with the third position 1202c, and so forth. Neighboring images may be stitched together in a database to create a full or partial retinal map. For example, two image can be stitched together in appropriate registration using features or portions of the feature (e.g., blood vessels or portions thereof) that are common to the multiple images. In various implementations, adjacent target positions would produce overlapping images that can be registered and stitched together. For example, target position 1202a and target position 1202b as well as target position 1202b and target position 1202c may produce overlapping and adjacent retinal images that can be stitched with each other. Accordingly, a number of different retinal images may be obtained with different eye gazes so as to assemble a larger image (e.g., a composite image or map) of the retina.

As discussed above, eye tracking can be performed using the composite retinal image or map. For example, after the target is no longer displayed, the user may move their eye gaze about as the user looks at different real objects in front of the user and head mounted display or augmented reality (virtual) image content displayed by the head mounted display. One or more retinal images may be obtained at these times. The term "instantaneous" or "real-time" images may be used herein to describe these images obtained subsequent to calibration that can be used for eye tracking (or other purpose such as obtaining biometric data). These "instantaneous" or "real-time" images likely correspond to a portion of the composite retinal image or map. The system may be configured to sufficiently match this "instantaneous" or "real-time" retinal image with a portion of the composite retinal image or retinal map. Such matching may be based on features or portions of features (blood vessels or portions thereof) that are common to both the "instantaneous" or "real-time" retinal image and the portion of the composite retinal image or map. Based on the location the portion of the composite retinal image or map to which this "instantaneous" or "real-time" retinal image coincides, a gaze direction may be deduced. Different gaze directions will result in retinal images that correspond to different portions of the retinal map. Accordingly, identifying the location of the "instantaneous" or "real-time" retinal image on the composite retinal image or map will provide information as to the direction of the user's gaze. Eye tracking, for example, tracking the movement of the eye and the change in eye gaze may be performed using such or similar methods. As discussed above, edge enhancement, edge detection, or other digital filtering and/or processing may be used to enhance and/or correlate features of different images with the composite retinal image or retinal map.

In various implementations after completion of the initial calibration process where the virtual target or fixation target is displayed (e.g., at a plurality of locations) to assemble a composite retinal image or map, the composite retinal image or map can still be refined. For example, as additional retinal images are obtained, the composite retinal image or map can be further refined or improved using the additional images. Accordingly as additional "instantaneous" or "real-time" retinal images are obtained, for example for the purpose of providing eye tracking, the composite retinal image or map can be further refined or improved using the "instantaneous" or "real-time". As a user continues to look at various positions in the display (with or without aid of a calibration target), the retinal composite image or map may be further refined using additional images are acquired subsequent to the initial calibration where the virtual target or fixation target was displayed. The quality of the composite retinal image or map may therefore be increased.

Additional non-limiting examples of how eye tracking may be accomplished and/or a composite retinal image or map may be produced and retinal images used are described in U.S. Publication No. 2017/0205875, titled "EYE IMAGE COLLECTION," filed on Jan. 17, 2017, the disclosure of which is hereby incorporated herein by reference in its entirety.

Accordingly, as discussed above larger portions of the retina may be recorded and mapped by obtaining retinal images and/or other images of the eye using imaging systems such as described herein and such images may facilitate eye tracking. For example, an image of the eye 210 shown in FIG. 13A may be captured when the eye is in an arbitrary position. The processing electronics or a processor (such as the same or different one described above as forming the composite image) may then compare captured images of the user's retina in real time to the stored composite or larger size (e.g., full-size) image of the user's retina to track eye movement. A given image of the user's retina captured in real time may show a specific portion of the user's retina. As described above, by comparing such a captured image to the stored image of the user's mapping a larger portion of the user's retina, the system can determine which portion of the user's retina is shown in the captured image, and can thereby determine the position/orientation of the eye that would produce such an image. See for example FIG. 13A, which shows two different images of portions of the retina that are produced when the eye is in two different positions and/or orientations. Accordingly, the position and/or orientation of the eye may be determined by capturing different images of the retina and determining which portion of the retina is visible. Such determination may be performed even if a composite image is not formed but rather multiple images of the retina for different eye positions/orientations are recorded and stored in a database. When a future image of the retina is obtained, that image may be compared to images in the database of stored images to determine which image in the database resembles the image of the eye recently obtained. Matching the recent image to one or more of the images in the database having associated positions and/or orientations associated with them can enable determination of the orientation and/or position of the more recent image. Other approaches to eye tracking may be used based on the images captured using the designs described herein.

As described herein, the retinal images may be employed for other purposes as well. For example, the retinal images may be used to verify that the user is the same user for which the composite retinal image or map was obtained. An image of the retina that is obtained when a user is wearing the head mounted display system (e.g., during the calibration process and/or during later use) may be compared with a previously obtained composite retinal image or map (e.g., created a prior day or when the head mounted display was previously booted up) that is stored. If the recently obtained retinal image does not match a portion of the composite retinal image or map sufficiently enough, a conclusion may be made that the current user is different than the previous user (e.g., for which the composite virtual image or map was created). Such methods may be used for security, e.g., to verify that the current user of the head mounted display device is the owner or typical user of the device. Accordingly, biometric data obtained via retinal imaging may be used for security purposes.

The retinal imaging may be used as well to collect biometric data for monitoring the user's health. Medically related data may be obtained from the retinal images. Such medical data may be useful for monitoring the health of the user.

Although various applications of eye imaging, such as eye tracking, collection of biometric data for heath monitoring and for security are discussed herein in the context of retinal imaging, imaging other parts of the user, for example, of the user's eye may be employed for these and other purposes.

Figure 14A:
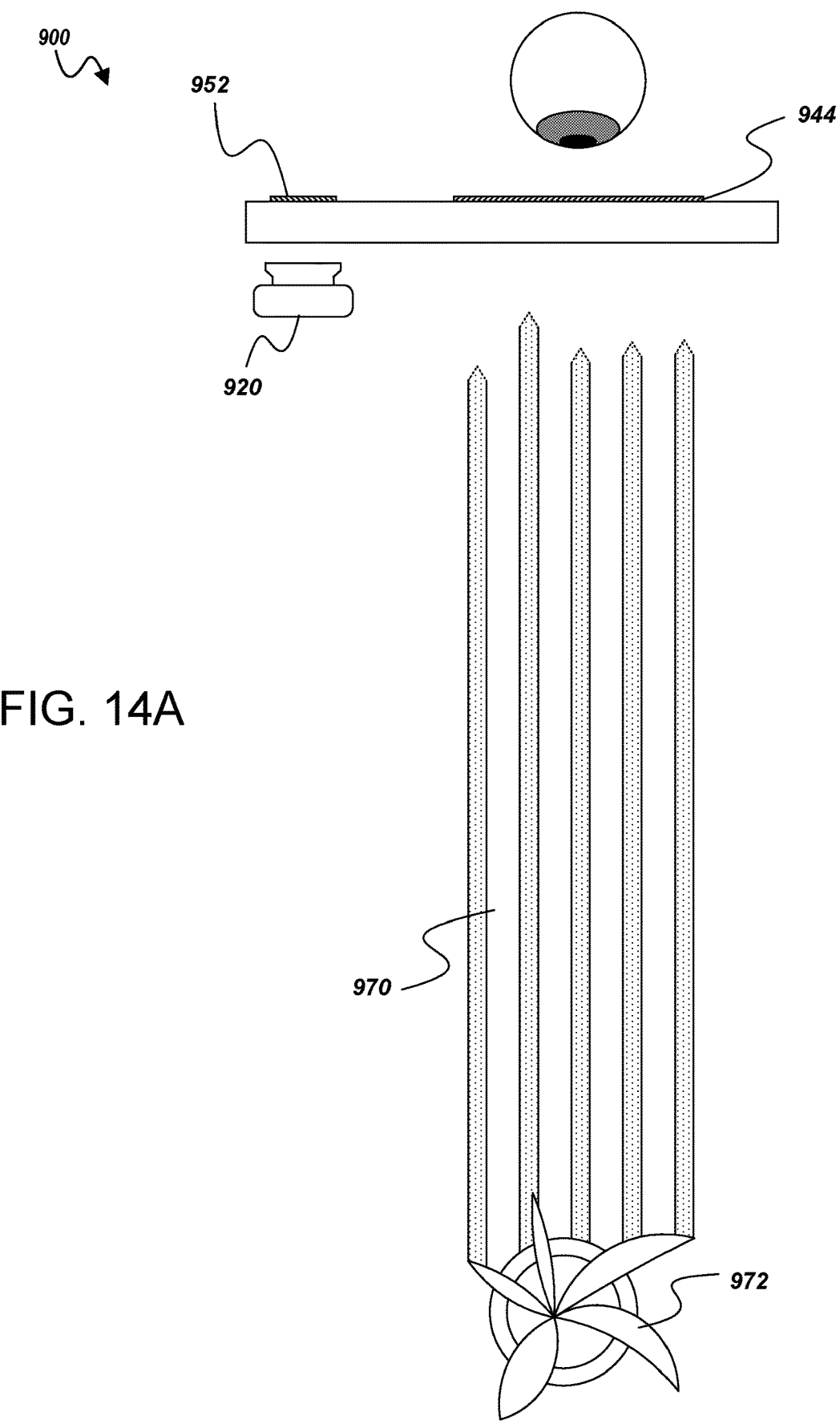
FIG. 14A schematically illustrates a cross-sectional view of an imaging system comprising an eyepiece and a camera for collecting light from the environment forward the eyepiece. Light from the environment is shown reflected off or emitted from one or more physical objects in the environment. Collection of light from objects in the environment in front of the eyepiece can enable images of the environment to be captured.
Figure 14B:
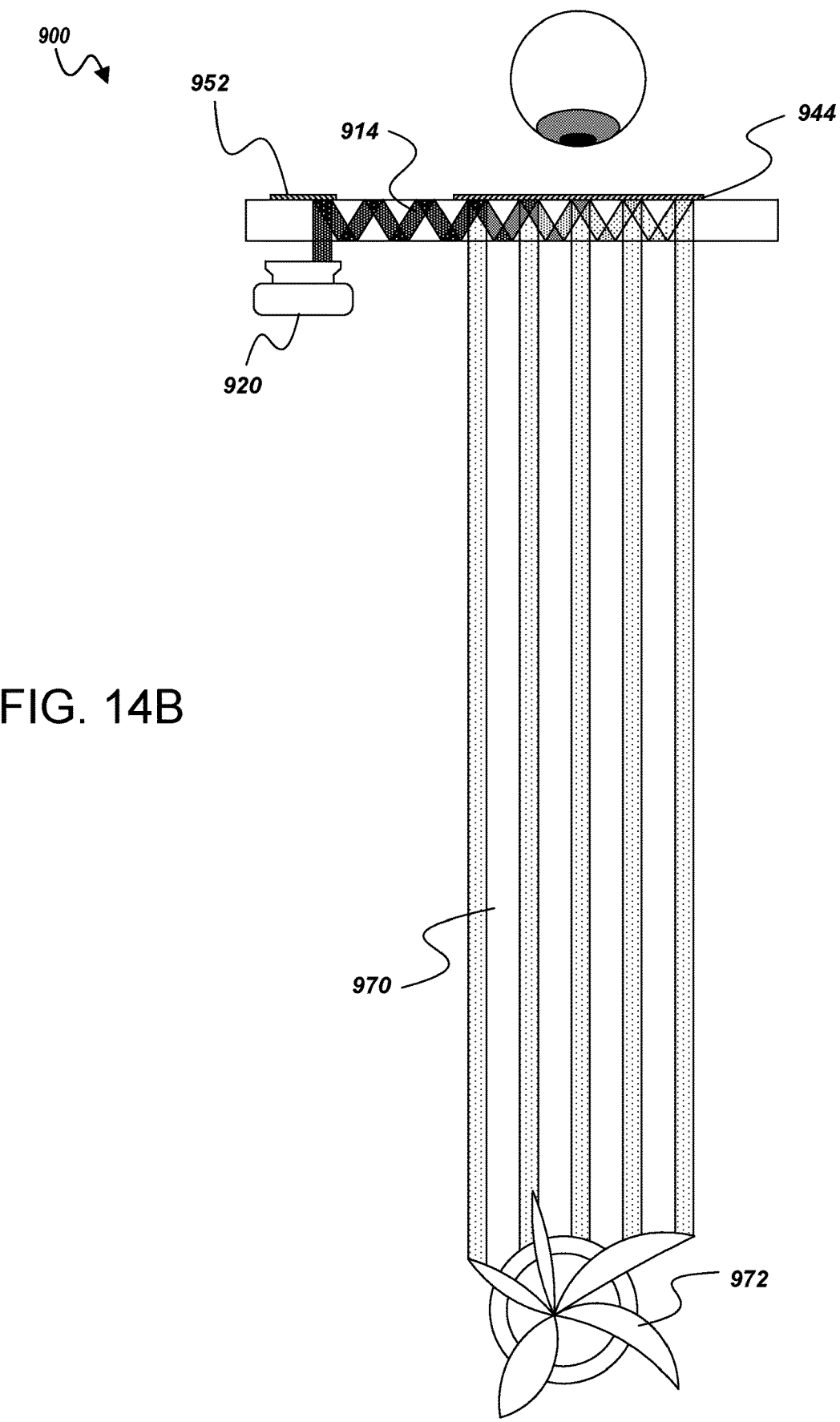
FIG. 14B schematically illustrates light from the environment being coupled by the coupling optical element into a waveguide of the eyepiece.

Although the eyepiece 950 is described above as capable of being utilized to facilitate imaging of the eye, the eyepiece can also be used to image the world in front of the user. FIGS. 14A-14B, for example, illustrate an example imaging system 900 that can be used to image a portion of an environment in front of the user and/or objects in the portion of the environment. The imaging system 900 used may be a similar system as described for FIGS. 11A-11E and/or for FIGS. 12A-12E except that light is collected by the eyepiece 950 from the environment forward the eyepiece and the user. FIG. 14A, for example, illustrates light 970 from the environment that is reflected off and/or emitted by one or more physical objects 972 in the environment forward the user and eyepiece 950. As shown, the light 970 from the environment may be approximately collimated (e.g., at infinity), for example because the physical object 972 in the environment may be located at a sufficiently large distance from the imaging system 900 for the light rays reaching the imaging system 900 to be collimated or approximately collimated. In some implementations, the imaging system 900 may be configured to image the environment and/or objects in the environment without the use of any optical elements having optical power (e.g., lenses, mirrors) in the imaging system 900.

The imaging system 900 shown in FIGS. 14A and 14B is similar to the imaging systems described above. The imaging system includes the eyepiece 950 comprising one or more waveguides 940 including the coupling optical element 944 configured to direct light from an image projector 930 (not shown) into the eye 210 to form images therein. The one or more waveguides may include a plurality of waveguides (e.g., a stack of waveguides) configured to incouple/outcouple a plurality of corresponding colors/wavelengths. Each waveguide in a stack of waveguides may be configured to direct light of a particular color (e.g., red, green, blue). For example, a distalmost waveguide (e.g., stack of waveguides) may be configured for visible light (e.g., red, blue, green) such that the waveguide is configured to incouple and outcouple the same wavelength(s) of visible light. Additionally or alternatively, a waveguide configured to incouple and outcouple invisible (e.g., infrared) light may be disposed proximal the eye 210. Such a plurality of waveguides corresponding to the waveguide 940 may be used in any other implementation described herein. The imaging system 900 may also include the imaging device (e.g., camera) 920 and outcoupling optical element 952 configured to turn light reflected from the eye 210 that is propagated within the waveguide 940 to the camera. In FIGS. 14A and 14B, the illumination source 960 is excluded since an illumination source may not be needed to image the environment in front of the user. However, an illumination source (e.g., the light source 960 described above) may be used in certain designs.

The eyepiece 950, waveguide 940, coupling optical element 944, outcoupling optical element 952 and camera 920 may be the same or similar to that describe above. For example, the coupling optical element 944 may be in physical engagement with the waveguide 940. For example, the coupling optical element 944 and/or outcoupling optical element 952 may be disposed in an optical path between the environment in front of the eyepiece 950 and camera 920 such that light from the environment is coupled into the waveguide 940 via the coupling optical element 944 and coupled out of the waveguide via the outcoupling optical element to be incident on the camera 210 (for example to form an image of at least a portion of the environment). The coupling optical element 944 may comprise a plurality of turning features configured to turn light guided within the waveguide out of the waveguide or turn light incident on the coupling optical element 944 at an angle into the waveguide to be guided therein by total internal reflection. The outcoupling optical element 952 may comprise a plurality of turning features configured to turn light (from the environment) that is guided within the waveguide at an angle such that the light is not guided in the waveguide by total internal reflection but is direct out toward the camera. The coupling optical element 944, outcoupling optical element 952 and the turning features associated with each may be in physical engagement with the waveguide 940. For example, the coupling optical element 944 and/or outcoupling optical element 952 may comprise one or more holographic or diffractive optical elements (e.g., surface relief gratings) patterned (e.g., etched) in or on the waveguide 940. The coupling optical element 944 and/or outcoupling optical element 952 may comprise a layer disposed on the waveguide 940 or may be formed be in the waveguide 940. For example, a volume holographic or diffractive optical element may be formed by changing the index of refraction of material comprising the waveguide or a layer disposed thereon. Accordingly, the coupling optical element 944 and/or outcoupling optical element 952 may be disposed in the volume of the waveguide 940 or a layer disposed thereon. Depending on the design, the coupling optical element 944 and/or outcoupling optical element 952 may be transmissive or reflective and may operate in transmission or reflection. For example, the coupling optical element 944 and/or outcoupling optical element 952 may include a transmissive or reflective diffractive optical element (e.g., grating) or holographical optical element that operates in transmission or reflection respectively, e.g., turning light via that is transmitted therethrough or that is reflected therefrom. The coupling optical element 944 and/or outcoupling optical element 952 can include a polarization optical element, such as a polarization selective turning element (e.g., polarizer). The polarization selective turning element may include one or more polarization gratings, diffractive optical elements, and/or holographic optical elements and may comprise liquid crystal structures such as liquid crystal polarization gratings. In some implementations, the reflective optical element may include a reflector (e.g., mirror). Other elements, such as for example the waveguide 940 may be similar to that described above as well.

FIG. 14B illustrates the operation of the imaging system 900 shown in FIG. 14A. Light 970 from the environment is coupled by the coupling optical element 944 into the waveguide 940. The coupling optical element 944 may be configured to turn collimated light at an angle that is greater than the critical angle of the waveguide 940 such that at least a portion of this collimated light is guided within the waveguide by total internal reflection toward the camera 920. The outcoupling optical element 952 can be configured to receive at least a portion of the light from the environment in front of the user that is coupled into the waveguide 940 via the coupling optical element 944 and guided therein. The outcoupling optical element 952 may be configured to couple the incoupled light out from the waveguide 940 to the camera 920 such that images of the environment may be captured by the camera 920. The images of the environment may be passed to processing electronics, (e.g., one or more processors), such as data module 140 (see FIG. 2). The data module 140 may be configured to reproduce a modified image of the environment in an augmented reality context. The processing electronics may be in communication with the camera 920 via a wired or wireless electronic signal. Additionally or alternatively, the processing electronics may communicate with the camera 920 using one or more remote receivers. The processing electronics may reside remotely (e.g., cloud computing devices, remote server, etc.).

This imaging system 900 may therefore be used for directly imaging the environment, which may be useful for a variety of reasons. For example, imaging the environment can be used to determine where to place augmented reality image content with respect to objects in the environment. For example, imaging the environment may provide the location of a table such that the head mounted display may render an image of person standing next to the table instead of on the table or in the table. The imaging system 900 described for imaging the environment may also be used to image the eye 210, such as is described for FIGS. 10, 11A-11E, and/or 12A-12E.

Figure 14C:
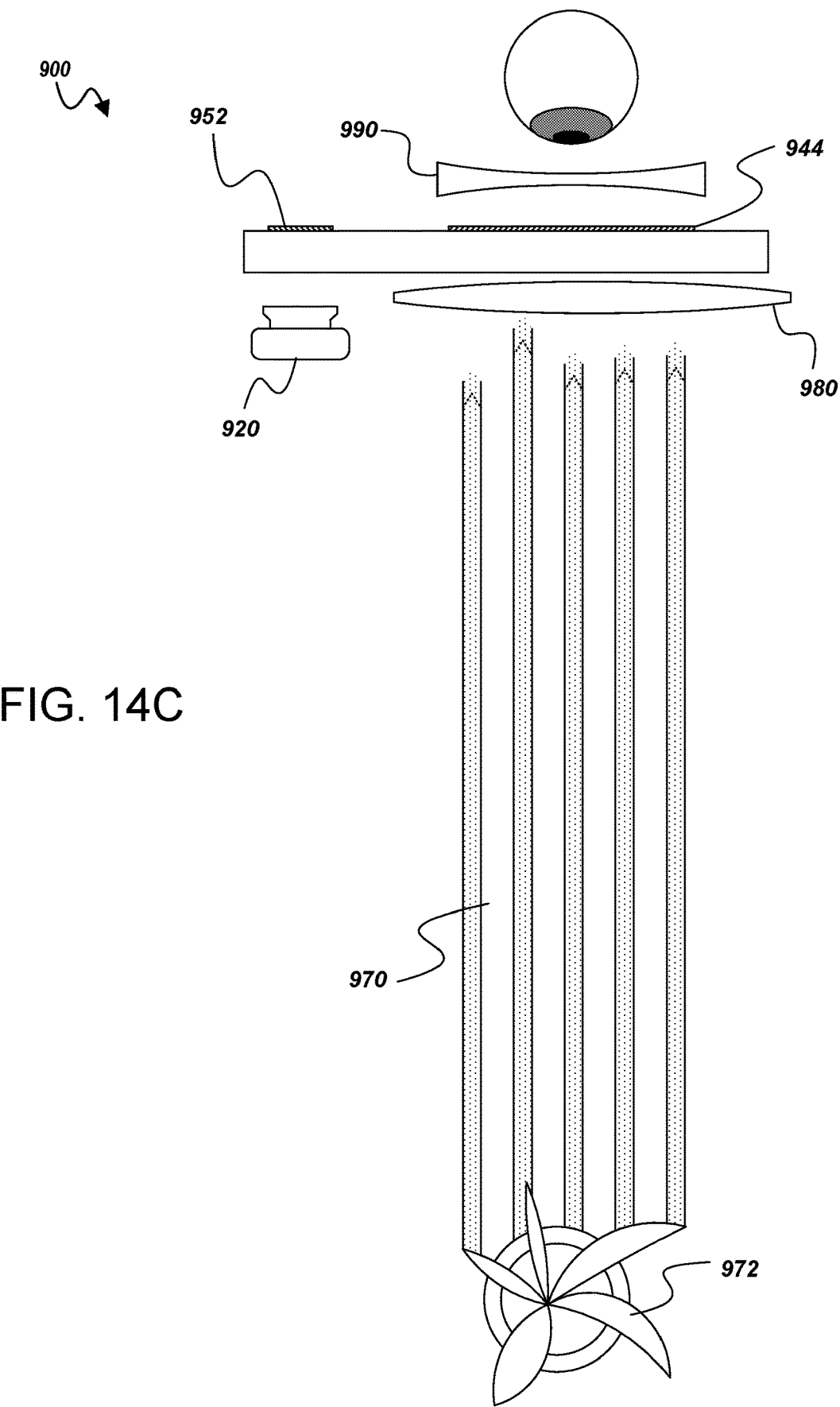
FIG. 14C schematically illustrates an imaging system for collecting light from the environment using a powered optical element, such as a refractive optical element (e.g., lens such as a wide field of view lens), forward the eyepiece.

It may be desirable to image a wide view of the environment using the imaging system 900. FIG. 14C schematically illustrates an imaging system 900 for collecting light from the environment using a powered optical element or lens such as refractive optical element 980 (e.g., a wide field of view lens) forward the eyepiece. The refractive optical element 980 may have a positive optical power. The refractive optical element 980 (e.g., positive lens) converges collimated light 970 from the environment toward the waveguide 940. Other types of lenses than the lens shown in FIG. 14C may be employed. Light that is transmitted (not shown) may pass through a powered optical element or lens such as refractive optical element 990 (e.g., negative lens) that is configured for a negative power equal and opposite of the refractive optical element 980. The negative lens 990 may have a similar or the same optical power as the positive lens 980 to offset or counter the optical power of the positive lens or a portion thereof. In this way, light from the environment (e.g., distal of the waveguide 940) may pass through the negative lens 990, the eyepiece 950, and the positive lens 980 with substantially no net change in optical power introduced by these two lenses to the eye. The negative lens 990 may be configured to offset or counter the optical power of the positive lens 980 such that a user's will not experience the power of the positive lens when viewing the environment in front of the eyepiece 950. The negative lens 990 will also counter the effect of the positive lens 980 to invert images of object in the environment in front of the wearer. Some light 970 from the environment may be incoupled into the waveguide 940 by the coupling optical element 944, in spite of some of the rays of light being convergent. The incoupled light incident on the outcoupling optical element 952 may be ejected out of the waveguide 940.

Implementations (e.g., those described by FIGS. 14A-14C) may be used outside an augmented reality context. For example, it is intended that an imaging system 900 configured to image the environment be implemented within a wearable device, such as, for example, eyeglasses (including unpowered glasses) or bifocals. Such an imaging system 900 may not require an image projector 930 and/or light source 960. Additionally or alternatively, such an imaging system 900 may not require an incoupling optical element configured for a corresponding image projector 930 and/or light source 960.

It may be advantageous to implement such an imaging system 900 for imaging the environment on a viewing screen (e.g., television screen, computer screen), such as a handheld device (e.g., cell phone, tablet). The imaging system 900 could improve video chat capabilities. For example, a viewer who is seeing a chat partner look into the screen may appear to be looking directly at the viewer. This would be possible since the light rays captured by the imaging system 900 would be captured in the same region where the user is looking (e.g., as opposed to viewing a screen but having the light rays captured by a separate outward-facing camera positioned at a different location).

In implementations where the imaging system 900 of FIG. 14C is also used to image the eye 210, a light source 960 and/or image projector 930 may be configured to inject light into the waveguide 940. Because the light reflected from the eye that is incoupled into the waveguide will pass through the refractive optical element 990 (e.g., negative lens), a positive powered refractive optical element may be disposed between the light source 960 and/or image projector 930 and between the waveguide 940. The positive lens can be configured to offset or counter any optical power provided by the refractive optical element 990 before the incoupled light from the light source and/or light projector is incident on the eye 210. Other types of lenses than shown in FIG. 14C may be uses as the optical element 990. Alternatively or additionally, processing electronics in communication with the light source and/or image projector can be configured to alter an image sufficient to present to the user an undistorted image after the light has passed through the refractive optical element 990. Corresponding incoupling optical element, outcoupling optical element, and/or coupling optical element may be configured to operate on non-collimated light (e.g., divergent, convergent light) in some designs.

In various implementations, the same waveguide 940 may be used to (i) propagate light from the environment in front of the eyepiece 950 and the user to the camera 940 and (ii) to propagate light from the image projector 930 to the eye 210 to form image content therein. Using the same waveguide 940 may simplify the system and/or the eyepiece and may make the system and/or eyepiece more compact possibly providing a reduced form factor. Reducing the thickness of the eyepiece 950 by reducing the number of waveguide 940 may be advantageous for other reasons as well. Lower cost and a more simplified manufacturing process may be some such advantages.

Also in various designs, the same or different imaging system may be used in the same head mounted display to image the eye by propagating light from the eye via a waveguide in the eyepiece 950 to the camera 940 such as, for example, described above. Such systems may also use the eyepiece to transfer light from an illumination source to the eye 210 to illuminate the eye. In some designs, the eyepiece may additionally be used to propagate light from the image projector 930 to the eye 210 to form image content therein. Using the eyepiece to assist in imaging the environment and image the eye (and possibly to illuminate the eye) may simplify the system and/or may make the system more compact possibly providing a reduced form factor.

Moreover, in some implementations, the same waveguide 940 may be used to (i) propagate light from the environment in front of the eyepiece 950 to the camera 940 and (ii) to propagate light from the eye 210 to the camera to capture images of the eye. The same waveguide may be used to propagate light from the image projector 930 to the eye 210 to form image content therein and/or to propagate light from the illumination source 960 to the eye 210 to illuminate the eye for image capture. Using the same waveguide 940 may simplify the system and/or the eyepiece and may make the system and/or eyepiece more compact possibly providing a reduced form factor. Reducing the thickness of the eyepiece 950 by reducing the number of waveguide 940 may be advantage for other reasons as well. Lower cost and a more simplified manufacturing process may be some such advantages.

Similarly, in addition to coupling light from the environment into the waveguide 940, the same coupling optical element 944 may be configured to direct light from the image projector 930 to the eye 210 to form image content therein and/or light from the eye into the waveguide 940 to be guided therein to the camera 920. Additionally or in the alternative, the same coupling optical element 944 may be configured to couple light from the illumination source 960 guided within the waveguide 940 out of the waveguide to the user's eye 210.

As discussed above, one or more of the coupling optical element 944, the in-coupling optical element 942, or the out-coupling optical element 952 may comprises polarization selective coupling elements. Accordingly, in various designs, light input into eyepiece 950 or waveguide 940 is polarized so as to acted on appropriately by the polarization selective turning elements.

Accordingly, in some embodiments the illumination source 960 comprises a polarized light source of suitable polarization to be acted on properly by the polarization selective coupling/turning elements.

Figure 15A:
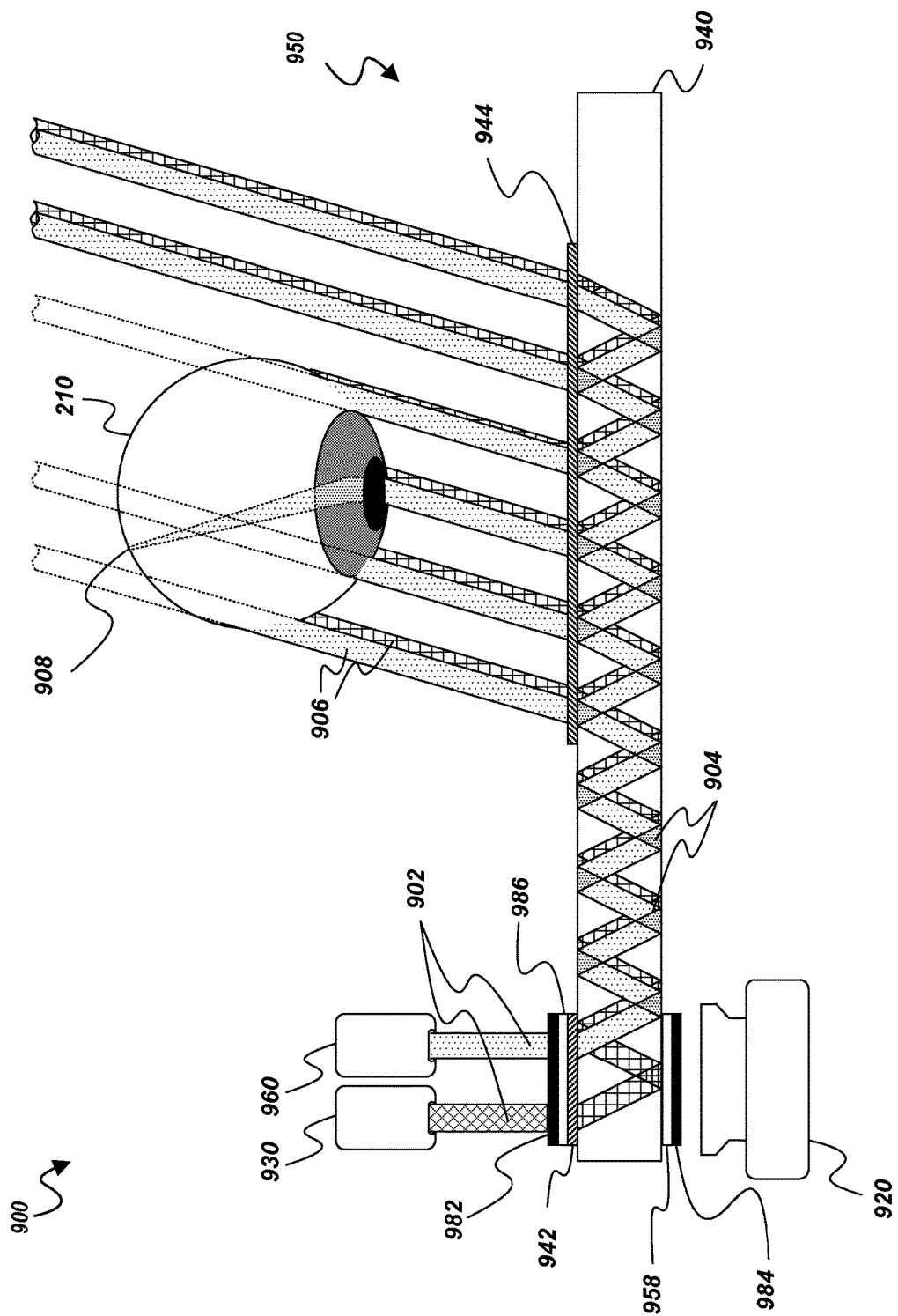
FIG. 15A schematically illustrates an example imaging system comprising a polarization selective incoupling optical element for receiving light a illumination source and coupling the light into a waveguide in an eyepiece. The eyepiece further includes a polarization selective light coupling element for coupling light out of the waveguide. A polarizer may be used to polarize the light from the illumination source and a half wave retarder may be used to rotate the orientation of the linearly polarized light so as to be turned into the waveguide by the polarization selective incoupling optical element.
Figure 15B:
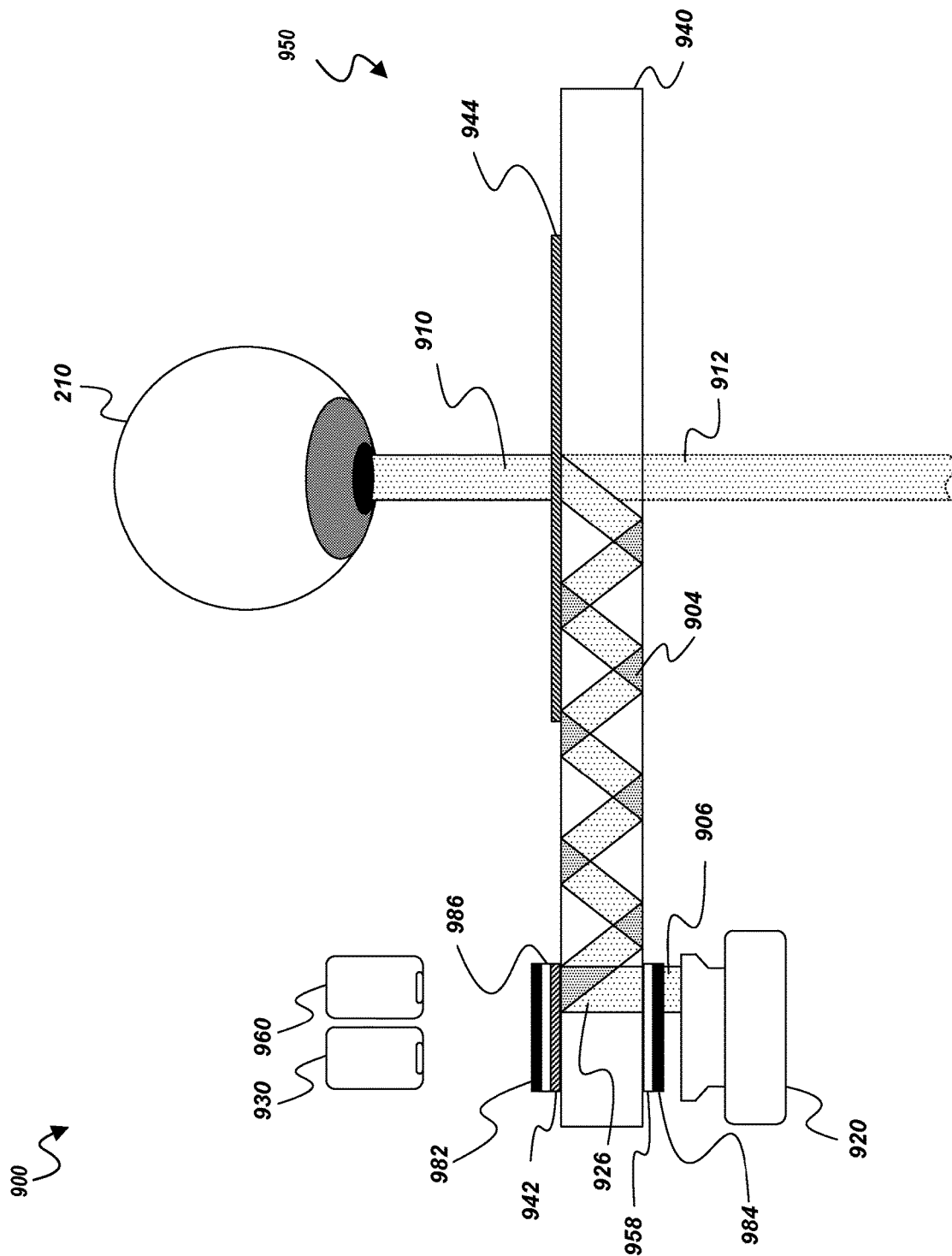
FIG. 15B schematically illustrates light from the eye (e.g., from the retina illuminated with infrared light from the illumination source) being coupled back into the waveguide and directed to a camera for image capture.

One or more polarization specific optical filters and polarization modifying elements may be included in various imaging systems 900, such as those where the image projector 930 and/or light source 960 are disposed directly opposite each other through the waveguide 940. The polarization sensitive elements may be helpful in reducing direction light emission into the imaging device 920 and/or to reduce saturation of the imaging device 920, for example, in configurations where these elements are aligned on opposite sides of the waveguide 940 at the same lateral position. FIGS. 15A-15B show such a configuration. The light source 960 such as shown in FIG. 15A can be configured to direct light through a polarization specific optical filter 982 such as a polarizer (e.g., a linear polarizer) and/or through a polarization modifying element 986 configured to alter a polarization state of incident light, such as a polarization rotator. A retarder such as a half wave retarder may, for example, rotate linear polarization. Accordingly, an appropriately oriented half wave retarder or half wave plate may rotate s-polarized light to p-polarized light or vice versa. Accordingly, in various implementations, the polarization specific optical filter 982 and/or a polarization modifying element 986 are disposed in an optical path between the light source 960 and the in-coupling optical element 942 so as to provide the properly oriented polarization to the in-coupling optical element. In some implementations, the imaging system 900 does not include polarization modifying elements but includes properly oriented polarization optical filters, such as polarizers.

The light emitted by the light source 960 may pass through an arrangement of optical elements in a particular order. For example, as shown in FIG. 15A, the light may pass first from the light source 960 through the polarization specific optical filter 982 (e.g., polarizer) and then through the polarization modifying element 986 (e.g. rotator). After the light has passed through the polarization modifying element 986, the light may be incident on an incoupling optical element 942, which may direct the light into the waveguide 940 to be guided therein.

For example, the light source 960 may be configured to emit light of a mixed polarization (e.g., s-polarization and p-polarization). The polarization specific optical filter 982 may be configured to transmit only light of a first polarization state (e.g., p-polarization). As the light continues, the polarization modifying element 986 may be configured to change the polarization state of the light (e.g., from p-polarized to s-polarized). The incoupling optical element may be configured to turn s-polarized light into an angle that is greater than the critical angle of the waveguide such that the s-polarized light is guided within the waveguide. The incoupled light 904 may be substantially polarized in the second polarization (s-polarization) as it propagates through the waveguide 940. The coupling optical element 944 may be configured to turn light only of the second polarization state (s-polarization). The coupling optical element 944 may be configured to couple the incoupled light 904 out of the waveguide 940 and to the eye 210 to provide illumination for image capture.

In order to prevent direct illumination (e.g., saturation) of the imaging device 920, a polarization modifying element 958 and/or a polarization specific optical filter 984 may be disposed in or on the waveguide 940 such that only light of a certain polarization state (e.g., p-polarized) can pass through the polarization specific optical filter 984 and to the imaging device 920. The polarization modifying element 958 (e.g., half waveplate) may be configured to change the state of the polarization (e.g., from s-polarized to p-polarized). The polarization specific optical filter 984 may be configured to transmit only light of a certain polarization (e.g., p-polarized light) therethrough. In this way, light passing through the polarization specific optical filter 982 will not be configured to transmit directly through the polarization specific optical filter 984. In any of the implementations above (e.g., where the image projector 930 and/or the light source 960 are on the same optical axis as shown in FIG. 15A), such as in FIGS. 10, 11A-11E, and 12A-12E, the configuration of the polarization specific optical filter 982, the polarization modifying element 986, the incoupling optical element 942, the polarization modifying element 958, and/or the polarization specific optical filter 984 may be implemented according to the design of FIG. 15A. The polarization specific optical filter 984 may be a transmissive-reflective polarizer (e.g., a polarizer beam splitter) configured to transmit light of a first polarization and to redirect or reflect light of a second polarization different from the first.

A partially reflective element (e.g., semi-transparent mirror) may be included to turn the incoupled light 904 to the imaging device 920. The partially reflective element may be disposed between the incoupling optical element 942 and the polarization modifying element 986 such that a portion of the incoupled light 914 is reflected toward the imaging device 920 while reducing leakage of the incoupled light 914 out of the waveguide 940. The portion of light that does not leak out may be any fraction between 0 and 1. For example, the portion may be 0.90, where 90% of the light rays propagating through the waveguide 940 along the coupling optical element 944 are maintained within the waveguide 940 at each reflection of the light rays. Other portions are possible (e.g., 0.10, 0.20, 0.30, 0.40, 0.50, 0.60, 0.70, 0.80, or any value in a range between these values).

FIG. 15B illustrates propagation of light reflected or scatter off the retina. Some of the light 910 reflected from the retina that is incident on the coupling optical element 944 having the second polarization (s-polarization) is turned by the coupling optical element 944 at angle greater than the critical angle of the waveguide 940 and thus may be guided therein. Some of the light may not be coupled into the waveguide 940 and will transmit therethrough as non-incoupled light 912. The incoupled light 904 may propagate through the waveguide 940 toward the camera.

Other implementations may benefit from use of polarization selective elements proximal the light source and camera. For example, various systems can be configured to provide illumination having a first polarization and capture images with the camera using light having a different polarization. For example, such a configuration may be used to reduce unwanted reflections, such as from the cornea when imaging the retina. Reflecton from the cornea will be specular. Accordingly, if light of a first polarization is incident on the cornea, the light reflected from the cornea will retain that first polarization. In contrast, the retina is diffuse. If light of a first polarization is incident on the retina, the light reflected from the retina does not retain solely the first polarization. The diffuse reflection more likely results in unpolarized light. Accordingly, a second polarization, different from the first polarization will be present in the reflected light. Likewise by illuminating with a first polarization and imaging with a second different polarization, the retina can be image with reduced glare from the cornea.

Accordingly, in various implementations, the polarization specific optical filters 982, 984 may be used together to reduce unwanted reflected light from the eye 210 (e.g., from the cornea). For example, unwanted light, glare, or glint may be reflected off the cornea that may saturate an image captured by the imaging device 920. Light reflected from the cornea may be specular and maintain its polarization. By contrast, light reflected off the retina may be more diffusely reflected and may be less homogenously polarized. Likewise, a combination of polarizers may be used to remove some or most of the unwanted reflected light. Initially polarized light can be used for illuminating the eye 210. In some designs, a polarized illumination source (e.g., the light source 960) may be used. Additionally or alternatively, a first polarizer (e.g., the polarization specific optical filter 982) may be positioned at the beginning of the optical path of the illumination source to provide initial polarization of the light. A second polarizer (e.g., the polarization specific optical filter 984) may be positioned at the optical path before the light enters the imaging device 920. The second polarizer may be rotated at 90° from the first polarizer (e.g. the polarizers 982, 984 may be "crossed"). As a result, the eye will be illuminated with the first polarization with some light of the first polarization reflected from the cornea. This light will not pass through the polarizer 984 proximal the camera. However, light reflected from the retina will include the second polarization. Likewise light diffusely reflected from the retina will pass through the polarize 984 proximal the camera and will enable an image of the retina to be captured by the camera. Thus, in such as configuration unwanted light received from the eye (e.g., from cornea) may be entering the imaging device 920 may be reduced or eliminated. Other configurations are possible. For example, a polarization selective incoupling optical element 942 for coupling light from the light source 960 into the waveguide 940 and a polarization selective outcoupling optical element for coupling light out of the waveguide to the camera 920 may be employed having different polarization selectivity properties. For example, the polarization selective incoupling optical element may selectively turn light from the illumination source having a first polarization into the waveguide while the outcoupling optical element may selectively turn light of a second different polarization out of the waveguide to the camera. The effect may again be to reduce or remove unwanted light received from the eye (e.g., from cornea) before entering the imaging device 920.

Figure 16:
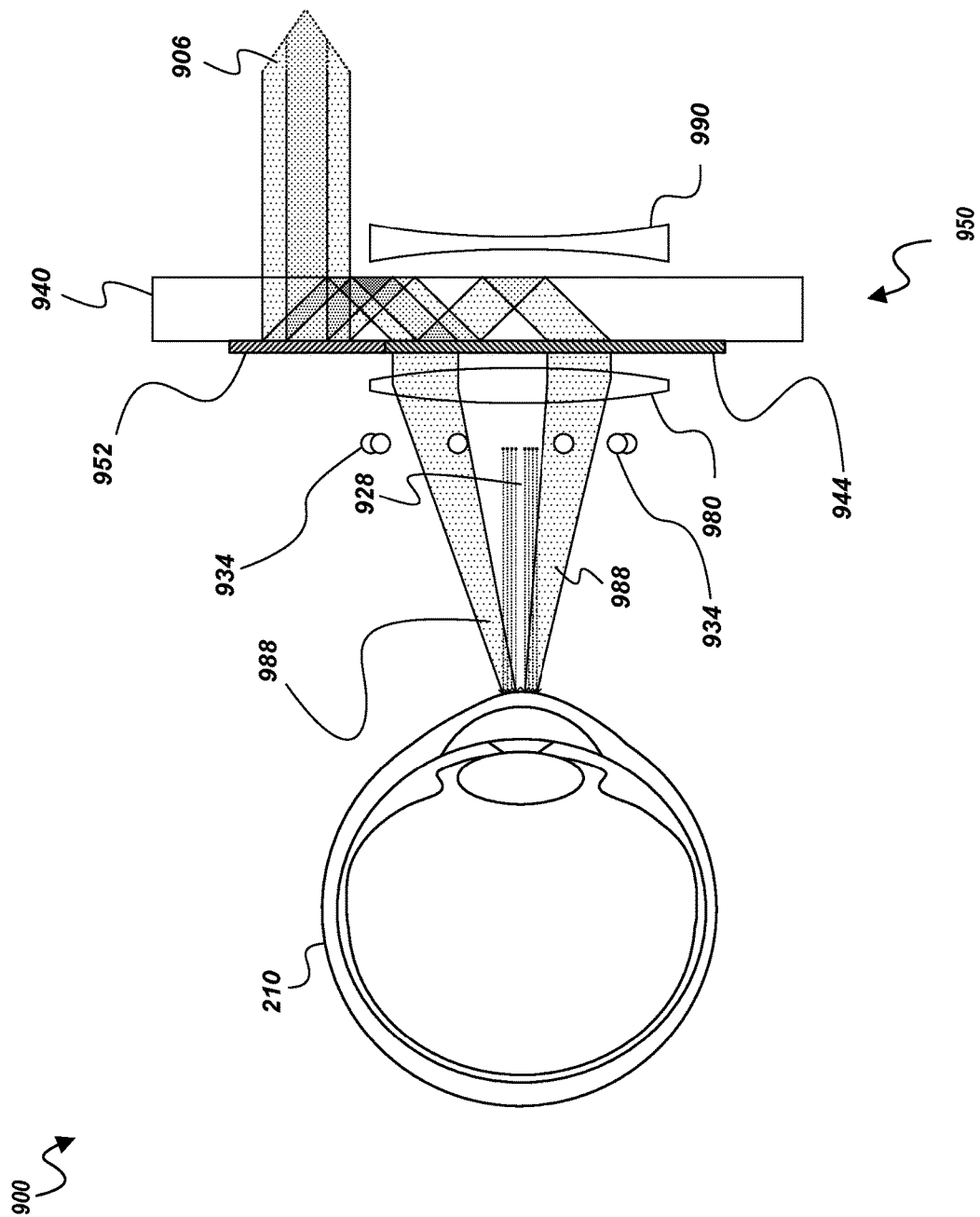
FIG. 16 schematically illustrates an imaging system configured for imaging an anterior portion (e.g., cornea) of an eye. The imaging system comprises an eyepiece such as described above. The imaging system further includes a positive lens for collimating light collect from the anterior portion of the eye for coupling via an optical coupling element into a waveguide and propagation to a camera for image capture. The system further comprises a negative lens to offset the positive power introduced by the positive lens and to prevent inversion of images of the environment in front of the eyepiece that would otherwise be caused by the positive lens.

Various imaging systems 900 are discussed herein that are capable of using the eyepiece 950 to collect light to image the retina. The imaging systems 900, however, can be configured to image other portions of the eye such as anterior portions of the eye. FIG. 16 illustrates how an imaging system 900 can be used for imaging an anterior portion (e.g., cornea) of an eye 210. The imaging system 900 may include one or more elements of the example imaging systems 900 described above. In addition, an example imaging system 900 may include one or more powered optical elements or lenses such as powered refractive optical elements 980, 990 having optical power. For example, a positive power lens or positive lens 980 may be disposed on a proximal side (e.g., closer to the eye 210) of the eyepiece 950 between the eye 210 and the eyepiece. A negative power lens or negative lens 990 may be disposed on a distal side of the eyepiece 950, between the eyepiece and the environment forward the user. One or both of the lenses 980, 990 may be variable focus elements (e.g., varifocal lenses) and/or may include a liquid crystal element. In some designs, one or both of the lenses 980, 990 includes a Fresnel lens. The lenses 980, 990 may incorporate liquid crystals to produce Fresnel lens functionality. Such functionality may allow for variable focus of one or both of the lenses 980, 990. In some designs, one or more of the lenses 980, 990 may be integrated with and/or manufactured (e.g., formed) on or into the eyepiece 950.

In various embodiments, the coupling optical element 944 is configured to turn collimated light reflected from the eye 210 into the light guide to be guided therein. Accordingly, the positive lens 980 may be configured to collimate light reflected from the eye 210, such as an anterior portion of the eye (e.g., the cornea). The positive lens 980 therefore may have a focal length that is equal or substantially equal to the distance of the lens to the portion of the eye 210 to be imaged, e.g., the cornea.

The negative lens 990 may have a similar or the same optical power as the positive lens 980 to offset or counter the optical power of the positive lens. In this way, light from the environment (e.g., distal of the waveguide 940) may pass through the negative lens 990, the eyepiece 950, and the positive lens 980 with substantially no net change in optical power introduced by these two lenses. Thus, the negative lens 990 may be configured to offset or cancel out the optical power of the positive lens 980 such that a user will not experience the power of the positive lens when viewing the environment in front of the eyepiece 950. The negative lens 990 will also counter the effect of the positive lens 980 to invert images of object in the environment in front of the wearer.

FIG. 16 illustrates light 928 that is incident on the cornea scattering therefrom. The imaging system 900 may be configured to capture this light 988 reflected from the cornea. For example, the positive lens 980 may collect a portion of the light 988 scattered from the cornea and collimate this light 988. This light 988, collimated by the positive lens 980, is incident on the coupling optical element 944, which is configured to turn collimated light into the waveguide 940 at an angle larger than the critical angle of the waveguide such that the light is guided therein by TIR. The coupling optical element 944, the outcoupling optical element 952, and/or the waveguide 940 may be as described above. Resultant outcoupled light 906 may be directed by the outcoupling optical element 952 out of the waveguide 940 to the camera (not shown).

FIG. 16 shows light 928, such as collimated light, which may be from the eyepiece 950 such as describe above. An illumination source 960 may couple light into the waveguide 940 and the coupling element 944 may couple this light from the illumination source 960 out of the waveguide. The coupling element 944 may be configured to couple light out of the waveguide 940 as collimated light. This light illuminates the anterior portion of the eye (e.g., the cornea) and scatters therefrom. As discussed above, this scattered light 988 can be collected by the positive lens 980 and the imaging system 900 to form an image of the anterior portion of the eye 210. Also as discussed above, this illumination 928 directed onto the eye 210 may be invisible (e.g., infrared) light.

FIG. 16 also shows an alternative arrangement for illuminating the eye 210. In some designs, one or more light sources 934 such as LEDs or emitters may be disposed with respect to the eye 210 to direct light thereon without being guided by TIR through the waveguide 940 and directed onto the eye 210. In some implementations, the eyepiece 950 or waveguide 940 is not in an optical path between the one or more light source 934 and the eye 210. In some designs, a plurality of such light sources 934 may be arranged in a pattern (e.g., circular or ring-like pattern) near and/or around the eye. In some designs, the pattern of light sources 934 may define an illumination axis parallel (e.g., coaxial) with the optical axis of the one or more lenses 980, 990. The one or more light sources 934 may be similar to the one or more light sources 960 described above and may, for example, be pulsed. Similarly, the one or more light sources 934 may comprise infrared light sources such as infrared LEDs or another type of invisible light. Alternatively, the one or more light sources may comprise visible light sources that emit visible light. Or the one or more light sources may emit both visible and invisible (e.g., infrared) light.

Figure 17:
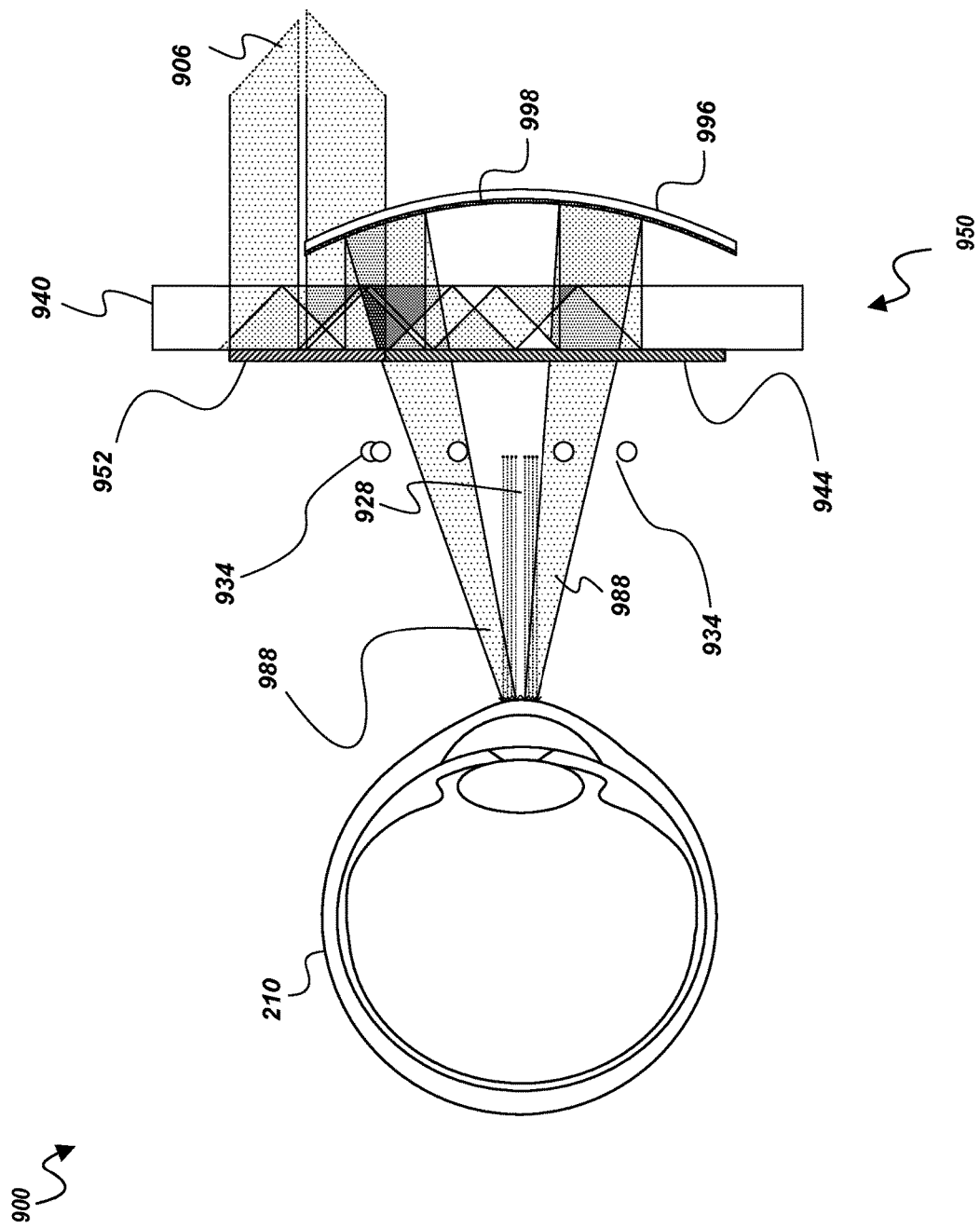
FIG. 17 schematically illustrates another example imaging system configured for imaging an anterior portion (e.g., cornea) of an eye. The imaging system comprises a curved wavelength selective reflector that collimates light from the anterior portion of the eye for coupling via an optical coupling element into a waveguide and propagation to a camera for image capture. The wavelength selective reflector may operate in reflection for infrared light reflected from the eye and in transmission for visible light from the environment in front of the user.

FIG. 17 illustrates another example imaging system 900 configured to image a portion of the eye 210 such as an anterior portion of the eye (e.g., cornea). The imaging system 900 shown in FIG. 17 employs a reflective optical element 996 configured to collimate the light from the eye, in contrast to the transmissive optical element (lens) 980 shown in FIG. 16. A reflective optical element will have less aberration than a transmissive optical element as chromatic aberration is not generally applicable to reflective optical elements such as the reflector 996 shown in FIG. 17. Accordingly, by using a reflective surface in collecting light from the eye 210, less (e.g., chromatic) aberration is introduced in the image captured of the eye.

FIG. 17 illustrates, for example, an imaging system 900 that includes a curved transmissive optical element 996 having a wavelength dependent reflective coating 998. The curved transmissive optical element 996 may be disposed distal the waveguide 940 (on the environment side of the eyepiece 950). Accordingly, the curved transmissive optical element 996 may be disposed between the environment forward the wearer and the waveguide 940 and/or the coupling optical element 944. Similarly, the waveguide 940 and/or the coupling optical element 944 may be disposed between the curved transmissive optical element 996 and the eye 210.

The wavelength dependent reflective coating 998 may be configured to reflect light of a certain wavelength or range of wavelengths. In some implementations, for example, the wavelength dependent reflective coating 998 may be configured to reflect invisible light (e.g., infrared light) within a certain range of wavelength, while the wavelength dependent reflective coating 998 may be configured to transmit visible light. The wavelength dependent reflective coating 998 may be disposed on a surface of the curved transmissive optical element 996, in some cases.

As discussed above, in various designs, the coupling optical element 944 is configured to turn collimated light reflected from the eye 210 into the waveguide 940 to be guided therein. Accordingly, the reflective optical element 996 may be configured to collimate light reflected from the eye 210, such as an anterior portion of the eye (e.g., the cornea). The curved reflective optical element 996 may therefore have a positive optical power for light that is incident on the proximal side thereof that is reflected from wavelength dependent reflective coating 998. In particular, in various designs, the reflective optical element 994 may have a focal length that is equal or substantially equal to the distance from the reflective optical element 996 to the portion of the eye 210 to be imaged, e.g., the cornea, iris, etc. Example values of focal lengths may be, for example, 2 cm to 8 cm. In some implementations, the focal length is between 4 cm and 6 cm. In some designs, the focal length is about 5 cm. The focal length may be in any range formed by any of these values or may be outside such ranges in different designs.

In various implementations, the reflective optical element 996 is disposed on the distal side of the eyepiece 950 forward the eyepiece. Accordingly, the reflective optical element 996 is disposed between the eyepiece 950 and the environment forward the user. Similarly, the eyepiece 950 is disposed between the reflective optical element 996 and the eye 210.

The curved transmissive optical element 996 may have a curved reflective surface having a curvature of any shape. In some implementations, the surface is rotationally symmetric. In some implementations, the surface may be spherical or aspheric (e.g., parabolic). Non-rotationally symmetric shapes are also possible. In various designs, however, the reflective surface has positive optical power. The reflective optical element 996 may comprise, for example, a concave mirror at least for some wavelengths and/or polarizations.

The curved transmissive optical element 996 may be configured to have negligible power in transmission. Likewise, the curved transmissive optical element 996 may be configured to transmit light without introducing convergence or divergence. In one example, the curved transmissive optical element 996 may have a curvature of an inner radius substantially the same as a curvature of an outer radius. A thin optical element 996 may reduce optical aberration, for example, for light transmitted therethrough, may be lighter and/or may be more compact.

In various designs, the reflective optical element 996 comprises material transmissive to visible light such that the user can see the environment in front of wearer. In some cases, to enhance transmission, the curved transmissive optical element 996 may be coated on an outer surface (e.g., the distal surface) with an anti-reflective coating. The anti-reflective coating may be configured to reduce reflection of, for example, of visible light such as red, green, and/or blue light. The reflective optical element 996, however, may be configured to reflect a portion of the light scattered from the eye 210 to form an image of the eye. Accordingly, the reflective optical element 996 may operate on different light differently. For example, the reflective optical element 996 may operate on different wavelengths differently. The reflective optical element 996 may be configured to reflect infrared light and transmit visible light.

As discussed above, one or more light sources 934 may be configured to illuminate the eye 210 with infrared light. Resultant light 988 reflected from the eye 210 (e.g., cornea) may be diverge, as schematically illustrated in FIG. 17. The curved transmissive optical element 996 may be disposed to receive this light 988 reflected from the eye (e.g., cornea, iris). The wavelength dependent reflective coating 998 may be configured to reflect the light 988 reflected from the eye because the wavelength illumination used to illuminate the eye is the same wavelength that is reflected by the reflective coating on the curved transmissive optical element 996 (e.g., 850 nm). For example the eye may be illuminated with infrared light (e.g., 850 nm) and the curved transmissive optical element 996 may be configured to reflect infrared light (e.g., 850 nm) and to pass visible light. The shape of the curved transmissive optical element 996 may also be configured to collimate the light 988 reflected from the eye and to reflect the light to the coupling optical element 944, which turns the collimated light into the waveguide 940 to be guided therein by TIR.

In FIG. 17, as in some other designs, one or more light sources 934 such as LEDs or emitters may be disposed with respect to the eye 210 to direct light thereon without being guided by TIR through the waveguide 940 and directed onto the eye 210. In some implementations, the eyepiece 950 or waveguide 940 is not in an optical path between the one or more light source 934 and the eye 210. In some designs, a plurality of such light sources 934 may be arranged in a pattern (e.g., circular or ring-like pattern) near and/or around the eye. In some designs, the pattern of light sources 934 may define an illumination axis parallel (e.g., coaxial) with the optical axis of the one or more lenses 980, 990. The one or more light sources 934 may be similar to the one or more light sources 960 described above and may, for example, be pulsed. Similarly, the one or more light sources 934 may comprise infrared light sources such as infrared LEDs or another type of invisible light. Other types of light sources, however, can be used.

Figure 18:
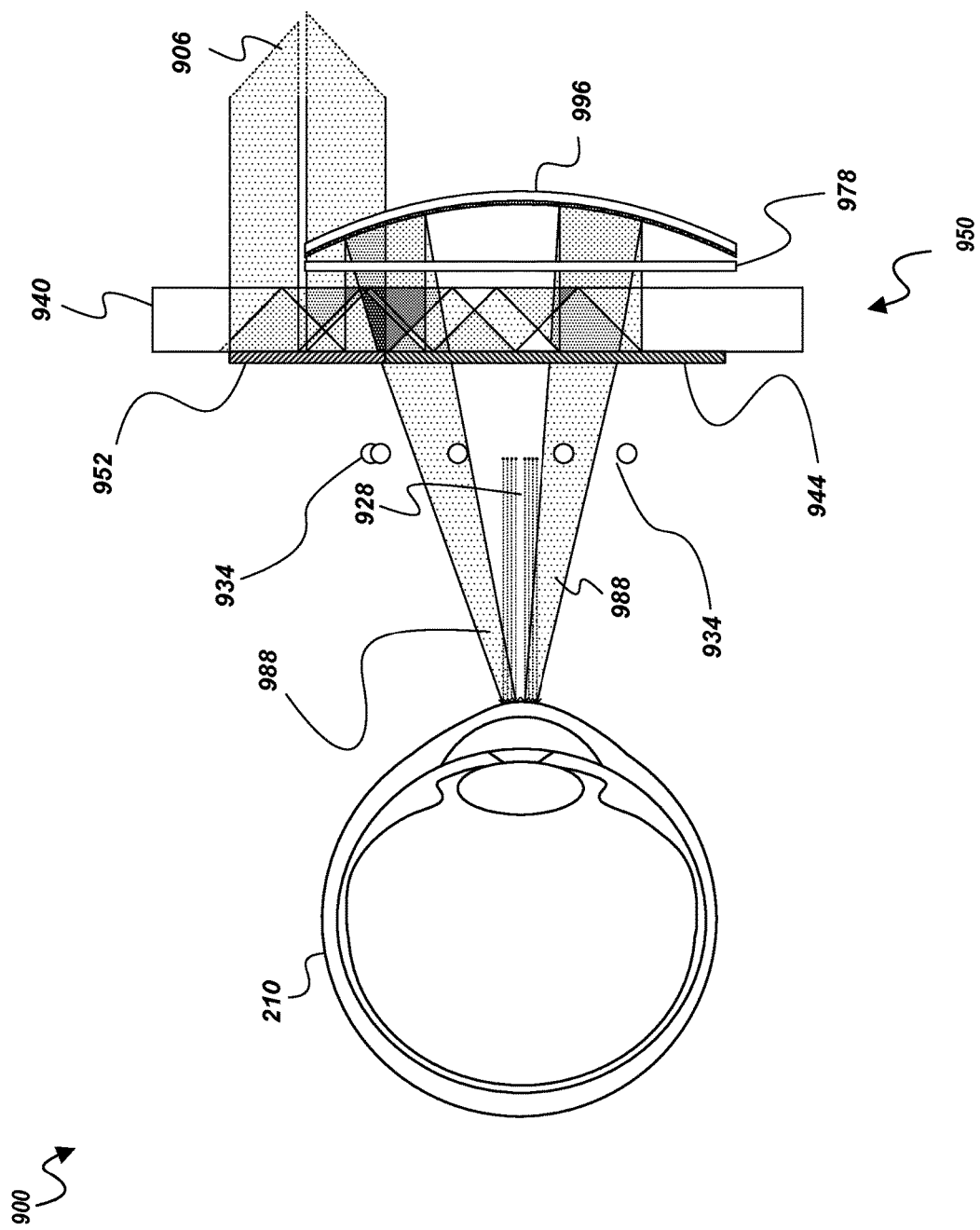
FIG. 18 schematically illustrates an example imaging system that also includes a curved wavelength selective reflector that collimates light from the anterior portion of the eye for coupling via an optical coupling element into a waveguide and propagation to a camera for image capture. Polarization selectivity may be employed to assist in controlling the path of the light reflected from the eye. Illumination of the eye is provided via the waveguide instead of a plurality of light source between the waveguide and the eye as shown in FIG. 18.

FIG. 18 illustrates another example imaging system 900 configured to image a portion of the eye 210 such as an anterior portion of the eye (e.g., cornea). In the implementation shown in FIG. 18, polarization selectivity is employed to assist in controlling the path of the light reflected from the eye. In particular, in various designs, the coupling optical element 944 is polarization selective. Light, for example, having a first polarization is transmitted through the coupling optical element 944 while light of a second different polarization is turned by the coupling optical element 944 into the waveguide 940 to be coupled therein by TIR. Accordingly, in various implementations the eye 210 is illuminated with polarized light or a polarizer (not shown) is disposed between the eye and the waveguide 940 such that the light from the eye incident on the waveguide is polarized. For example, the emitters 934 may emit polarized light or a polarizer may be disposed in front of the emitters 934 such that the eye 210 is illuminated with polarized light. Accordingly, in various designs, the polarization of the polarized light incident and/or reflected from the eye 210 that is received by the optical coupling element 944 may the first polarization such that said light is directed to the reflector 996.

Likewise, in various implementations, the coupling optical element 944 (and/or an outcoupling optical element 952) is configured to transmit light of a first polarization state such as a first linear, circular, or elliptical polarization state (e.g., p-polarization, left handed circular or elliptical polarization, etc.) and turn light of a second polarization state such as a second linear, circular, or elliptical (e.g., s-polarization, right handed circular or elliptical polarization, etc.) into and/or out of the waveguide, respectively. In some implementations, the eye illuminators 934 may emit only or primarily the first polarization (e.g., p polarization) or further include a polarization modifying element (e.g., polarizer) that is configured to transmit only light of the first polarization state (e.g., p-polarization). Additionally, the coupling optical element 944 and/or outcoupling optical element 952 may be configured to turn light of a second polarization (e.g., s-polarization) into and/or out of the waveguide, respectively.

Similar to the imaging system 900 shown in FIG. 17, an imaging system 900 the curved reflector 998 shown in FIG. 17 comprises a curved transmissive optical element 996 having a wavelength dependent reflective coating 998. The wavelength dependent reflective coating 998 may be configured to reflect light of a certain wavelength or range of wavelengths. In some implementations, for example, the wavelength dependent reflective coating 998 may be configured to reflect invisible light (e.g., infrared light) within a certain range of wavelength, while the wavelength dependent reflective coating 998 may be configured to transmit visible light. The wavelength dependent reflective coating 998 may be disposed on a surface of the curved transmissive optical element 996, in some cases.

In various implementations, the curved transmissive optical element 996 is disposed on the distal side of the eyepiece 950 forward the eyepiece. Accordingly, the reflective optical element 996 is disposed between the eyepiece 950 and the environment forward the user. Similarly, the eyepiece 950 is disposed between the reflective optical element 996 and the eye 210.

Accordingly, light having the first polarization (e.g., p-polarization) from the eye 210 is incident on the coupling optical element 944 and passes therethrough to the curved transmissive optical element 996. The imaging system 900 further included a polarization modifying optical element 978, such as a retarder (e.g., a quarter-wave retarder). This retarder 978 is transmissive and imparts a quarter wave of retardance on the light transmitted therethrough. This light is incident on and reflected from the curved transmissive optical element 996. The wavelength dependent reflective coating 998 may be configured to reflect the wavelength of light reflected from the eye. Consequently, this light is reflected from the curved surface of the curved transmissive optical element 996 and is collimated. This collimated light passes again through the retarder 978, thereby imparting another quarter wave of retardance on the light transmitted therethrough. The retardance introduced on these two passes through the retarder (e.g., a full wave of retardance) causes the polarization to rotate. Accordingly, the first polarization (e.g., p-polarization) transmitted through the polarization selective coupling optical element 944 on the first pass, is transformed into the second polarization (s-polarization) and is turned into the waveguide 940 to be guided to the camera 920 by TIR. As discussed above, in various designs, the coupling optical element 944 is configured to turn collimated light reflected from the eye 210 into the waveguide 940 to be guided therein. Accordingly, the reflective optical element 996 may be configured to collimate light reflected from the eye 210, such as an anterior portion of the eye (e.g., the cornea). The curved reflective optical element 996 may therefore have a positive optical power. In particular, in various designs, the reflective optical element 994 may have a focal length that is equal or substantially equal to the distance from the reflective optical element 996 to the portion of the eye 210 to be imaged, e.g., the cornea, iris, etc. Example values of focal lengths may be for example, 2 cm to 8 cm. In some implementations, the focal length is between 4 cm and 6 cm. In some designs, the focal length is about 5 cm.

In various designs, the reflective optical element 996 may comprise a curved surface that is configured to reflect light. The curved surface may be spherical or rotationally symmetric in certain cases. The reflective optical element 996 may comprise, for example, a concave mirror at least for some wavelengths and/or polarizations.

In various designs, the reflective optical element 996 comprises material transmissive to visible light such that the user can see the environment in front of wearer. The wavelength dependent reflective coating 998 disposed on a surface of the curved transmissive optical element 996 may therefore be transmissive to visible light or at least certain wavelength of visible light. The curved transmissive optical element 996 may also be coated on an outer surface (e.g., the distal surface) with an anti-reflective coating. The anti-reflective coating may be configured to reduce reflection of red, green, and/or blue light. The reflective optical element 994, however, may be configured to reflect a portion of the light scattered from the eye 210 to form an image of the eye. Accordingly, the reflective optical element 996 may operate on different light differently. For example, the reflective optical element 996 may operate on different polarization states (and/or wavelengths) of light differently. The reflective optical element 996 may be configured to transmit visible light and reflect infrared light.

As shown in FIG. 17, the one or more light sources 934 such as LEDs or emitters in FIG. 18 may be disposed with respect to the eye 210 to direct light thereon without being guided by TIR through the waveguide 940 and directed onto the eye 210. Accordingly, n some implementations, the eyepiece 950 or waveguide 940 is not in an optical path between the one or more light sources 934 and the eye 210. In some designs, a plurality of such light sources 934 may be arranged in a pattern (e.g., circular or ring-like pattern) near and/or around the eye. The one or more light sources 934 may be similar to the one or more light sources 960 described above and may, for example, be pulsed. Similarly, the one or more light sources 934 may comprise infrared light sources such as infrared LEDs or another type of invisible light. In particular, in various implementations the light sources 934 may emit light that is reflected by the wavelength dependent reflective coating 998 and/or the curved transmissive optical element 996. Other types of light sources, however, can be used.

Although the polarization selective coupling optical element 944 is configured to be polarization selective depending on the type of linear polarization incident thereon, other polarization selective coupling optical elements may be polarization selective to other types of polarization states such as different types of circular or elliptical polarization. The polarization selective coupling optical element 944 may, for example, be configured such that the first polarization, such as a first circular or elliptical polarization (e.g., left handed polarization or LHP-polarization), is transmitted through the polarization selective coupling optical element 944 and the second polarization, such as second circular or elliptical polarization (e.g., right handed polarization or RHP), is turned into the light guide, or vice versa. Such a polarization selective coupling optical element 944 may comprise liquid crystal such as cholesteric liquid crystal. Examples of some liquid crystal optical elements are discussed below in the section titled "Cholesteric Liquid Crystal Mirror," in U.S. Publication No. 2018/0164627, titled "DIFFRACTIVE DEVICES BASED ON CHOLESTERIC LIQUID CRYSTAL," filed on Dec. 7, 2017; in U.S. Publication No. 2018/0239147, titled "DISPLAY SYSTEM WITH VARIABLE POWER REFLECTOR," filed on Feb. 22, 2018; in U.S. Publication No. 2018/0239177, titled "VARIABLE-FOCUS VIRTUAL IMAGE DEVICES BASED ON POLARIZATION CONVERSION," filed on Feb. 22, 2018; each of which is hereby incorporated by reference in its entirety and for all purposes.

A polarization modification element or retarder such as a circular polarizer may be disposed between the eye and the polarization selective coupling optical element 944 to convert the light reflected from the eye to the first polarization (e.g., LHP). The LHP light will pass through the polarization selective coupling optical element 944, reflect from the reflector 998, change polarization into RHP and be turned by the polarization selective coupling optical element 944 into the waveguide to the camera.

In some implementations, the reflector 996 may be polarization selective in its reflectivity such that only light of a certain polarization state is reflected and/or that light of a different polarization state is transmitted. Such an optical element may comprise liquid crystal such as cholesteric liquid crystal. Examples of such optical elements are discussed below in the section titled "Cholesteric Liquid Crystal Mirror," in U.S. Publication No. 2018/0164627, titled "DIFFRACTIVE DEVICES BASED ON CHOLESTERIC LIQUID CRYSTAL," filed on Dec. 7, 2017; in U.S. Publication No. 2018/0239147, titled "DISPLAY SYSTEM WITH VARIABLE POWER REFLECTOR," filed on Feb. 22, 2018; in U.S. Publication No. 2018/0239177, titled "VARIABLE-FOCUS VIRTUAL IMAGE DEVICES BASED ON POLARIZATION CONVERSION," filed on Feb. 22, 2018; each of which is hereby incorporated by reference in its entirety and for all purposes. Such optical elements may reflect light of a first polarization state such as a first circular or elliptical polarization state (left handed circular or elliptical polarization) and transmit light of a second polarization state such as a second circular or elliptical polarization state (e.g. right handed circular or elliptical polarization) or vice versa. In some embodiments, the liquid crystal is disposed on a curved surface of the reflector 996 such that in reflection, the reflector has optical power such as positive optical power. In various other implementations, the liquid crystal optical element may be flat or planar. For example, the liquid crystal may be disposed on a flat or planar substrate or layer. Despite being flat, optical power may be included in the liquid crystal optical element. Such an element may be referred to as a cholesteric liquid crystal reflective lens. Accordingly, light from the eye may be collimated and reflected to the coupling optical element 998. The reflector, for example, may reflect light of a first polarization state (e.g., left handed circular or elliptical) and transmit light of a second polarization (e.g., right handed circular or elliptical polarization). Accordingly, the eye 210 is illuminated with left handed circular polarized light or the light reflected from the eye is transmitted through a polarizer (e.g., a circular or elliptical polarizer) that transmits light having the first polarization (e.g., left handed circular or elliptical polarized light). The coupling optical element 944 may also be polarization selective and may transmit LHP light and turn RHP light into the waveguide. The LHP light from the eye passes through the coupling optical element 944. This transmitted LHP light also is incident on the wavelength-selective liquid crystal reflector 996 and reflected therefrom. In certain designs, the wavelength-selective liquid crystal reflector 996 transforms the first polarization state (e.g. LHP) into the second polarization state (e.g. RHP) upon reflection. This light of the second polarization state (e.g., RHP light) is directed to the coupling optical element 944, which turns light of the second polarization state (RHP) into the waveguide 940 to the camera 920.

In some designs, the coupling optical element 944 does not comprise a liquid crystal grating but instead comprises, for example a surface relief diffraction grating or holographic grating. As discussed above, these coupling optical element 944 that do not comprise cholesteric liquid crystal may also comprise a volume diffractive or holographic optical elements or grating.

Accordingly, light scattered from the eye, is reflected by the reflective optical element 996 back to the waveguide 940 for coupling into the waveguide by the coupling element 944. In contrast, however, a portion of the unpolarized light from the environment in front of the wearer corresponding to the second polarization state (e.g., RHP) would be transmitted through the reflective optical element 996. Thus, the wearer could see objects through the reflective optical element 996.

In various designs, however, the reflective optical element 996 would have negligible power in transmission. For example, the reflective optical element 996 may have curved surfaces on both sides of the optical element having the same curvature such that the aggregate power of the optical element for light transmitted therethrough would be negligible.

As discussed above, in various implementations, the reflective optical element 996 comprises a cholesteric liquid crystal reflective lens, a cholesteric liquid crystal reflective element such as discussed below in the section titled "Cholesteric Liquid Crystal Mirror," in U.S. Publication No. 2018/0164627, titled "DIFFRACTIVE DEVICES BASED ON CHOLESTERIC LIQUID CRYSTAL," filed on Dec. 7, 2017; in U.S. Publication No. 2018/0239147, titled "DISPLAY SYSTEM WITH VARIABLE POWER REFLECTOR," filed on Feb. 22, 2018; in U.S. Publication No. 2018/0239177, titled "VARIABLE-FOCUS VIRTUAL IMAGE DEVICES BASED ON POLARIZATION CONVERSION," filed on Feb. 22, 2018; each of which is hereby incorporated by reference in its entirety and for all purposes. Such optical element may operate on a particular wavelength or wavelength range. Accordingly, light such as infrared light reflected from the eye may be acted on by the cholesteric liquid crystal reflective element. However, light not in that wavelength range such as visible light from the environment may be passed through the cholesteric liquid crystal reflective element without being operated on by the cholesteric liquid crystal reflective element. Accordingly, the cholesteric liquid crystal reflective element may have negligible power for this visible light from the environment passing therethrough As discussed above, in certain implementations, the illumination source 960 couples light into the waveguide 940 that is turned out of the waveguide to illuminate the eye 210. In such embodiments, the coupling optical element 944 may be polarization selective. For example, the coupling optical element 944 may transmit a first polarization (p-polarization) and transmit a second polarization (s-polarization).

Accordingly, if light from the illumination source 906 propagates through the waveguide 940 and is turned by the coupling optical element 944, this illumination will be s-polarization. A polarization modifying optical element (e.g., a quarter wave retarder) may be disposed between the waveguide 940 and the eye 210 so as to cause rotation of the polarized light reflected from the eye. Light from the light source 960 that is reflected from the eye 210 will pass twice through the quarter wave retarder and as a result the s-polarized light ejected from the waveguide by the coupling element 944 to illuminate the eye will be transformed into p-polarized light.

This p-polarized light will be transmitted through the coupling optical element 944 and the waveguide and be incident on the reflective optical element 996.

The imaging system 900 may further comprise a second polarization modifying element 978 which may comprise, for example, a retarder or waveplate as discussed above. This retarder may comprise for example a quarter wave retarder. The second polarization modifying element 978 may be disposed distal of the waveguide 940, between the waveguide and the reflector 996. The second polarization modifying element 978 may also be disposed between the coupling element light 944 and the reflector 996. Light (p-polarized) from the eye 210 that is transmitted through the coupling element light 944 passes through second polarization modifying element 978 is transformed into circular polarization. If the reflector 996 reflects circular polarized light, this light will be reflected back to the waveguide 940 after passing again through the polarization modifying element 978. Two passes through this polarization modifying element (e.g., quarter wave retarder) 978 will cause the light to be transformed into s-polarized light, which will be turned by the coupling element 944 into the waveguide to be guide therein to the camera (not shown).

As illustrated in FIG. 18, the light 988 reflected from the eye 210 is diverging. This light is incident on the reflector 996, which is curved or otherwise has positive optical power, and may be collimated thereby. The coupling optical element 944, which is configured to turn collimated into the waveguide 940, will therefore direct this collimated light from the curved reflective optical element 996 toward the imaging device 920 (not shown). Accordingly, the light reflected from the eye 210 that is collimated by the curved reflective optical element 996 is coupled into the waveguide 940 and guided therein toward the outcoupling optical element 952. The outcoupling optical element 952 may be configured to direct the light out of the eyepiece 950 to the camera (not shown).

A wide variety of variations are possible in the configurations of the imaging system. Different types of reflectors 996 and coupling elements 944 may be employed. The reflectors 996 and coupling elements 944 may, for example, be configured to operate on linear polarized light or circular or elliptical polarized light. As discussed, the reflectors 996 have optical power. The reflectors 996 and coupling elements 944 may comprise cholesteric liquid crystal grating reflectors and/or lenses with our without optical power. Polarization modifying elements 978 such as retarders may be included between the coupling elements 944 and the reflector and/or between the coupling elements 944 and the eye. In some embodiments, a polarizer such as a circular polarizer or a linear polarizer may be disposed between the eye and the coupling elements 944. If for example unpolarized light is reflected from the eye, a polarizer (e.g., circular polarizer or linear polarizer) may be disposed between the eye and the coupling elements 944. In some such cases the coupling elements 944 are polarization selective.

In configurations such as shown in FIGS. 17 and 18, where light reflected from the eye passes through the waveguide 940 to the curved reflective optical element 996 to be collimated and redirected back to the waveguide, background noise is introduced. This background noise results from light passing initially from the eye through the coupling optical element 944. As discussed above, the coupling optical element 944 may be configured to turn collimated light into the waveguide 940 to be guided therein to the camera 920 where an image is formed. The coupling optical element 944 will, however, turn some non-collimated light incident thereon. Accordingly, on the initial pass through the coupling optical element 944 and the waveguide 940 to the curved reflective optical element 996, some of the non-collimated (diverging) light reflected from the eye will be coupled by the coupling optical element 944 into the waveguide and contribute background noise to image of the eye formed at by the camera 920. This noise will be superimposed on the image formed by the collimated light retro-reflected by the curved reflective optical element 996 that is coupled by the coupling optical element 944 into the waveguide to be guided therein to the camera 920.

In certain designs, this noise can be subtracted out from the image. The process for subtracting out the noise from the signal may involve (a) measuring the amount of light coupled by the coupling optical element 944 on the initial pass through the coupling optical element 944 to the curved reflective optical element 996 that is turned and reaches the camera 920 (referred to as N) and (b) measuring the total signal at the camera 920 when light passes through coupling optical element 944 and the waveguide 940 to the curved reflective optical element 996, is collimated, and reflected back to the coupling optical element and turned to the camera. This total signal will also include some noise, N, as the uncollimated light reflected from the eye will have passed through the coupling optical element 944 to get to the curved reflective optical element 996 and thus some of uncollimated light will be turned by the coupling optical element 944 to the camera 920. If the noise, N, can be measured separately from the total signal, T, that includes the noise superimposed over the image of the eye, the noise, N, can be subtracted out from the total signal, T, as represented by the formula below:

$$I = T - N$$

where I represents the image with the noise component, N, removed.

Figure 19:
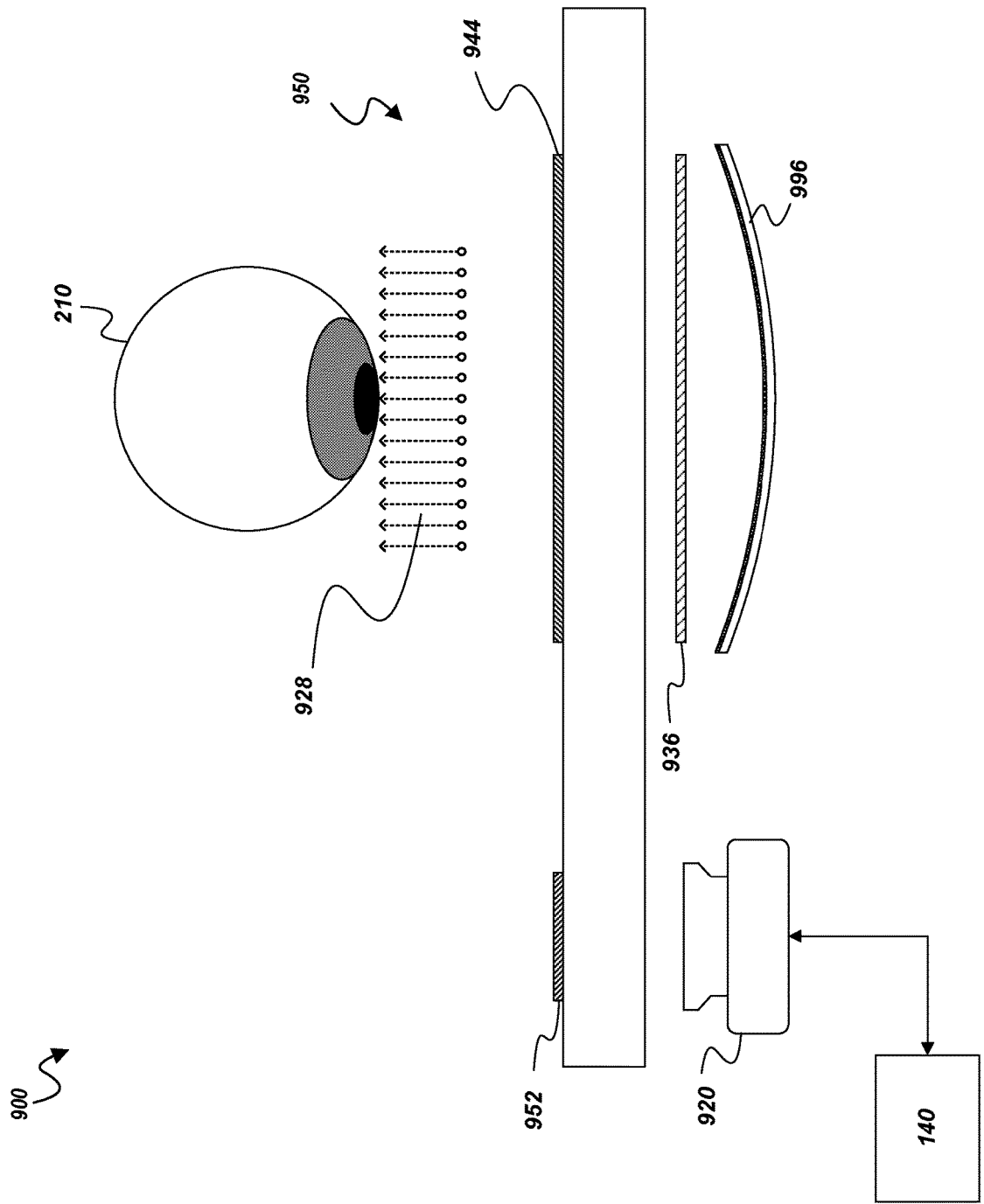
FIG. 19 schematically illustrates an imaging system that includes a shutter to assist in a procedure for subtracting out noise.

The two measurements (a) and (b) above can be obtained in various ways. For example, as shown in FIG. 19, a shutter 936 can be disposed between the curved reflective optical element 996 and the waveguide 940 and coupling optical element 944. This shutter 936 may be configured to block light when the shutter is in a first state and to transmit light when the shutter is in a second state. This shutter 936 may comprise, for example, a liquid crystal shutter.

Accordingly, the noise component N can be measured when the shutter 936 is in the first state where light reflected from the eye 210 is incident on the coupling optical element 944, passes therethrough toward the curved reflective optical element 996, however, is prevented from reaching the curved reflective optical element by the closed shutter. As discussed above, some of the light reflected from the eye 210, although mainly uncollimated, does couple into the coupling optical element 944 and is turned into the waveguide and guided therein to the camera 920. As referenced above, this light does not contribute to formation of an image, but will be background noise. The camera 920 may record this noise, N, when the shutter 936 is closed.

The total signal, T, including both the noise, N, and the image, can be measured when the shutter 936 is in the second state where the shutter is open. Light reflected from the eye 210 is again incident on the coupling optical element 944. Some of this light reflected from the eye 210, although mainly uncollimated, couples into the coupling optical element 944 and is turned into the waveguide and guided therein to the camera 920. Most of this light reflected from the eye 210, however, passes through the coupling optical element 944, through the open shutter 936 and to the curved reflective optical element 996. The curved reflective optical element 996 collimates and reflects at least a portion of this light back to the coupling optical element 944, which turns this collimated light into the waveguide 920 to be guided to the camera 920 to form an image of the eye 210. The camera 920 can capture this image of the eye 210.

Processing electronics (such as processing electronics 140) in communication with the camera 920 can receive the noise component, N, measured when the shutter 936 was in the first closed state as well as the total signal, T, measured when the shutter was in the second open state and can subtract the two (T-N). In this manner, the noise, N, contributed by the non-collimated light reflected from the eye 210 that is coupled into the coupling optical element 944 on the initial pass therethrough, can be subtracted from the total image signal, T. The processing electronics may be in communication with the camera 920 via a wired electronic signal. Additionally or alternatively, the processing electronics may communicate with the camera 920 using one or more remote receivers. The processing electronics may reside remotely (e.g., cloud computing devices, remote server, etc.).

Other ways may be employed to perform the measurement of (a) and (b) to obtain N and T and subtract N from T. For example, if the curved reflective optical element 996 is wavelength selective such as shown in FIG. 18, the eye can be illuminated with light of different wavelength at different times. For example, to perform the measurement (a) and quantify the noise, N, the eye can be illuminated with a wavelength that is not reflected by the curved reflective optical element 996. However, to perform the measurement (b) and quantify the total signal, T, the eye can be illuminated with a wavelength that is reflected by the curved reflective optical element 996. The noise, N, can then be subtracted from the total T, as discussed above (e.g., T−N).

Figure 20A:
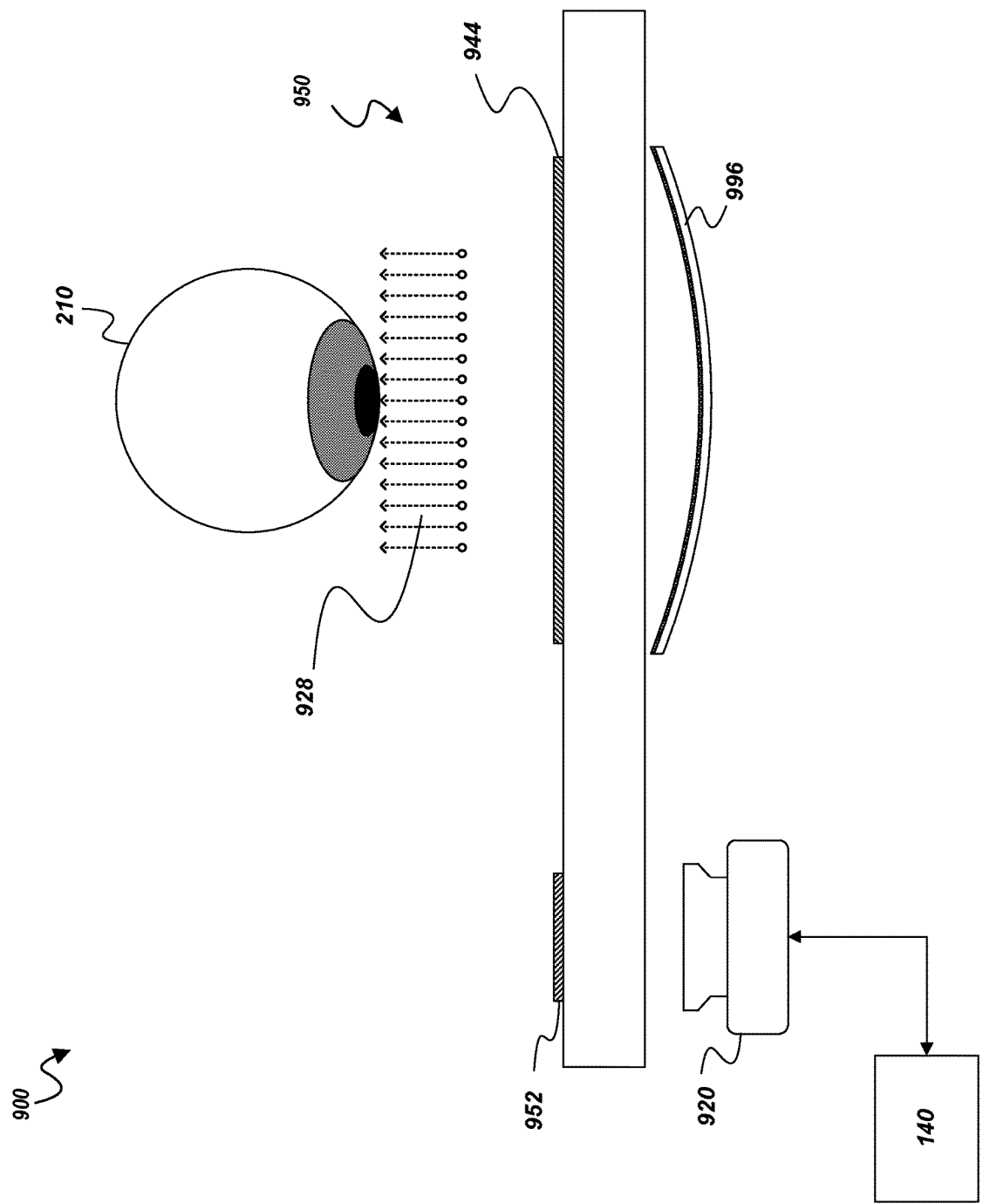
FIGS. 20A-20E schematically illustrate an alternative procedure for subtracting out noise using wavelength modulation in conjunction with a curved wavelength selective reflector.
Figure 20B:
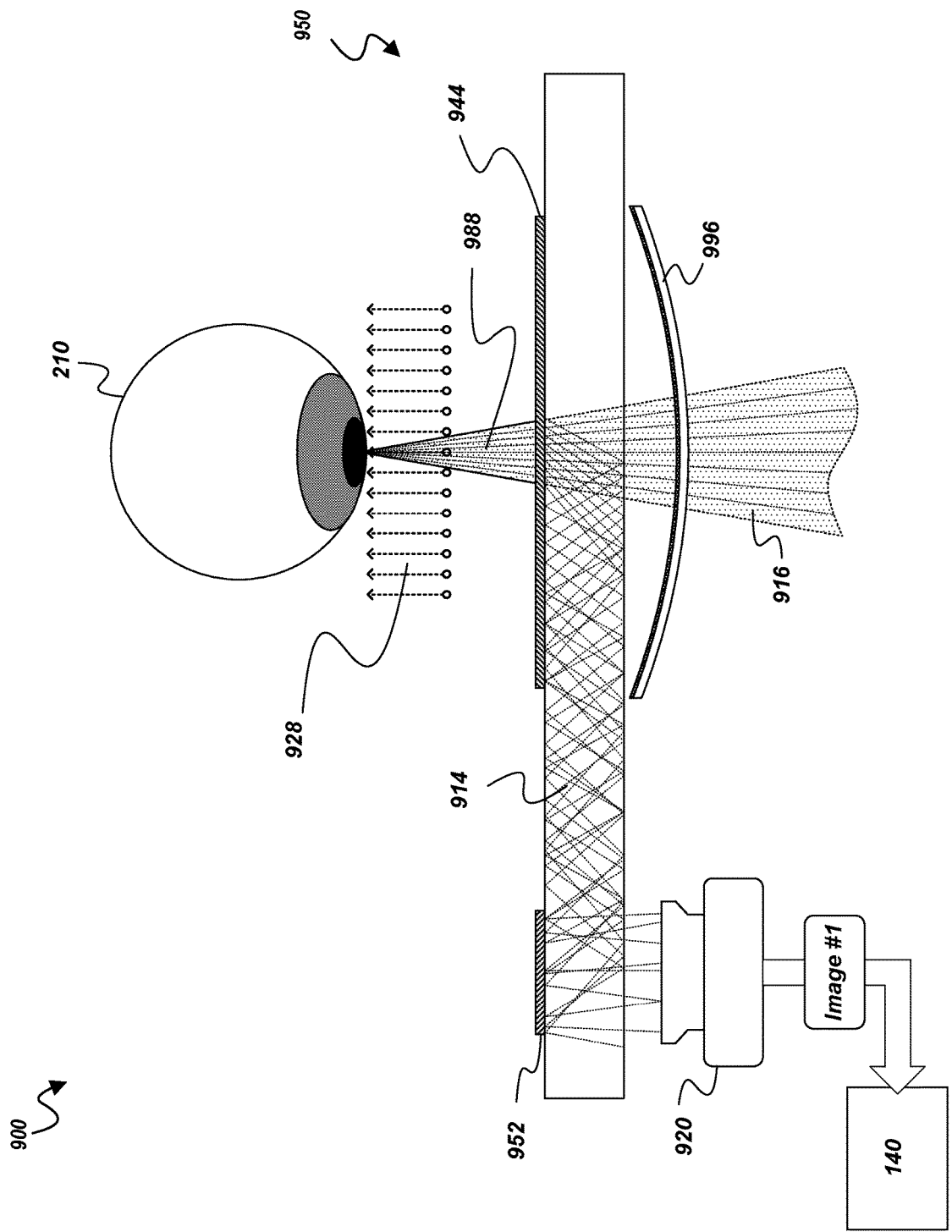
Figure 20C:
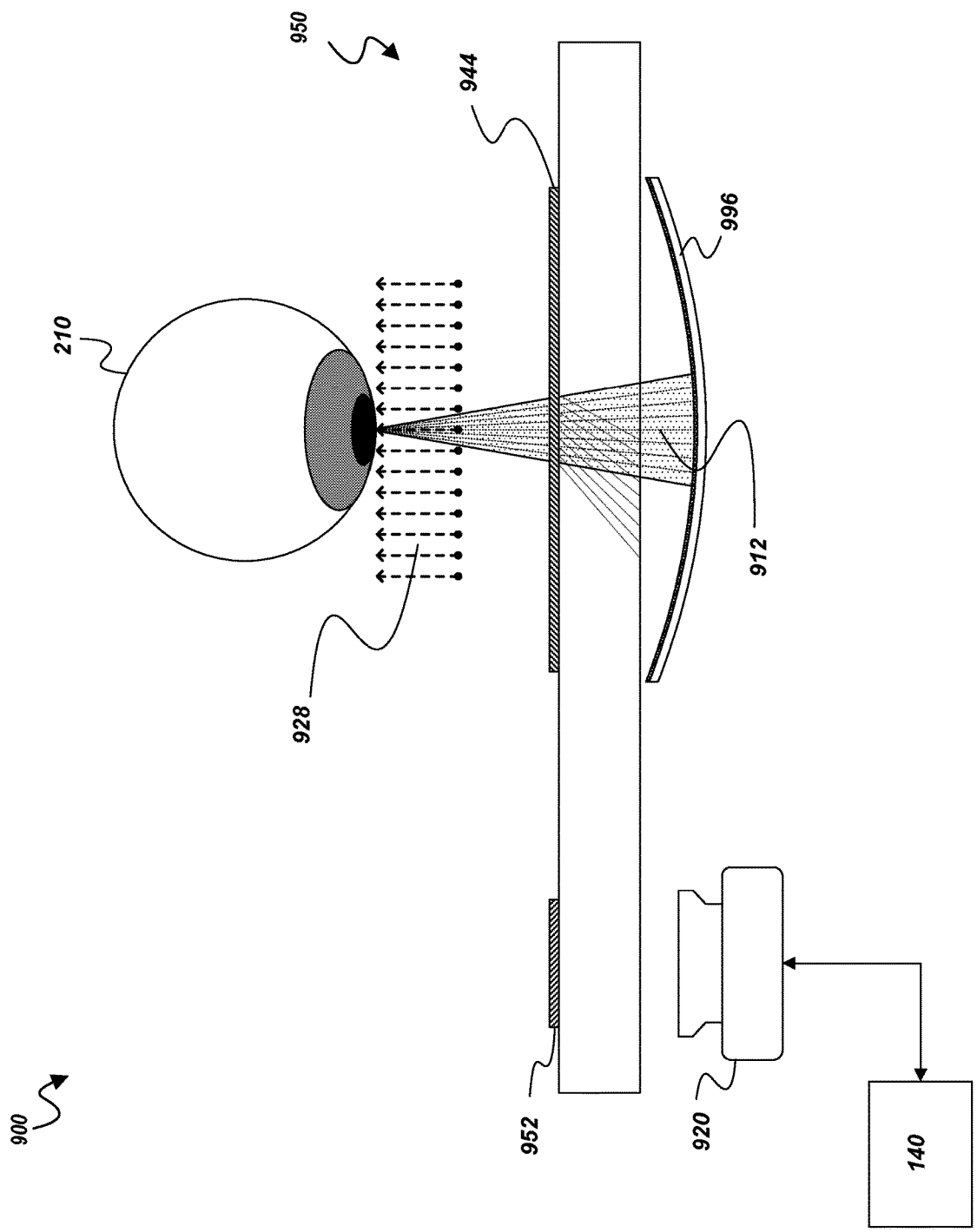
Figure 20D:
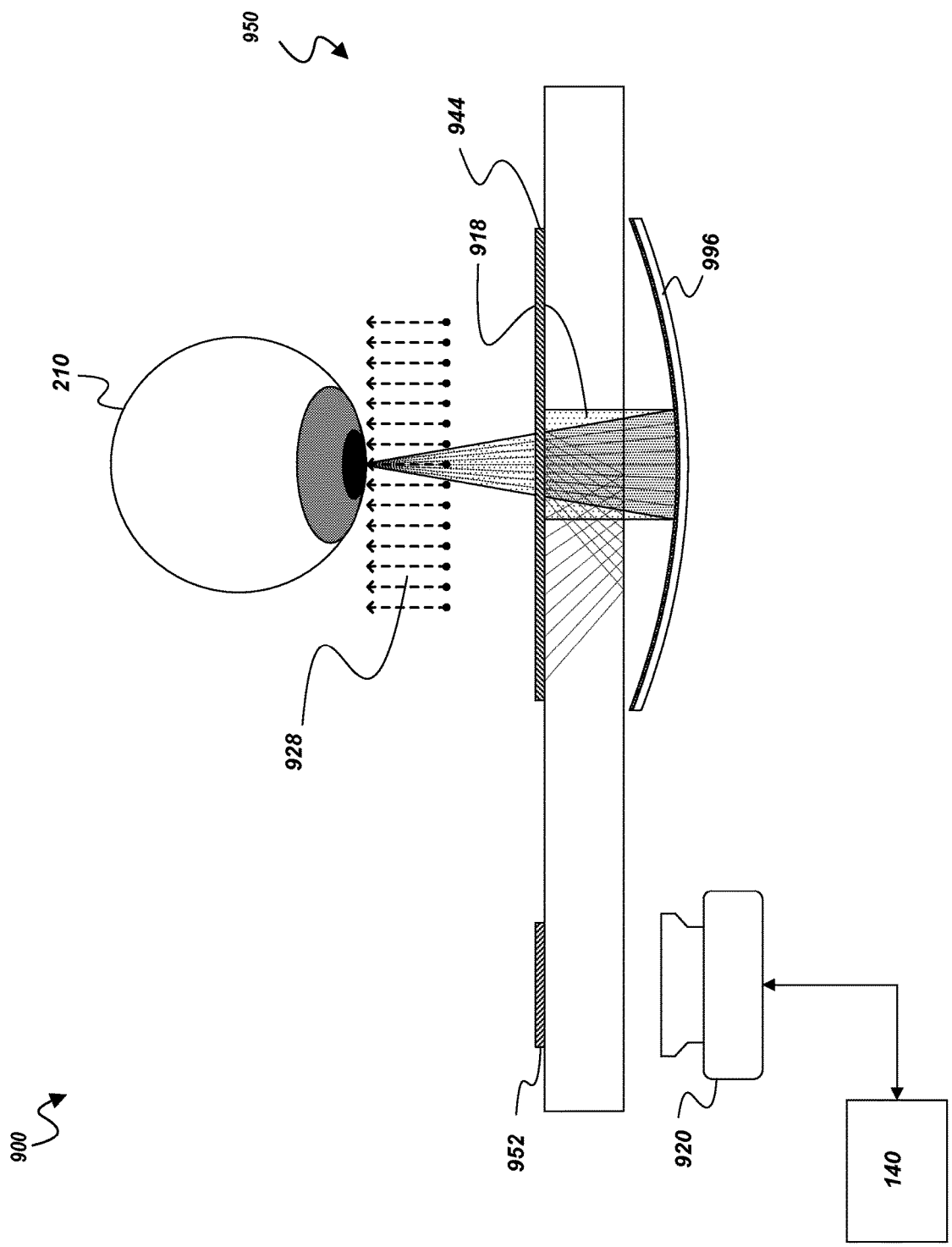
Figure 20E:
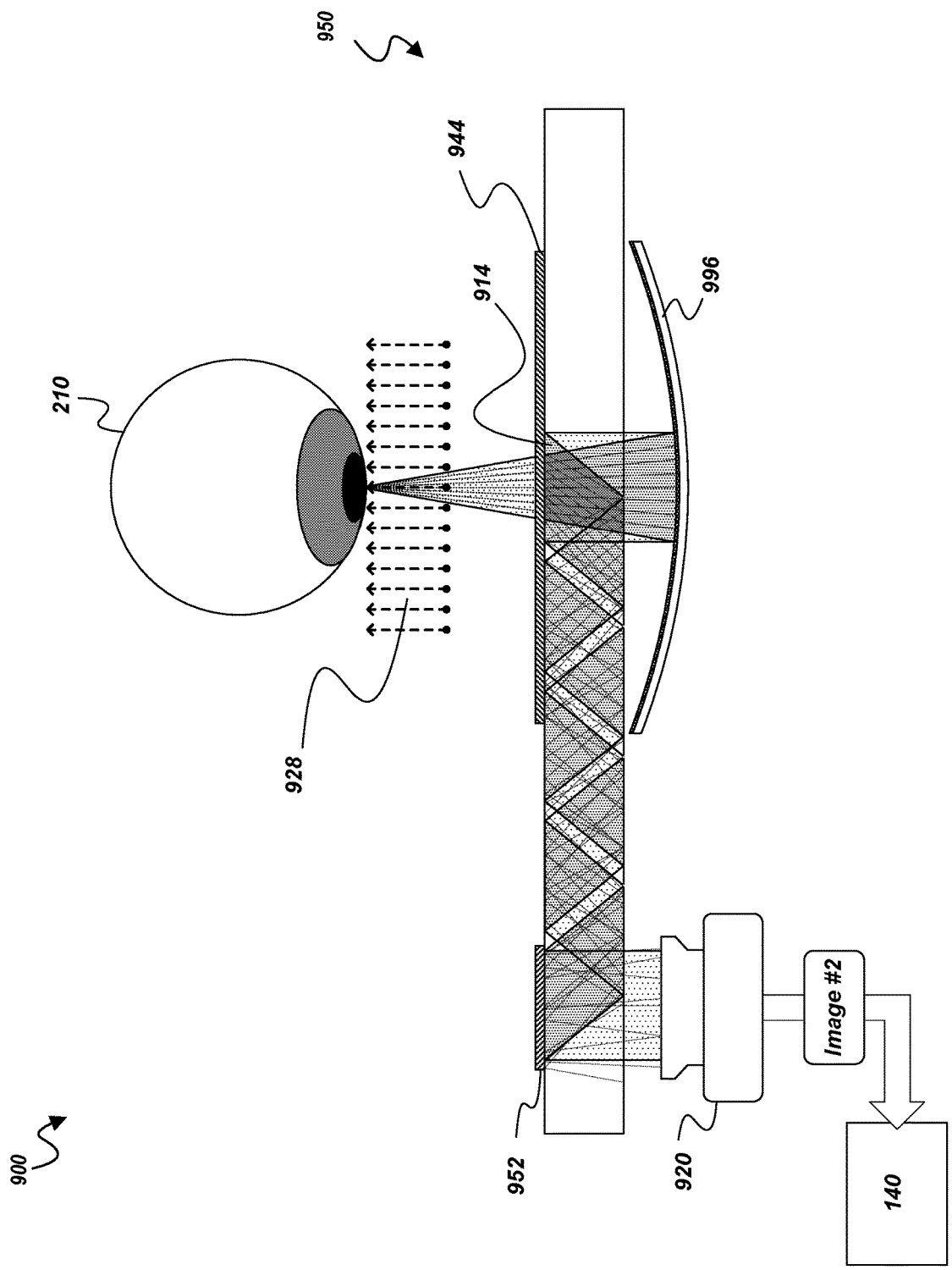

FIGS. 20-20E illustrate an example imaging system 900 configured to use wavelength modulation to measure and subtract out the noise component, N, as discussed above. The imaging system 900 in FIGS. 20A-20E includes a curved transmissive optical element 996 that is wavelength selective (such as described with reference to FIGS. 17 and 18 above). For example, the curved transmissive optical element 996 has a wavelength dependent reflective coating 998 on a curved surface thereof. The imaging system 900 may also include one or more light sources or illumination sources (not shown) configured to illuminate the eye 210. The one or more light sources may be configured to emit infrared light. The one or more light sources, however, can be configured to emit different color or wavelength light at different times. Such wavelength modulation can enable the measurement of N separately so as to be subtracted out from the total signal, T.

In various implementations, for example, the one or more illumination sources 960, 934 may be configured in a first state to emit one or more wavelengths that are reflected by the curved reflective optical element, $\lambda_{Reflect}$, and in a second state one or more wavelengths that are not reflected $\lambda_{Not\ Reflect}$. In the second state, no more than negligible amounts of wavelengths that are reflected by the curved reflective optical element, $\lambda_{Reflect}$, are emitted. Similarly, in the first state, no more than negligible amounts of wavelengths that are not reflected $\lambda_{Not\ Reflect}$ are emitted.

In some examples, the reflected wavelength(s), $\lambda_{Reflect}$, may be between about 800 nm and 950 nm. The reflected wavelength(s), $\lambda_{Reflect}$, may be between about 835 nm and 915 nm. The reflected wavelength(s), $\lambda_{Reflect}$, may be between about 840 nm and 870 nm. In some designs, the reflected wavelength, $\lambda_{Reflect}$, is about 850 nm. The light emission 928 from the one or more light sources 960 may illuminate the eye.

As shown in FIG. 20B, light 988 having the wavelength(s) that are not reflected by the curved reflective optical element 944, $\lambda_{Not\ Reflect}$, (and no more than negligible amounts of light that is reflected by the curved reflective optical element 944, $\lambda_{Reflect}$) is reflected off part of the eye 210 (e.g., the cornea). Because this light comprises wavelength(s) that are not reflected by the curved reflective optical element 944, $\lambda_{Not\ Reflect}$, rays of light 916 are shown propagating through the curved reflective optical element 996 to the environment forward the user.

Although the light 988 incident on the coupling optical element 944 is not collimated, the coupling optical element nevertheless couples at least some light 914 into the waveguide 940 to be guided to the camera 920. According, the camera 920 may capture an image (Image #1) corresponding to the noise component, N, that results from uncollimated light that is turned by the coupling optical element 944 on the initial pass to the curved reflective optical element 996. This image (Image #1) is background noise and does is not a recognizable image of the eye. Processing electronics 140 is shown as receiving this first image (Image #1).

In FIGS. 20C-20E, the illumination sources (not shown) emit one or more wavelengths that are reflected by the curved reflective optical element, $\lambda_{Reflect}$, and no more than negligible amounts of wavelengths that are not reflected $\lambda_{Not\ Reflect}$. This wavelength, $\lambda_{Reflect}$, may be, for example, 850 nm.

As shown in FIG. 20C, some of the light 988 reflected from the eye 210 that is incident on coupling optical element 944 in the first pass through the coupling optical element 944 is coupled by the coupling optical element 944 into the waveguide 940 (as in FIG. 20B) and directed toward the camera 920. Additionally, the curved transmissive optical element 996, which selectively reflect light of wavelength $\lambda_{Reflect}$, reflects and collimates the non-incoupled light 918 reflected from the eye 210 that is incident on the curved transmissive optical element. As illustrated in FIG. 20E, the coupling optical element 944 turns and couples this collimated reflected light into the waveguide 940 toward the camera 920. FIG. 20E shows both components reaching the camera 920, light 988 reflected from the eye 210 that is incident on coupling optical element 944 in the first pass through the coupling optical element 944 is coupled by the coupling optical element into the waveguide 940 and light reflected and collimate by the curved transmissive optical element 996 that is coupled by the coupling optical element into the waveguide. The camera 920 may capture an image (Image #2) corresponding to this total image component, T. Processing electronics 140 is shown as receiving this second image (Image #2).

As discussed above, the processing electronics may subtract the noise from the image, T−N. In this example, Image #1 can be subtracted from Image #2. Accordingly, the processing electronics 140 may be configured to modify the second image based on the first image. Other approaches, however, are possible. For example, the processing electronics 140 may be configured to create a new image that represents a version of the second image with reduced optical noise. Implementations for subtracting noise from the image may be used in implementations described above. For example, implementations shown in FIGS. 10, 11A-11E, and/or FIGS. 12A-12E can include a shutter 936 and/or a curved transmissive optical element 996 having a wavelength dependent reflective coating 998 configured to selectively reflect non-incoupled light 912 and to direct the light to an imaging device 920.

As discussed above, the Image #1 was obtained for the case where the light was illuminated with one or more wavelengths that are not reflected by the curved reflective optical element, $\lambda_{Not\ Reflect}$, and no more than negligible amounts of wavelengths that are reflected $\lambda_{Reflect}$. Image #2 was obtained for the case where the light was illuminated with one or more wavelengths that are reflected by the curved reflective optical element, $\lambda_{Reflect}$, and no more than negligible amounts of wavelengths that are not reflected $\lambda_{Not\ Reflect}$. Accordingly, the one or more illumination sources 960, 934 may be configured to modulate in wavelength. For example, in certain designs the one or more illumination sources 960, 934 may comprise a first illumination source configured to output one or more wavelengths not reflected by the curved reflective optical element, $\lambda_{Not\ Reflect}$, and no more than negligible amounts of wavelengths that are reflected $\lambda_{Reflect}$. The one or more illumination sources may further comprise a second illumination source configured to output one or more wavelengths that are reflected by the curved reflective optical element, $\lambda_{Reflect}$, and no more than negligible amounts of wavelengths that are not reflected $\lambda_{Not\ Reflect}$. The intensity of the first and second illumination sources can be alternately increased and decreased, turned on and off, attenuated and not attenuated, passed and blocked to provide modulation in the wavelength of light illuminating the eye. For example, during a first time interval the first illumination source can be blocked while the second illumination source is not blocked. During a subsequent second time interval, the second illumination source can be blocked while the first illumination source is not blocked. This process can be repeated to provide modulation of the wavelength of light illuminating the eye. In other designs, the wavelength of a light source may be tuned and detuned to shifted the wavelength back and forth between $\lambda_{Reflect}$ and $\lambda_{Not\ Reflect}$. Other arrangements are possible.

As described above, imaging systems 900 may be included in head mounted displays such as augmented reality displays that additionally provide the ability to image the eye by collecting light with the eyepiece 950. Such imaging systems 900 may be used for eye tracking. Multiple images of the retina or an anterior portion of the eye may be obtained. Movement and/or repositioning of the eye can be ascertained from these images to track the eye position and/or orientation. These imaging system may also be use as for biometric imaging and/or for identifying the user. For example, an image of the user's eye such as of the retina or iris may be obtained and recorded. A subsequent image of the eye (e.g., retina, or iris) of the wearer may be obtained at a later time. The two images may be compared to determine whether the wearer in that later instance was the wearer in the first instance. Other uses for the imaging systems however are possible.

Although illumination systems may be described above as waveguide based and comprising one or more waveguides, other types of light turning optical elements may be employed instead of a waveguide. Such light turning optical elements may include turning features to eject the light out of the light turning optical element, for example, onto the spatial light modulator. Accordingly, in any of the examples described herein as well as any of the examples below, any reference to waveguide may be replaced with light turning optical element instead of a waveguide. Such a light turning optical element may comprise, for example, a polarizing beam splitter such as a polarizing beam splitting prism.

As discussed above the systems described herein can allow for collection of biometric data and/or biometric identification. For example, the eye or portions thereof (e.g., the retina) can be imaged to provide such biometric data and/or biometric identification. Images of the eye such as of the retina may be obtained at various times when the head mounted display system is being worn by a user, presumably the same user. A collection of such images can be recorded, for example, in a database. These images may be analyzed to collect biometric data. Such biometric data may be useful for monitoring the user's health or medical status. Different medical parameters can be monitored by imaging the patient, for example, the patient eye (e.g., retina). The medical parameters can be recorded and compared with subsequent measurements obtained when the user is wearing the head mounted display system.

In addition, if a person begins wearing the head mounted display system and an image of the user's eye is captured that does not match the images stored in the database a conclusion may be drawn that the person currently wearing the head mounted display system is different from the previous user. This can be useful in determining whether the intended user is wearing the headset or if it is being worn by a new user. Such a feature may allow for certain medical, security, and/or convenience-in-use applications or functionality. For example, the head mounted display may be configured to identify a wearer based on characteristics of the wearer's eye. For example, the system can be configured to determine an individual based on features of a wearer's retina (e.g. blood vessels), cornea, or other eye features. In some implementations for example, a series of markers may be determined for a particular wearer. Based on the series of markers, the system may be able to determine that the previous user is wearing the headset or, alternatively, that another user is wearing the headset. The markers may include a shape or center of a user's cornea, a configuration of blood vessels in the user's retina, an intensity and/or position of a reflection of light from the cornea, a shape of an aspect of the eye, and/or any other biometric marker. In certain implementations a confusion matrix can be determined. As discussed above for example in the discussion of developing a retinal map using a virtual/fixation target at a variety of location (see, e.g., FIG. 13B), the system may have a user look in a set of pre-determined directions or eye poses and develop a matrix of characteristics of the eye or part of the eye (e.g., cornea, retina, etc.) associated with each direction or eye pose. Using such a matrix, the system can determine an identity of the individual. Other methods are possible.

Figure 21:
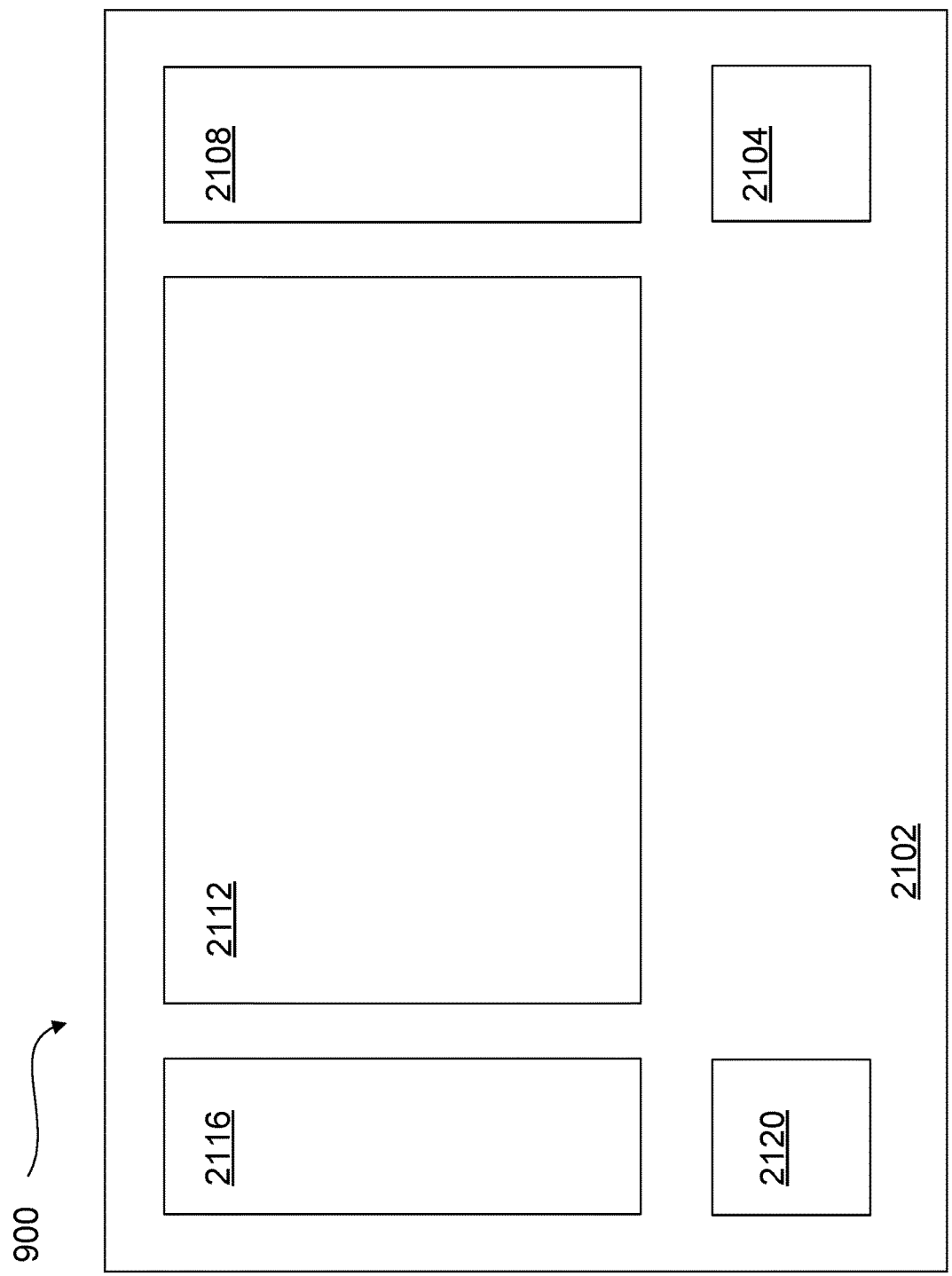
FIG. 21 shows an example eyepiece that can be used to simultaneously project light into a user's eye to provide image content thereto while receiving image data of the user's eye or of the environment in front of the user.

Similarly, as discussed above, a wide variety of configurations of the system are possible. For example, FIG. 21 shows an example eyepiece 900 that can be used to simultaneously project light into a user's eye while imaging the user's eye. The eyepiece 900 shown includes an incoupling optical element 2104, a light distributing element 2108, and a light consolidating element 2116, and an outcoupling optical element 2120 on opposite sides of a coupling optical element 2112. Each of these optical elements may be disposed within or on a waveguide 2102. The waveguide 2102 may correspond, for example, to one of the waveguides 670, 680, 690 described herein (see, e.g., FIG. 9A-9C). The incoupling optical element 2104 may correspond to one of incoupling optical elements 700, 710, 720 described herein and/or to the incoupling optical element 942 (see, e.g., FIG. 10) and may be configured to inject image content from a projector into the waveguide and/or illumination from a light source 960. The light distributing element 2108 may correspond to one of the light distributing elements 730, 740, 750 described herein (see, e.g., FIGS. 9A-9C and may be used to spread light in a given direction and redirect the light from the incoupling optical element 2104 to the coupling optical element 2112. The coupling optical element 2112 may correspond to the coupling optical element 944 described herein (see, e.g., FIG. 10). In some designs, the coupling optical element 2112 includes functionality described herein with respect to the outcoupling optical elements 800, 810, 820 (see FIGS. 9A-9C). The light consolidating element 2116 may be configured to reduce the lateral spatial extent of light received from the coupling optical element 2112 and redirect said light toward the outcoupling optical element 2120. The outcoupling optical element 2120 may correspond to the outcoupling optical element 952 described herein (see, e.g., FIG. 10).

The incoupling optical element 2104 may be disposed within or on the waveguide 2102 so as to receive light, such as from a projector (e.g., the image projector 930) and/or an illuminator (e.g., the light source 960). The light may be passed via the waveguide 2102 to the associated light distributing optical element 2108. Any of the incoupling optical element 2104, light distributed optical element 2108 or coupling optical element 2112 may be disposed on a major surface of (e.g., on a top or bottom surface) of the waveguide or within the waveguide. Similarly, any one or combination of the light consolidating element 2116, and/or the outcoupling optical element 2120 may be disposed on the major surface (e.g., a top or both major surface) of the waveguide 2102 or within the waveguide.

The coupling optical element 2112 may receive the light (e.g., via TIR) from the light distributing element 2108 and expand the light to enter the user's eye. Thus, the coupling optical element 2112 may be disposed in front of a user's eye and project image content therein. Additionally or alternatively, the coupling optical element 2112 may be configured to provide illuminating light onto and/or into the user's eye.

Light that is reflected from the eye (e.g., the illumination light from the illumination source) may be reflected and captured by the coupling optical element 2112. Thus, in some embodiments, the coupling optical element 2112 can serve to both outcouple light received from the light distributing element 2108 and incouple light received from the eye into the waveguide 2102.

In some embodiments, the coupling optical element 2112 may include one or more diffractive optical elements (DOEs) such that the coupling optical element 2112 has dual functionality. A first DOE (e.g., a grating, holographic region) may be configured to outcouple light as well and a second DOE may be configured to incouple reflected light from the eye into the waveguide 2102. In some embodiments, both the first and second DOEs are superimposed (e.g., occupy the same or approximately the same volume) within the waveguide 2102.

Alternatively, in some embodiments, the coupling optical element 2112 includes at least two DOEs that are stacked on over or in front of the other. For example, with reference to FIG. 21, the first DOE of the coupling optical element 2112 may be disposed over, whereas the second diffractive element may be disposed under the first DOE. The order of each DOE may be reversed in other implementations.

Cholesteric Liquid Crystal Mirror

Some liquid crystals are in a phase referred to as a chiral phase or a cholesteric phase. In a cholesteric phase, the liquid crystals can exhibit a twisting of the molecules along an axis perpendicular to the director, where the molecular axis is parallel to the director. As described herein, a cholesteric liquid crystal (CLC) layer comprises a plurality of liquid crystal molecules in a cholesteric phase that extend in a direction, e.g., a direction perpendicular to the director such as a layer depth direction, and that are successively rotated or twisted in a rotation direction, e.g., clockwise or counterclockwise. The directors of the liquid crystal molecules in a chiral structure can be characterized as a helix having a helical pitch (p), which corresponds to a length in the layer depth direction corresponding to a net rotation angle of the liquid crystal molecules of the chiral structures by one full rotation in the first rotation direction. In other words, the helical pitch refers to the distance over which the liquid crystal molecules undergo a full 360° twist. The liquid crystals displaying chirality can also be described as having a twist angle, or a rotation angle ($\phi$), which can refer to, for example, the relative azimuthal angular rotation between successive liquid crystal molecules in the layer normal direction, and as having a net twist angle, or a net rotation angle, which can refer to, for example, the relative azimuthal angular rotation between an uppermost liquid crystal molecule and a lowermost liquid crystal molecule across a specified length, e.g., the length of a chiral structure or the thickness of the liquid crystal layer. As described herein, a chiral structure refers to a plurality of liquid crystal molecules in a cholesteric phase that extend in a direction, e.g., a direction perpendicular to the director such as a layer depth direction, and are successively rotated or twisted in a rotation direction, e.g., clockwise or counterclockwise. In one aspect, the directors of the liquid crystal molecules in a chiral structure can be characterized as a helix having a helical pitch.

Figure 22:
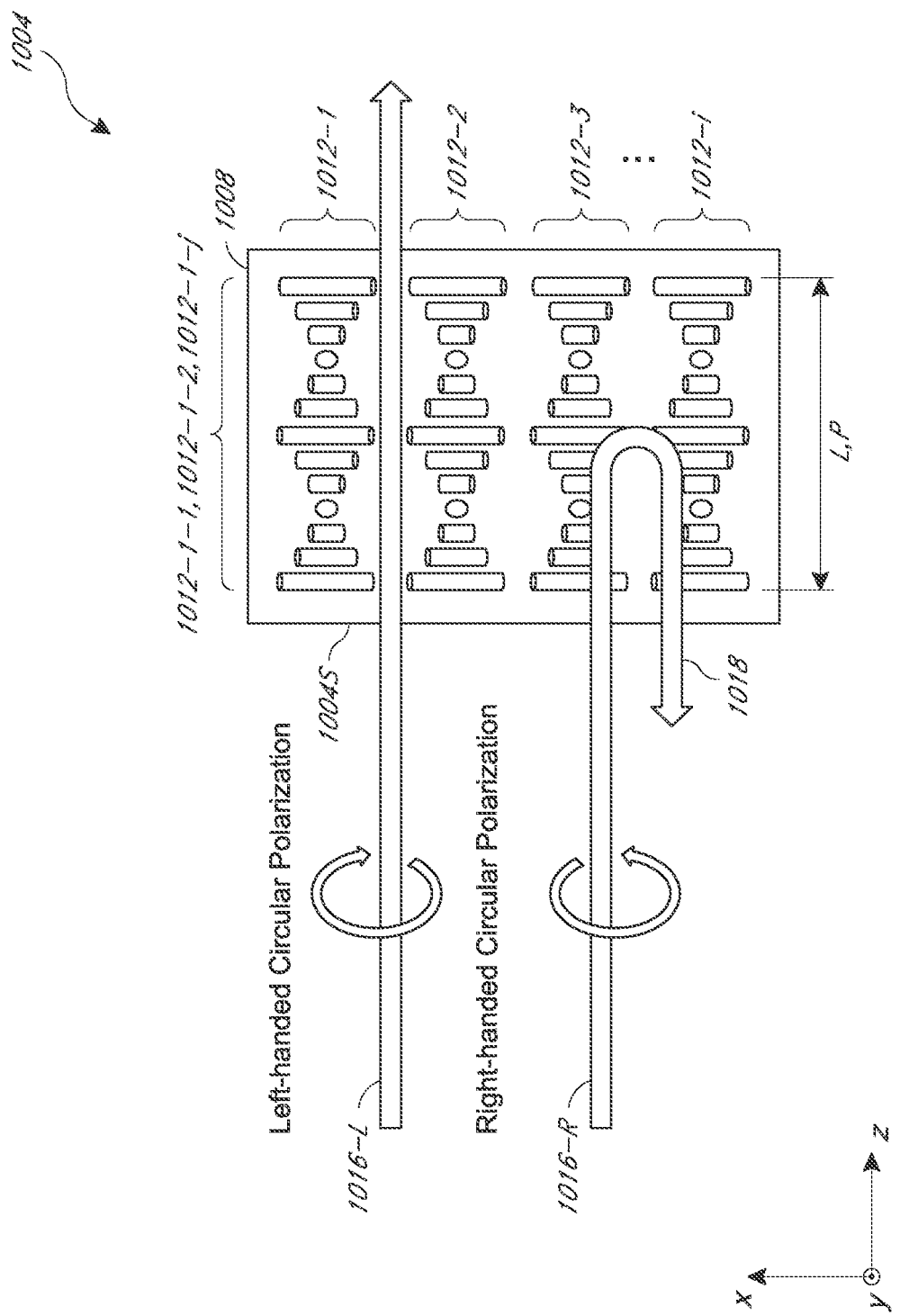
FIG. 22 illustrates a cross-sectional side view of an example of a cholesteric liquid crystal diffraction grating (CLCG) having a plurality of uniform chiral structures.

FIG. 22 illustrates a cross-sectional side view of a cholesteric liquid crystal (CLC) layer 1004 comprising a plurality of uniform chiral structures, according to embodiments. In the CLC layer 1004, the chiral structures that are adjacent in a lateral direction, e.g., x-direction, have similarly arranged liquid crystal molecules. In the illustrated embodiment, the chiral structures 1012-1, 1012-2, . . . 1012-$i$ are similarly configured such that liquid crystal molecules of the different chiral structures that are at about the same depth, e.g., the liquid crystal molecules closest to the light-incident surface 1004S, have the same rotation angle, as well as successive rotation angles of successive liquid crystal molecules at about the same depth, as well as the net rotation angle of the liquid crystal molecules of each chiral structure.

The CLC 1004 comprises a CLC layer 1008 comprising liquid crystal molecules arranged as a plurality of chiral structures 1012-1, 1012-2, . . . 1012-i, wherein each chiral structure comprises a plurality of liquid crystal molecules, where i is any suitable integer greater than 2. In operation, when incident light having a combination of light beams having left-handed circular polarization and light beams having right-handed circular polarization are incident on the surface 1004S of the CLC layer 1008, by Bragg-reflection, light with one of the circular polarization handedness is reflected by the CLC layer 1004, while light with the opposite polarization handedness is transmitted through the CLC layer 1008 without substantial interference. As described herein and throughout the disclosure, the handedness is defined as viewed in the direction of propagation. According to embodiments, when the direction of polarization, or handedness of the polarization, of the light beams 1016-L, 1016-R is matched such that it and has the same direction of rotation as the liquid crystal molecules of the chiral structures 1012-1, 1012-2, . . . 1012-i, the incident light is reflected. As illustrated, incident on the surface 1004S are light beams 1016-L having left-handed circular polarization and light beams 1016-R having a right-handed circular polarization. In the illustrated embodiment, the liquid crystal molecules of the chiral structures 1012-1, 1012-2, . . . 1012-i are rotated in a clockwise direction successively in the direction in which incident light beams 1016-L, 1016-R travel, i.e., positive x-direction, which is the same rotation direction as the light teams 1016-R having right-handed circular polarization. As a result, the light beams 1016-R having right-handed circular polarization are substantially reflected, whereas the light beams 1016-L having left-handed circular polarization are substantially transmitted through the CLC layer 1004.

As described supra, by matching the handedness of polarization of incident elliptically or circularly polarized light with the direction of rotation as the liquid crystal molecules of the chiral structures of a CLC layer, the CLC layer can be configured as a Bragg reflector. Furthermore, one or more CLC layers having different helical pitches can be configured as a wave-length selective Bragg reflector with high bandwidth. Based on the concepts described herein with respect to various embodiments, the CLC layers can be configured as an off-axis or on-axis mirror configured to selectively reflect a first range of wavelengths, for example, infrared wavelengths (e.g., the near infrared), while transmitting another range of wavelengths, e.g., visible wavelengths.

Figure 23:
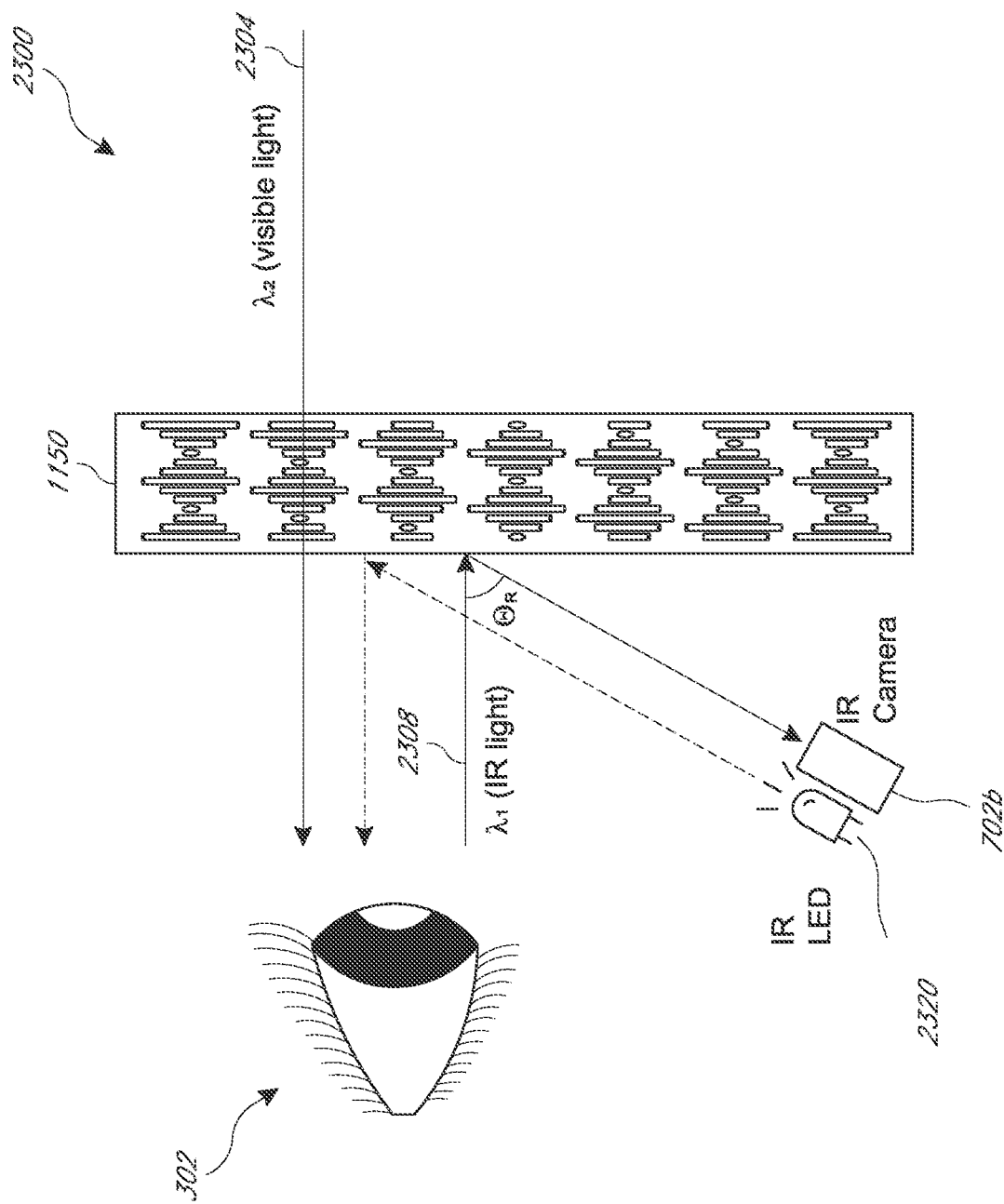
FIG. 23 illustrates an example of an imaging system comprising a forward-facing camera configured to images a wearer's eye using a cholesteric liquid crystal (CLC) off-axis mirror.

FIG. 23 illustrates an example of an eye-tracking system 2300 employing a cholesteric liquid crystal reflector (CLCR), e.g., a wavelength-selective CLCR 1150 configured to image an eye 302 of a viewer, according to various embodiments. Unlike the CLC layer 1004 described above with respect to FIG. 22, the chiral structures in the wavelength-selective CLCR 1150 that are adjacent in a lateral direction, e.g., x-direction, have differently arranged liquid crystal molecules. That is, the chiral structures are configured such that liquid crystal molecules of the different chiral structures that are at about the same depth, e.g., the liquid crystal molecules closest to the light-incident surface 1004S, have different rotation angle. As a result, light incident on the CLCR 1150 is reflected at an angle ($\theta_R$) relative to the layer depth direction, as described further below in the context of the eye-tracking system 2300.

Eye tracking can be a useful feature in interactive vision or control systems including wearable display systems described elsewhere in the specification, for virtual/augmented/mixed reality display applications, among other applications. To achieve effective eye tracking, it may desirable to obtain images of the eye 302 at low perspective angles, for which it may in turn be desirable to dispose an eye-tracking camera 702b near a central position of viewer's eyes. However, such position of the camera 702b may interfere with user's view. Alternatively, the eye-tracking camera 702b may be disposed to a lower position or a side. However, such position of the camera may increase the difficulty of obtaining robust and accurate eye tracking since the eye images are captured at a steeper angle. By configuring the CLCR 1150 to selectively reflect infrared (IR) light 2308 (e.g., having a wavelength of 850 nm) from the eye 302 while transmitting visible light 2304 from the world, the camera 702b can be placed away from the user's view while capturing eye images at normal or low perspective angles. Such configuration does not interfere with user's view since visible light is not reflected. The same CLCR 1150 can also be configured as an IR illumination source 2320 by reflecting IR light from an IR source, e.g., IR LED, into the eye 302, as illustrated. A low perspective angle of IR illuminator can results in less occlusions, e.g., from eye lashes, which configuration allows more robust detection of specular reflections, which can be useful feature in modern eye-tracking systems.

Still referring to FIG. 23, according to various embodiments, the CLCR 1150 comprises one or more cholesteric liquid crystal (CLC) layers each comprising a plurality of chiral structures, wherein each chiral structure comprises a plurality of liquid crystal molecules that extend in a layer depth direction (e.g., z-direction) and are successively rotated in a first rotation direction, as described supra. The arrangements of the liquid crystal molecules of the chiral structures vary periodically in a lateral direction perpendicular to the layer depth direction such that the one or more CLC layers are configured to substantially Bragg-reflect a first incident light having a first wavelength ($\lambda_1$) while substantially transmitting a second incident light having a second wavelength ($\lambda_2$). As described above, each of the one or more CLC layers are configured to substantially Bragg-reflect elliptically or circularly polarized first and second incident light having a handedness of polarization that is matched to the first rotation direction, when viewed in the layer depth direction, while being configured to substantially transmit elliptically or circularly polarized first and second incident light having a handedness of polarization that is opposite to the first rotation direction, when viewed in the layer depth direction. According embodiments, the arrangements of the liquid crystal molecules varying periodically in the lateral direction are arranged to have a period in the lateral direction such that a ratio between the first wavelength and the period is between about 0.5 and about 2.0. According to embodiments, the first wavelength is in the near infrared range between about 600 nm and about 1.4 μm, for instance about 850 nm and the second wavelength in is in the visible range having one or more colors as described elsewhere in the specification. According to various embodiments, the liquid crystal molecules of the chiral structures are pre-tilted relative to a direction normal to the layer depth direction. As configured, the one or more CLC layers are configured such that the first incident light is reflected at an angle ($\theta_R$) relative to the layer depth direction (z-direction) exceeding about 50°, about 60°, about 70° or about 80° degrees relative to the layer depth direction.

Thus configured, the wavelength-selective CLCR 1150 comprises one or more cholesteric liquid crystal (CLC) layers each comprising a plurality of liquid crystal molecules that extend in a layer depth direction and are successively rotated in a first rotation direction, wherein arrangements of the liquid crystal molecules of the chiral structures vary periodically in a lateral direction perpendicular to the layer depth direction such that the one or more CLC layers are configured to substantially Bragg-reflect a first incident light having a first wavelength, e.g., an IR wavelength, while substantially transmitting a second incident light having a second wavelength, e.g., a visible wavelength.

Similar liquid crystal layers and structures may be used for the reflector 996 and coating 998 described above in connection with FIGS. 17-20E. The coating 998 may for example comprise a liquid crystal coating and may be wavelength and/or polarization selective in certain implementations. Other types of coatings 998 and reflectors 996, however, may be employed.

As discussed above, for example, in connection with FIG. 16, a lens 980 may be used to alter the propagation of (e.g., collimate) light directed to the coupling optical element 944. This light may be light reflected from, for example, the user's eye such as an anterior surface (e.g., corneal surface) of the user's eye. The distance from the eye, e.g., the anterior surface (e.g., corneal surface) to the coupling optical element 944 may be for example about 20 mm. A positive lens 980 such as a lens having a focal length of about 20 mm may be configured to collimate light reflected from the eye 210, such as an anterior portion of the eye (e.g., the cornea). Light reflected form the anterior surface eye may be coupled into the waveguide 940 and guided therein to a camera. With the focal length set at the distance to the anterior surface of the eye, the camera can image such surfaces. Accordingly, in various implementations the positive lens 980 therefore may have a focal length that is equal or substantially equal to the distance of the lens to the portion of the eye 210 to be imaged, e.g., the cornea.

Although a refractive optical element is shown, other types of lenses or optical elements with optical power such as positive optical power may be used. For example, the lens may comprises a diffractive optical element such as a diffractive lens or hologram. Such a lens may be disposed between the eye and the coupling optical element 944 in some implementations.

In various implementations, the coupling optical element 944 may include optical power. The coupling optical element 944 may, for example, comprise a diffractive optical element having optical power. The diffractive optical element may comprises, for example, a diffractive grating. The diffractive optical element may comprise a holographic optical element or a hologram. The diffractive optical element may have diffractive features such as for example surface features that are configured to both turn light into the waveguide and to provide optical power. Other types of diffractive optical elements are possible. In various implementations, the diffractive optical elements may comprise liquid crystal and may comprises liquid crystal gratings. The diffractive optical elements may also comprise polarization grating. Additionally, the diffractive optical elements may comprise liquid crystal polarization gratings. Some nonlimiting examples of liquid crystal gratings, liquid crystal polarization gratings and other liquid crystal optical elements are discussed in the following published applications, each of which is hereby incorporated by reference herein in its entirety and for all purposes: U.S. Publication No. 2018/0143438, titled "MULTILAYER LIQUID CRYSTAL DIFFRACTIVE GRATINGS FOR REDIRECTING LIGHT OF WIDE INCIDENT ANGLE RANGES," filed on Nov. 16, 2017; U.S. Publication No. 2018/0143485, titled "SPATIALLY VARIABLE LIQUID CRYSTAL DIFFRACTION GRATINGS," filed on Nov. 16, 2017; U.S. Publication No. 2018/0143509, titled "WAVEGUIDE LIGHT MULTIPLEXER USING CROSSED GRATINGS," filed on Nov. 16, 2017; U.S. Publication No. 2018/0239177, titled "VARIABLE-FOCUS VIRTUAL IMAGE DEVICES BASED ON POLARIZATION CONVERSION," filed on Feb. 22, 2018; and U.S. Publication No. 2018/0164627, titled "DIFFRACTIVE DEVICES BASED ON CHOLESTERIC LIQUID CRYSTAL," filed on Dec. 7, 2017.

This diffractive optical element may have optical power that alters on the propagation of light incident thereon. The diffractive optical element, may for example, collimate light reflected from as surface having a distance from said diffractive optical element corresponding to the focal length of the diffractive optical element. Such distance may be for example from about 15 to 20 mm (e.g., 20 mm or thereabouts). Such a focal length may provide for collimating light reflected from an anterior surface of the eye such as a corneal surface (e.g., cornea). Other distances are possible. For example the distance may be in a range from about 10 to 40 mm or 10 to 50 mm, 5 to 40 mm or 5 to 50 mm or any range between any of the distance values herein. Values outside these ranges are also possible.

Figure 24:
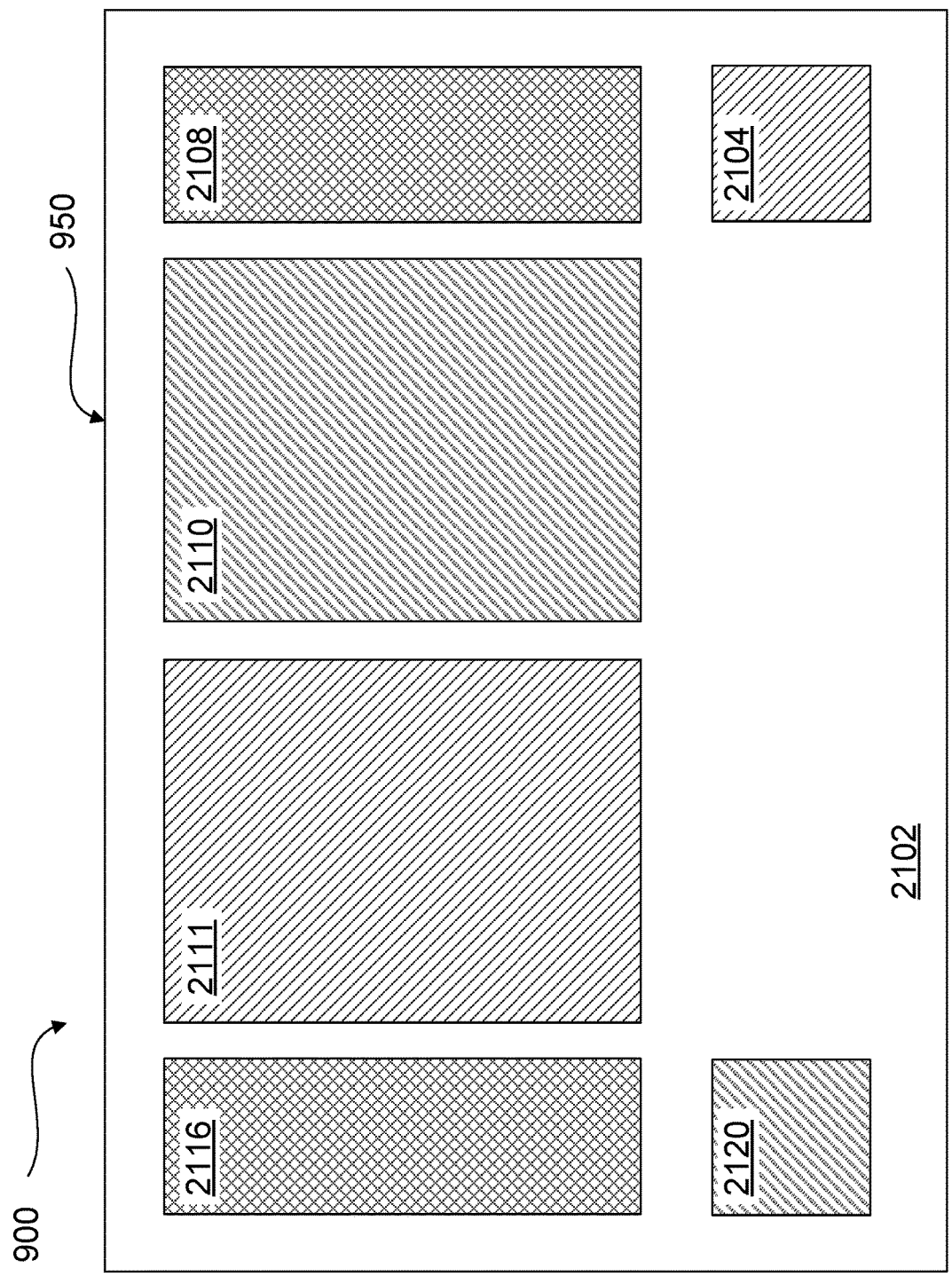
FIG. 24 shows another example eyepiece that can be used to simultaneously project light into a user's eye to provide image content thereto while receiving image data of the user's eye or of the environment in front of the user. In this example, the coupling optical element configured to receive light in from the user's or from the environment in front of the user is displaced laterally from the image content outcoupling optical element (e.g., exit pupil expander).

FIG. 24 shows an example, of a coupling optical element (e.g., coupling grating) 2111 disposed on a waveguide 2102 of an eyepiece 950. The coupling optical element 2111 comprises a diffractive optical element configured to couple light incident thereon into the waveguide 2102. The diffractive optical element also includes optical power. For example, the diffractive optical element includes diffractive features such as surface diffractive features that are configured to provide optical power, for example, to collimate light incident thereon from an anterior surface of the eye (e.g., corneal surface). A light consolidating element 2116, and an outcoupling optical element 2120 are also shown disposed on the waveguide 2102. The light consolidating element 2116 is disposed to receive light coupled into the waveguide 2102 by the coupling element 2111. The light consolidating element 2116 is configured to redirect light incident thereon from the coupling optical element 2111 to the out-coupling optical element 2120. The light consolidating element 2116 is configured to reduce lateral spatial extent of light (e.g., the light beam) from said at least one coupling element prior to reaching said at least one out-coupling optical element, and an outcoupling optical element 2120. In certain configurations, fewer optical elements may be used, possibly, for example, to reduce cost and/or optical losses or for other reasons. For example, the light consolidating element 2116 may be omitted in certain embodiments. In such embodiments, light may be incoupled from the input coupling element 2111 (e.g., after being reflected from the eye 210) and directly coupled to the outcoupling optical element 2120. The light may propagate through the eyepiece 950 between the input coupling element 2111 and the outcoupling optical element 2120. Other configurations are possible. A camera is disposed with respect to the out-coupling optical element 2120 to receive light therefrom. The outcoupling optical element 2120 is configured to direct light received from the light consolidating element 2116 to the camera for capturing an image.

FIG. 24 also shows incoupling optical element 2104, a light distributing element 2108, and an image content outcoupling optical element 2110 disposed on the waveguide

2102. The incoupling optical element 2104 may be configured to couple light received from an image projector into the waveguide 2102. The light distribution element 2108 may be configured to redirect light received from the incoupling optical element 2104 to the out-coupling optical element 2110, additionally increasing the spatial extent of the light as discussed above. The out-coupling optical element 2110 may be configured to couple light guided within the waveguide 2102 out of the waveguide and direct such light to the eye for viewing image content from the projector.

In various implementations one or more of these optical elements 2111, 2116, 2120, 2110, 2108, 2104 may be disposed within or on a waveguide 2102. Similarly, as discussed above, one or more of these optical elements 2111, 2116, 2120, 2110, 2108, 2104 may comprise diffractive optical elements.

In the implementation illustrated in FIG. 24, the coupling optical element (e.g., coupling grating) 2111 may be displaced lateral from the out-coupling optical element 2110 on the waveguide 2102. In the implementation shown, a space laterally separates the coupling optical element 2111 from the out-coupling optical element 2110.

Figure 25:
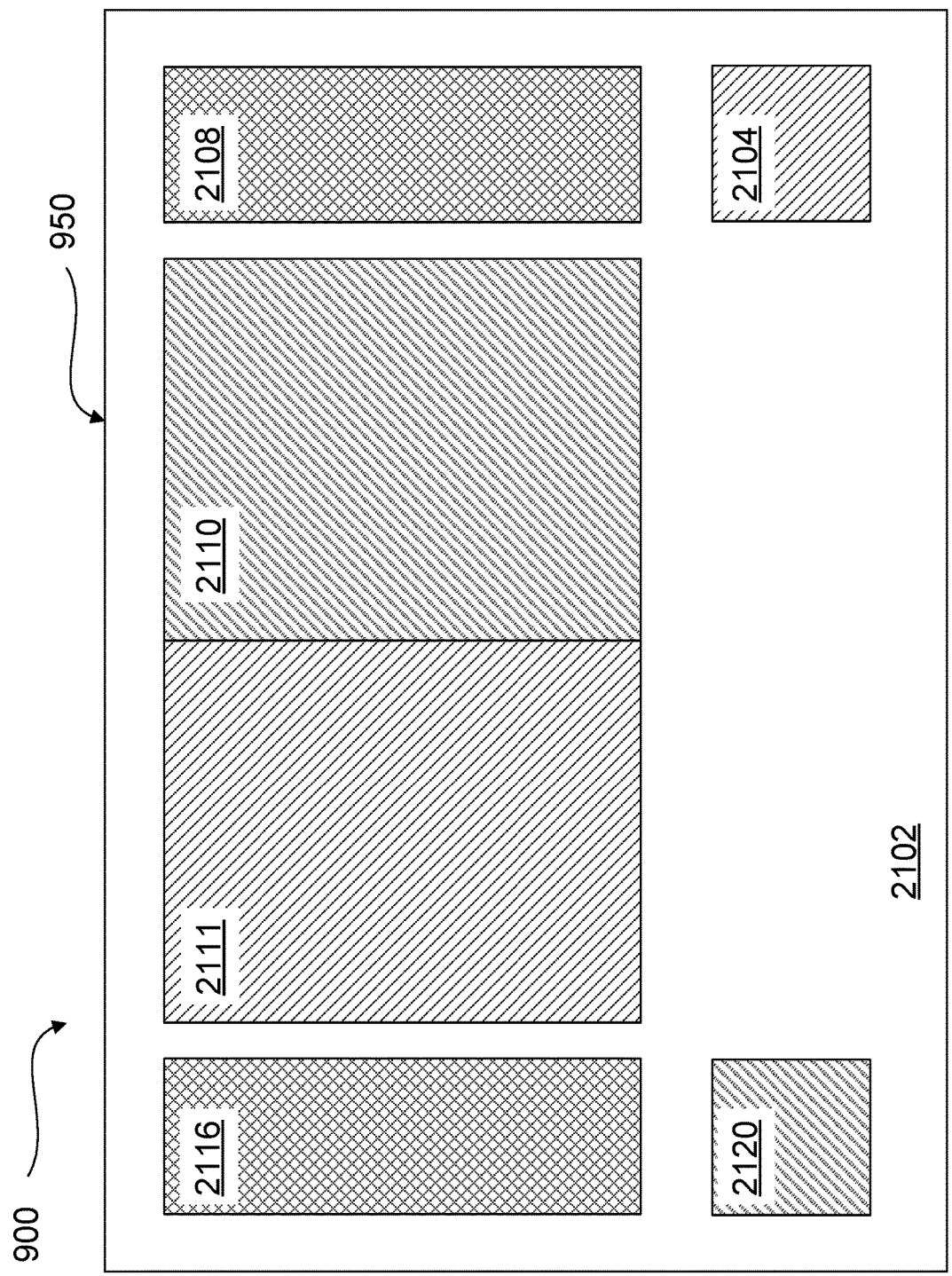
FIG. 25 shows another example eyepiece similar to that shown in FIG. 24 wherein the coupling optical element configured to receive light in from the user's or from the environment in front of the user is laterally spaced apart from the image content out-coupling optical element (e.g., exit pupil expander). In the implementation shown in FIG. 25, however, a space does not laterally separate the coupling optical element 2111 from the out-coupling optical element 2110.

FIG. 25 shows another similar implementations wherein the coupling optical element (e.g., coupling grating) 2111 is displaced laterally from the out-coupling optical element 2110 on the waveguide 2102. In the implementation shown in FIG. 25, however, a space does not laterally separate the coupling optical element 2111 from the out-coupling optical element 2110.

Having the coupling optical element (e.g., coupling grating) 2111 displaced laterally from the out-coupling optical element 2110 on the waveguide 2102 can enable the coupling optical element to include optical power, for example, that collimates light received from an anterior surface of the eye (e.g., corneal surface) such that this optical power does not affect the propagation of light from and/or through the out-coupling optical element 2110 to the eye. Images presented to the eye from the image projector as well as the view of the environment in front of the user and the head mounted display, need not therefore be affected (e.g., distorted or defocused, etc.) by the optical power of the coupling optical element 2111.

Figure 26:
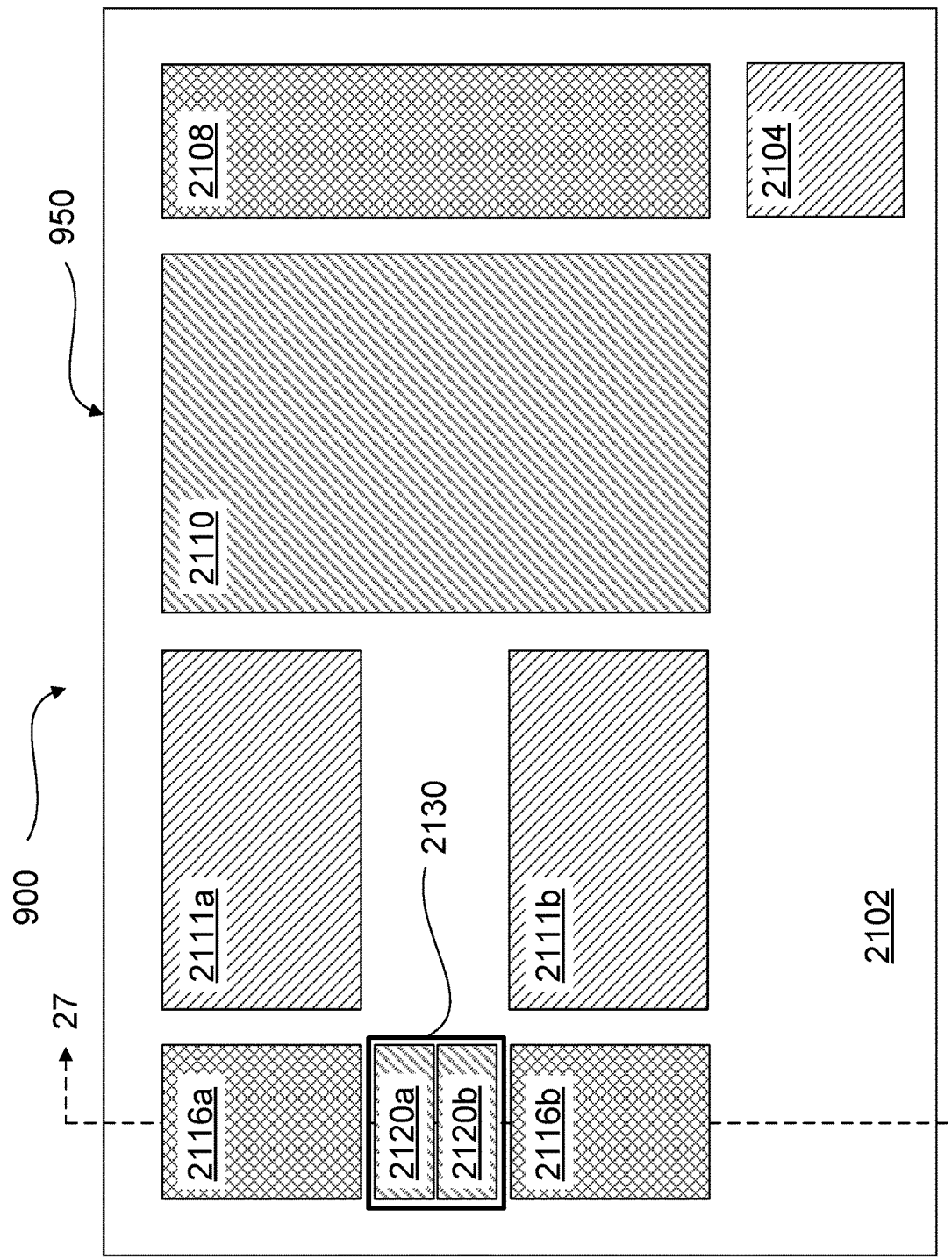
FIG. 26 shows an example eyepiece including first and second coupling optical elements configured to couple light received from the user's eye or from the environment into a waveguide to be guided therein as well as first and second out-coupling optical elements configured to couple light guided within the waveguide out of said waveguide to one or more cameras.

FIG. 26 illustrates an implementation of an imaging system 900 configured to image multiple portions of the eye. For example, an imaging system 900 such as shown in FIG. 26 may be configured to image both anterior surfaces of the eye (e.g., corneal surfaces) as well as the retina. The imaging system 900 includes a pair of incoupling optical elements, a first incoupling optical element 2111a and a second incoupling optical element, disposed on the waveguide 2102 of the eyepiece. The imaging system 900 additionally includes a pair of light consolidating elements, a first light consolidating optical element 2116a and a second light consolidating element 2116b, disposed on the waveguide 2102. In certain configurations, fewer optical elements may be used, possibly, for example, to reduce cost and/or optical losses or for other reasons. For example, the light consolidating elements 2116a, 2116b may be omitted in certain embodiments. In such embodiments, light may be incoupled from the first and second input coupling elements 2111a, 2111b (e.g., after being reflected from portions the eye 210 such as the retina and/or cornea) and directly coupled to corresponding first and second outcoupling optical elements 2120a, 2120b. The light may propagate through the eyepiece 950 (e.g., via a waveguide such as the waveguide 2102) between the first and second input coupling elements 2111a, 2111b and the corresponding outcoupling optical elements 2120a, 2120b. Other configurations are possible. In addition, the imaging system 900 additionally includes a pair of light out-coupling optical elements, a first out-coupling optical element 2120a and a second out-coupling optical element 2120b, disposed on the waveguide 2102.

The first coupling optical element 2111a is configured to couple light incident thereon into the waveguide 2102. The first light consolidating element 2116a is disposed to receive light coupled into the waveguide 2102 by the first coupling element 2111a. The first light consolidating element 2116a is configured to redirect light incident thereon from the first coupling optical element 2111a to the first out-coupling optical element 2120a. The first light consolidating element 2116a is also configured to reduce the lateral spatial extent of light (e.g., the light beam) from the first coupling element 2111a prior to reaching the first out-coupling optical element 2120a. A camera is disposed with respect to the first out-coupling optical element 2120a to receive light therefrom. Although the camera is not shown in FIG. 26, an area corresponding to the detection area 2130 of the camera is shown. The first out-coupling optical element 2120a is configured to direct light received from the first light consolidating element 2116a to the camera and, in particular, to the detection area 2130 shown in FIG. 26, for capturing an image.

Likewise, the second coupling optical element 2111b is configured to couple light incident thereon into the waveguide 2102. The second light consolidating element 2116b is disposed to receive light coupled into the waveguide 2102 by the second coupling element 2111b. The second light consolidating element 2116b is configured to redirect light incident thereon from the second coupling optical element 2111b to the second out-coupling optical element 2120b. The second light consolidating element 2116b is also configured to reduce the lateral spatial extent of light (e.g., the light beam) from the second coupling element 2111a prior to reaching the second out-coupling optical element 2120a. A camera is disposed with respect to the second out-coupling optical element 2120b to receive light therefrom. Although the camera is not shown in FIG. 26, an area corresponding to the detection area 2130 of the camera is shown. The second out-coupling optical element 2120b is configured to direct light received from the second light consolidating element 2116b to the camera and, in particular, to the detection area 2130 shown in FIG. 26 for capturing an image.

FIG. 26 also shows incoupling optical element 2104, a light distributing element 2108, and an image content out-coupling optical element 2110 disposed on the waveguide 2102. The incoupling optical element 2104 may be configured to couple light received from an image projector into the waveguide 2102. The light distribution element 2108 may be configured to redirect light received from the incoupling optical element 2104 to the out-coupling optical element 2110, additionally increasing the spatial extent of the light as discussed above. The out-coupling optical element 2110 may be configured to couple light guided within the waveguide 2102 out of the waveguide and direct such light to the eye for viewing image content from the projector.

In the implementation illustrated in FIG. 26, the first and second coupling optical elements (e.g., coupling gratings) 2111a, 2111b are displaced lateral from the out-coupling optical element 2110 on the waveguide 2102. In the implementation shown, a space laterally separates the first and second coupling optical elements 2111a, 2111b from the out-coupling optical element 2110. Furthermore, in the example of FIG. 26, the first and second coupling optical elements 2111a, 2111b are displaced lateral from each other on the waveguide 2102. In other implementations, two or more of the first coupling optical element (e.g., coupling grating) 2111a, the second coupling optical element 2111b, and the out-coupling optical element 2110 need not be displaced laterally from each other on the waveguide 2102.

In various implementations one or more of these optical elements 2111a, 2111b, 2116a, 2116b, 2120a, 2120b, 2110, 2108, 2104 may be disposed within or on a waveguide 2102. Similarly, as discussed above, one or more of these optical elements 2111a, 2111b, 2116a, 2116b, 2120a, 2120b, 2110, 2108, 2104 may comprise diffractive optical elements.

The imaging system 900 of FIG. 26 can be configured to image multiple portions of the eye. For example, an imaging system 900 may be configured to image both anterior surfaces of the eye (e.g., corneal surfaces) as well as the retina. The first incoupling optical element 2111a may, for example, have optical power or have a lens disposed in front thereof with optical power. The first coupling optical element 2111a may, for example, comprise a diffractive optical element configured to couple light into the waveguide 2102 but also configured to impart optical power thereto. Additionally or alternatively, a lens having optical power may be disposed in front of the first coupling optical element 2111a. The optical power may be configured to alter the propagation of light received by the first incoupling optical element 2111a such that a particular portion of the eye may be imaged. In some examples, the optical power may be positive optical power. Moreover, the optical power may be such that an anterior surface of the eye may be imaged. The optical power may, for example, correspond to a focal length of between about 15 to 25 mm (e.g., about 20 mm). As a result, light reflected from an anterior surface of the eye, which may be about 15 to 25 mm (e.g., about 20 mm) from the first coupling optical element 2111a may be collimated and coupled into the waveguide. Other focal lengths are possible. For example the focal length may be in a range from about 10 to 40 mm or 10 to 50 mm, 5 to 40 mm or 5 to 50 mm or any range between any of the distance values herein. Values outside these ranges are also possible.

In contrast, in various implementations, the second coupling optical element 2111b may neither have optical power nor include a lens disposed in front thereof. The lack of optical power associated with the second coupling optical element 2111b will result in light from the anterior portion of the eye (e.g., corneal surfaces) not being collimated and not being imaged by the camera. However, light reflected from the retina may upon passing through the natural lens of the eye of the user may be collimated. This light collimated by the natural lens of the eye may be coupled into the waveguide 2102 by the second coupling optical element 2111b and imaged by the camera. In this manner, light collected by the first coupling optical element 2111a may image an anterior surface of the eye (e.g., a corneal surface of the eye) and the second coupling optical element 2111b may image the retina of the eye of the user. In some implementations, such a configuration enables light collected by the first coupling optical element 2111a to form images of glint on the eye, for example, on an anterior surface of the eye (e.g., a corneal surface of the eye). The second coupling optical element 2111b may image the retina of the eye of the user as discussed above. In some examples, the second coupling optical element 2111b and/or a lens disposed in front thereof may have some amount of net optical power (e.g., a non-zero amount of net optical power) that is weaker than that of the first coupling optical element 2111a and/or a lens disposed in front of the first coupling optical element 2111a. In particular, the second coupling optical element 2112b can have optical power and/or a lens associated therewith, however, total optical power of the second coupling optical element 2112b and/or any lens associated second coupling optical element is less than the optical power of the first coupling optical element and/or any lens associated with the first coupling optical element).

In some implementations, the images formed by light collected by the first coupling optical element 2111a are next to (e.g., not superimposed over) images formed by light collected by the second coupling optical element 2111b. For example, images of the anterior surface(s) of the user's eye (e.g., cornea) may be formed next to (e.g., not superimposed over) images of the retina.

Polarization techniques can be used to attenuate or remove light from the anterior surfaces (e.g., corneal surfaces) from affecting images formed by light collected by the second coupling optical element 2111b. For example, the eye can be illuminated with polarized light having a first polarization and the camera can form an image using light from the second out-coupling optical element 2120b using light of a second different polarization. For example, the second out-coupling optical element 2111b may be a polarization selective coupling element that selectively couples out light of the second polarization different than the first polarization. Additionally or alternatively, a polarizer 2140 that filters out the first polarization (e.g., selectively transmits the second polarization) may be included between the second out-coupling optical element 2120b and the camera 920 as illustrated in FIG. 27, which is a cross-section through the waveguide 950, 2102, consolidating optical elements 2116a, 2116b, and out-coupling optical elements 2120a, 2120b shown in FIG. 26.

Such a configuration may be used to reduce unwanted reflections (e.g., glint), such as from the cornea when imaging the retina. Reflection from the cornea will be specular. Accordingly, if light of the first polarization is incident on the cornea, the light reflected from the cornea will retain that first polarization. In contrast, the retina is diffuse. If light of the first polarization is incident on the retina, the light reflected from the retina does not retain solely the first polarization. The diffuse reflection more likely results in unpolarized light. Accordingly, the second polarization, different from the first polarization will be present in the light reflected from the retina. As a result, by forming images with light coupled out of the second out-coupling optical element 2120b using light of the second polarization, images of the retina will be obtained while images of the cornea or glint will be suppressed. Likewise, by illuminating with a first polarization and imaging with a second different polarization, the retina can be image with reduced glare from the cornea.

Accordingly, in various implementations, polarization specific optical filters or polarization selective optical elements (e.g. coupling gratings) may be used to reduce unwanted reflected light from the eye 210 (e.g., from the cornea). For example, unwanted light, glare, or glint may be reflected off the cornea that may saturate an image captured by the camera. As discussed above, light reflected from the cornea may be specular and maintain its polarization. By contrast, light reflected off the retina may be more diffusely reflected and may be less homogenously polarized. Likewise, a combination of polarizers may be used to remove some or most of the unwanted light reflected from the cornea. Initially polarized light can be used for illuminating the eye of the user. In some designs, a polarized illumination source (e.g., the light source) may be used. Additionally or alternatively, a first polarizer (e.g., a polarization specific optical filter or a polarization selective optical coupling element coupling illumination light into an illumination waveguide) may be positioned at the beginning of the optical path of the illumination source to provide initial polarization of the light to the eye. A second polarizer (e.g., a polarization specific optical filter or polarization selective coupling element) may be positioned at the optical path before the light enters the camera. The second polarizer may be rotated at 90° from the first polarizer (e.g. the polarizers may be "crossed"). As a result, the eye will be illuminated with the first polarization with some light of the first polarization reflected from the cornea. This light will not pass through the crossed polarizer (that preferentially passes light of the second polarization) located proximal the camera. However, light reflected from the retina will include the second polarization. Likewise, light diffusely reflected from the retina will pass through the polarizer 2140 proximal the camera and will enable an image of the retina to be captured by the camera. Thus, in such configurations, unwanted light received from the eye (e.g., from cornea) and entering the camera may be reduced or eliminated from the images captured using light from the second coupling optical element 2111*b*. Other configurations are possible. For example, a polarization selective coupling elements 2111*b* and/or a polarization selective out-coupling optical elements 2120*b* may be used in addition or in alternative to polarizers such as the polarizer 2140 proximal the camera. Additionally or alternatively, a polarized light source may be used for illumination (e.g., illuminating the eye). The effect may again be to reduce or remove unwanted light received from the eye (e.g., from cornea) before entering the imaging device 920.

Figure 27:
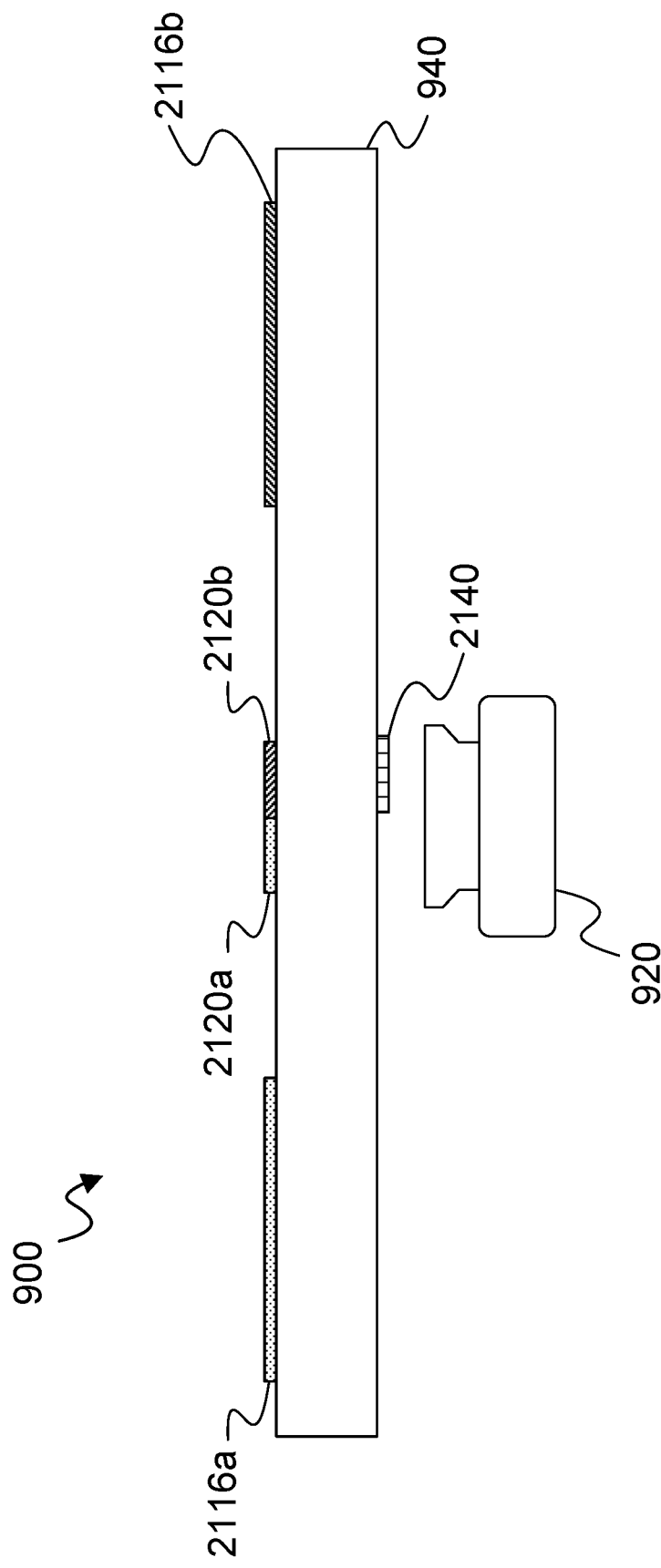
FIG. 27 is a cross-section through the waveguide, consolidating optical elements, and out-coupling optical elements shown in FIG. 26 showing a polarizer in an optical path between one of the out-coupling optical elements and the camera. The polarizer may be used to remove unwanted glint reflections from the cornea when obtaining images of the retina.

As illustrated in FIG. 27, in various implementations, such polarizers are not used in an optical path from the first coupling optical element 2111*a* and the camera or between the first out-coupling optical element 2120*a* and the camera. As a result, images of the cornea and glint may be obtained from light coupled by the first coupling optical element 2111*a* into the waveguide and/or light coupled out of the waveguide from the first out-coupling optical element 2120*a*. As discussed above, this first coupling optical element 2111*a* may have optical power or a lens associated therewith that is specifically used to image the cornea and/or glint. Likewise, polarization selective coupling optical elements 2111*a* or polarization selective out-coupling optical element 2120*a* that filter out light of the first polarization would not be used as the first coupling optical element 2111*a* and out-coupling optical element 2120*a*, respectively. Additionally, polarizers 2140 between the coupling optical element 2111*a* and the camera 920 or between the out-coupling optical element 2111*a* and the camera 920 that filter out light of the first polarization would not be used.

A wide variety of variations are possible. For example, although the first and second out-coupling optical elements 2120*a*, 2120*b* are described above as coupling light and forming images on a single camera (e.g., a single detection area 2130), in other implementations, the first and second out-coupling optical elements 2120*a*, 2120*b* can coupling light and forming images on respective first and second cameras. Other variations are possible.

Additionally, in some implementations, one or more of the eyepieces described above (e.g., the eyepiece 950) with reference to FIGS. 24-27 may be a dedicated imaging eyepiece layer (e.g., omitting the incoupling optical element 2104, the light distributing element 2108, and/or the output coupling element 2110). In such implementations, the imaging eyepiece layer may be included as a layer in a stack of waveguides. The one or more other layers in the stack of waveguides may include the incoupling optical element 2104, the light distributing element 2108, and/or the output coupling element 2110.

In some embodiments, the dedicated imaging eyepiece layer can be configured to capture images of the environment. In some such embodiments, the imaging eyepiece layer may be disposed most proximal to the environment when installed in the head-mounted display. In some such configurations, the dedicated imaging eyepiece layer may be the outermost layer in the waveguide stack such that it is positioned between the other layers (e.g., waveguides) and the environment. In some embodiments, the dedicated imaging eyepiece layer can be configured to capture images of the user's eye 210. In some such embodiments, the imaging eyepiece layer may be disposed most proximal to the user when installed in the head-mounted display. In some implementations, the dedicated imaging eyepiece layer may be the innermost layer in the waveguide stack such that it is positioned between the other layers (e.g., waveguides) and the user. Other configurations are possible.

In certain embodiments, the first and second coupling elements 2111*a*, 2111*b* may be laterally aligned but displaced in depth (e.g., along the z-axis or into the page of FIG. 26). For example, in such embodiments, the first and second coupling elements 2111*a*, 2111*b* may be positioned on opposite sides of the same waveguide. In certain embodiments, the first input coupling element 2111*a* may be disposed on or within a first waveguide and the second input coupling element 2111*b* may be disposed on or within a second waveguide. Additionally or alternatively, the first and second light consolidating elements 2116*a*, 2116*b* and/or the first and second outcoupling optical elements s 2120*a*, 2120*b* may be disposed on opposite sides of the same waveguide and/or may be disposed on or in corresponding separate waveguides.

One or more of the coupling optical elements 2111, 2111*a*, 2111*b* described above with reference to FIGS. 24-27 may be wavelength-selective such that the optical elements are configured to interact only with a certain wavelength or band of wavelengths. The wavelength or band of wavelengths may include invisible light (e.g., infrared light, or a specific band thereof). In some implementations, the first input coupling element 2111*a* may be configured to operate on a wavelength lower than that for the second input coupling element 2111*b* (or vice versa). For example, the first coupling optical element 2111*a* may be configured to interact with about 800 nm light, and/or the second coupling optical element 2111*b* may be configured to interact with about 950 nm light (or vice versa). Optical filters may also be use to effectuate similar wavelength selectivity. In various implementations, therefore, light coupled into the waveguide by the first coupling optical element that reaches the at least one camera can be of a different wavelength than light coupled into the waveguide by the second optical element that reaches the at least one camera. Other configurations are possible.

A wide variety of variations are possible in the structure and design of the coupling optical elements 2120 and the out-coupling optical elements 2012. For example, the size and shape of the coupling optical element 2120 for coupling light into the waveguide 2102 and the out-coupling optical element 2112 for coupling light out of the waveguide 2102 to a camera, and in particular the size and shape of the coupling areas of the coupling optical element 2120 and out-coupling optical element 2112, can be varied. Coupling area as used herein refers to the area of the optical element that is configured to receive light and couple said light into the waveguide or out of the waveguide for use by the system for example for imaging (e.g., the eye or the environment in front of the user). In some implementations, the coupling area may corresponds to the area of the optical element in its entirety or to a portion of the area of the optical element that is configured to be used in the system to couple light into or out of the waveguide for use by the system. For example, in some implementations, the coupling area of a coupling element comprising a diffractive optical element used to couple light (from the eye or the environment in front of the user) into the waveguide is that area of the diffractive optical element used by the system to couple light into the waveguide. The coupling optical element, for example, the diffractive grating or diffractive optical element may be larger than the coupling area in some cases. For example, opaque objects such as an opaque element or layer having a small aperture therein may obstruct the propagation of light to portions of the diffractive grating or diffractive optical element thereby reducing the coupling area. Accordingly, the size and shape of the coupling area may be controlled by the size and perimeter of the optical element (e.g., the spatial extent of the diffractive optical element or grating) as well as other optical elements or other components or features that may block light from reaching portions of the optical element. Other factors may potentially reduce, alter or otherwise influence the size and shape of the coupling area.

Figure 28B:
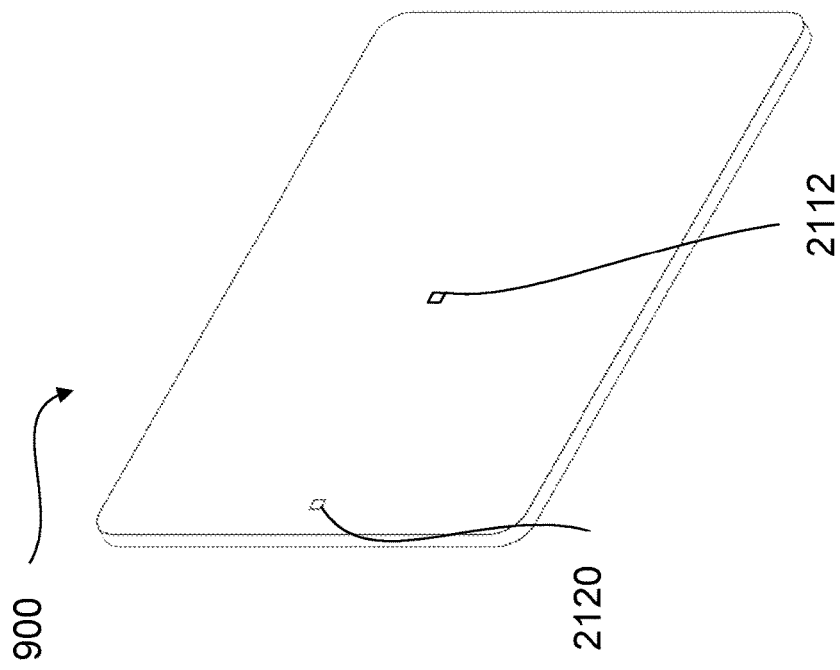
FIGS. 28A and 28B are front and perspective views of a coupling optical element for coupling light into the waveguide and an out-coupling optical element for coupling light out of the waveguide to a camera wherein the coupling optical element has a pinhole coupling area. The outcoupling optical element is similarly sized and shaped in this implementation.
Figure 28A:
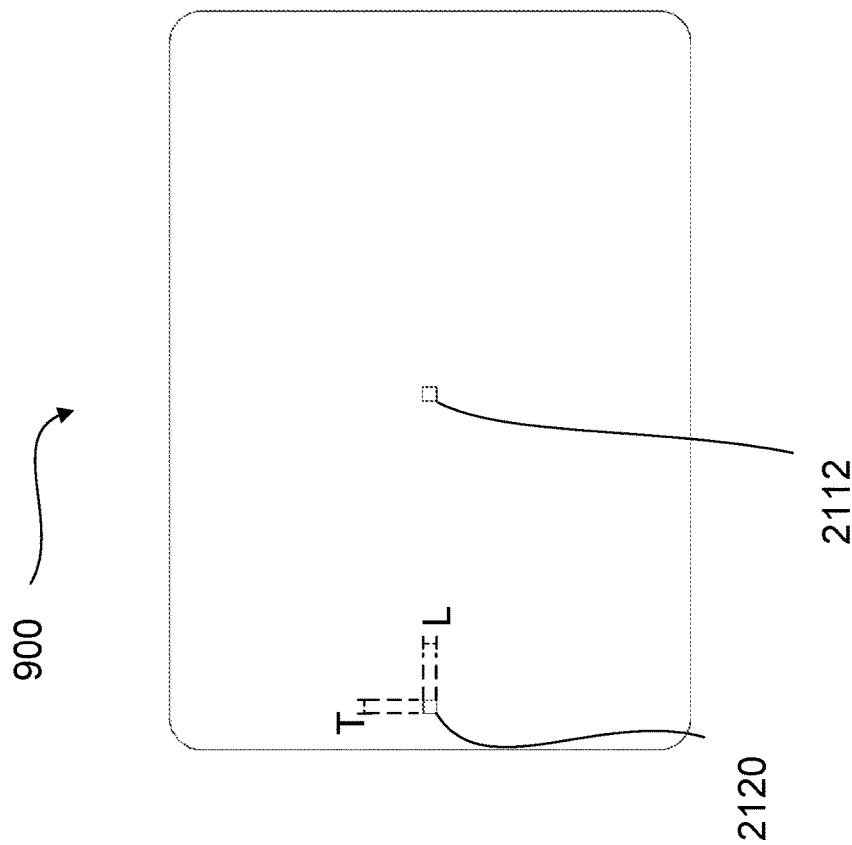

FIGS. 28A and 28B show a coupling optical element 2120 for coupling light into the waveguide 2102 wherein the coupling optical element has a reduced size. In particular, the coupling optical element 2120 has a pinhole size coupling area. The size of the coupling area may for example be about 1.5 mm×1.5 mm. As illustrated in FIG. 28A, for example, coupling area of the coupling optical element 2120 may have a length, L, and thickness, T. The length and thickness may both be about 1.5 mm in certain implementations. The reduced size of the coupling area removes multiple (e.g. ghost) images from being collected by the coupling optical element 2120. The pinhole size coupling area of the coupling optical element 2120 for coupling light from an object such as the user's eye or an object in the environment in front of the user and the eyewear has an effect similar to that of a pinhole camera on the collection of light and resultant imaging. The reduced coupling area size of the coupling optical element 2120 is akin to the reduced size of a pinhole camera coupling area. The result is that a large depth of focus or depth of field is provided without the need for a lens. The coupling optical element 2120 also need not have optical power nor does a lens need to be provided at the coupling optical element 2120. Nevertheless a large range of object distances are in focus with such a design.

The out-coupling optical element 2112 shown in FIGS. 28A and 28B for coupling light out of the waveguide 2102 to a camera is also of reduced size. In this particular implementation, the size and shape of the coupling optical element 2120 and the out-coupling optical element 2112 are similar or the same. The out-coupling optical element 2112 may also be 1.5×1.5 mm.

As discussed above, the coupling optical element 2120 and the out-coupling optical element 2112 may comprise diffractive optical elements such as diffraction gratings. The coupling optical element 2120 and the out-coupling optical element 2112 may comprise holograms or holographic optical elements. As discussed herein, the coupling optical element 2120 and the out-coupling optical element 2112 may comprise liquid crystal, liquid crystal gratings, polarization gratings and/or liquid crystal polarization gratings. The coupling optical element 2120 may be configured to receive light (e.g., from the eye of the user or from the environment in front of the user) and couple at least a portion of that light into the waveguide 2102. The coupling optical element 2120 may also be configured to turn and direct a portion of the light to the out-coupling optical element 2112. The out-coupling optical element 2112 may be configured to couple light received from the coupling optical element 2120 and guided within the waveguide 2102 out of the waveguide, for example, to a camera. In the configuration shown, a light consolidating optical element such as described above is not included.

The size and shape of the coupling area of the coupling optical element 2120 and the out-coupling optical element 2112 may vary. For example, although the coupling optical element 2120 and the out-coupling optical element 2112 are shown as squares, the shapes of either or both may be different. In some implementations, the size and relative placement of each of optical elements 2120, 2112 may be selected based at least in part on the desired distance from the user's eye (i.e., focal length), the wavelength of the light to be captured, or both. The desired distance between the waveguide and the user's eye may be, for example, from about 15 mm to 25 mm. Other configurations are possible. In some embodiments, the optical elements 2120, 2112 may, for example, be disposed 15 mm to 25 mm away from each other on or in the waveguide. The shape of the coupling area may, for example, be circular or otherwise round. The size of the coupling area may also be different. For example, the dimension (e.g., average or maximum) along one direction of the coupling area (e.g., length, L, or thickness, T) may be from 0.1 to 3 mm, 0.1 to 0.3 mm, 0.1 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. Similarly, dimensions (e.g., maximum or average) along another direction of the coupling area (e.g., length, L, or thickness, T) may be from 0.1 to 3 mm, 0.1 to 0.3 mm, 0.1. to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. These two directions may be orthogonal in some implementations. The dimensions along the two directions need not be the same. Accordingly, the coupling area may be symmetrical or asymmetrical. For example, the aspect ratio of the coupling area (e.g., as measured by the ratio of the length to thickness such as maximum length to maximum thickness or average length to average thickness) may be from 1 to 2, from 1 to 1.75, from 1 to 1.5, from 1 to 1.3, from 1 to 1.2, from 1 to 1.1 or any range formed by any of these values. Values outside these ranges are also possible.

Figure 29B:
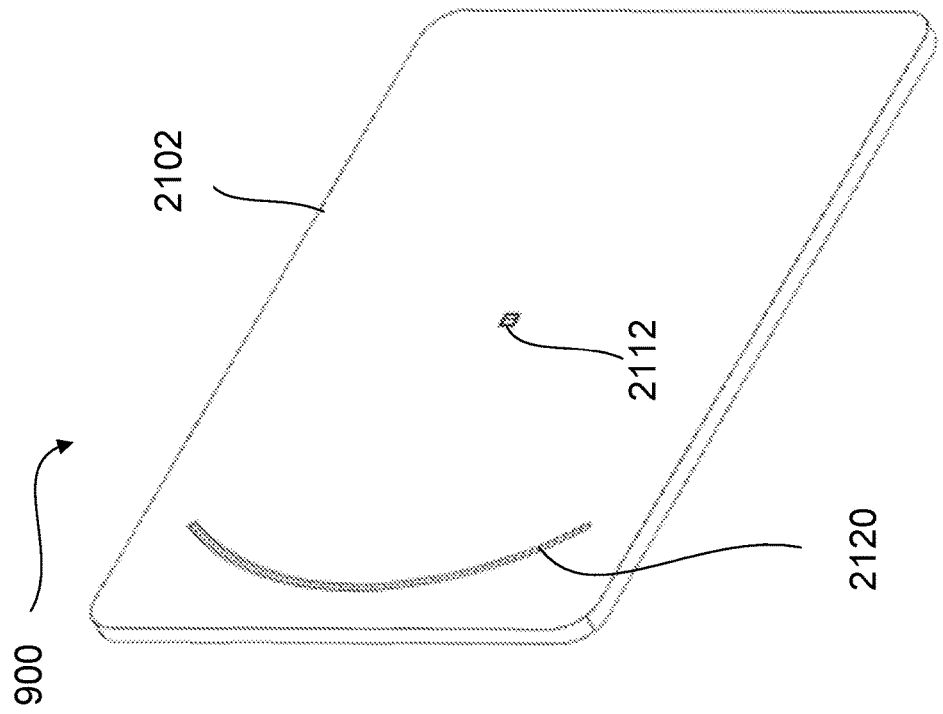
FIGS. 29A and 29B are front and perspective views of a coupling optical element for coupling light into the waveguide and an out-coupling optical element for coupling light out of the waveguide to a camera wherein the coupling optical element has an arcuate slit-shaped coupling area. The outcoupling optical element is has a pinhole size coupling area.
Figure 29A:
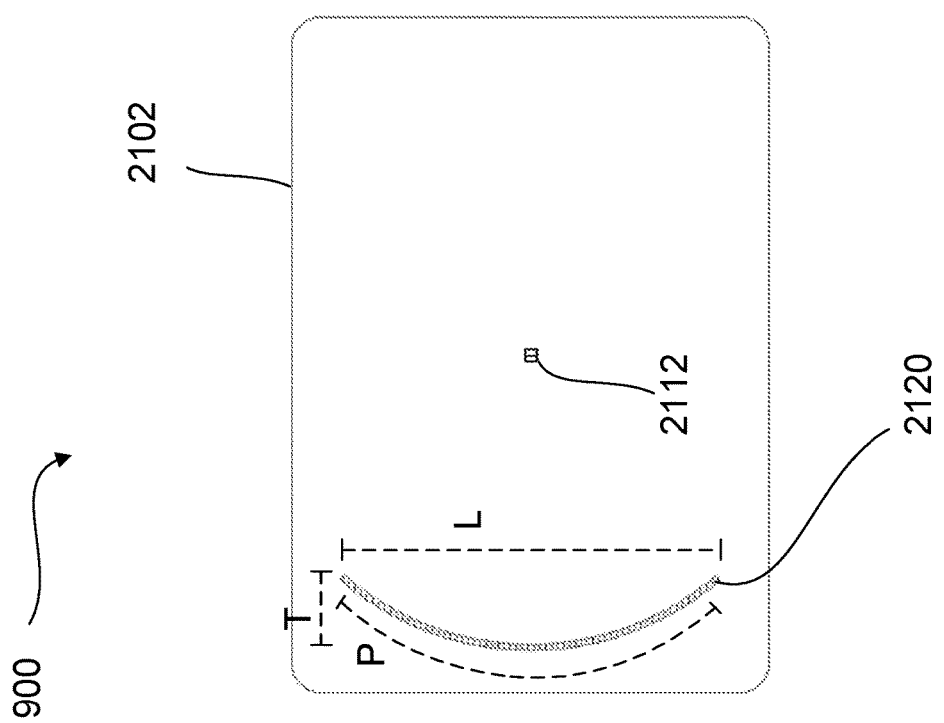

As discussed above, other shapes are possible. FIGS. 29A and 29B, for example, show a coupling optical element 2120 for coupling light into the waveguide 2102 and an out-coupling optical element 2112 for coupling light out of the waveguide to a camera wherein the coupling optical element 2120 has an arcuate slit-shaped coupling area. (The outcoupling optical element 2112 has a pinhole coupling area similar to that shown in FIGS. 28A and 28B.)

A slit may be advantageous in being larger than a pinhole and therefore may collect more light. However, the narrowness of the slit provides a similar effect as a pinhole. For example, the reduced thickness, T, of the coupling area may remove multiple images from being collected by the coupling optical element 2120. Ghost images and/or blur can thereby be reduced. As illustrated in FIG. 25A, the coupling area of the coupling optical element 2120 may have a length, L, and thickness, T. The thickness, T, may be about 1.0 mm or 1.5 mm in certain implementations. The pinhole size thickness, T, of the coupling optical element 2120 for coupling light from an object such as the eye or an object in the environment in front of the user and the eyewear has an effect similar to that of a pinhole camera on the collection of light and resultant imaging. The reduced size of the coupling area of the coupling optical element 2120 is akin to the reduce size of a pinhole camera coupling area. The result is that a large depth of focus or depth of field is provided without the need for a lens. The coupling optical element 2120 also need not have optical power nor does a lens need to be provided at the coupling optical element 2120. Nevertheless, a large range of object distances are in focus with such a design.

The out-coupling optical element 2112 shown in FIGS. 29A and 29B for coupling light out of the waveguide to a camera is also of reduced size. In this particular implementation, the size and shape of the out-coupling optical element 2112 are similar or the same as that described above in connection with FIGS. 28A and 28B. The out-coupling optical element 2112, for example, may also be 1.5×1.5 mm.

As discussed above, the coupling optical element 2120 and the out-coupling optical element 2112 may comprise diffractive optical elements such as diffraction gratings. The coupling optical element 2120 and the out-coupling optical element 2112 may comprise holograms or holographic optical elements. As discussed herein, the coupling optical element 2120 and the out-coupling optical element 2112 may comprise liquid crystal, liquid crystal gratings, polarization gratings, liquid crystal polarization gratings or any combination thereof. The coupling optical element 2120 may be configured to receive light (e.g., from the eye of the user or from the environment in front of the user) and couple at least a portion of that light into the waveguide 2102. The coupling optical element 2120 may also be configured to turn and direct a portion of the light to the out-coupling optical element 2112. The out-coupling optical element 2112 may be configured to couple light received from the coupling optical element 2120 and guided within the waveguide 2102 to the out-coupling optical element 2112 out of the waveguide, for example, to a camera. In the configuration shown, a light consolidating optical element such as described above is not included.

The shape of the coupling area of the coupling optical element 2120 and the out-coupling optical element 2112 may vary. In theory, a curved slit may potentially facilitate directing the light from the coupling optical element 2120 to the out-coupling optical element. Moreover, in some implementations, the arcuate slit may have a curvature described by a radius of curvature and a center of curvature. The curvature of the slit may be such that the out-coupling optical element 2112 is at the center of curvature of the arcuate-shape slit. However, the curvature may be different, for example, larger or smaller. Still other variations in the shape are possible. For example, the edges of the arcuate shaped slit may be rounded.

The size of the coupling area may also be different. For example, the shorter dimension, the thickness, T, along one direction of the coupling area may be from 0.1 to 0.3 mm, 0.1 to 0.5 mm, 0.3 to 0.5 mm, 0.2 to 0.5 mm, 0.1 to 1.0 mm, 0.3. to 1.0 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. This dimension, the thickness, T, may be smaller than the other dimension, the length, L. The other dimension, length, L, may correspond to the length or resultant displacement from one end to another. Alternately, a path length, P, or in this case an arc length, may be used to provide a measure of the larger dimension of the coupling area. In some implementations, the length, L, or path length or arc length, P, may be from 5 mm to 40 mm, 10 to 40 mm, from 10 to 30 mm, from 15 to 30 mm, from 15 to 25 mm, from 1 to 5 mm, from 3 to 5 mm, or any range formed by any of these values. Values outside these ranges are also possible. These two directions may be orthogonal in some implementations, however, the directions need not be orthogonal. The slit is asymmetric. For example, the aspect ratio of the coupling area (e.g., as measured by the ratio of the length, L, to thickness where length can be either the resultant displacement from one end to another or the path length such as the arc length, P) may be from 5 to 100, from 10 to 100, from 15 to 100, from 20 to 100, from 10 to 40, from 10 to 50 or any range formed by any of these values. Values outside these ranges are also possible. In some embodiments, the dimension along one direction of the coupling area of the coupling optical element 2120 may be less than or equal to 2.5% of the distance between the center of the coupling optical element 2120 and the center of the out-coupling optical element 2112. By way of example, the center-to-center distance between optical elements 2120, 2112 may be about 20 mm and said dimension (e.g., thickness, T) may be less than or equal to about 0.5 mm (e.g., 2.5% of 20 mm). Other configurations or values are possible. For example, said dimension (e.g., thickness, T) may be less than or equal to 2%, 1.5%, and/or 1% of the distance between the center of the coupling optical element 2120 and the center of the out-coupling optical element 2112. The dimensions referred to herein such as thickness, T, length, L, path length P, may be single measurements, averages, maximums or minimums.

The shape and size of the out-coupling optical element 2112 may also be vary. For example, although the out-coupling optical element 2112 are shown as squares, the shapes may be different. The shape of the coupling area may, for example, be circular or otherwise round. The size of the coupling area may also be different. For example, the dimension, e.g. thickness, T, along one direction of the coupling area may be from 0.1 to 0.3 mm, 0.1 to 0.5 mm, 0.3 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. Similarly, dimension e.g. length, L, along another direction of the coupling area may be from 0.1 to 0.3 mm, 0.1 to 0.5 mm, 0.3 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. These two directions may be orthogonal in some implementations. The dimensions along the two directions need not be the same. Accordingly, the coupling area may be symmetrical or asymmetrical. For example the aspect ratio of the coupling area (e.g., as measured by the ratio of the length, L, to thickness, T, where length can be either the resultant displacement from one end to another or the path length such as the arc length, P) may be from 1 to 2, from 1 to 1.75, from 1 to 1.5, from 1 to 1.3, from 1 to 1.2, from 1 to 1.1 or any range formed by any of these values. Values outside these ranges are also possible.

As stated above, the dimension referred to herein such as thickness, T, length, L, path length P, may be single measurements, averages, maximums or minimums.

Figure 30B:
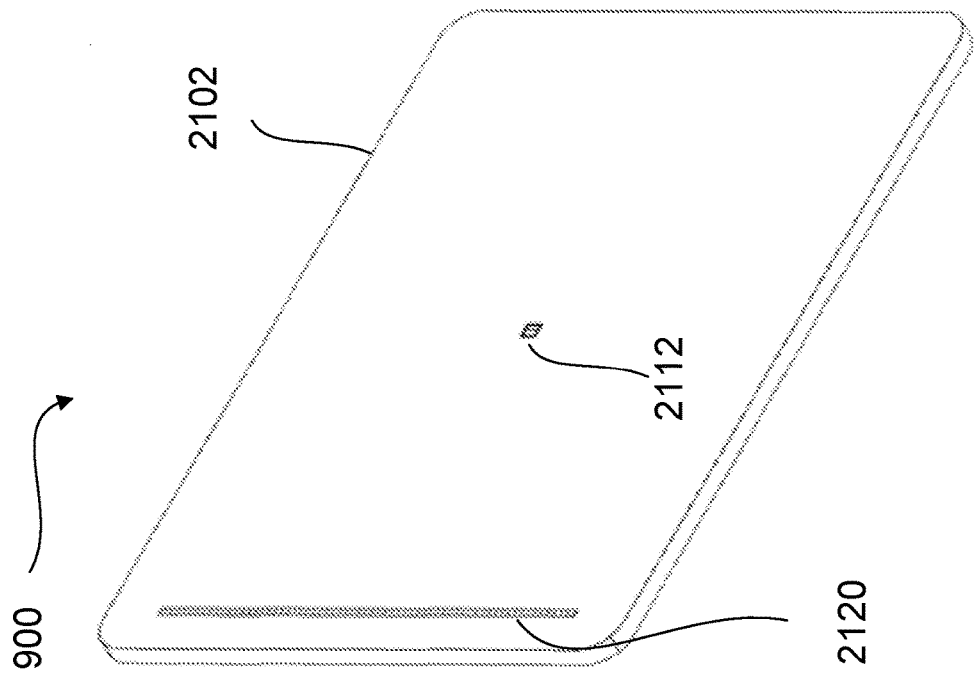
FIGS. 30A and 30B are front and perspective views of a coupling optical element for coupling light into the waveguide and an out-coupling optical element for coupling light out of the waveguide to a camera wherein the coupling optical element has a non-arcuate (e.g. straight rectangular) slit-shaped coupling area. The outcoupling optical element has a pinhole size coupling area.
Figure 30A:
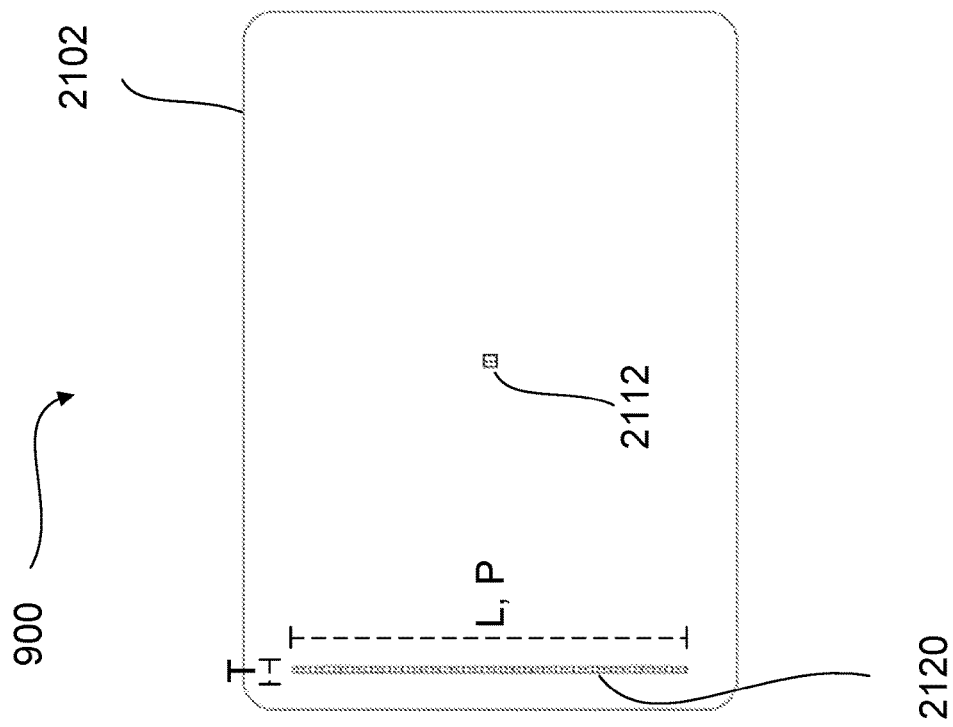

As discussed above, different shapes and sizes of the coupling area are possible. FIGS. 30A and 30B show a coupling optical element 2120 for coupling light into the waveguide 2102 having a non-arcuate slit-shaped coupling area. In particular, the coupling optical element 2120 has a straight slit coupling area. The slit is rectangularly shaped. In contrast, the outcoupling optical element 2112 comprises a pinhole size coupling area similar to that shown in FIGS. 28A and 28B as well as FIGS. 29A and 29B.

As discussed above, a slit may be advantageous in being larger than a pinhole and therefore collect more light. However, the narrowness of the slit provides a similar effect as a pinhole. For example, the reduced thickness, T, of the coupling area may remove multiple images from being collected by the coupling optical element 2120. Ghost images and/or blur can thereby be reduced. As illustrated in FIG. 30A, the coupling area of the coupling optical element 2120 may have a length, L, and thickness, T. The thickness, T, may be about 1.0 mm or 1.5 mm in certain implementations. The pinhole size thickness, T, of the coupling optical element 2120 for coupling light from an object such as the eye or an object in the environment in front of the user and the eyewear has an effect similar to that of a pinhole camera on the collection of light and resultant imaging. The reduced size of the coupling area of the coupling optical element 2120 is akin to the reduce size of a pinhole camera aperture. The result is that a large depth of focus or depth of field is provided without the need for a lens. The coupling optical element 2120 also need not have optical power nor does a lens need to be provided at the coupling optical element 2120. Nevertheless, a large range of object distances are in focus with such a design.

The out-coupling optical element 2112 shown in FIGS. 30A and 30B for coupling light out of the waveguide to a camera is also of reduced size. In this particular implementation, the size and shape of the out-coupling optical element 2112 are similar or the same as that described above in connection with FIGS. 28A and 28B and 29A and 29B. The out-coupling optical element 2112, for example, may also be 1.5×1.5 mm.

As discussed above, the coupling optical element 2120 and the out-coupling optical element 2112 may comprise diffractive optical elements such as diffraction gratings. The coupling optical element 2120 and the out-coupling optical element 2112 may comprise holograms or holographic optical elements. As discussed herein, the coupling optical element 2120 and the out-coupling optical element 2112 may comprise liquid crystal, liquid crystal gratings, polarization gratings, liquid crystal polarization gratings or any combination thereof. The coupling optical element 2120 may be configured to receive light (e.g., from the eye of the user or from the environment in front of the user) and couple at least a portion of that light into the waveguide 2102. The coupling optical element 2120 may also be configured to turn and direct a portion of the light to the out-coupling optical element 2112. The out-coupling optical element 2112 may be configured to couple light received from the coupling optical element 2120 and guided within the waveguide 2102 to the out-coupling optical element 2112 out of the waveguide, for example, to a camera. In the configuration shown, a light consolidating optical element such as described above is not included.

As illustrated, the shape of the coupling area of the coupling optical element 2120 and the out-coupling optical element 2112 may vary. As discussed above, in theory, a curved slit may potentially facilitate directing the light from the coupling optical element 2120 to the out-coupling optical element. However, a non-arcuate slit can also be used. A straight slit or a rectangular slit such as shown in FIGS. 30A and 30B can direct sufficient light to the outcoupling optical element 2112 so as to capture images with the camera. Nevertheless, other variations in the shape are possible. For example, the edges of the slit may be rounded.

The size of the coupling area may also be different. For example, the shorter dimension, the thickness, T, along one direction of the coupling area may be from 0.1 to 0.3 mm, 0.1 to 0.5 mm, 0.3 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. This dimension, the thickness, T, may be smaller than the other dimension, the length, L. The other dimension, length, L, may correspond to the length or resultant displacement from one end to another. As discussed above, alternately, a path length, P, may be used to provide a measure of the larger dimension of the coupling area. In this example, where the slit is straight, the length, L, as measured by the displacement from one end to another is the same as the path length, P. In some implementations, the length, L, or path length or arc length, P, may be from 1 to 5 mm, 1 to 3 mm, 5 mm to 40 mm, 10 to 40 mm, from 10 to 30 mm, from 15 to 30 mm, from 15 to 25 mm, or any range formed by any of these values. Values outside these ranges are also possible. As discussed, these two directions may be orthogonal in some implementations such as for the straight or rectangular slit, however, the directions need not be orthogonal. The slit is asymmetric. For example, the aspect ratio of the coupling area (e.g., as measured by the ratio of the length, L, to thickness, T, where length can be either the resultant displacement from one end to another or the path length such as the arc length, P) may be from 5 to 100, from 10 to 100, from 15 to 100, from 20 to 100, from 10 to 40, from 10 to 50 or any range formed by any of these values. Values outside these ranges are also possible. As stated above, the dimensions referred to herein such as thickness, T, length, L, path length P, may be single measurements, averages, maximums, or minimums.

The shape and size of the out-coupling optical element 2112 may also vary. For example, although the out-coupling optical element 2112 are shown as squares, the shapes of either or both may be different. The shape of the coupling area may, for example, be circular or otherwise round. The size of the coupling area may also be different. For example, the dimension, e.g. thickness, T, along one direction of the coupling area may be from 0.1 to 0.3 mm, 0.1 to 0.5 mm, 0.3 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. Similarly, dimension e.g. length, L, along another direction of the coupling area may be from 0.1 to 0.3 mm, 0.1 to 0.5 mm 0.3 to 0.5 mm, 0.5 to 3 mm, 0.5 to 2 mm, from 1 to 3 mm, from 1 to 2 mm, from 0.5 to 2.5 mm, from 1.0 to 2.5 mm, from 1.0 mm to 1.5 mm or 1.5 mm to 2 mm or any range formed by any of these values. Values outside these ranges are also possible. These two directions may be orthogonal in some implementations. The dimensions along the two directions need not be the same. Accordingly, the coupling area may be symmetrical or asymmetrical. For example the aspect ratio of the coupling area (e.g., as measured by the ratio of the length, L, to thickness, T, where length can be either the resultant displacement from one end to another or the path length such as the arc length, P) may be from 1 to 2, from 1 to 1.75, from 1 to 1.5, from 1 to 1.3, from 1 to 1.2, from 1 to 1.1 or any range formed by any of these values. Values outside these ranges are also possible. The dimensions referred to herein such as thickness, T, length, L, path length P, may be single measurements, averages, maximums or minimums (e.g., average thickness, maximum thickness, average length, maximum length).

Figure 31:
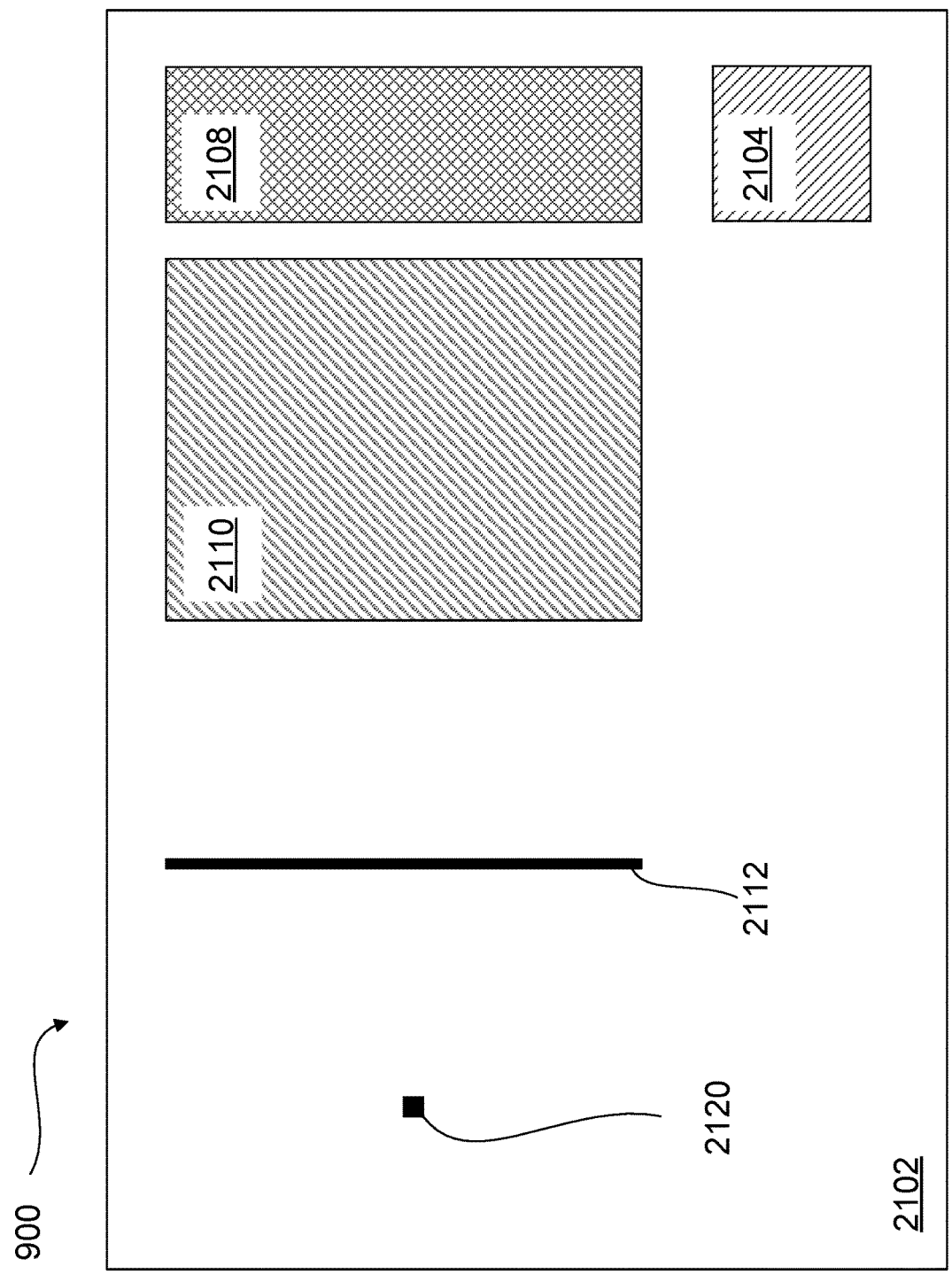
FIG. 31 is a front view of an eyepiece including a coupling optical element for coupling light into the waveguide and an out-coupling optical element for coupling light out of the waveguide to a camera wherein the coupling optical element has a non-arcuate (e.g. straight rectangular) slit-shaped coupling area. The eyepiece further includes an image content incoupling optical element for receiving light from an image projector, a light distribution element for directing light from the incoupling optical element to an out-coupling optical element for coupling light guided within the waveguide to a user for viewing image content.

FIG. 31 shows an eyepiece including a coupling optical element 2112 for coupling light into the waveguide 2102 and an out-coupling optical element 2120 for coupling light out of the waveguide 2102 to a camera wherein the coupling optical element 2112 has a non-arcuate (e.g. straight rectangular) slit-shaped coupling area included together with an image content incoupling optical element 2104 for receiving light from an image projector, a light distribution element 2108 for directing light from the image content incoupling optical element 2104 to an out-coupling optical element 2110, and an out-coupling optical element 2110 for coupling light guided within the waveguide to a user for viewing image content. In some implementations, the coupling optical element 2112 includes optical power or has a lens associated therewith that provides optical power. This optical power may collimate light from objects at a particular distance, such as from the anterior surface of the eye (e.g., cornea) to facilitate image capture of that object (e.g., glint on the cornea). The optical power the first coupling optical element 2112a and/or a lens associated therewith, may correspond to a focal length in a range from about 15 to 25 mm, 10 to 40 mm or 10 to 50 mm, 5 to 40 mm or 5 to 50 mm or any range between any of the distance values herein. Values outside these ranges are also possible.

The slit coupling optical element 2112 is displaced laterally from the out-coupling optical element 2110. In other embodiments such as shown in FIGS. 30A and 30B, the system 900 need not be included on an eyepiece with such components for presenting images to a user.

Figure 32B:
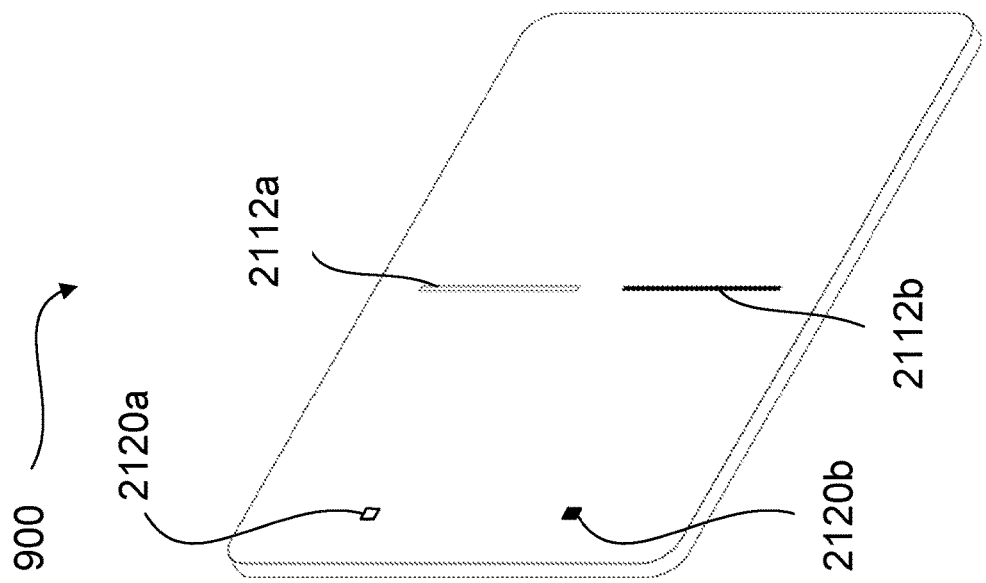
FIGS. 32A and 32B are front and perspective views a pair of coupling optical elements for coupling light into the waveguide and a pair of out-coupling optical element for coupling light out of the waveguide to a camera wherein the coupling optical elements has a non-arcuate (e.g. straight rectangular) slit-shaped coupling area. Such a configuration may be useful for imaging different portions of the eye such as the retina and the cornea (or glint thereon).
Figure 32A:
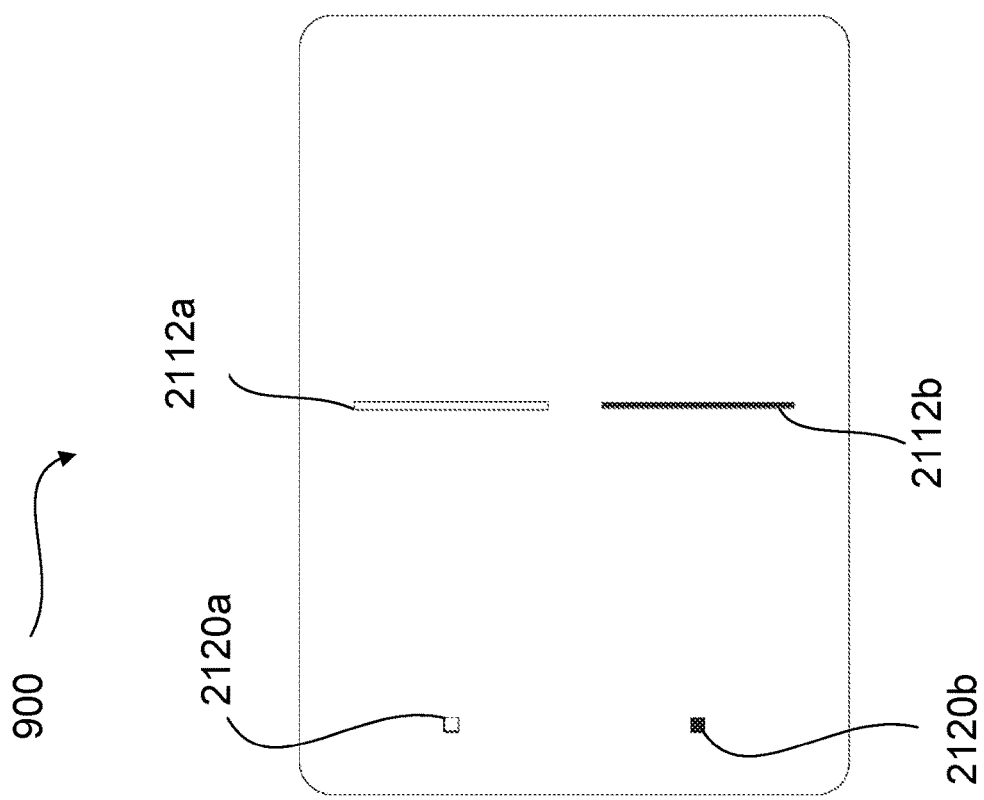

FIGS. 32A and 32B show first and second coupling optical elements 2112a, 2112b for coupling light into the waveguide 2102 and first and second out-coupling optical elements 2120a, 2120b for coupling light out of the waveguide to a camera wherein the coupling optical elements 2112am 2112b have non-arcuate (e.g. straight rectangular) slit-shaped coupling areas. Such a configuration may be useful for imaging different objects simultaneously. In some implementations, for example, different portions of the eye such as the retina and the cornea (or glint thereon) can be imaged with the pair of coupling optical elements 2112a, 2112b, the pair of out-coupling optical elements 2120a, 2120b and one or more cameras. In some implementations, the first coupling optical element 2112a has optical power or is associated with a lens while the second coupling optical element 2112b does not have a similar optical power or a similar lens (e.g., has no optical power and no lens associated therewith). In some implementations, the second coupling optical element 2112b could have optical power and/or a lens associated therewith, however, total optical power of the second coupling optical element 2112b and/or any lens associated second coupling optical element is less than the optical power of the first coupling optical element and/or any lens associated with the first coupling optical element). As discussed above, such a system 900 may be configured, for example, to image an anterior portion of the eye using the first coupling optical element 2112a and image the retina using the second coupling optical element 2112b. As discussed above, in some implementations, the eye is illuminated with light having a first polarization and the second out-coupling optical element 2120b is polarization selective or has associated therewith a polarizer configured to filter out light of the first polarization so as to remove reflections from the cornea such as glint from degrading images of the retina.

Figure 33:
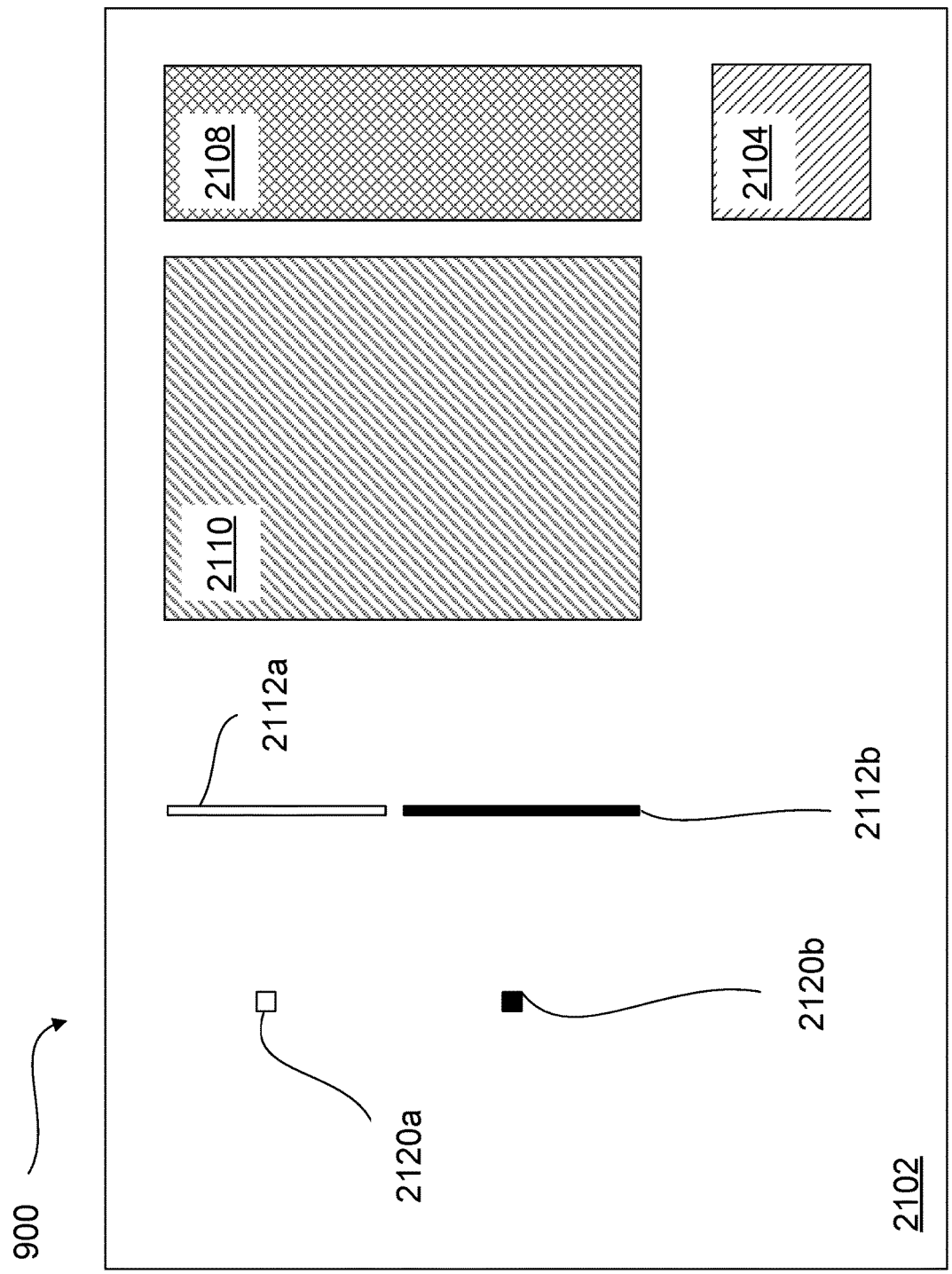
FIG. 33 is a front view of an eyepiece including a pair of coupling optical elements for coupling light into the waveguide and a pair of out-coupling optical element for coupling light out of the waveguide to a camera wherein the coupling optical elements has a non-arcuate (e.g. straight rectangular) slit-shaped coupling area. The eyepiece further includes an image content incoupling optical element for receiving light from an image projector, a light distribution element for directing light from the incoupling optical element to an out-coupling optical element for coupling light guided within the waveguide to a user for viewing image content.

FIG. 33 shows the first and second coupling optical elements 2112a, 2112b for coupling light into the waveguide 2102 and first and second out-coupling optical elements 2120a, 2120b for coupling light out of the waveguide 2102 to a camera wherein the coupling optical elements 2112am 2112b comprise a non-arcuate (e.g. straight rectangular) slit-shaped coupling area integrated on an eyepiece. The eyepiece further includes an image content incoupling optical element 2104 for receiving light from an image projector, a light distribution element 2108 for directing light from the incoupling optical element 2104 to an out-coupling optical element 2110 for coupling light guided within the waveguide 2102 to a user for viewing image content. In other embodiments such as shown in FIGS. 32A and 32B, the system 900 need not be included on a waveguide with such components 2104, 2108, 2110 for presenting images to a user.

Figure 34B:
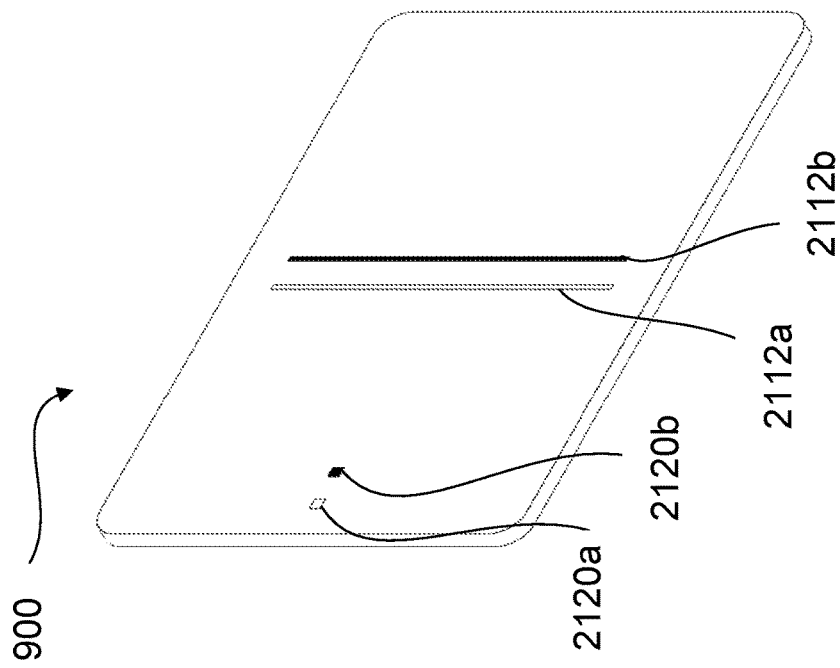
FIGS. 34A and 34B are front and perspective views of a pair of coupling optical elements for coupling light into the waveguide and a pair of out-coupling optical element for coupling light out of the waveguide to a camera wherein the coupling optical elements has a non-arcuate (e.g. straight rectangular) slit-shaped coupling area. The arrangement is different than that shown in FIGS. 32A and 32B.
Figure 34A:
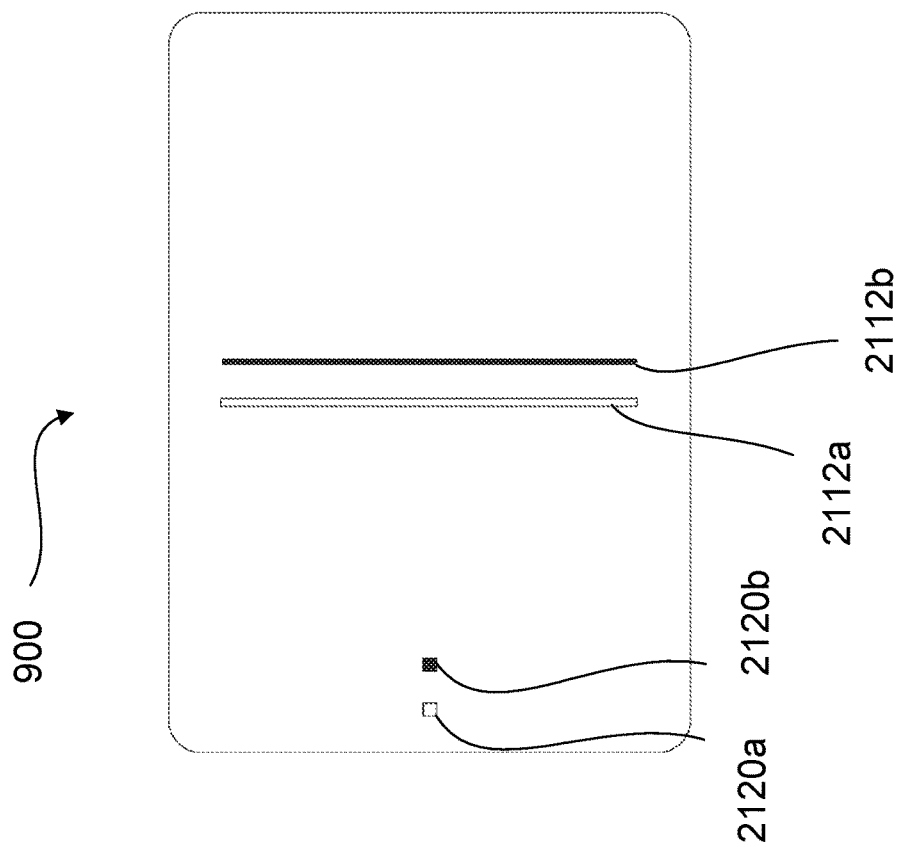

FIGS. 34A and 34B show first and second coupling optical elements 2112a, 2112b for coupling light into the waveguide 2102 and first and second out-coupling optical elements 2120a, 2120b for coupling light out of the waveguide to a camera wherein the coupling optical elements 2112a, 2112b comprise a non-arcuate (e.g. straight rectangular) slit-shaped coupling area. Such a configuration may be useful for imaging different objects simultaneously. In some implementations, for example, different portions of the eye such as the retina and the cornea (or glint thereon) can be imaged with the pair of coupling optical elements 2112a, 2112b, the pair of out-coupling optical elements 2120a, 2120b and one or more cameras. In some implementations, the first coupling optical element 2112a has optical power or is associated with a lens while the second coupling optical element 2112b does not have a similar optical power or a similar lens (e.g., has no optical power and no lens associated therewith). In particular, as discussed above, in some implementations, the second coupling optical element 2112b could have optical power and/or a lens associated therewith, however, total optical power of the second coupling optical element 2112b and/or any lens associated second coupling optical element is less than the optical power of the first coupling optical element and/or any lens associated with the first coupling optical element). The optical power of the first coupling optical element 2112a and/or a lens associated therewith, may correspond to a focal length in a range from about 15 to 25 mm, 10 to 30 mm, 10 to 40 mm or 10 to 50 mm, 5 to 40 mm or 5 to 50 mm or any range between any of the distance values herein. Values outside these ranges are also possible.

As discussed above, such a system 900 may be configured, for example, to image an anterior portion of the eye using the first coupling optical element 2112a and image the retina using the second coupling optical element 2112b. As discussed above, in some implementations, the eye is illuminated with light having a first polarization and the second out-coupling optical element 2120b is polarization selective or has associated therewith a polarizer configured to filter out light of the first polarization so as to remove reflections from the cornea such as glint from degrading images of the retina. The arrangement shown in FIGS. 34A and 34B is different than that shown in FIGS. 32A and 32B. The first and second coupling optical elements 2112a, 2112b and the first and second out-coupling optical elements 2120a, 2120b are aligned on the same axis.

Figure 35:
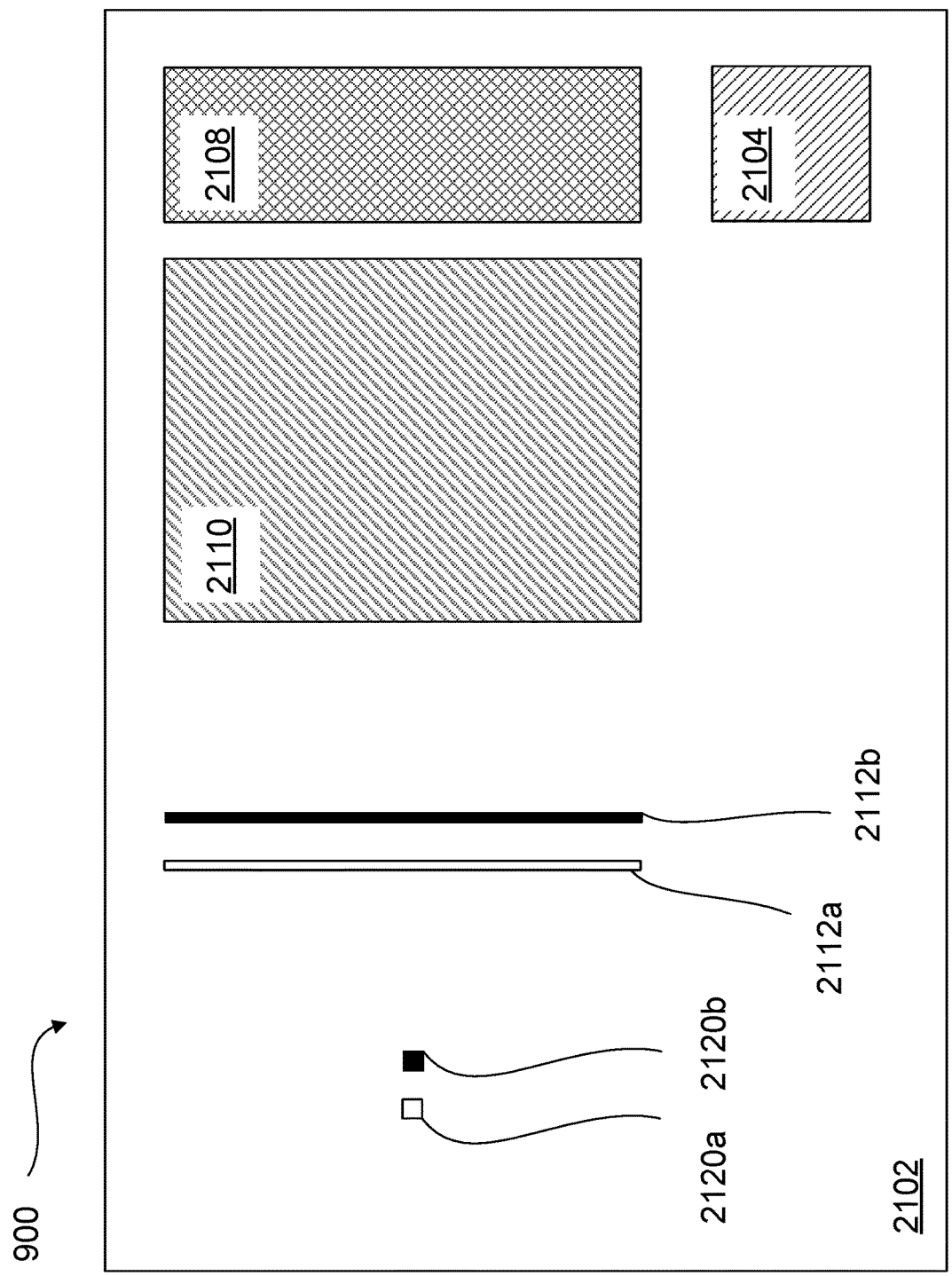
FIG. 35 is a front view of an eyepiece including a pair of coupling optical elements for coupling light into the waveguide and a pair of out-coupling optical element for coupling light out of the waveguide to a camera similar to that shown in FIGS. 30A and 30B. The eyepiece further includes an image content incoupling optical element for receiving light from an image projector, a light distribution element for directing light from the incoupling optical element to an out-coupling optical element for coupling light guided within the waveguide to a user for viewing image content.

FIG. 35 shows the first and second coupling optical elements 2112a, 2112b for coupling light into the waveguide 2102 and first and second out-coupling optical elements 2120a, 2120b for coupling light out of the waveguide 2102 to a camera similar to that shown in FIGS. 33A and 33B. The coupling optical elements 2112am 2112b comprise non-arcuate (e.g. straight rectangular) slit-shaped coupling areas aligned along a common axis and integrated on an eyepiece. The eyepiece further includes an image content incoupling optical element 2104 for receiving light from an image projector, a light distribution element 2108 for directing light from the image content incoupling optical element 2104 to an out-coupling optical element 2110 for coupling light guided within the waveguide 2102 to a user for viewing image content. In other implementations, such as shown in FIGS. 34A and 34B, the system 900 need not be included on a waveguide with such components 2104, 2108, 2110 for presenting images to a user.

As discussed above, polarization techniques can be used to attenuate or remove light from the anterior surfaces (e.g., corneal surfaces) from affecting images formed by light collected by the second coupling optical element 2112b. For example, the eye can be illuminated with polarized light having a first polarization and the camera can form an image using light from the second out-coupling optical element 2120b using light of a second different polarization. For example, the second out-coupling optical element 2112b may be a polarization selective coupling element that selectively couples out light of the second polarization different than the first polarization. Additionally or alternatively, a polarizer 2140 that filters out the first polarization (e.g., selectively transmits the second polarization) may be included between the second out-coupling optical element 2120b and the camera 920 as illustrated in FIG. 27.

Such a configuration may be used to reduce unwanted reflections (e.g., glint), such as from the cornea when imaging the retina. Reflection from the cornea will be specular. Accordingly, if light of the first polarization is incident on the cornea, the light reflected from the cornea will retain that first polarization. In contrast, the retina is diffuse. If light of the first polarization is incident on the retina, the light reflected from the retina does not retain solely the first polarization. The diffuse reflection more likely results in unpolarized light. Accordingly, the second polarization, different from the first polarization will be present in the light reflected from the retina. As a result, by forming images with light coupled out of the second out-coupling optical element 2120b using light of the second polarization, images of the retina will be obtained while images of the cornea or glint will be suppressed. Likewise, by illuminating with a first polarization and imaging with a second different polarization, the retina can be image with reduced glare from the cornea.

Accordingly, in various implementations, polarization specific optical filters or polarization selective optical elements (e.g. coupling gratings) may be used to reduce unwanted reflected light from the eye 210 (e.g., from the cornea). For example, unwanted light, glare, or glint may be reflected off the cornea that may saturate an image captured by the camera. As discussed above, light reflected from the cornea may be specular and maintain its polarization. By contrast, light reflected off the retina may be more diffusely reflected and may be less homogenously polarized. Likewise, a combination of polarizers may be used to remove some or most of the unwanted light reflected from the cornea. Initially polarized light can be used for illuminating the eye of the user. In some designs, a polarized illumination source (e.g., the light source) may be used. Additionally or alternatively, a first polarizer (e.g., a polarization specific optical filter or a polarization selective optical coupling element coupling illumination light into an illumination waveguide) may be positioned at the beginning of the optical path of the illumination source to provide initial polarization of the light to the eye. A second polarizer (e.g., a polarization specific optical filter or polarization selective coupling element) may be positioned at the optical path before the light enters the camera. The second polarizer may be rotated at 90° from the first polarizer (e.g. the polarizers may be "crossed"). As a result, the eye will be illuminated with the first polarization with some light of the first polarization reflected from the cornea. This light will not pass through the crossed polarizer (that preferentially passes light of the second polarization) located proximal the camera. However, light reflected from the retina will include the second polarization. Likewise, light diffusely reflected from the retina will pass through the polarizer 2140 proximal the camera and will enable an image of the retina to be captured by the camera. Thus, in such configurations, unwanted light received from the eye (e.g., from cornea) and entering the camera may be reduced or eliminated from the images captured using light from the second coupling optical element 2112b. Other configurations are possible. For example, a polarization selective coupling elements 2112b and/or a polarization selective out-coupling optical elements 2120b may be used in addition or in alternative to polarizers such as the polarizer 2140 proximal the camera. Additionally or alternatively, a polarized light source may be used for illumination (e.g., illuminating the eye). The effect may again be to reduce or remove unwanted light received from the eye (e.g., from cornea) before entering the imaging device 920.

As illustrated in FIG. 27, in various implementations, such polarizers are not used in an optical path from the first coupling optical element 2112a and the camera or between the first out-coupling optical element 2120a and the camera. As a result, images of the cornea and glint may be obtained from light coupled by the first coupling optical element 2112a into the waveguide and/or light coupled out of the waveguide from the first out-coupling optical element 2120a. As discussed above, this first coupling optical element 2112a may have optical power or a lens associated therewith that is specifically used to image the cornea and/or glint. Likewise, polarization selective coupling optical elements 2112a or polarization selective out-coupling optical element 2120a that filter out light of the first polarization would not be used as the first coupling optical element 2112a and out-coupling optical element 2120a, respectively. Additionally, polarizers 2140 between the coupling optical element 2112a and the camera 920 or between the out-coupling optical element 2112a and the camera 920 that filter out light of the first polarization would not be used.

Systems for Illuminating the Eye

As mentioned above, eye tracking can be a useful feature in augmented and mixed reality technologies. Glint-based eye tracking systems can utilize the reflections of light off of the eye, e.g., the cornea, potentially to provide a determination of the gaze direction of the eye. Systems described herein may be configured to direct light to the eye from a light output that is relatively close to the eye. Having the light output closer to the eye may reduce system level complexities of the glint based eye tracking system. However, placing a light output too near to the eye may result in unwanted visual occlusion. The view of the environment in front of the wearer of the head mounted display may, for example, be occluded by a light source if disposed in front of the viewer close to the eye. Therefore, in some embodiments, various systems described herein include a structure that is configured to be placed in front of the eye so as to provide eye illumination without substantially occluding the viewer's field of view of the environment in front of the head mounted display.

For example, a thin layer of material that may be transparent can be disposed in front of the eye without excessive visual occlusion. A light output for directing light onto the eye, e.g., for glint based tracking, can be incorporated into the transparent layer that is placed in front of the eye. As will be discussed below, for example, an elongate light guide such as an optical fiber or optical rod may be included in the transparent layer to output light to the eye. In some implementations, the transparent layer itself may comprise a planar waveguide for conveying light to the eye. Such configurations may reduce obstructions to the user's field of view.

The transparent layer can be included in a head mounted display configured to project light to a user to display augmented reality image content in a field of vision of the user. The head mounted display may comprise a frame configured to be supported on the head of the user. The transparent layer may be supported on the frame and disposed at a location in front of the user's eye when the user wears the head-mounted display such that the transparent portion transmits light from an environment in front of the user to the user's eye to provide a view of the environment in front of the user.

Figure 36A:
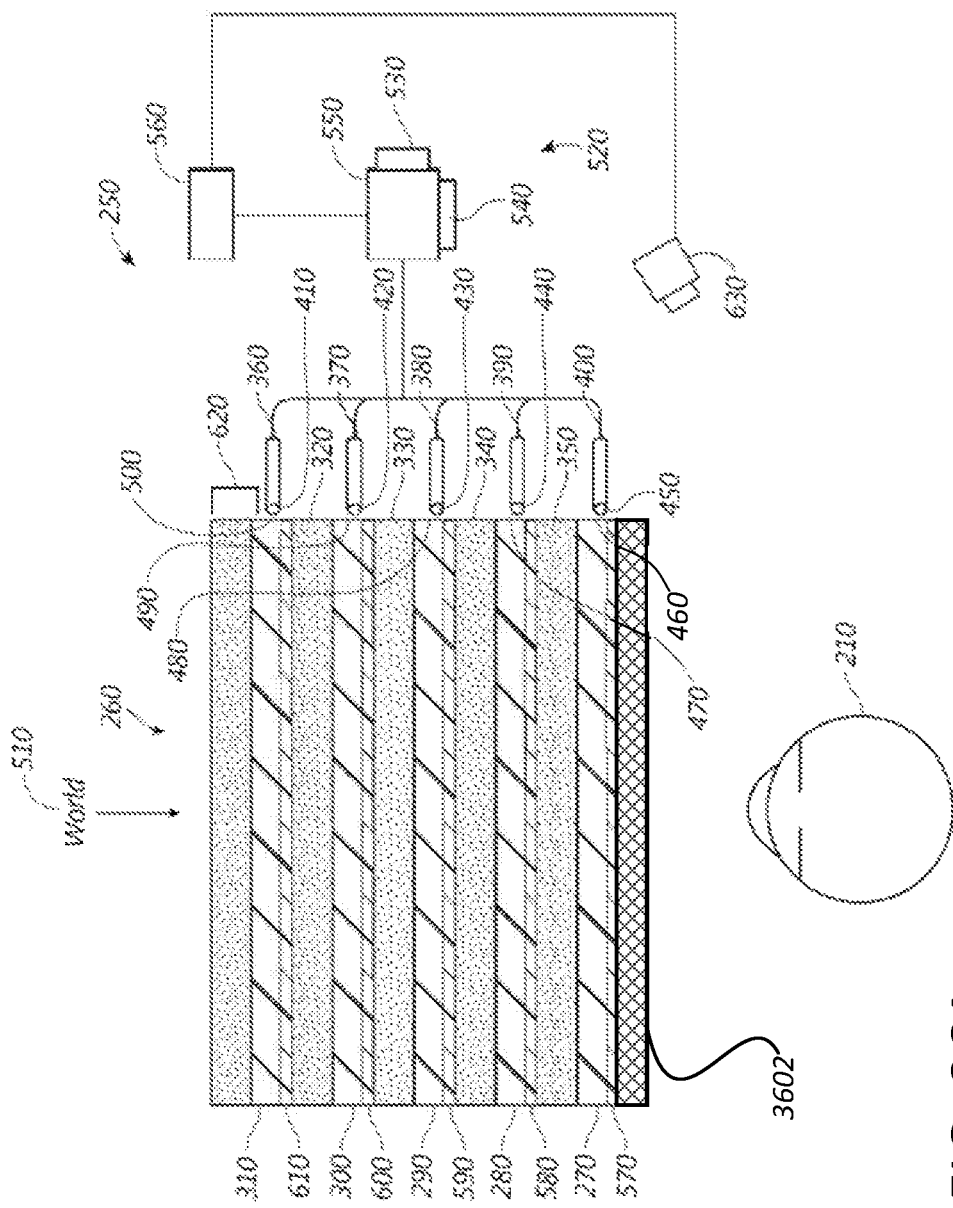
FIGS. 36A and 36B are side views of transparent layers that can be integrated into an eyepiece to direct light to the eye and used, for example, for glint based gaze tracking.
Figure 36B:
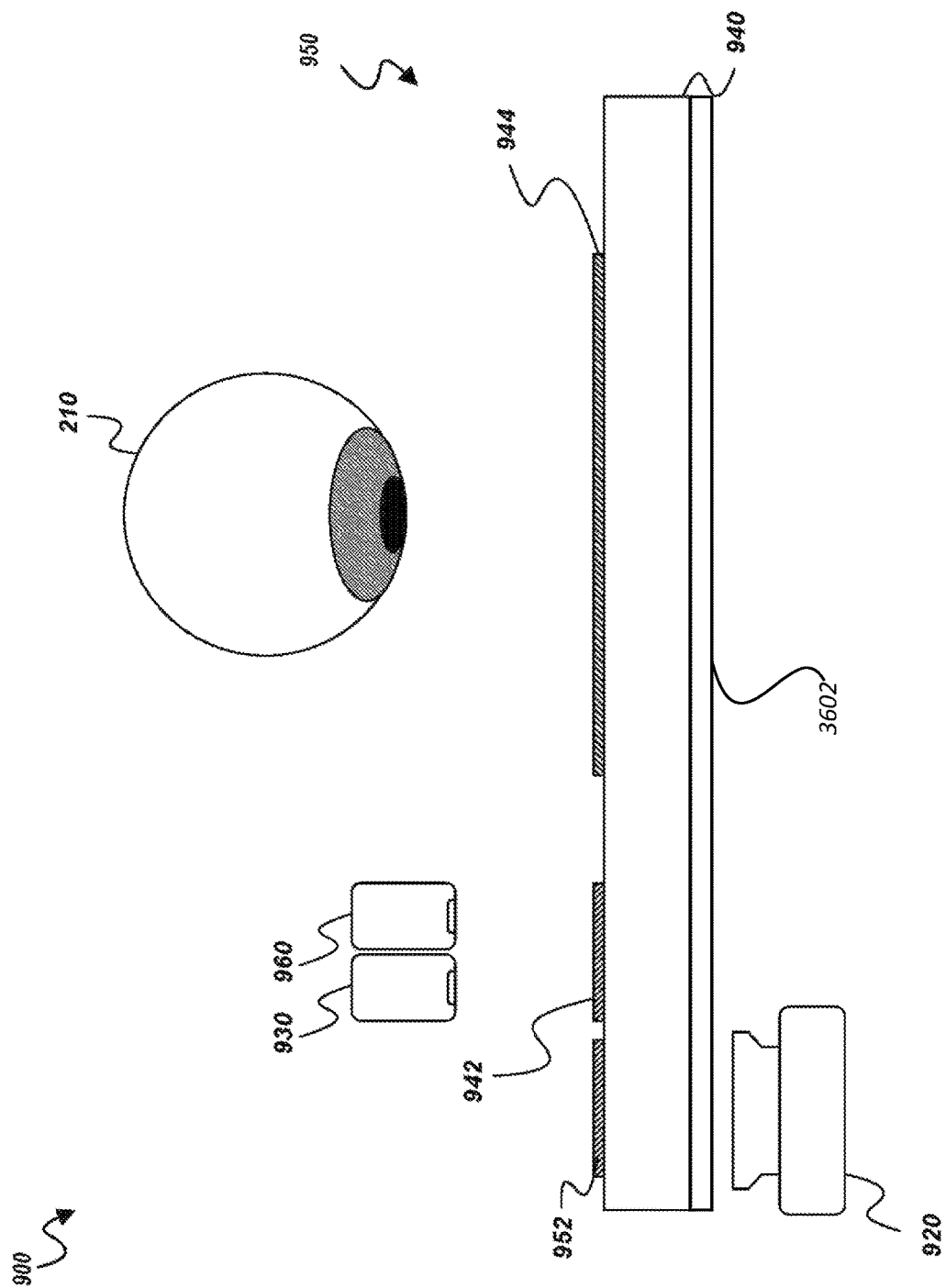

As shown in FIG. 36A, the transparent layer 3602 may be included as part of a stacked waveguide assembly 260 similar to that shown in FIG. 6. The layer 3602 is in front of the user's eye 210 such that light can be directed onto the eye potentially from a relatively short distance from the eye. The transparent layer 3602, however, may be disposed at any number of positions within an eyepiece. For example, FIG. 36B, which shows an eye eyepiece 950 similar to that shown in FIG. 10, depicts the transparent layer 3602 disposed on the opposite side of the waveguide 940 as the eye 210. The waveguide 940, therefore, is between the transparent layer 3602 and the eye 210. In many implementations, however, the waveguide 940 is sufficiently thin such that the transparent layer 3602 and the light output associated therewith is nevertheless sufficiently close to the eye. As discussed above, the waveguide 940 can be used to both project image content into the eye 210 as well as collect light reflected from the eye 210 to image the eye on a camera 920.

Figure 37A:
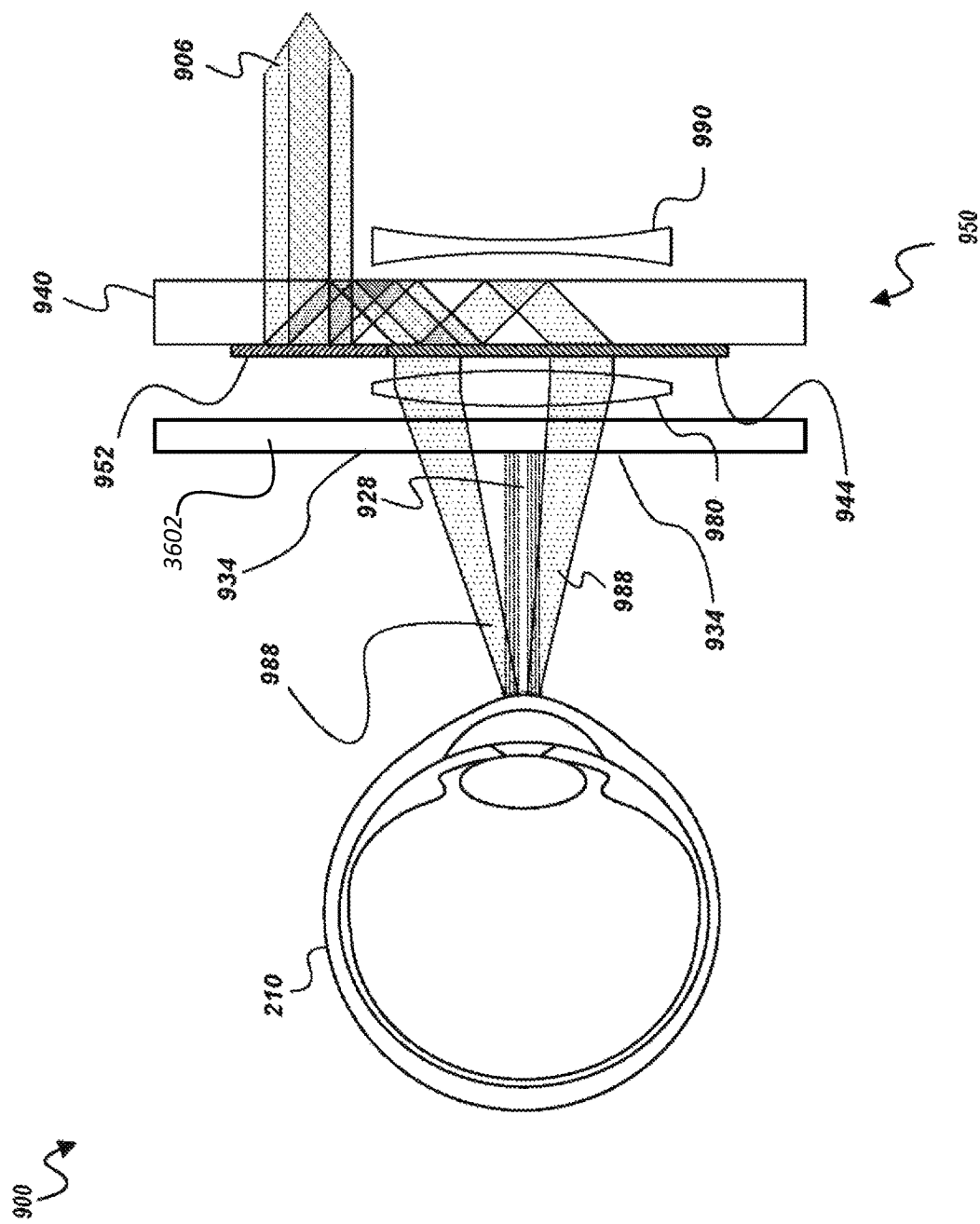
FIGS. 37A and 37B are side views showing example transparent layers for directing light to the user's eye positioned at different locations in an eyepiece.
Figure 37B:
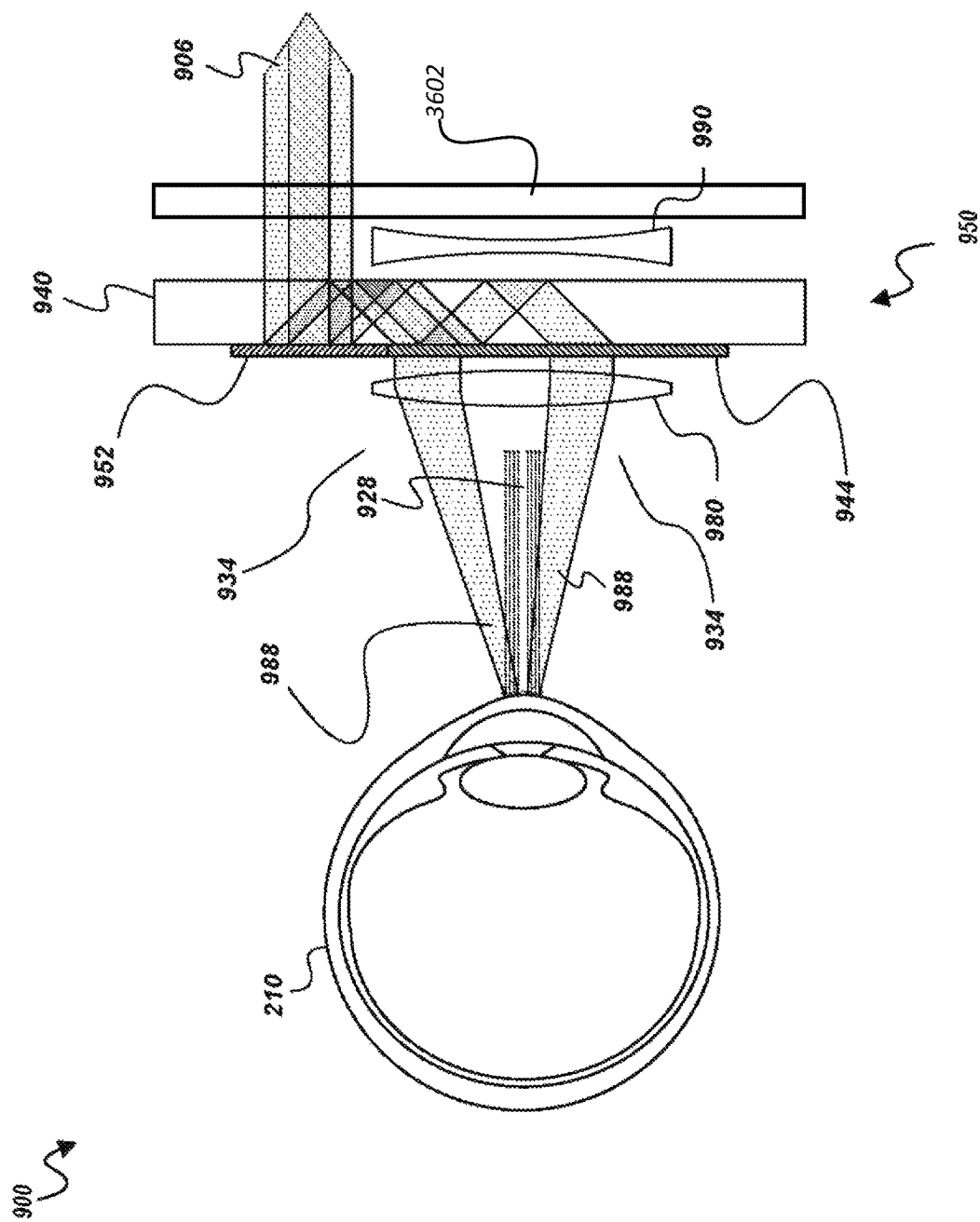

FIGS. 37A and 37B also show eyepieces 950, similar to the configurations shown in FIG. 16, including a waveguide 940 for collecting light reflected from the eye to obtain images the eye. The eyepiece 950, however, further comprises a transparent layer 3602 configured to direct light to the eye 210. In the design shown in FIG. 37A, the transparent layer 3602 is disposed rearward of the waveguide 940 (e.g., closer to the eye 210) and is thus between the waveguide and the eye. Alternatively, FIG. 37B illustrates the transparent layer 3602 disposed forward the waveguide 940 (e.g., closer to the environment in front of the user) such that the waveguide is between the transparent layer and the eye 210.

Examples Illumination Structures

The transparent layer 3602 may comprise a material or combination of materials that are transparent to visible light (e.g., glass, plastic). For example, the transparent layer 3602 may comprise a polymer substrate, such as a polycarbonate layer. In some implementations, the transparent layer 3602 comprises multiple sublayers stacked together. For example, the transparent layer 3602 may comprise an inner region sandwiched between outer regions forward and rearward of the inner region. In some designs, for example, an inner light guiding region (e.g., UV cured adhesive) is disposed between sheets (e.g., of plastic or glass). In some implementations, the inner region comprises plastic and the outer regions may comprise glass. Other configurations, however, are possible.

Figure 38A:
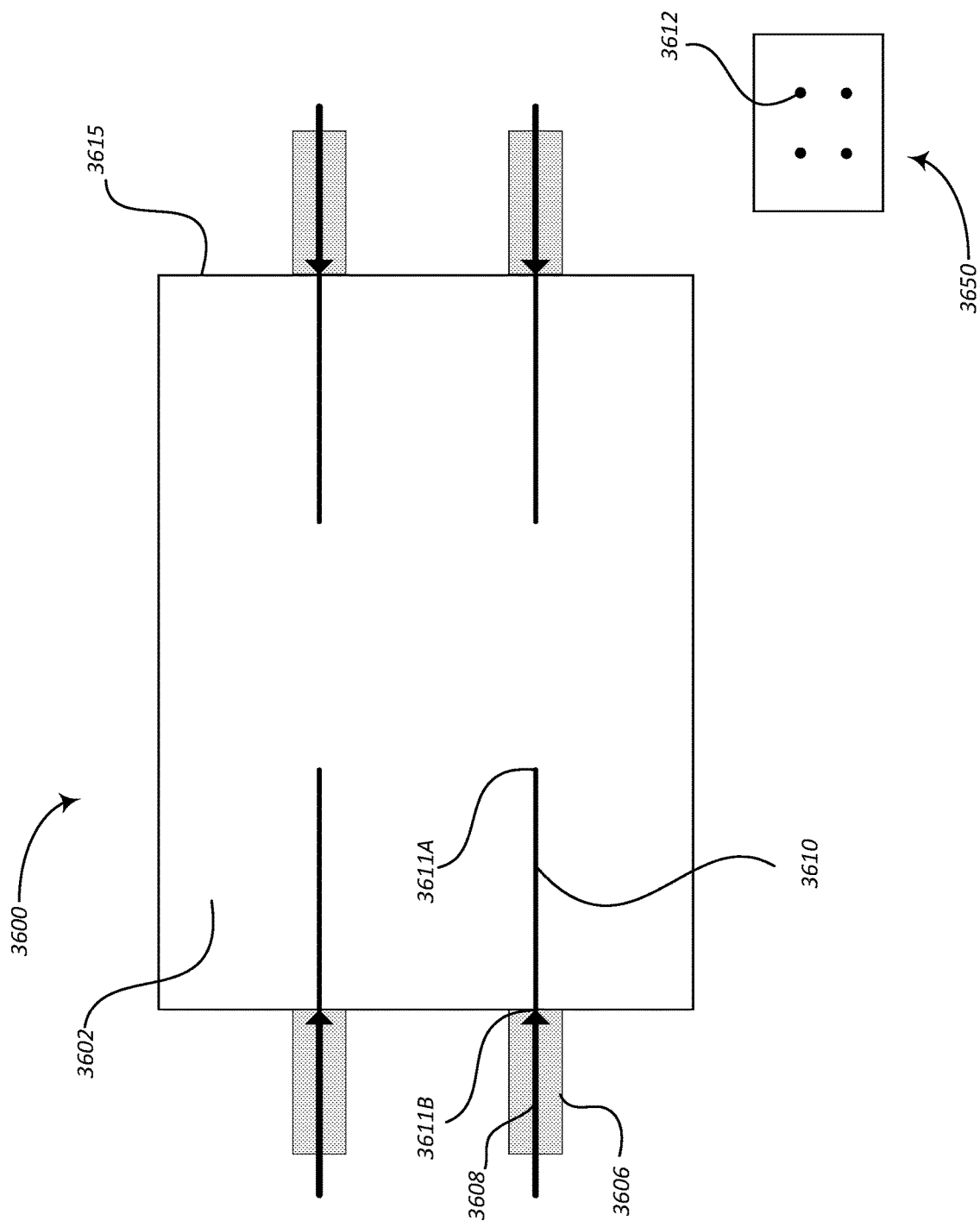
FIGS. 38A and 38B are front and side views of an example transparent layer including a plurality of optical fibers therein that can be configured to direct light towards the eye.
Figure 38B:
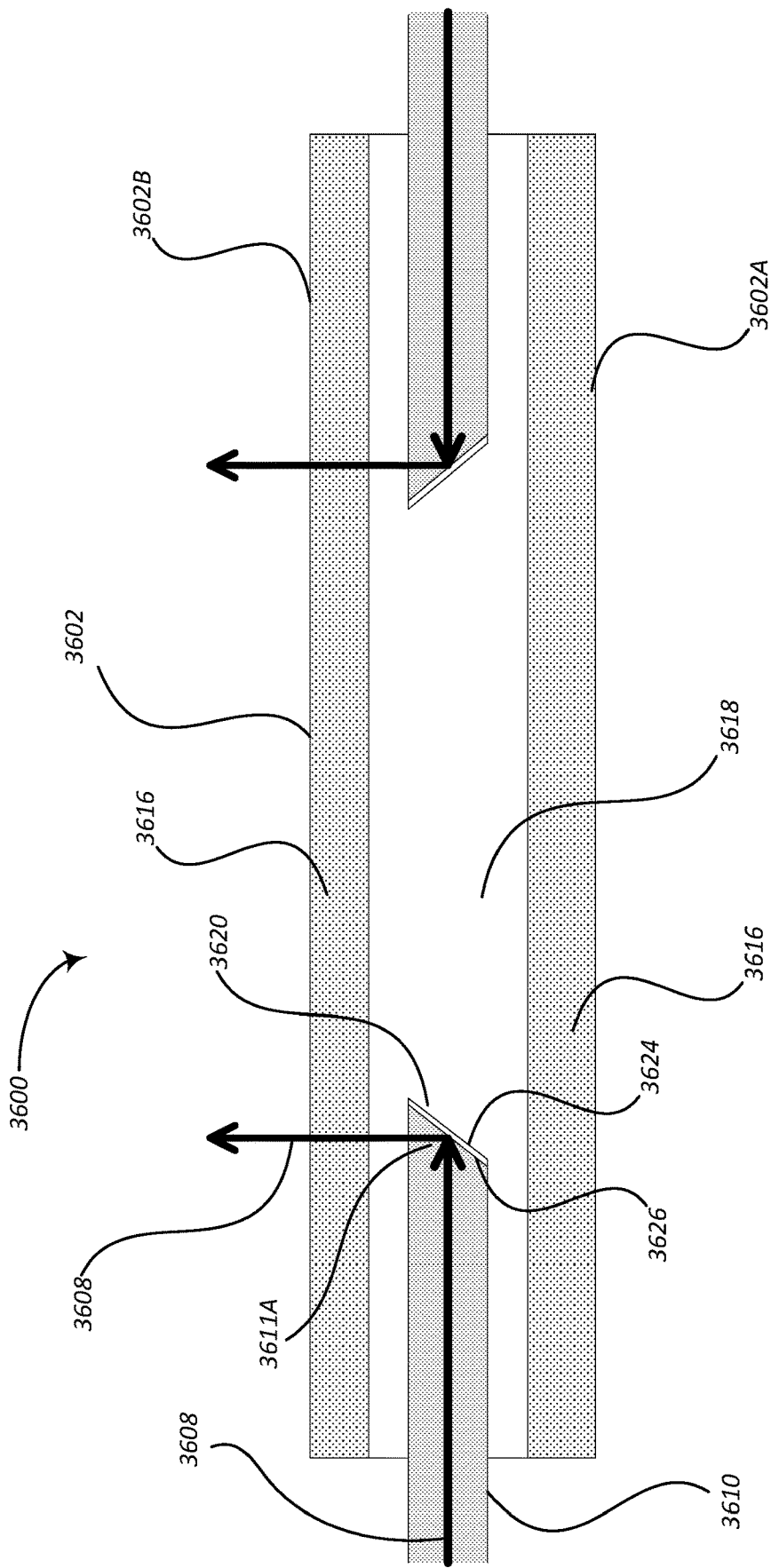

FIGS. 38A-38B illustrate two views of an eye illumination system 3600 comprising a transparent layer 3602 with elongate light guides 3610 included therein for conveying and directing light to the eye. The elongate light guide may have a length, a width, and thickness where the length is much longer than the width and/or thickness. For example, an elongate light guide may have a length at least 10 times as long as the width and/or thickness, possibly 50 times as long, 100 times as long or more or may be within any range formed by any of these values. The elongate light guide may include dimensions or range of dimensions outside these ranges in some implementations.

In the example of FIGS. 38A-38B, the elongate light guides 3610 comprise optical fibers 3610 within the transparent layer 3602. As shown in FIG. 38A, the elongate light guide 3610, in this case the optical fiber, has a first end 3611a and a second end 3611b, the first end being disposed within the transparent layer 3602 and more centrally located than the second end. In this implementation, the second end 3611b is disposed at the perimeter or edge 3615 of the transparent layer 3602.

The second end 3611b includes an input for receiving light, for example, from a light source 3606 such as an LED, laser, or another optical fiber or optical coupler. In some embodiments, the second end 3611b may be physically coupled to the light source or may be physically coupled to an optical coupler, which may, in turn, be physically coupled to the light source. In some implementations, the optical fiber may be relatively long or may extend outward beyond the surface of the transparent layer such that the second end 3611b may be substantially displaced from the transparent layer. In some of these implementations, two or more optical fibers may be routed to a same or common light source. The first end 3611a of the optical fiber 3610 may have an output for emitting light such that the light is directed to the eye 210. The light output may comprise a relatively small aperture, for example, the light output may have an aperture size between 5 µm and 160 µm (e.g., 9 µm, 50 µm, 62.5 µm, 100 µm) or any range formed by any of these values. The aperture size may also be outside these ranges in some implementations. Accordingly, in some implementations, the output of the optical fiber 3610 at the first end may be treated as a point source.

FIG. 38A shows four elongate light guides 3610 (e.g., four optical fibers) in the transparent layer 3602. In some implementations, the optical fibers 3610 may be arranged so that the first ends 3611a of the optical fibers 3610 form four corners of a square or rectangular shape. However, the optical fibers 3610 may be arranged in any number of configurations and the ends 3611a, 3611b may be disposed at any location.

Additionally, the number of elongate light guides 3610 (e.g., optical fibers) may be more or less than four. In some implementations, a lens or other optics may be included at the first end 3611a, e.g., to collimated the light. In some implementations, a diffuser may be included at the output to diffuse the light output from the first end 3611a of the fiber. As discussed above, in various implementations, the plurality of elongate light guides (optical fibers) 3610 may have outputs that create point sources illuminating the eye 210. For example, as illustrated in inset 3650 of FIG. 38A, a set of four elongate light guides (e.g. optical fibers) 3610 in a transparent layer 3602 having four respective outputs may form a square pattern of outputs (e.g. bright spots, point sources) 3612. As discussed above, the number and/or arrangement of the outputs, however, may be different.

As discussed above, one or more elongate light guide 3610 may comprise one or more optical fibers. The optical fiber 3610 may comprise a core and cladding that surrounds the core. Light can be guided within the core via total internal reflection off the cladding. The optical fiber 3610 may comprise a single-mode or multi-mode optical fiber. The optical fiber 3610 may have a core diameter having a range of, for example, between about 8 µm and 110 µm such as, e.g., approximately 9 µm, 50 µm, 62.5 µm, or 100 µm, or any ranges formed by any of these values. The core diameter of the optical fiber 3610 may be outside these ranges as well. The optical fiber 3610 may comprise material that is transparent to visible light and in some implementations index matching material may be included around the optical fiber to reduce reflection from the optical fiber. Accordingly, when the user views the environment in front of the head mounted display device through the transparent layer 3602, the optical fiber 3610 may obstruct vision to a relatively minor extent.

In various implementations, the elongate light guides 3610 are embedded in the transparent layer 3602. Additionally, as discussed above, the transparent layer 3602 may comprise multiple layers in certain designs. FIG. 38B, for example, shows the transparent layer 3602 comprising a plurality of layers, namely, a pair of outer layers or regions 3616 on opposite sides of an inner layer or region 3618. In particular, the transparent layer 3602 may comprise a pair of transparent covers 3616 and transparent material in which elongate light guides (e.g., optical fibers) 3610 are embedded. The transparent material comprising the inner region 3618 is sandwiched between the transparent covers 3616. The transparent covers 3616 may comprise a material that is transparent to visible light (e.g., glass, plastic) and may comprise sheets that provide mechanical support, for example, during and/or after manufacturing in certain cases. The transparent material comprising the inner region 3618 may comprise material that is also transparent to visible light and that may provide index matching to the optical fiber (e.g., with the cladding of the optical fiber) and/or with the covers to reduce reflection and obscuration of the view of the eye. In some implementations, this material in the inner region 3618 comprises a liquid or gel, possibly an adhesive, during the manufacture stage. The liquid, gel, or adhesive, may solidify prior to use of the eye illumination system 3600. The material in the inner region 3618 in which the elongate light guide (e.g., optical fiber) 3610 is embedded may be cured to transform the material, for example, into a stronger, or more solid, rigid, or stable structure. This material may comprise, for example, a curable adhesive such as a UV curable adhesive. The elongate light guide 3610 may be disposed between the covers 3616 in the curable material, and the material may be cured or otherwise solidified, hardened, or stabilized to fix the elongate light guide in place in the transparent layer 3602. Other methods of fabricating the device, however, are possible.

In various implementations, a reflecting or light deflecting surface or element 3620 is provided at the first end 3611a of the elongate light guide 3610 to eject light out of the elongate light guide 3610 toward the user's eye. FIG. 38B, for example shows, the first end 3611a of the elongate light guide (e.g. optical fiber) 3610 has a reflective surface or reflector 3620 configured to couple light through the output of said optical fiber 3610 in a particular direction. In particular, the reflective surface or reflector 3620 may be positioned at an angle with respect to the length of the elongate waveguide guide 3610 and/or with respect to the front and/or rear surfaces 3602a, 3602b of the transparent layer 3602. The angled reflector 3620 may reflect incident light 3608 that is guided within the optical fiber 3610 from a light source 3606 towards the eye 210. In some implementations such as shown in FIG. 38B, the reflective surface or reflector 3620 may be angled to direct light out through the rear surface 3602b of the transparent layer 3602 toward the user's eye. The angled reflector 3620 may comprise an angled end 3626 of the elongate light guide 3610 such as an angled end of the optical fiber. For example, the angled reflector 3620 may comprise a cleaved or beveled surface at the first end 3611a of said optical fiber 3610. The angled surface 3626 of the optical fiber 3610 may have an angle between 35 and 55 degrees (e.g., 45 degrees) with respect to the length of the optical fiber 3610 that extends along the length of the transparent layer 3602. The angled end surface 3626 of the optical fiber 3610 may be polished in some implementations. The angled reflector 3620 may additionally comprise a reflective coating 3624 to increase reflectivity. For example, the reflective coating 3624 may comprise metal or other type of coating that increases the efficiency of the reflection of incident light 3608 off of the angled reflector 3620. This reflective coating 3624 may be disposed on to the angled surface 3626 as shown in FIG. 38B. In some embodiments, a diffuser may be used at the angled end 3626 of the elongate light guide 3610 or the end of the elongate light guide may otherwise be configured to diffuse the light exiting therefrom. A diffuser may, in some cases, advantageously increase the output cone angle of the light 3608 out of the transparent layer 3602 towards the eye 210.

Figure 39:
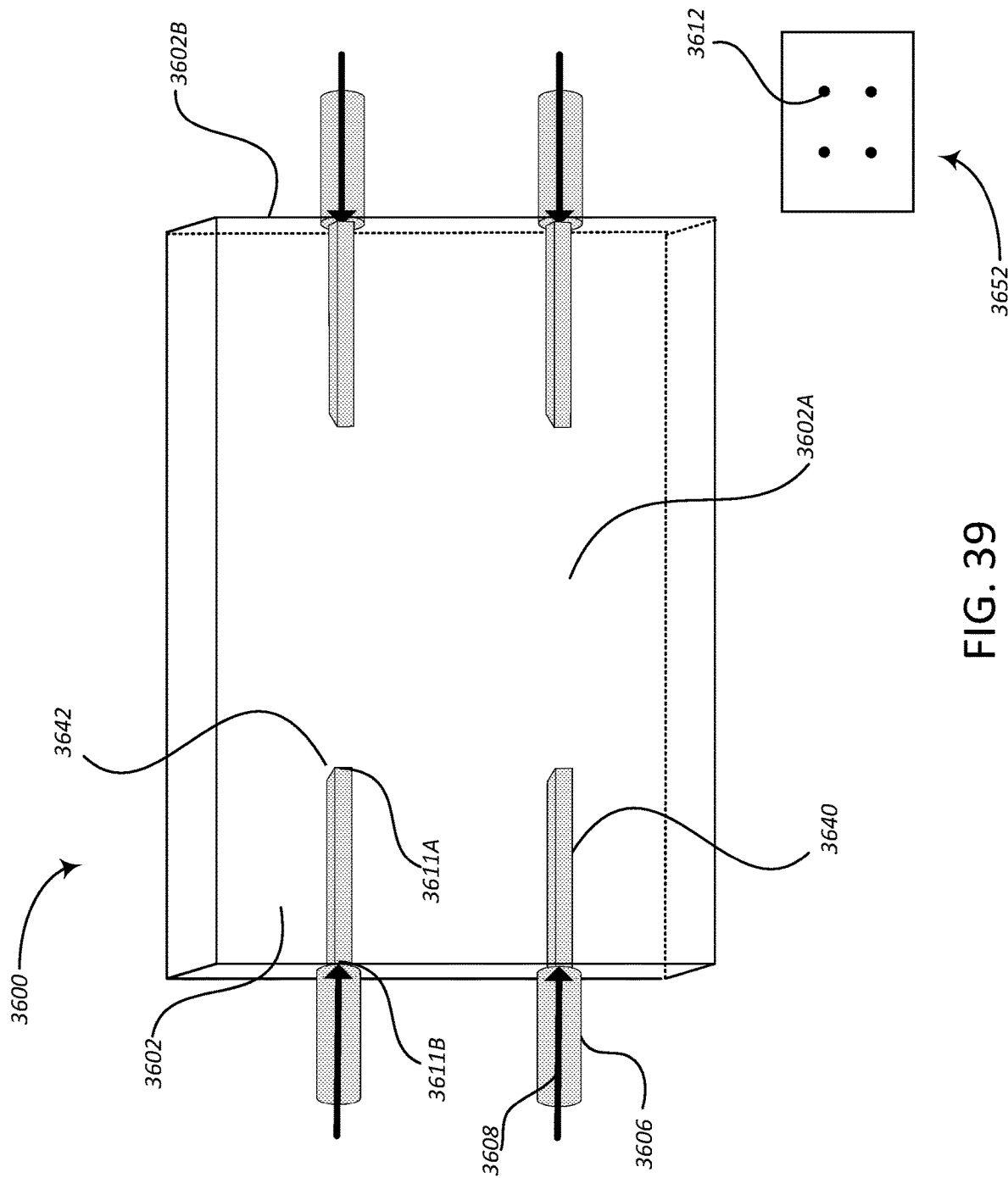
FIG. 39 is a perspective view of an example transparent layer including a plurality of optical rods therein that can be configured to direct light towards the eye.

As discussed above, the elongate light guide 3610 may comprise optical fibers as shown in FIGS. 38A-38B, however, the elongate light guide 3610 may comprise other types of light guides or light pipes. For example, FIG. 39 illustrates a perspective view of an eye illumination system 3600 employing at least one optical rod 3640 embedded in a transparent layer 3602. The optical rod 3640 may comprise a material whose index of refraction is different from the surrounding waveguide such that light may be guided therein along the length of the optical rod 3640 by total internal reflection. This material may be transparent to visible light and may comprise, for example, glass or plastic in some designs. As discussed above, the elongate light guide, in this case an optical rod 3640, may have a length and a width and thickness where the length is much longer than the width and/or thickness. For example, an elongate light guide may have a length at least 10 times as long as a width and/or thickness, possibly 50 times as long, 100 times as long, 150 times as long, 200 times as long or more, or any range formed by any of these values. The elongate light guide may also include dimensions or ranges of dimensions outside these ranges. In some implementations, an optical rod 3640 may be more rigid than an optical fiber. In some implementations, the rod 3640 may be larger (wider or thicker) than the core of an optical fiber. The optical rod 3640 may comprise any number of shapes. The rod 3640 may, for example, comprise a cylindrical shape such as a right circular cylinder or a rectangular prism. Accordingly, for some designs, the rod may have a circular or rectangular cross-section perpendicular to its length. Other shapes are possible. For example, the rod 3640 may be conical in some cases. The width and/or thickness of the rod 3640 may be from 50 µm to 400 µm or 250 µm to 350 µm (e.g., 300 µm) or any range between any of these values. The dimensions (e.g., width and/or thickness) of the rod 3640 may be outside these ranges as well.

FIG. 39 shows the optical rod 3640 having first end 3611a that is embedded in transparent layer 3602. In some implementations, the rod 3640 comprises material having a higher index than the material comprising the transparent layer 3602. This configuration may cause light to be guided within the rod 3640. The light reflects off sidewalls of the rod 3640 as a result of totally internally reflection at the interface between the high index rod and the lower index material of the transparent layer 3602. Other configurations, however, may be employed.

Also as shown in FIG. 39, the rod 3640 may have a reflective surface or reflector 3642 configured to direct light out of the rod at an angle with respect to the length of the rod. In various implementations such as shown, this reflector 3642 may be angled with respect to the length of the optical rod 3640 and/or the front and/or rear surfaces 3602a, 3602b of the transparent layer 3602. In particular, the reflector 3642 may comprise an angled surface that may be configured to reflect light 3608 from a light source 3606 that is guided within the optical rod 3640 towards the eye 210. For example, the angled surface may comprise a beveled surface at the first end 3611a of the optical rod 3640. The angled surface may comprise a surface with an angle between 35 and 55 degrees (e.g. 45 degrees) with respect to the length of the optical rod 3640 that extends along the length of the transparent layer 3602. In various implementations, a reflective coating may be applied to the angled end. The reflective coating may comprise metal or other type of coating that increases the efficiency of reflection of the incident light 3608 off of the angled reflector 3642 out of the transparent layer 3602. As discussed above, in some implementations, a diffuser can be included at the first end 3611a of the optical rod 3640, for example, possibly to increase the output cone angle of the light directed towards the eye 210.

As discussed above, the elongate light guide such as the optical rod 3640 may be embedded in transparent layer 3602. The optical rod 3640 may, for example, be embedded in transparent material within the transparent layer 3602. In some implementations, for instance, the material in the inner region in which the elongate light guide (e.g., rod) 3640 is embedded may be cured to transform the material, for example, into a stronger, or more solid, rigid, or stable structure that solidifies, hardens, and/or stabilizes to fix the rod in place in the transparent layer 3602.

In other implementations, the elongate light guide (e.g., rod) 3640 may be disposed within a channel or cavity of the transparent layer 3602. The transparent layer 3602 may, for example, have a channel or cavity designed to accept or house the elongate light guide 3640. The channel or cavity may be larger than the diameter or width of the elongate light guide 3640. For example, the elongate light guide 3640 may be a rectangular prism with a width or height of 150 µm and the transparent layer 3602 may have a channel or cavity with a width or height of 200 µm. The elongate light guide 3610 may be secured in the channel or cavity with a transparent material within the channel or cavity. Other methods of fabricating the device, however, are possible.

As shown in FIG. 39, at least one optical rod 3640 may be included in the transparent layer 3602. Although four such rods 3640 are shown, more or less rods may be employed. In some embodiments, the optical rod 3640 may be placed within the transparent layer 3602 so that the first ends 3611a of the optical rod 3640 form four corners of a square or a rectangle. However, the optical rod 3640 may be placed in any number of arrangements or configurations within the transparent layer 3602.

The first end of the at least one optical rod 3640 may comprise an output that creates a point source or the like illuminating the eye 210. Likewise, the plurality of optical rods 3640 may each have outputs that create point sources illuminating the eye 210. For example, as illustrated in inset 3652 of FIG. 39, a set of four optical rod 3640 embedded in a transparent layer 3602 may create a square pattern of outputs (e.g., bright spots, point sources) 3612. Other patterns, however, may be used. Such arrangements may be useful in eye tracking or estimation of the location, dimensions, or other characteristics of anatomical features of the user's eye such as the center of curvature of the cornea.

Accordingly, as discussed above, the transparent layer 3602 may include a plurality of optical outputs 3612. These optical outputs 3612 may comprise the optical output of elongate light guides 3610, 3640 such as the outputs of optical fibers or optical rods. These optical outputs 3612 may have a height and/or width of between 5 µm and 600 µm. For example, these optical outputs 3612 may have a height and/or width of between 5 µm and 160 µm (e.g., 9 µm, 35 µm, 50 µm, 62.5 µm, or 100 µm), 160 µm and 600 µm (e.g., 200 µm, 300 µm, or 400 µm), or any range between any of these values. The dimensions (e.g., width and/or thickness) of the elongate light guide (e.g., fibers, rods) 3610, 3640 may be outside these ranges as well. Angled reflective surfaces may, in part, establish the dimensions of the optical outputs 3612. As discussed above, the angled reflective surface may comprise an angled cleaved optical fiber, an engineered optical rod, or other angled surface. The angled reflective surface may be disposed in the transparent layer.

The light may be provided by one or more light sources 3606 optically connected to the elongate light guides 3610, 3640. The one or more light sources 3606 may comprise one or more infrared light sources. The one or more light sources 3606 may comprise one or more light emitting diodes (LEDs) or lasers. Other types of light sources 3606 may possibly be used. In some implementations, the one or more light sources 3606 may have outputs that are disposed at or proximal to the edge 3615 of the transparent layer 3602 to couple light therein.

The transparent layer 3602 may, however, be configured differently to direct light to the user's eye. FIGS. 40A-40E, for example, illustrate variants, eye illumination systems 3600 employing at least one tilted reflective surface 3630 embedded in a transparent layer 3602 to direct light out of the transparent layer to the eye. The transparent layer 3602 may comprise at least one tilted reflective surface 3630 included therein to receive light guided, for example, by total internal reflection within the transparent layer. The at least one tilted reflective surface 3630 may be angled such that light guided within the transparent layer 3602 is reflected from the tilted surface 3630 and directed through the rear major surface 3602b out of the transparent layer 3602 to the eye 210.

The transparent layer 3602 may comprise a plurality of waveguide regions or optical channels 3632, 3636 therein that receive light from one or more light sources 3606 and guide light from the light source within the waveguide regions by total internal reflection. The waveguide regions 3632, 3636 may, for example, comprise optically transparent material having an index of refraction higher than that surrounding the waveguide region such the light is reflected from sidewalls of the waveguide regions by total internal reflection. Additionally, the waveguide regions 3632, 3636 may include tilted reflective surfaces 3630 that deflect the light guided within the waveguide region out, for example, the rear surface 3602b of the transparent layer 3602 toward the eye.

Figure 40A:
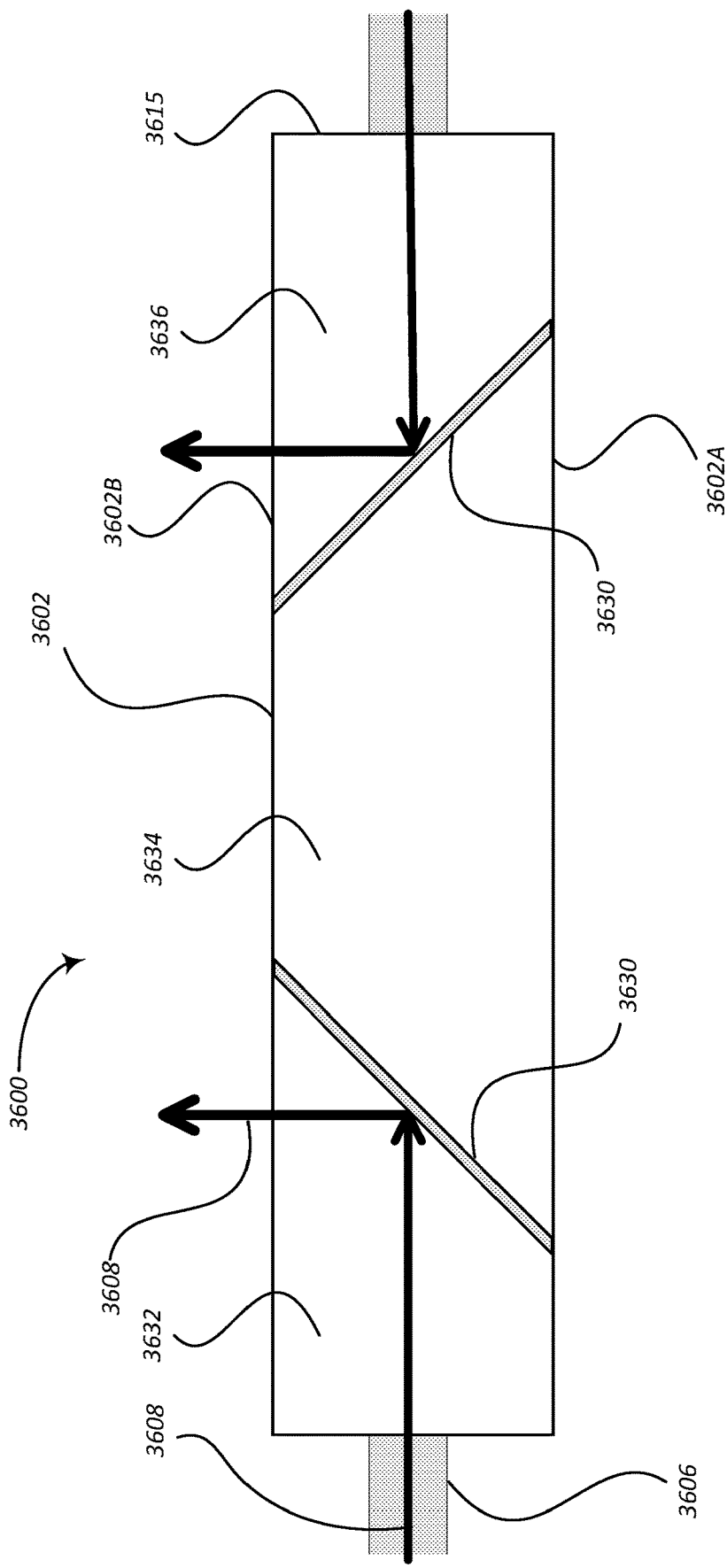

For example, as illustrated in FIG. 40A, which is a cross-section through an example transparent layer 3602, the transparent layer may comprise a set of regions: first and second waveguide regions 3632, 3636, and a third transparent region 3634 therebetween. The first waveguide region 3632 has a first tilted (e.g., inclined) reflective surface 3630 and the second waveguide region 3636 has a second tilted (e.g., inclined) reflective surface 3630. The third transparent region 3634 can also have first and second counter-part tilted (e.g., declined) surfaces. In some implementations, the inclined reflective surfaces 3630 of the first and second waveguide regions 3632, 3636 abut the first and second counterpart declined surfaces of the third transparent region 3634. In some implementations, one or more intervening layers may be included between the first waveguide region 3632 and the third transparent region 3634 as well as between the second waveguide region 3636 and the third transparent region. For example, the one or more intervening layers may include a tilted surface 3630. The tilted surface 3630 may comprise a reflective coating. For example, the reflective coating may be an IR-reflective coating. For example, the reflective coating may be a metallization. In some embodiments, the tilted surface 3630 may be transparent to some or all of the visible spectrum. In various implementations, the first and second waveguide regions 3632, 3636 and the third transparent region 3634 comprise a material or materials that are transparent to visible light such as glass or plastic. In various implementations, the first and second waveguide regions 3632, 3636 may comprise material having a refractive index such that light may be guided therein by total internal reflection between major surfaces.

Figure 40B:
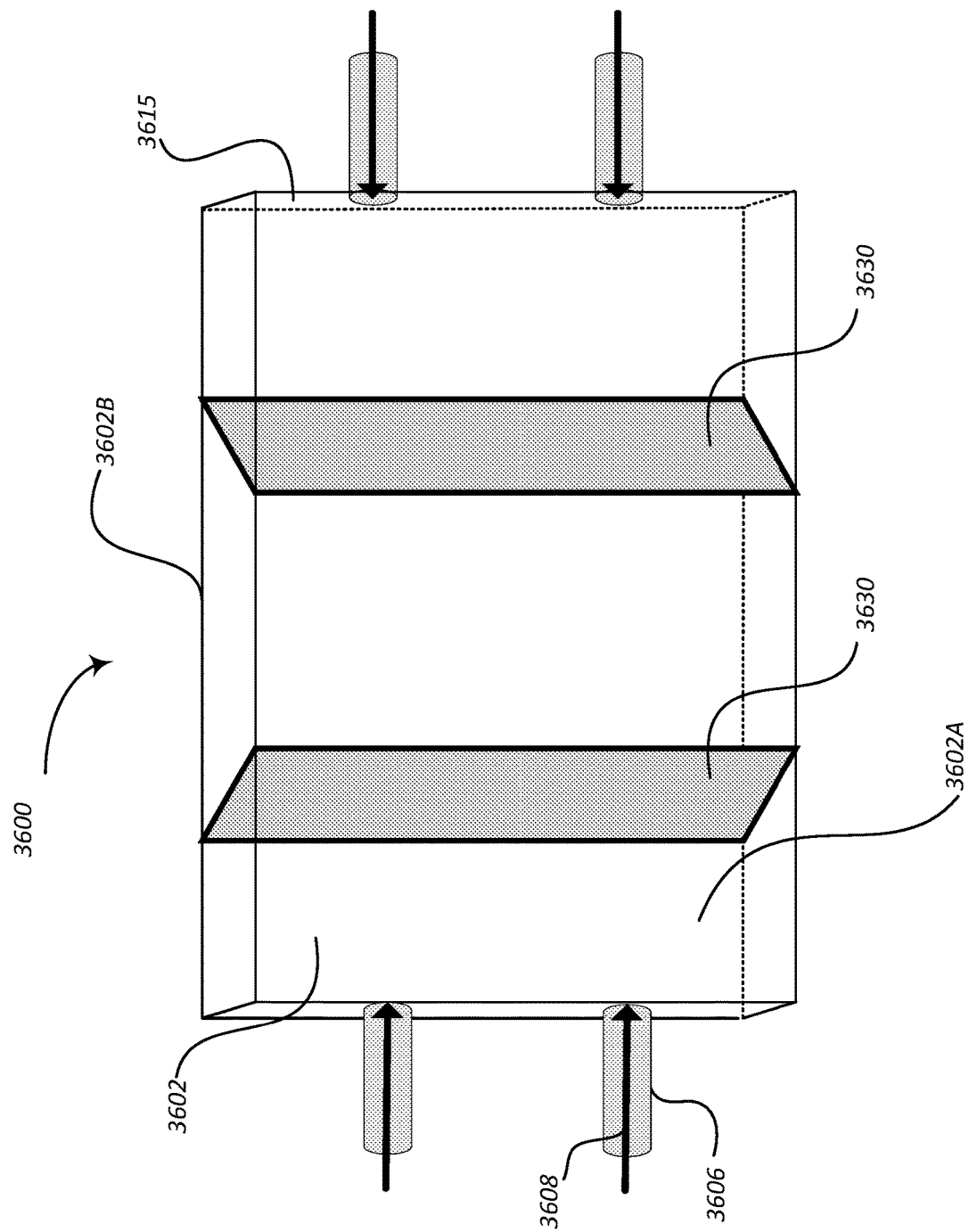

FIGS. 40B and 40C are perspective and top views, respectively, of an example transparent layer 3202 showing at least one light source 3606 disposed with respect to at least one edge 3515 of the transparent layer such that light 3608 from the at least one light source 3606 is injected into the at least one transparent layer, e.g., into the first and second waveguide regions 3632, 3636. Light 3608 may propagate through first and second waveguide regions 3632, 3636, be incident on a tilted surfaces 3630 and reflected therefrom through the rear surface 3602b and toward the eye 210. The tilted reflective surface 3630 may comprise a surface that is angled with respect to a major surface (e.g., front and rear surfaces 3602a, 3602b) of the transparent layer 3602. The tilted surface 3630 may be angled such that light 3608 guided within the transparent layer 3602 is reflected from the tilted surface 3630 and directed through a major surface (e.g., rear surface 3602b) of the transparent layer 3602 towards the eye 210. For example, the tilted surface 3630 may comprise a surface that forms an angle between 35 and 55 degrees (e.g., 45 degrees) with respect to a major surface of the transparent layer 3602. The tilted surface 3630 may comprise a polished surface. A reflective coating may be applied to portions of the tilted surface 3630.

The reflective coating may comprise metal or other coating that increases the efficiency of reflection of light propagated through the waveguide or set of waveguides. In some embodiments, the reflective coating may be an IR reflective coating. As illustrated in the top view shown in FIG. 40C, the tilted reflective surface 3630 is oriented vertically (e.g., extends superiorly-inferiorly) with respect to the head mounted display and the user's head as opposed, for example, to extending horizontally (e.g., nasally-temporally) and having light sources on the upper and lower edges 3615.

As shown, the at least one light source 3606 may comprise a plurality of spaced apart light sources 3606 such as lasers and/or LEDs disposed at the edge 3615 of the transparent layer 3602. In some implementations, reflection of light output from the discrete light sources 3606 off the tilted reflective surface 3630 may create a plurality of outputs 3612 (possibly corresponding to point sources) illuminating the eye 210. Accordingly, the geometry (e.g., shape, orientation) of the at least one tilted reflective surface 3630 may affect the resultant arrangement and/or location of the outputs 3612 (e.g., point source(s)). For example, as illustrated in the inset 3654A of FIG. 40C, the two tilted surfaces 3630 embedded in a transparent layer 3602 (also shown in FIGS. 40A and 40B) may create a square arrangement of outputs (e.g., bright spots, point sources) 3612 when paired with the set of four light sources 3606 shown. A similar pattern of reflections or glints may be observed on the eye. Variation in the number and/or position of the light sources 3606 may alter the arrangement. For example, the pattern of outputs (e.g., point sources) and corresponding reflection off the eye (e.g., glints) may be rectangular, triangular, or otherwise, depending possibly on the location and number of light sources.

Figure 40D:
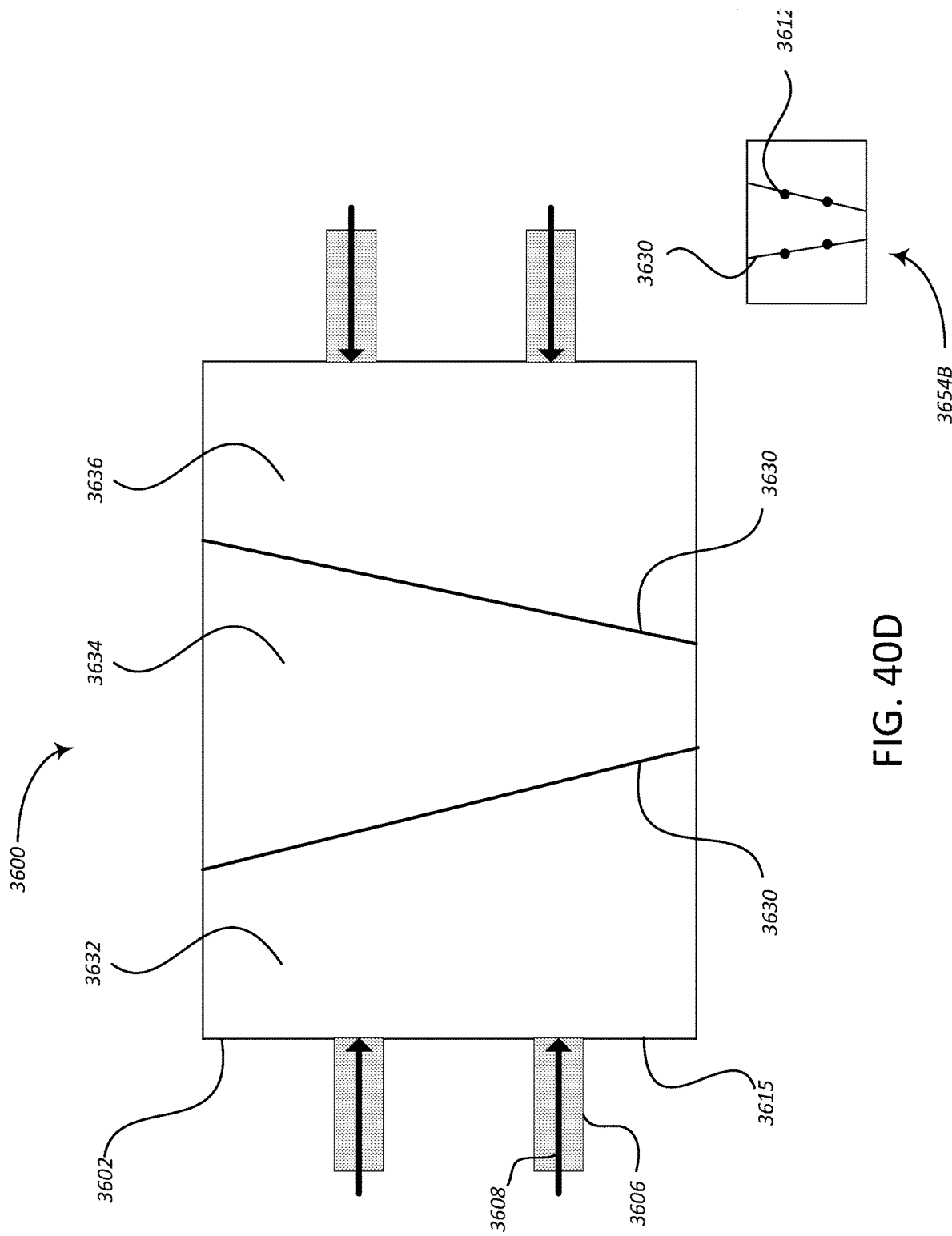
FIGS. 40D-40F are top views of additional example designs of transparent layers that include a plurality of tilted surfaces configured to reflect light guided through the transparent layer towards the eye.
Figure 40E:
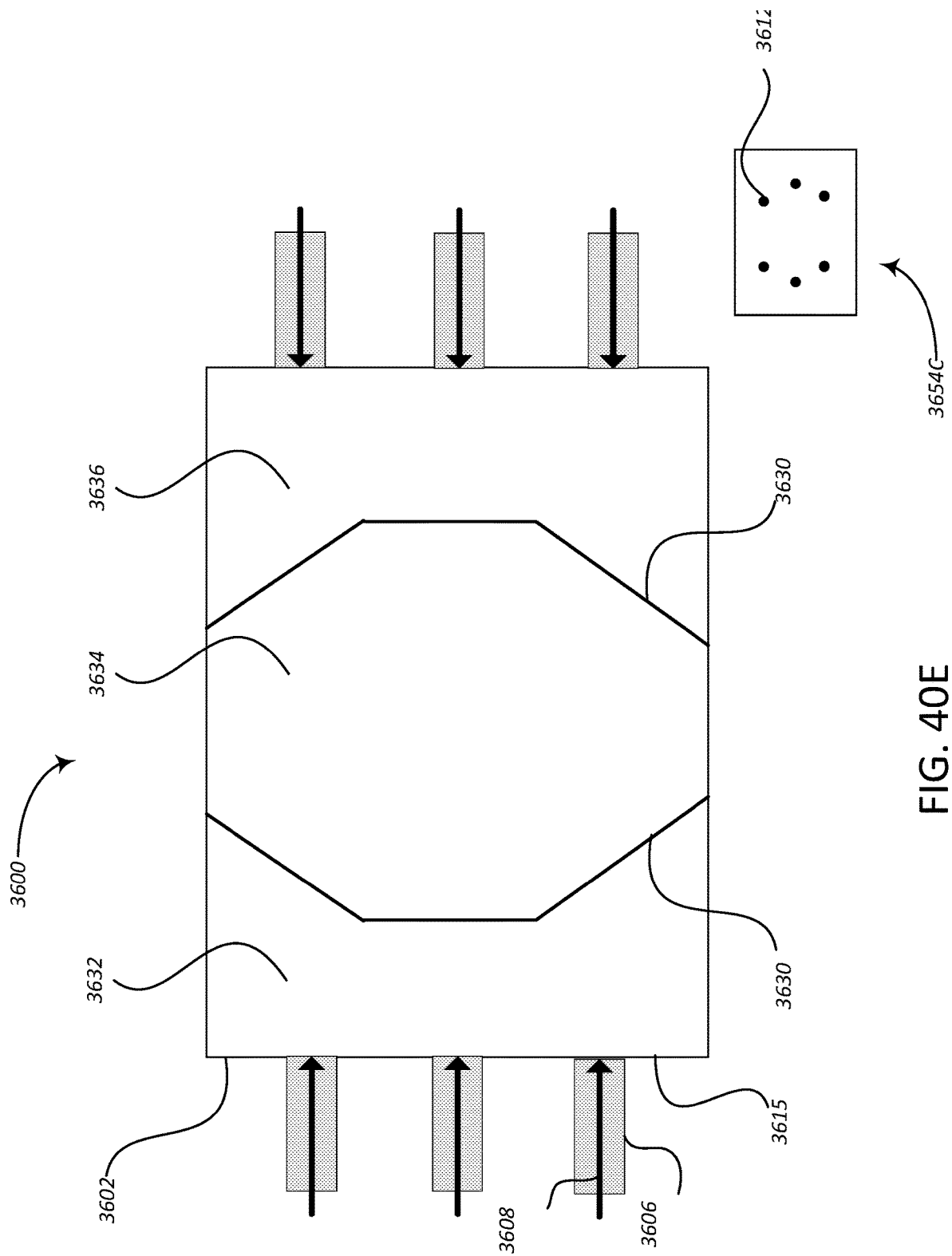
Figure 40F:
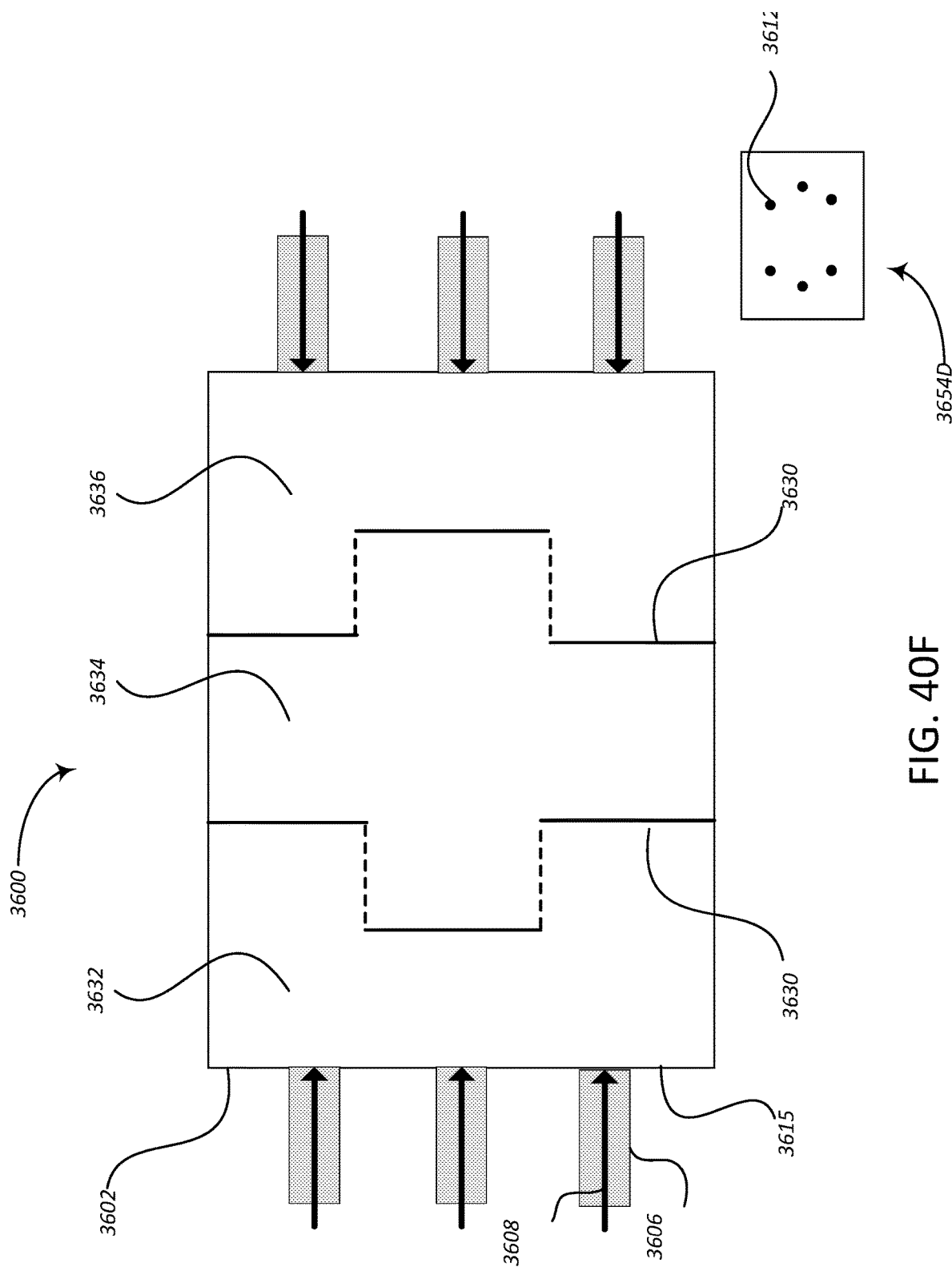

Variations in the number, shape, position, and/or orientation of the at least one tilted reflective surfaces 3630 are also possible. For example, although two tilted reflective surfaces 3630 are shown in FIGS. 40B and 40C, only one tilted surface may be employed in some implementations. The light sources 3606 may be included on only one side of the transparent layer 3602 in such an example design. As another example, the orientations (with respect to the vertical and horizontal directions) of the tilted reflective surface 3630 may be different. Moreover, the orientations (with respect to the vertical and horizontal directions) need not be the same for different tilted reflective surfaces included in a single transparent layer 3602. FIG. 40D, for example shows a transparent layer 3602 including a pair of tilted reflective surfaces 3630 oriented at an angle (e.g., by +15 and −15 degrees) with respect to the vertical direction of the head mounted display and head of the user. Two light sources 3606 are disposed on opposite sides of the transparent layer 3602 in the example shown. The orientation of the tilted reflective surfaces 3630 with respect to the vertical of the head mounted display and the user's head is such that an upper pair of the resultant outputs (e.g., bright spots, point sources, etc.) 3612 may be farther apart than a lower pair of outputs (e.g., bright spots, point sources, etc.) as illustrated in the inset 3654B of FIG. 40D. A similar pattern of reflections or glints may be observed on the eye. Although four light sources 3606 are shown, more or less light sources and hence outputs (e.g., bright spots, point sources, etc.) 3612 may be employed. Similarly, the number of light sources 3606 on each side of the transparent layer 3602 need not be the same. Additionally, the tilted reflective surfaces 3630 may be oriented differently with respect to the vertical of the head mounted display and the user's head. Any angle from horizontal to vertical may be possible. In another example, a hexagonal pattern of outputs (e.g., bright spots, point source, etc.) 3612 may be created by having a hexagonal arrangement of tilted reflective surfaces 3630 such as shown in FIG. 40E and the respective inset 3654C. A similar pattern of reflections or glints may be observed on the eye. As illustrated, six light sources 3606 are used, three on each side of the transparent layer 3602. A hexagonal pattern of outputs (e.g., bright spots, point sources) 3612 may also be produced by another configuration of tilted reflective surfaces 3630 illustrated by the top view of the transparent layer 3602 shown in FIG. 40F. Again, six light sources 3606 are used. The lateral (e.g., nasal versus temporal) position of the tilted reflective surfaces 3630 may result in the outputs (e.g., bright spots, point sources, etc.) 3612 produced by the light sources 3606 being displaced with respect to each other causing the laterally displaced light outputs (e.g., bright spots, point sources, etc.) 3612 shown in the inset 3654D of FIG. 40F. Again, similar pattern of reflections or glints may be observed on the eye.

As discussed above, the tilted reflective surfaces 3630 may be oriented differently with respect to the vertical and horizontal. For example, instead of the tilted reflected surfaces 3630 being vertical, the tilted reflective surfaces may be horizontal in some designs. In such cases, the light sources 3606 may be included on the upper and/or lower sides of the transparent layer 3602.

In any of the design discussed herein, a light source 3606 may be optically coupled to the transparent layer 3602 thereby injecting light therein. One or more optical coupling element, for example, lens or other optics may be used in various implementations. The light source 3606 may be configured to emit a wavelength or band of wavelengths of light, which may include invisible (e.g. infrared, near infrared, etc.) or visible light.

As described herein, the eye illumination system 3600 may be used to transmit light 3608 towards the eye 210 such that the light reflected off of the angled reflector 3620 of the optical fiber 3610, angled reflector 3642 of the optical rod 3640, or tilted reflective surface 3630 of the waveguide regions or optical channels may produce reflections off the cornea of the eye 210. In some cases, the light from the transparent layer 3602 corresponds to point sources. Similarly, the reflection 3612 off the cornea may comprise localized points or glints. The light reflected off of the cornea may then be received by a camera. In various implementations, by analyzing the corneal reflections, the gaze direction of the eye 210 may be determined.

EXAMPLES

Any of the following Examples or Additional Examples can be combined. Additionally, any of the following Examples or Additional Examples can be integrated with a head mounted display. In addition, any of the following Examples or Additional Examples can be implemented with a single depth plane and/or with one or more depth planes and/or one or more variable depth planes (e.g., one or more elements with variable focusing power that provide accommodation cues that vary over time).

Example Section I

1. A head mounted display system configured to project light to an eye of a user to display augmented reality image content in a vision field of said user, said head-mounted display system comprising:

a frame configured to be supported on a head of the user;
an image projector configured to project images into the user's eye to display image content in the vision field of the user;
a camera;
at least one waveguide;
at least one coupling optical element configured such that light is coupled into said waveguide and guided therein; and
at least one out-coupling element configured to couple light guided within said waveguide out of said waveguide and direct said light to said camera,
wherein the camera is disposed in an optical path with respect to said at least one out-coupling optical element to receive at least a portion of the light that is coupled into said waveguide via the coupling element and guided therein and that is coupled out from said waveguide by said outcoupling coupling element such that images may be captured by said camera.

2. The system of Example 1, wherein said at least one coupling optical element is configured such that light from the environment in front of the user wearing the head mounted display system is coupled into said at least one waveguide and guided therein such that images of said environment may be captured by said camera.

3. The system of any of the Examples above, wherein said at least one coupling optical element is configured such that light reflected from the eye of the user wearing the head mounted display system is coupled into said at least one waveguide and guided therein such that images of said eye may be captured by said camera.

4. The system of any of the Examples above, wherein said at least one coupling optical element is configured such that light reflected from the eye of the user wearing the head mounted display system is coupled into said waveguide and guided therein such that images of said eye may be captured by said camera, said system configured to image an anterior portion of said eye.

5. The system of any of the Examples above, wherein said at least one coupling optical element is configured such that light reflected from the eye of the user wearing the head mounted display system is coupled into said waveguide and guided therein such that images of said eye may be captured by said camera, said system configured to image a corneal surface of said eye.

6. The system of any of the Examples above, wherein said at least one coupling optical element is configured such that light reflected from the eye of the user wearing the head mounted display system is coupled into said waveguide and guided therein such that images of said eye may be captured by said camera, said system configured to image the retina of said user's eye.

7. The system of any of the Examples above, further comprising an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user.

8. The system of Example 7, wherein said eyepiece is configured to receive light from said image projector and to direct said light into said user's eye to display augmented reality image content to the user's vision field.

9. The system of any of Examples 7-8, wherein said eyepiece comprises said at least one waveguide.

10. The system of any of Examples 7-9, wherein said image projector is configured to direct light into an edge of said eyepiece.

11. The system of Examples 9 or 10, wherein said image projector is configured to direct light into an edge of said at least one waveguide.

12. The system of any of the Examples above, further comprising at least one in-coupling optical element configured to in-couple light from said image projector into said at least one waveguide so as to guide light from said image projector for providing said image content to said user's eye.

13. The system of any of the Examples above, wherein said at least one coupling optical element is also configured to couple light from said image projector guided within said waveguide out of said at least one waveguide such that image content can be viewed by the user's eye.

14. The system of any of the Examples above, wherein the same coupling optical element is configured to couple light from said image projector guided within said waveguide out of said waveguide such that image content can be viewed by the user's eye and to couple light into said at least one waveguide to be guided therein to said camera.

15. The system of any of Examples 1 to 12, further comprising at least one image content out-coupling optical element configured to couple light from said image projector guided within said waveguide out of said at least one waveguide such that image content can be viewed by the user's eye.

16. The system of any of the Examples above, wherein said at least one coupling optical element faces the eye of the user wearing the head mounted imaging system to receive light from said eye.

17. The system of any of the Examples above, wherein said at least one coupling optical element is configured such that light from the environment in front of the user wearing the head mounted imaging system is coupled into said at least one waveguide and guided therein such that images of said environment may be captured by said camera.

18. The system of any of the Examples above, wherein said at least one coupling optical element faces the environment in front of the user wearing the head mounted imaging system to receive light from said environment.

19. The system of Example 15, wherein said at least one image content out-coupling optical element configured to couple light from said image projector guided within said waveguide out of said at least one waveguide and said at least one coupling optical element configured such that light is coupled into said waveguide and guided therein to said camera are superimposed on each other.

20. The system of Example 15, wherein said at least one image content out-coupling optical element configured to couple light from said image projector guided within said waveguide out of said at least one waveguide and said at least one coupling optical element configured such that light is coupled into said waveguide and guided therein to said camera are stacked over the other.

21. The system of Example 15, wherein said at least one image content out-coupling optical element configured to couple light from said image projector guided within said waveguide out of said at least one waveguide and said at least one coupling optical element configured such that light is coupled into said waveguide and guided therein to said camera are integrated in the same diffractive optical element.

22. The system of Example 15, wherein said at least one coupling optical element is configured such that light is coupled into a first waveguide and guided therein to said camera and said at least one image content out-coupling optical element is configured to couple light from said image projector guided within a second waveguide out of said second waveguide.

23. The system of any of the Examples above, wherein said at least one coupling optical element is configured such that light is coupled into a first waveguide and guided therein to said camera and said image projector is configured to couple light into a second waveguide to provide image content to said eye.

24. The system of any of the Examples above, wherein said image projector comprises a light source, a modulator, and projection optics.

25. The system of any of the Examples above, wherein the image projector comprises scanning optical fiber.

26. The system of any of Examples 24 or 25, wherein the modulator comprises a light modulator.

27. The system of Example 26, wherein the light modulator comprises a spatial light modulator.

28. The system of any of the Examples above, wherein said camera comprises a detector array and imaging optics.

29. The system of Example 28, wherein said imaging optics is configured to focus collimated light onto said detector array.

30. The system of any of the Examples above, wherein said at least one waveguide comprises material that is transparent to visible light having a refractive index sufficient to guide light in said waveguide by total internal reflection.

31. The system of any of the Examples above, wherein said at least one waveguide comprises a stack of waveguides.

32. The system of Example 31, wherein different waveguides of the stack of waveguides are configured to output light with different wavefront divergence as if projected from different distances from the user's eye.

33. The system of Example 31 or 32, wherein different waveguides of the stack of waveguides are configured to output light with different colors.

34. The system of any of Examples 31, 32, or 33, wherein different waveguides comprise first, second, and third waveguides, said system is configured such that the first is for red color light, the second for is green color light, and the third is for blue color light.

35. The system of any of the Examples 12 to 34, wherein the in-coupling optical element comprises a diffractive optical element or reflector.

36. The system of any of the Examples 12 to 34, wherein the in-coupling optical element comprises a diffractive optical element.

37. The system of any of the Examples above, wherein the coupling optical element comprises a diffractive optical element.

38. The system of any of the Examples above, wherein the coupling optical element comprises liquid crystal.

39. The system of any of the Examples above, wherein the coupling optical element comprises a liquid crystal polarization grating.

40. The system of any of the Examples above, wherein the out-coupling optical element comprises a diffractive optical element.

41. The system of any of the Examples above, wherein the coupling optical element comprises liquid crystal.

42. The system of any of the Examples above, wherein the coupling optical element comprises a liquid crystal polarization grating.

43. The system of any of the Examples above, wherein the coupling element is configured to increase a dimension of the eyebox along at least one axis.

44. The system of Example 43, further comprising an orthogonal pupil expander comprising at least one light redirecting element in or on said at least one waveguide that is configured to increase a dimension of an eyebox along an axis that is orthogonal to the at least one axis.

45. The system of Example 44, wherein said at least one light redirecting element comprises a diffractive optical element.

46. The system of any of the Examples above, wherein the same coupling element is configured to (a) couple light into said at least one waveguide to be received by said camera and to (b) couple light from said image projector out from said at least one waveguide to said user's eye.

47. The system of any of the Examples above, wherein the same coupling element is configured to (a) couple light from said environment into said at least one waveguide to be received by said camera and to (b) couple light from said image projector out from said at least one waveguide to said user's eye.

48. The system of any of the Examples above, wherein the same coupling element is configured to (a) couple light from said eye into said at least one waveguide to be received by said camera and to (b) couple light from said image projector out from said at least one waveguide to said user's eye.

49. The system of any of the above Examples, further comprising a reflective surface having optical power disposed to receive light reflected from the user's eye that passes through said eyepiece and to direct said light back to said eyepiece.

50. The system of Example 49, wherein said at least one coupling element is configured such that light from the user's eye that passes through the at least one waveguide and is reflected from the reflective surface back to the at least one waveguide is coupled into said at least one waveguide and guided therein.

51. The system of any of Examples 49 to 50, wherein the camera is disposed in an optical path with respect to said at least one out-coupling optical element to receive at least a portion of the light from the user's eye that is reflected from the reflective surface and coupled into said waveguide via the coupling element and guided therein and that is coupled out from said waveguide by said outcoupling coupling element.

52. The system of any of Examples 49 to 51, wherein the reflective surface reflects infrared light but transmits visible light.

53. The system of any of Examples 49 to 52, wherein the reflective surface is curved.

54. The system of any of Examples 49 to 53, wherein the reflective surface is disposed on a curved optical element.

55. The system of any of Examples 49 to 54, wherein the reflective surface is disposed on a concave mirror.

56. The system of any of Examples 49 to 55, wherein the reflective surface has positive optical power in reflection and negligible optical power in transmission.

57. The system any of Examples 49 to 56, wherein the reflective surface is configured to collimated light from the user's eye.

58. The system of any of Examples 49 to 57, wherein the reflective surface is configured to collimate light from the retina of the user's eye.

59. The system of any of Examples 49 to 58, wherein the reflective surface is configured to collimate light from an anterior region of the user's eye.

60. The system of any of Examples 49 to 59, wherein the reflective surface is configured to collimate light from the cornea of the user's eye.

61. The system of any of Examples 49 to 60, wherein the reflective surface is formed on a curved optical element and comprises an infrared reflective coating.

62. The system of Example 61, wherein the curved optical element has negligible power for light transmitted therethrough.

63. The system of Example 61 or 62, wherein the curved optical element has first and second curved surfaces on opposite sides of the curved optical element, said first and second curved surfaces having the same curvature.

64. The system of any of Examples 49 to 63, further comprising a retarder disposed with respect to the reflective surface and the coupling optical element so as to rotate the polarization of light passing through the at least one waveguide and reflected from the reflective surface back to the at least one waveguide and the coupling optical element.

65. The system of any of the Examples above, wherein the at least one coupling element comprises a polarization selective turning element.

66. The system of any of the Examples above, wherein the at least one coupling element comprises a polarization grating.

67. The system of any of the Examples above, wherein the at least one coupling element is configured to turn light guided within the at least one waveguide out of the waveguide to the eye as collimated light directed to the eye of the user.

68. The system of any of the Examples above, wherein the at least one coupling element is configured to turn collimated light from the reflective surface into the at least one waveguide.

69. The system of any of the Examples above, wherein the at least one out-coupling element comprises an off-axis reflector.

70. The system of any of the Examples above, wherein the at least one out-coupling element comprises a polarization selective turning element.

71. The system of any of the Examples above, wherein the at least one out-coupling element comprises a polarization grating.

72. The system of any of the Examples above, wherein the at least one out-coupling element comprises liquid crystal.

73. The system of any of the Examples above, wherein the at least one out-coupling element comprises a liquid crystal polarization grating.

74. The system of any of the Examples above, further comprising a circular polarizer.

75. The system of any of the Examples above, wherein the in-coupling element comprises a polarization selective turning element.

76. The system of any of the Examples above, wherein the in-coupling element comprises a polarization grating.

77. The system of any of the Examples above, wherein the at least one in-coupling element comprises a diffractive optical element.

78. The system of any of the Examples above, wherein the at least one in-coupling element comprises a diffraction grating.

79. The system of any of the Examples above, wherein the in-coupling element comprises an off-axis reflector.

80. The system of any of Examples 49 to 79, wherein the reflective surface comprises a liquid crystal reflector.

81. The system of any of Examples 49 to 80, wherein the reflective surface comprises a cholesteric liquid crystal reflective lens.

82. The system of any of the Examples above, wherein the same waveguide (a) guides light coupled from the user's eye into said at least one waveguide to be received by said camera so as to capture an image of at least a portion of the eye of the user, and (b) guides light coupled from said image projector such that light from said projector can be directed to said user's eye such that said image from said image projector is in the vision field of said the user.

83. The system of any of the Examples above, wherein the same coupling element (a) couples light from said user's eye into said at least one waveguide to be received by said camera and (b) couples light from said image projector out from said at least one waveguide to said user's eye.

84. The system of any of Examples 49 to 83, further comprising electronics configured to cause the camera to capture a first image when light reflected from the reflective surface is blocked.

85. The system of Example 84, wherein said electronics is configured to cause the camera to capture a second image when light reflected from the reflective surface is not blocked.

86. The system of Example 85, wherein said electronics is configured to use the first image to modify the second image.

87. The system of Examples 85 or 86, wherein said electronics is configured to subtract from the second image based on the first image.

88. The system of any of the Examples above, wherein said system is configured to perform eye tracking based images of said eye.

89. The system of Example 88, wherein performing eye tracking based on said images of said eye comprises storing an image of the retina of said eye.

90. The system of any of any of the Examples above, wherein said system is configured to:
obtain an image of a portion of said retina of said eye using said camera;
compare one or more stored images of said retina with the image of said portion of said retina; and
determine a gaze of the user based on the comparison of the one or more stored images and the image of the portion of the retina obtained from the camera.

91. The system of Example 90, wherein determining a gaze of the user comprises determining to which portion of the retina corresponds to the image of said portion of the retina.

92. The system of any of Examples 90 to 91, wherein determining a gaze of the user comprises determining an orientation of the eye.

93. The system of any of the Examples above, wherein said system is configured to obtain biometric data based on one or more images of the user's eye obtained with said camera.

94. The system of any of the Examples above, wherein said system is configured to identify the user via biometric sensing based on one or more images of said eye obtained with said camera.

95. The system of any of the above Examples, wherein said system is configured to provide illumination of a first polarization and to preferentially capture images with said camera using light of a second polarization different than said first polarization.

96. The system of any of the above Examples, wherein said system is configured to illuminate said user's eye with light of a first polarization and to preferentially capture images of said user's eye with said camera using light of a second polarization different than said first polarization.

97. The system of Examples 95 or 96, wherein said first and second polarizations are orthogonal.

98. The system of any of the above Examples, further comprising a light source disposed so as to provide illumination so as to capture images with said camera.

99. The system of any of the above Examples, further comprising a light source disposed so as to illuminate of the user's eye.

100. The system of Examples 98 or 99, wherein said light source comprises one or more infrared light sources.

101. The system of any of Examples 98 to 100, wherein said light source comprises one or more infrared light emitting diodes (LEDs).

102. The system of any of Examples 98 to 101, wherein said light source is pulsed.

103. The system of any of Examples 98 to 102 further comprising an off-axis reflector disposed to receive light from said light source and illuminate said user's eye with said light.

104. The system of any of Examples 98 to 103, wherein said light source is configured to input light into a waveguide to provide said illumination.

105. The system of any of Examples 98 to 104, wherein said light source is configured to input light into a waveguide disposed with respect to said eye to provide illumination to said eye.

106. The system of Examples 104 or 105, further comprising an illumination in-coupling optical element configured to couple light from said light source into said waveguide.

107. The system of any of Examples 98 to 103, wherein said light source is configured to input light into said at least one waveguide to provide illumination.

108. The system of Example 107, further comprising an illumination in-coupling optical element configured to couple light from said light source into said at least one waveguide to provide illumination.

109. The system of any of Examples 98 to 103, wherein said light source is configured to input light into the same waveguide as used to project image content to the user's eye.

110. The system of any of Examples 98 to 104, wherein said light source is configured, to provide illumination to the user's eye, to input light into the same waveguide as used to guide light to the camera.

111. The system of any of Examples 98 to 105, wherein said light source is configured to input light into the same waveguide as used to guide light from the user's eye to the camera.

112. The system of any of Examples 109 to 111, further comprising an illumination in-coupling optical element configured to couple light from said light source into said waveguide.

113. The system of any of Examples 106, 108, or 112, wherein said illumination in-coupling optical element is polarization selective, in-coupling light of a first polarization.

114. The system of Example 98 to 113, wherein said light source is a polarized light source configured to output polarized light having a first polarization.

115. The system of any of Examples 98 to 114, wherein said light source is configured to direct polarized light having a first polarization onto said eye.

116. The system of Example 98 to 115, further comprising an illumination polarizer having a first polarization disposed in the optical path between said light source and said eye to polarize light directed to said eye.

117. The system of Example 116, wherein the illumination polarizer is disposed in the optical path between said light source and said waveguide configured to provide illumination.

118. The system of any of Examples 98 to 117, further comprising an image acquisition polarizer in an optical path between said eye and said camera.

119. The system of Example 118, wherein said image acquisition polarizer is proximal said camera.

120. The system of Examples 118 or 119, wherein said image acquisition polarizer is disposed in an optical path between (a) said at least one waveguide configured guide light to said camera and (b) said camera.

121. The system of any of Examples 118 to 120, wherein said image acquisition polarizer reduces the amount of light said first polarization that reaches said camera.

122. The system of Examples 118 to 121, wherein said image acquisition polarizer comprises a polarizer configured to selectively coupling light of a second polarization different than said first polarization to said camera.

123. The system of any of the Examples above, further comprising at least one light consolidating element disposed in an optical path between said at least one coupling element and said at least one out-coupling optical element to reduce lateral spatial extent of light from said at least one coupling element prior to reaching said at least one out-coupling optical element.

124. The system of any of the Examples above, wherein said at least one light consolidating element comprises a diffractive optical element.

125. The system of any of the Examples above, wherein said at least one light consolidating element comprises a hologram or diffraction grating.

126. The system of any of the Examples above, wherein said at least one waveguide comprises material that is transparent to infrared light having a refractive index sufficient to guide infrared light in said waveguide by total internal reflection.

127. The system of any of the Examples above, wherein said at least one coupling optical element comprises an exit pupil expander.

128. The system of any of the Examples above, wherein the system includes optical power to increase collimation of light reflected from the eye that is coupled into the waveguide to be guided to the camera.

129. The system of any of the Examples above, wherein the system includes optical power to increase collimation of light reflected from an anterior portion of the eye that is coupled into the waveguide to be guided to the camera.

130. The system of any of the Examples above, wherein the system includes optical power to increase collimation of light reflected from the cornea of the eye that is coupled into the waveguide to be guided to the camera.

131. The system of any of Examples 128 to 130, wherein the optical power comprises positive optical power.

132. The system of any of Examples 128 to 131, wherein the optical power is provided by a lens.

133. The system of any of Examples 88 to 132, wherein the one or more stored images of the retina of the eye comprise a composite image of the retina of the eye generated using a plurality of images of different portions of the retina of the eye.

134. The system of any of Examples 88 to 133, wherein the composite image of the retina comprises a plurality of images of the retina stitched together.

135. The system of any of Examples 88 to 134, wherein the plurality of images of the retina stitched together comprises images obtained when a fixation target was displayed in the vision field of the user at various locations, respectively.

136. The system of any of Examples 88 to 135, wherein the one or more stored images of the retina comprises images obtained when a fixation target was displayed in the vision field of the user at various locations, respectively.

137. The system of any of Examples 88 to 136, wherein the system is further configured to use the obtained image of the portion of the retina of the eye to update the composite image.

138. The system of any of Examples 88 to 137, wherein using the obtained image of the portion of the retina to update the composite image of the retina comprises stitching the obtained image into a section of the composite image corresponding to the portion of the retina shown in the obtained image.

139. The system of any of Examples 88 to 138, wherein the system is further configured to apply a digital filter to the obtained image of the portion of the retina of the eye to obtain a filtered image of the portion of the retina.

140. The system of Examples 139, wherein the system is further configured to compare one or more stored images of the retina with the filtered image of the portion of the retina.

141. The system of any of Examples 139 to 140, wherein the digital filter comprises a Frangi Filter.

142. The system of any of Examples 88 to 139, wherein the system is configured to apply edge enhance the obtained image of the portion of the retina.

143. The system of any of the Examples above, wherein said system is configured to perform user identification verification using images of the retina.

144. The system of any of the Examples above, wherein said system is configured to:
  obtain an image of a portion of said retina of said eye using said camera;
  compare one or more stored images of said retina with the image of said portion of said retina.

145. The system of Example 144, wherein the one or more stored images of the retina of the eye comprise a composite image of the retina of the eye generated using a plurality of images of different portions of the retina of the eye.

146. The system of any of Examples 144 to 145, wherein the composite image of the retina comprises a plurality of images of the retina stitched together.

147. The system of any of Examples 144 to 146, wherein the plurality of images of the retina stitched together comprises images obtained when a fixation target was displayed in the vision field of the user at various locations, respectively.

148. The system of any of Examples 144 to 146, wherein the one or more stored images of the retina comprises images obtained when a fixation target was displayed in the vision field of the user at various locations, respectively.

149. The system of any of Examples 144 to 148, wherein the system is further configured to use the obtained image of the portion of the retina of the eye to update the composite image.

150. The system of any of Examples 144 to 149, wherein using the obtained image of the portion of the retina to update the composite image of the retina comprises stitching the obtained image into a section of the composite image corresponding to the portion of the retina shown in the obtained image.

151. The system of any of Examples 144 to 150, wherein the system is further configured to apply a digital filter to the obtained image of the portion of the retina of the eye to obtain a filtered image of the portion of the retina.

152. The system of Examples 151, wherein the system is further configured to compare one or more stored images of the retina with the filtered image of the portion of the retina.

153. The system of any of Examples 144 to 152, wherein the digital filter comprises a Frangi Filter.

154. The system of any of Examples 144 to 153, wherein the system is configured to apply edge enhance the obtained image of the portion of the retina.

155. The system of any of the Examples above, wherein said at least one coupling optical element comprises a diffractive optical element having a coupling area for coupling light into said waveguide, said coupling area having an average thickness in a range from 0.1 to 3 millimeters across, and wherein the light is coupled into said waveguide via the coupling area of the coupling element.

156. The system of any of the Examples above, wherein said average thickness of said coupling area is in a range from 0.5 to 2 millimeters.

157. The system of any of the Examples above, wherein said average thickness of said coupling area is in a range from 1 to 2 millimeters.

158. The system of any of the Examples above, wherein said coupling area is slit shaped.

159. The system of any of the Examples above, wherein said coupling area has a rectangular shape.

160. The system of any of the Examples above, wherein said coupling area has an arcuate shape.

161. The system of any of the Examples above, wherein said coupling area has an aspect ratio in a range from 5 to 100.

162. The system of any of the Examples above, wherein said coupling area has an aspect ratio in a range from 10 to 100.

163. The system of any of the Examples above, wherein said coupling area has an aspect ratio in a range from 15 to 100.

164. The system of any of the Examples above, wherein said coupling area has an aspect ratio in a range from 20 and 100.

165. The system of any of the Examples above, wherein said out-coupling optical element comprises a diffractive optical element.

166. The system of any of the Examples above, wherein said out-coupling optical element has a coupling area for coupling light out of said waveguide having an average thickness in a range from 0.5 mm to 3.0 millimeters.

167. The system of any of the Examples above, wherein said out-coupling optical element has a coupling area for coupling light out of said waveguide having an average thickness in a range from 1 mm to 2.5 millimeters.

168. The system of any of the Examples above, wherein said out-coupling optical element has a coupling area for coupling light out of said waveguide having a dimension in a range from 0.5 mm to 3.0 millimeters across in two orthogonal directions.

169. The system of any of the Examples above, wherein said out-coupling optical element has a coupling area for coupling light out of said waveguide having a dimension in a range from 1.0 mm to 2.5 millimeters across in two orthogonal directions.

170. The system of any of the Examples above, wherein said coupling area of said out-coupling optical element has an aspect ratio in a range from 1 to 2.

171. The system of any of the Examples above, wherein said coupling area of said out-coupling optical element has an aspect ratio in a range from 1 to 1.75.

172. The system of any of the Examples above, wherein said coupling area of said out-coupling optical element has an aspect ratio of in a range from 1 to 1.5.

173. The system of any of the Examples above, wherein said coupling area of said out-coupling optical element has an aspect ratio of in a range from 1 to 1.3.

174. The system of any of the Examples above, wherein said coupling area of said out-coupling optical element has an aspect ratio of in a range from 1 to 1.2.

175. The system of any of the Examples above, wherein said coupling area of said out-coupling optical element has an aspect ratio of in a range from 1 to 1.1.

176. The system of any of the Examples above, wherein said at least one coupling optical element is configured such that light reflected from the eye of the user wearing the head mounted display system is coupled into said at least one waveguide and guided therein such that images of said eye may be captured by said at least one camera.

177. The system of any of the Examples above, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

178. The system of any of the Examples above, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

179. The system of any of the Examples above, wherein the coupling optical element has optical power.

180. The system of any of the Examples above, wherein the optical power of the coupling optical element is configured to increase collimation of light reflected from the eye that is coupled into the waveguide to be guided to the camera.

181. The system of any of the Examples above, wherein the optical power of said coupling optical element is configured to increase collimation of light reflected from an anterior portion of the eye that is coupled into the waveguide to be guided to the camera.

182. The system of any of the Examples above, wherein the optical power of said coupling optical element is configured to increase collimation of light reflected from the cornea of the eye that is coupled into the waveguide to be guided to the camera.

183. The system of any of Examples above, wherein the optical power comprises positive optical power.

184. The system of any of Examples above, wherein the optical power corresponds to a focal length of in a range from 15 mm and 25 mm.

185. The system of any of Examples above, further comprising at least one image content out-coupling optical element configured to couple light from said image projector guided within said at least one of said at least one waveguide out thereof such that image content can be viewed by the user's eye.

186. The system of any of Examples above, wherein said at least one image content out-coupling optical element and said at least one coupling optical element are disposed laterally with respect to each other.

187. The system of any of Example 186, wherein said at least one image content out-coupling optical element is disposed more nasally than said at least one out-coupling element.

188. The system of any of Example 186, wherein said at least one image content out-coupling optical element is disposed more temporally than said at least one out-coupling element.

189. The system of any of Examples above, wherein said at least one coupling optical element comprises:
   a first coupling optical element configured such that light is coupled into said at least one waveguide and guided therein to at least one of said at least one cameras; and
   a second coupling optical element configured such that light is coupled into said at least one waveguide and guided therein to at least one of said at least one cameras,
   wherein first coupling optical element and said second coupling optical element are disposed laterally with respect to each other.

190. The system of any of Example 189, wherein said first coupling optical element comprising a diffractive optical element having optical power.

191. The system of any of the Examples above, further comprising a lens disposed with respect to said first coupling optical element to provide optical power to light received by said first coupling optical element.

192. The system of any of the Examples above, wherein said optical power is configured to increase collimation of light reflected from the eye that is coupled into the waveguide to be guided to the camera.

193. The system of any of the Examples above, wherein said optical power is configured to increase collimation of light reflected from an anterior portion of the eye that is coupled into the waveguide to be guided to the camera.

194. The system of any of the Examples above, wherein said optical power is configured increase collimation of light reflected from the cornea of the eye that is coupled into the waveguide to be guided to the camera.

195. The system of any of the Examples above, wherein the optical power comprises positive optical power.

196. The system of any of the Examples above, wherein the optical power corresponds to a focal length about the distance of the eye to first coupling optical element.

197. The system of any of any the Examples above, wherein the optical power corresponds to a focal length in a range from 15 mm to 25 mm.

198. The system of any of the Examples above, wherein said first coupling optical element is configured such that light reflected from an anterior portion of the eye of the user wearing the head mounted display system is coupled into said waveguide and guided therein such that images of said anterior portion of said eye may be captured by said camera.

199. The system of any of the Examples above, wherein said first coupling optical element is configured such that light reflected from a corneal surface of the eye of the user wearing the head mounted display system is coupled into said waveguide and guided therein such that images of the corneal surface said eye may be captured by said camera.

200. The system of any of the Examples above, wherein said second coupling optical element is configured such that light reflected from the retina of the eye of the user wearing the head mounted display system is coupled into said waveguide and guided therein such that images of the retina of said eye may be captured by said camera.

201. The system of any of the Examples above, wherein said second coupling optical element does not include optical power.

202. The system of any of the Examples above, wherein said second coupling optical element does not include a lens in an optical path between the eye and said second coupling optical element.

203. The system of any of the Examples above, wherein at least one coupling optical element is configured such that light is coupled into said waveguide and guided therein, said at least one coupling optical element comprising a diffractive optical element having a slit shaped coupling area for coupling light into said waveguide, and wherein the camera is disposed in an optical path with respect to said at least one out-coupling optical element to receive at least a portion of the light that is coupled into said waveguide via the coupling area of the coupling element.

204. The system of any of the Examples above, wherein said coupling area has an average thickness of in a range from 0.5 to 3 millimeters.

205. The system of any of the Examples above, wherein said coupling area has an average thickness in a range from 0.5 to 2 millimeters.

206. The system of any of the Examples above, wherein said coupling area has an average thickness in a range from 1 to 2 millimeters.

207. The system of any of the Examples above, wherein said coupling area has a rectangular shape.

208. The system of any of the Examples above, wherein said coupling area has an arcuate shape.

209. The system of any of the Examples above, wherein said coupling area has a non-arcuate shape.

210. The system of any of the Examples above, wherein said coupling area that has a length and a width, the length longer than the width and said coupling area is straight along said the length.

211. The system of any of the Examples above, wherein said coupling area has an aspect ratio in a range from 5 to 100.

212. The system of any of the Examples above, wherein said coupling area has an aspect ratio in a range from 10 to 100.

213. The system of any of the Examples above, wherein said coupling area has an aspect ratio in a range from 15 to 100.

214. The system of any of the Examples above, wherein said coupling area has an aspect ratio in a range from 20 to 100.

215. The system of any of the Examples above, wherein said out-coupling optical element has a coupling area for coupling light out of said waveguide having a thickness from 0.5 mm to 3.0 millimeters across.

216. The system of any of the Examples above, wherein said out-coupling optical element has a coupling area for coupling light out of said waveguide having an average thickness in a range from 1 mm to 2.5 millimeters across.

217. The system of any of the Examples above, wherein said out-coupling optical element has a coupling area for coupling light out of said waveguide having a dimension along one direction of in a range from 0.5 mm to 3.0 millimeters across in two orthogonal dimensions.

218. The system of any of the Examples above, wherein said out-coupling optical element has an coupling area having a dimension along one direction in a range from 1.0 mm to 2.5 millimeters across in two orthogonal dimensions.

219. The system of any of the Examples above, wherein said at least one out-coupling optical element has a coupling area for coupling light out of said waveguide having an aspect ratio in a range from 1 to 2.

220. The system of any of the Examples above, wherein said at least one out-coupling optical element has a coupling area for coupling light out of said waveguide having an aspect ratio in a range from 1 to 1.75.

221. The system of any of the Examples above, wherein said at least one out-coupling optical element has a coupling area for coupling light out of said waveguide having an aspect ratio in a range from 1 to 1.5.

222. The system of any of the Examples above, wherein said at least one out-coupling optical element has a coupling area for coupling light out of said waveguide having an aspect ratio in a range from 1 to 1.3.

223. The system of any of the Examples above, wherein said at least one out-coupling optical element has a coupling area for coupling light out of said waveguide having an aspect ratio in a range from 1 to 1.2.

224. The system of any of the Examples above, wherein said at least one out-coupling optical element has a coupling area for coupling light out of said waveguide having an aspect ratio in a range from 1 to 1.1.

225. The system of any of the Examples above, said at least one out-coupling element has a coupling area for coupling light out of said waveguide that is not a slit.

226. The system of any of the Examples above, wherein said average thickness of said coupling area is in a range from 0.1 to 0.3 millimeters.

227. The system of any of the Examples above, wherein said average thickness of said coupling area is in a range from 0.1 to 2 millimeters.

228. The system of any of the Examples above, wherein said average thickness of said coupling area is in a range from 0.1 to 1.5 millimeters.

229. The system of any of the Examples above, wherein said average thickness of said coupling area is in a range from 0.1 to 1 millimeters.

230. The system of any of the Examples above, wherein said average thickness of said coupling area is in a range from 0.2 to 2 millimeters.

231. The system of any of the Examples above, wherein said average thickness of said coupling area is in a range from 0.3 to 2 millimeters.

232. The system of any of the Examples above, wherein said average thickness of said coupling area is in a range from 0.2 to 1.5 millimeters.

233. The system of any of the Examples above, wherein said average thickness of said coupling area is in a range from 0.2 to 1 millimeters.

234. The system of any of the Examples above, wherein said average thickness of said coupling area is in a range from 0.3 to 1.5 millimeters.

235. The system of any of the Examples above, wherein said average thickness of said coupling area is in a range from 0.3 to 1 millimeters.

236. The system of any of the Examples above, wherein said average thickness of said coupling area is in a range from 0.1 to 0.5 millimeters.

237. The system of any of the Examples above, wherein said average thickness of said coupling area is in a range from 0.1 to 0.8 millimeters.

238. The system of any of the Examples above, wherein said average thickness of said coupling area is in a range from 0.2 to 0.5 millimeters.

239. The system of any of the Examples above, wherein said average thickness of said coupling area is in a range from 0.2 to 0.8 millimeters.

240. The system of any of the Examples above, wherein said average thickness of said coupling area is in a range from 0.1 to 0.2 millimeters.

241. The system of any of the Examples above, wherein said average thickness of said coupling area is in a range from 0.1 to 0.3 millimeters.

242. The system of any of the Examples above, wherein said average thickness of said coupling area is in a range from 0.2 to 0.3 millimeters.

243. The system of any of the Examples above, wherein said average thickness of said coupling area is in a range from 0.3 to 0.5 millimeters.

244. The system of any of the Examples above, wherein said average thickness of said coupling area is in a range from 0.3 to 0.8 millimeters.

245. The system of any of the Examples above, wherein said coupling area has a length of from 20 mm to 50 mm.

246. The system of any of the Examples above, wherein said coupling area has a length of from 10 mm to 40 mm.

247. The system of any of the Examples above, wherein said coupling area has a length of from 2 mm to 20 mm.

248. The system of any of the Examples above, wherein said coupling area has a length of from 5 mm to 20 mm.

249. The system of any of the Examples above, wherein said coupling area has a length of from 1 mm to 10 mm.

250. The system of any of the Examples above, wherein said coupling area has a length of from 0.5 mm to 2 mm.

251. The system of any of the Examples above, wherein said coupling area has a length of from 10 mm to 20 mm.

252. The system of any of the Examples above, wherein said coupling area has a length of from 10 mm to 30 mm.

253. The system of any of the Examples above, wherein said coupling area has a length of from 6 mm to 18 mm.

254. The system of any of the Examples above, wherein said system is configured such that light coupled into said waveguide by said first coupling optical element is acted on by a first total optical power and light coupled into said waveguide by said second coupling optical element is acted on by a second total optical power and said first total optical power is larger than said second total optical power.

255. The system of any of the Examples above, wherein said first coupling optical element has a first optical power and said second coupling optical element has a second optical power, and said first optical power is larger than said second optical power.

256. The system of any of the Examples above, wherein said first coupling optical element has a first lens associated therewith having has a first optical power and said second coupling optical element has associated therewith a second lens having a second optical power, and said first optical power is larger than said second optical power.

Example Section II

1. A head mounted display system configured to project light to an eye of a user to display augmented reality image content in a vision field of said user and to image at least a portion of an environment in front of the user wearing the head mounted display system, said head-mounted display system comprising:
   a frame configured to be supported on a head of the user;
   an image projector configured to project an image;
   a camera; and
   an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from the environment in front of the user to the user's eye to provide a view of the environment in front of the user, said eyepiece comprising:
(a) at least one waveguide;
(b) at least one in-coupling optical element configured to in-couple light from said image projector into said at least one waveguide so as to guide light from said image projector therein;
(c) at least one coupling optical element configured to couple light from said image projector guided within said waveguide out of said waveguide and direct said light to the user's eye; and
(d) at least one out-coupling element configured to couple light within said waveguide out of said waveguide and direct said light to said camera,
wherein the image projector is disposed in an optical path with respect to said at least one in-coupling optical element to couple light from said image projector into said waveguide to be guided therein such that said light is coupled out from said waveguide by said at least one coupling element to said user's eye such that said image from said projector is in the vision field of said the user,
wherein said coupling element is configured such that light from the environment in front of the user wearing the head mounted display is coupled into said waveguide and guided therein,
wherein the camera is disposed in an optical path with respect to said at least one out-coupling optical element to receive at least a portion of the light from the environment in front of the user that is coupled into said waveguide via the coupling element and guided therein and that is coupled out from said waveguide by said outcoupling coupling element such that images of said environment may be captured by said camera, and
wherein the same waveguide (a) guides light coupled from said environment into said waveguide to be received by said camera so as to capture an image of at least a portion of the environment in front of the user, and (b) guides light coupled from said projector such that light from said projector can be directed to said user's eye so that said image from said projector is in the vision field of said the user.

2. The system of Example 1, wherein said image projector comprises a light source, a modulator, and projection optics.

3. The system of Example 1 or 2, wherein the image projector comprises scanning optical fiber.

4. The system of any of Examples 2 or 3, wherein the modulator comprises a light modulator.

5. The system of Example 4, wherein the light modulator comprises a spatial light modulator.

6. The system of any of the Examples above, wherein said camera comprises a detector array and imaging optics.

7. The system of Example 6, wherein said imaging optics is configured to focus collimated light onto said detector array.

8. The system of any of the Examples above, wherein said at least one waveguide comprises material that is transparent to visible light having a refractive index sufficient to guide light in said waveguide by total internal reflection.

9. The system of any of the Examples above, wherein said at least one waveguide comprises a stack of waveguides.

10. The system of Example 9, wherein different waveguides of the stack of waveguides are configured to output light with different wavefront divergence as if projected from different distances from the user's eye.

11. The system of Example 9 or 10, wherein different waveguides of the stack of waveguides are configured to output light with different colors.

12. The system of any of Examples 9, 10, or 11, wherein different waveguides comprise first, second, and third waveguides, said system is configured such that the first is for red color light, the second for is green color light, and the third is for blue color light.

13. The system of any of the Examples above, wherein the in-coupling optical element comprises a diffractive optical element or reflector.

14. The system of any of the Examples above, wherein the coupling optical element comprises a diffractive optical element.

15. The system of any of the Examples above, wherein the out-coupling optical element comprises a diffractive optical element.

16. The system of any of the Examples above, wherein the coupling element is configured to increase a dimension of the eyebox along at least one axis.

17. The system of Example 16, further comprising an orthogonal pupil expander comprising at least one light redirecting element in or on said at least one waveguide that is configured to increase a dimension of an eyebox along an axis that is orthogonal to the at least one axis.

18. The system of Example 17, wherein said at least one light redirecting element comprises a diffractive optical element.

19. The system of any of the Examples above, wherein the same coupling element (a) couples light from said environment into said at least one waveguide to be received by said camera and (b) couples light from said image projector out from said at least one waveguide to said user's eye.

20. The system of any of the above Examples, further comprising a reflective surface having optical power disposed to receive light reflected from the user's eye that passes through said eyepiece and to direct said light back to said eyepiece.

21. The system of Example 20, wherein said at least one coupling element is configured such that light from the user's eye that passes through the eyepiece and is reflected from the reflective surface back to the eyepiece is coupled into said waveguide and guided therein.

22. The system of any of Examples 20 to 21, wherein the camera is disposed in an optical path with respect to said at least one out-coupling optical element to receive at least a portion of the light from the user's eye that is reflected from the reflective surface and coupled into said waveguide via the coupling element and guided therein and that is coupled out from said waveguide by said outcoupling coupling element.

23. The system of any of Examples 20 to 22, wherein the reflective surface reflects infrared light but transmits visible light.

24. The system of any of Examples 20 to 23, wherein the reflective surface is curved.

25. The system of any of Examples 20 to 24, wherein the reflective surface is disposed on a curved optical element.

26. The system of any of Examples 20 to 25, wherein the reflective surface is disposed on a concave mirror.

27. The system of any of Examples 20 to 26, wherein the reflective surface has positive optical power in reflection and negligible optical power in transmission.

28. The system any of Examples 20 to 27, wherein the reflective surface is configured to collimated light from the user's eye.

29. The system of any of Examples 20 to 28, wherein the reflective surface is configured to collimate light from the retina of the user's eye.

30. The system of any of Examples 20 to 29, wherein the reflective surface is configured to collimate light from an anterior region of the user's eye.

31. The system of any of Examples 20 to 30, wherein the reflective surface is configured to collimate light from the cornea of the user's eye.

32. The system of any of Examples 20 to 31, wherein the reflective surface is formed on a curved optical element having an infrared reflective coating on said reflective surface.

33. The system of Example 33, wherein the curved optical element has negligible power for light transmitted therethrough.

34. The system of Example 32 or 33, wherein the curved optical element has first and second curved surface on opposite sides of the curved optical element, said first and second curved surfaces having the same curvature.

35. The system of any of the Examples above, further comprising a retarder disposed with respect to the reflective surface and the coupling optical element so as to rotate the polarization of light passing through the eye piece and reflected from the reflective surface back to the eye piece and the coupling optical element.

36. The system of any of the Examples above, wherein the at least one coupling element comprises a polarization selective turning element.

37. The system of any of the Examples above, wherein the at least one coupling element comprises a polarization grating.

38. The system of any of the Examples above, wherein the at least one coupling element is configured to turn light guided within the at least one waveguide out of the waveguide to the eye as collimated light directed to the eye of the user.

39. The system of any of the Examples above, wherein the at least one coupling element is configured to turn collimated light from the reflective surface into the at least one waveguide.

40. The system of any of the Examples above, wherein the at least one out-coupling element comprises an off-axis reflector.

41. The system of any of the Examples above, wherein the at least one out-coupling element comprises a polarization selective turning element.

42. The system of any of the Examples above, wherein the at least one out-coupling element comprises a polarization grating.

43. The system of any of the Examples above, further comprising a circular polarizer.

44. The system of any of the Examples above, wherein the in-coupling element comprises a polarization selective turning element.

45. The system of any of the Examples above, wherein the in-coupling element comprises a polarization grating.

46. The system of any of the Examples above, wherein the in-coupling element comprises an off-axis reflector.

47. The system of any of Examples 20 to 34, wherein the reflective surface comprises a liquid crystal reflector.

48. The system of any of Examples 20 to 34 or 47, wherein the reflective surface comprises a cholesteric liquid crystal reflective lens.

49. The system of any of the Examples above, wherein the same waveguide (a) guides light coupled from the user's eye into said at least one waveguide to be received by said camera so as to capture an image of at least a portion of the eye of the user, and (b) guides light coupled from said image projector such that light from said projector can be directed to said user's eye such that said image from said image projector is in the vision field of said the user.

50. The system of any of the Examples above, wherein the same coupling element (a) couples light from said user's eye into said at least one waveguide to be received by said camera and (b) couples light from said image projector out from said at least one waveguide to said user's eye.

51. The system of any of the Examples above, further comprising electronics configured to cause the camera to capture a first image when light reflected from the reflective surface is blocked.

52. The system of Example 51, wherein said electronics is configured to cause the camera to capture a second image when light reflected from the reflective surface is not blocked.

53. The system of Example 52, wherein said electronics is configured to use the first image to modify the second image.

54. The system of Example 53, wherein said electronics is configured to subtract from the second image based on the first image.

55. The system of any of the Examples above, wherein said system is configured to perform eye tracking based on said image of said eye.

56. The system of Example 55, wherein performing eye tracking based on said image of said eye comprises storing an image of the retina of said eye.

57. The system of any of any of the Examples above, wherein said system is configured to:
store an image of the retina of said eye;
capture an image of a portion of said retina of said eye;
compare the stored image of said retina with the image of said portion of said retina; and
determine a gaze of the user based on the comparison of the stored image and image of the portion of the retina.

58. The system of Example 57, wherein determining a gaze of the user comprises determining to which portion of the retina corresponds to the image of said portion of the retina.

59. The system of any of Examples 57 to 58, wherein determining a gaze of the user comprises determining an orientation of the eye.

60. The system of any of the above Examples, further comprising a light source disposed so as to illuminate of the user's eye.

61. The system of Example 60, wherein said light source comprises one or more infrared light sources configured to direct infrared light to the user's eye.

62. The system of Examples 60 or 61, wherein said light source comprises one or more infrared light emitting diodes (LEDs).

63. The system of any of Examples 60 to 62, wherein said light source is pulsed.

64. The system of any of the Examples above, further comprising an off-axis reflector disposed to receive light from said light source and illuminate said eye with said light.

65. A head mounted imaging system configured to image at least a portion of an environment in front of a user wearing the head mounted imaging system, said head-mounted imaging system comprising:

a frame configured to be supported on a head of the user;
a camera; and
an eyepiece disposed on the frame, at least a portion of said eyepiece being transparent and disposed at a location in front of the user's eye when the user wears said head-mounted imaging system such that said transparent portion transmits light from the environment in front of the user to the user's eye to provide a view of the environment in front of the user, said eyepiece comprising:
(a) at least one waveguide;
(b) at least one coupling optical element configured such that light from the environment in front of the user wearing the head mounted imaging system is coupled into said waveguide and guided therein; and
(c) at least one out-coupling element configured to couple light within said waveguide out of said waveguide and direct said light to said camera,
wherein the camera is disposed in an optical path with respect to said at least one out-coupling optical element to receive at least a portion of the light from the environment in front of the user that is coupled into said waveguide via the coupling element and guided therein and that is coupled out from said waveguide by said outcoupling coupling element such that images of said environment may be captured by said camera.

66. The system of Example 65, wherein said camera comprises a detector array and imaging optics.

67. The system of Example 66, wherein said imaging optics is configured to focus collimated light onto said detector array.

68. The system of any of Examples 65 to 67, wherein said at least one waveguide comprises material that is transparent to visible light having a refractive index sufficient to guide light in said waveguide by total internal reflection.

69. The system of any of Examples 65 to 68, wherein said at least one waveguide comprises a stack of waveguides.

70. The system of Example 69, wherein different waveguides of the stack of waveguides are configured to output light with different wavefront divergence as if projected from different distances from the user's eye.

71. The system of Example 69 or 70, wherein different waveguides of the stack of waveguides are configured to output light with different colors.

72. The system of any of Examples 69 to 71, wherein different waveguides comprise first, second, and third waveguides, said system is configured such that the first is for red color light, the second for is green color light, and the third is for blue color light.

73. The system of any of Examples 65 to 72, wherein the coupling optical element comprises a diffractive optical element.

74. The system of any of Examples 65 to 73, wherein the out-coupling optical element comprises a diffractive optical element.

75. The system of any of Examples 65 to 74, wherein the coupling element is configured to increase a dimension of the eyebox along at least one axis.

76. The system of Example 75, further comprising an orthogonal pupil expander comprising at least one light redirecting element in or on said at least one waveguide that is configured to increase a dimension of an eyebox along an axis that is orthogonal to the at least one axis.

77. The system of Example 76, wherein said at least one light redirecting element comprises a diffractive optical element.

78. The system of any of Examples 65-77, wherein said at least one coupling optical element comprises a diffractive optical element having a coupling area for coupling light into said waveguide, said coupling area having an average thickness in a range from 0.1 to 3 millimeters across, and wherein the light is coupled into said waveguide via the coupling area of the coupling element.

79. The system of Example 78, wherein said average thickness of said coupling area is in a range from 0.5 to 2 millimeters.

80. The system of any of Examples 78-79, wherein said average thickness of said coupling area is in a range from 1 to 2 millimeters.

81. The system of any of Examples 78-80, wherein said coupling area is slit shaped.

82. The system of any of Examples 78-81, wherein said coupling area has a rectangular shape.

83. The system of any of Examples 78-81, wherein said coupling area has an arcuate shape.

84. The system of any of Examples 78-83, wherein said coupling area has an aspect ratio in a range from 5 to 100.

85. The system of any of Examples 78-83, wherein said coupling area has an aspect ratio in a range from 10 to 100.

86. The system of any of Examples 78-83, wherein said coupling area has an aspect ratio in a range from 15 to 100.

87. The system of any of Examples 78-83, wherein said coupling area has an aspect ratio in a range from 20 and 100.

88. The system of any of Examples 78-87, wherein said out-coupling optical element comprises a diffractive optical element.

89. The system of any of Examples 78-88, wherein said out-coupling optical element has a coupling area for coupling light out of said waveguide having an average thickness in a range from 0.5 mm to 3.0 millimeters.

90. The system of any of Examples 78-88, wherein said out-coupling optical element has a coupling area for coupling light out of said waveguide having an average thickness in a range from 1 mm to 2.5 millimeters.

91. The system of any of Examples 78-88, wherein said out-coupling optical element has a coupling area for coupling light out of said waveguide having a dimension in a range from 0.5 mm to 3.0 millimeters across in two orthogonal directions.

92. The system of any of Examples 78-88, wherein said out-coupling optical element has a coupling area for coupling light out of said waveguide having a dimension in a range from 1.0 mm to 2.5 millimeters across in two orthogonal directions.

93. The system of any of Examples 78-92, wherein said coupling area of said out-coupling optical element has an aspect ratio in a range from 1 to 2.

94. The system of any of Examples 78-92, wherein said coupling area of said out-coupling optical element has an aspect ratio in a range from 1 to 1.75.

95. The system of any of Examples 78-92, wherein said coupling area of said out-coupling optical element has an aspect ratio of in a range from 1 to 1.5.

96. The system of any of Examples 78-92, wherein said coupling area of said out-coupling optical element has an aspect ratio of in a range from 1 to 1.3.

97. The system of any of Examples 78-92, wherein said coupling area of said out-coupling optical element has an aspect ratio of in a range from 1 to 1.2.

98. The system of any of Examples 78-92, wherein said coupling area of said out-coupling optical element has an aspect ratio of in a range from 1 to 1.1.

99. The system of any of Examples 78-98, wherein said at least one coupling optical element is configured such that light reflected from the eye of the user wearing the head mounted display system is coupled into said at least one waveguide and guided therein such that images of said eye may be captured by said at least one camera.

100. The system of any of Examples 78-99, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

101. The system of any of Examples 78-100, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

102. The system of any of Examples 78-101, wherein the coupling optical element has optical power.

103. The system of Example 102, wherein the optical power of the coupling optical element is configured to increase collimation of light reflected from the eye that is coupled into the waveguide to be guided to the camera.

104. The system of any of Examples 102-103, wherein the optical power of said coupling optical element is configured to increase collimation of light reflected from an anterior portion of the eye that is coupled into the waveguide to be guided to the camera.

105. The system of any of Examples 102-104, wherein the optical power of said coupling optical element is configured to increase collimation of light reflected from the cornea of the eye that is coupled into the waveguide to be guided to the camera.

106. The system of any of Examples above, wherein the optical power comprises positive optical power.

107. The system of any of Examples above, wherein the optical power corresponds to a focal length of in a range from 15 mm and 25 mm.

108. The system of any of Examples above, further comprising at least one image content out-coupling optical element configured to couple light from said image projector guided within said at least one of said at least one waveguide out thereof such that image content can be viewed by the user's eye.

109. The system of any of Examples above, wherein said at least one image content out-coupling optical element and said at least one coupling optical element are disposed laterally with respect to each other.

110. The system of any of Example 109, wherein said at least one image content out-coupling optical element is disposed more nasally than said at least one out-coupling element.

111. The system of any of Example 109, wherein said at least one image content out-coupling optical element is disposed more temporally than said at least one out-coupling element.

112. The system of any of Examples above, wherein said at least one coupling optical element comprises:
 a first coupling optical element configured such that light is coupled into said at least one waveguide and guided therein to at least one of said at least one cameras; and
 a second coupling optical element configured such that light is coupled into said at least one waveguide and guided therein to at least one of said at least one cameras,
 wherein first coupling optical element and said second coupling optical element are disposed laterally with respect to each other.

113. The system of any of Example 112, wherein said first coupling optical element comprising a diffractive optical element having optical power.

114. The system of any of Examples 112-113, further comprising a lens disposed with respect to said first coupling optical element to provide optical power to light received by said first coupling optical element.

115. The system of any of Examples 113-114, wherein said optical power is configured to increase collimation of light reflected from the eye that is coupled into the waveguide to be guided to the camera.

116. The system of any of Examples 113-115, wherein said optical power is configured to increase collimation of light reflected from an anterior portion of the eye that is coupled into the waveguide to be guided to the camera.

117. The system of any of Examples 113-116, wherein said optical power is configured increase collimation of light reflected from the cornea of the eye that is coupled into the waveguide to be guided to the camera.

118. The system of any of Examples 113-117, wherein the optical power comprises positive optical power.

119. The system of any of Examples 113-119, wherein the optical power corresponds to a focal length about the distance of the eye to first coupling optical element.

120. The system of any of any the Examples above, wherein the optical power corresponds to a focal length in a range from 15 mm to 25 mm.

121. The system of any of Examples 112-120, wherein said first coupling optical element is configured such that light reflected from an anterior portion of the eye of the user wearing the head mounted display system is coupled into said waveguide and guided therein such that images of said anterior portion of said eye may be captured by said camera.

122. The system of any of Examples 112-121, wherein said first coupling optical element is configured such that light reflected from a corneal surface of the eye of the user wearing the head mounted display system is coupled into said waveguide and guided therein such that images of the corneal surface said eye may be captured by said camera.

123. The system of any of Examples 112-122, wherein said second coupling optical element is configured such that light reflected from the retina of the eye of the user wearing the head mounted display system is coupled into said waveguide and guided therein such that images of the retina of said eye may be captured by said camera.

124. The system of any of Examples 112-123, wherein said second coupling optical element does not include optical power.

125. The system of any of Examples 112-124, wherein said second coupling optical element does not include a lens in an optical path between the eye and said second coupling optical element.

126. The system of any of Examples 112-125, wherein at least one coupling optical element is configured such that light is coupled into said waveguide and guided therein, said at least one coupling optical element comprising a diffractive optical element having a slit shaped coupling area for coupling light into said waveguide, and wherein the camera is disposed in an optical path with respect to said at least one out-coupling optical element to receive at least a portion of the light that is coupled into said waveguide via the coupling area of the coupling element.

127. The system of any of Examples 78-126, wherein said coupling area has an average thickness of in a range from 0.5 to 3 millimeters.

128. The system of any of Examples 78-126, wherein said coupling area has an average thickness in a range from 0.5 to 2 millimeters.

129. The system of any of Examples 78-126, wherein said coupling area has an average thickness in a range from 1 to 2 millimeters.

130. The system of any of Examples 78-129, wherein said coupling area has a rectangular shape.

131. The system of any of Examples 78-129, wherein said coupling area has an arcuate shape.

132. The system of any of Examples 78-130, wherein said coupling area has a non-arcuate shape.

133. The system of any of Examples 78-132, wherein said coupling area that has a length and a width, the length longer than the width and said coupling area is straight along said the length.

134. The system of any of Examples 78-133, wherein said coupling area has an aspect ratio in a range from 5 to 100.

135. The system of any of Examples 78-133, wherein said coupling area has an aspect ratio in a range from 10 to 100.

136. The system of any of Examples 78-133, wherein said coupling area has an aspect ratio in a range from 15 to 100.

137. The system of any of Examples 78-133, wherein said coupling area has an aspect ratio in a range from 20 to 100.

138. The system of any of Examples 78-137, wherein said out-coupling optical element has a coupling area for coupling light out of said waveguide having a thickness from 0.5 mm to 3.0 millimeters across.

139. The system of any of Examples 78-137, wherein said out-coupling optical element has a coupling area for coupling light out of said waveguide having an average thickness in a range from 1 mm to 2.5 millimeters across.

140. The system of any of Examples 78-139, wherein said out-coupling optical element has a coupling area for coupling light out of said waveguide having a dimension along one direction of in a range from 0.5 mm to 3.0 millimeters across in two orthogonal dimensions.

141. The system of any of Examples 78-139, wherein said out-coupling optical element has an coupling area having a dimension along one direction in a range from 1.0 mm to 2.5 millimeters across in two orthogonal dimensions.

142. The system of any of Examples 78-141, wherein said at least one out-coupling optical element has a coupling area for coupling light out of said waveguide having an aspect ratio in a range from 1 to 2.

143. The system of any of Examples 78-142, wherein said at least one out-coupling optical element has a coupling area for coupling light out of said waveguide having an aspect ratio in a range from 1 to 1.75.

144. The system of any of Examples 78-142, wherein said at least one out-coupling optical element has a coupling area for coupling light out of said waveguide having an aspect ratio in a range from 1 to 1.5.

145. The system of any of Examples 78-142, wherein said at least one out-coupling optical element has a coupling area for coupling light out of said waveguide having an aspect ratio in a range from 1 to 1.3.

146. The system of any of Examples 78-142, wherein said at least one out-coupling optical element has a coupling area for coupling light out of said waveguide having an aspect ratio in a range from 1 to 1.2.

147. The system of any of Examples 78-142, wherein said at least one out-coupling optical element has a coupling area for coupling light out of said waveguide having an aspect ratio in a range from 1 to 1.1.

148. The system of any of Examples 78-147, said at least one out-coupling element has a coupling area for coupling light out of said waveguide that is not a slit.

149. The system of any of Examples 78-148, wherein said average thickness of said coupling area is in a range from 0.1 to 0.3 millimeters.

150. The system of any of Examples 78-148, wherein said average thickness of said coupling area is in a range from 0.1 to 2 millimeters.

151. The system of any of Examples 78-148, wherein said average thickness of said coupling area is in a range from 0.1 to 1.5 millimeters.

152. The system of any of Examples 78-148, wherein said average thickness of said coupling area is in a range from 0.1 to 1 millimeters.

153. The system of any of Examples 78-148, wherein said average thickness of said coupling area is in a range from 0.2 to 2 millimeters.

154. The system of any of Examples 78-148, wherein said average thickness of said coupling area is in a range from 0.3 to 2 millimeters.

155. The system of any of Examples 78-148, wherein said average thickness of said coupling area is in a range from 0.2 to 1.5 millimeters.

156. The system of any of Examples 78-148, wherein said average thickness of said coupling area is in a range from 0.2 to 1 millimeters.

157. The system of any of Examples 78-148, wherein said average thickness of said coupling area is in a range from 0.3 to 1.5 millimeters.

158. The system of any of Examples 78-148, wherein said average thickness of said coupling area is in a range from 0.3 to 1 millimeters.

159. The system of any of Examples 78-148, wherein said average thickness of said coupling area is in a range from 0.1 to 0.5 millimeters.

160. The system of any of Examples 78-148, wherein said average thickness of said coupling area is in a range from 0.1 to 0.8 millimeters.

161. The system of any of Examples 78-148, wherein said average thickness of said coupling area is in a range from 0.2 to 0.5 millimeters.

162. The system of any of Examples 78-148, wherein said average thickness of said coupling area is in a range from 0.2 to 0.8 millimeters.

163. The system of any of Examples 78-148, wherein said average thickness of said coupling area is in a range from 0.1 to 0.2 millimeters.

164. The system of any of Examples 78-148, wherein said average thickness of said coupling area is in a range from 0.1 to 0.3 millimeters.

165. The system of any of Examples 78-148, wherein said average thickness of said coupling area is in a range from 0.2 to 0.3 millimeters.

166. The system of any of Examples 78-148, wherein said average thickness of said coupling area is in a range from 0.3 to 0.5 millimeters.

167. The system of any of Examples 78-148, wherein said average thickness of said coupling area is in a range from 0.3 to 0.8 millimeters.

168. The system of any of Examples 78-167, wherein said coupling area has a length of from 20 mm to 50 mm.

169. The system of any of Examples 78-167, wherein said coupling area has a length of from 10 mm to 40 mm.

170. The system of any of Examples 78-167, wherein said coupling area has a length of from 2 mm to 20 mm.

171. The system of any of Examples 78-167, wherein said coupling area has a length of from 5 mm to 20 mm.

172. The system of any of Examples 78-167, wherein said coupling area has a length of from 1 mm to 10 mm.

173. The system of any of Examples 78-167, wherein said coupling area has a length of from 0.5 mm to 2 mm.

174. The system of any of Examples 78-167, wherein said coupling area has a length of from 10 mm to 20 mm.

175. The system of any of Examples 78-167, wherein said coupling area has a length of from 10 mm to 30 mm.

176. The system of any of Examples 78-167, wherein said coupling area has a length of from 6 mm to 18 mm.

Example Section III

1. A head mounted display system configured to project light to an eye of a user to display augmented reality image content in a vision field of said user and to image at least a portion of the eye of the user wearing the head mounted display system, said head-mounted display system comprising:
 a frame configured to be supported on a head of the user;
 an image projector configured to project an image;
 a camera;
 an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from the environment in front of the user to the user's eye to provide a view of the environment in front of the user, said eyepiece comprising:
  (a) at least one waveguide;
  (b) at least one in-coupling optical element configured to in-couple light from said image projector into said at least one waveguide so as to guide light from said image projector therein;
  (c) at least one coupling optical element configured to couple light from said image projector guided within said waveguide out of said waveguide and direct said light to the user's eye; and
  (d) at least one out-coupling element configured to couple said light guided within said waveguide out of said waveguide and direct said light to said camera; and
 a reflective surface having optical power disposed to receive light reflected from the user's eye that passes through said eyepiece and to direct said light back to said eyepiece;
 wherein the image projector is disposed in an optical path with respect to said at least one in-coupling optical element to in-couple light from said image projector into said waveguide to be guided therein such that said light is coupled out from said waveguide by said at least one coupling element to said user's eye such that said image from said projector is in the vision field of said the user,
 wherein said at least one coupling element is configured such that light from the user's eye that passes through the eyepiece and is reflected from the reflective surface back to the eyepiece is coupled into said waveguide and guided therein, and
 wherein the camera is disposed in an optical path with respect to said at least one out-coupling optical element to receive at least a portion of the light from the user's eye that is reflected from the reflective surface and coupled into said waveguide via the coupling element and guided therein and that is coupled out from said waveguide by said outcoupling coupling element.

2. The system of Example 1, further comprising a light source disposed so as to illuminate of the user's eye.

3. The system of Example 2, wherein said light source comprises one or more infrared light sources configured to direct infrared light to the user's eye.

4. The system of Examples 2 or 3, wherein said light source comprises one or more infrared light emitting diodes (LEDs).

5. The system of any of Examples 2 to 4, wherein said light source is pulsed.

6. The system of any of the Examples above, further comprising an off-axis reflector disposed to receive light from said light source and illuminate said eye with said light.

7. The system of any of the Examples above, wherein the reflective surface reflects infrared light but transmits visible light.

8. The system of any of the Examples above, wherein the reflective surface is curved.

9. The system of any of the Examples above, wherein the reflective surface is disposed on a curved optical element.

10. The system of any of the Examples above, wherein the reflective surface is disposed on a concave mirror.

11. The system of any of the Examples above, wherein the reflective surface has positive optical power in reflection and negligible optical power in transmission.

12. The system of any of the Examples above, wherein the reflective surface is configured to collimated light from the user's eye.

13. The system of any of the Examples above, wherein the reflective surface is configured to collimate light from the retina of the user's eye.

14. The system of any of the Examples above, wherein the reflective surface is configured to collimate light from an anterior region of the user's eye.

15. The system of any of the Examples above, wherein the reflective surface is configured to collimate light from the cornea of the user's eye.

16. The system of any of the Examples above, wherein the reflective surface is formed on a curved optical element having an infrared reflective coating on said reflective surface.

17. The system of Example 9 or 16, wherein the curved optical element has negligible power for light transmitted therethrough.

18. The system of any of Examples 9 or 16 or 17, wherein the curved optical element has first and second curved surface on opposite sides of the curved optical element, said first and second curved surfaces having the same curvature.

19. The system of any of the Examples above, further comprising a retarder disposed with respect to the reflective surface and the coupling optical element so as to rotate the polarization of light passing through the eye piece and reflected from the reflective surface back to the eye piece and the coupling optical element.

20. The system of any of the Examples above, wherein the at least one coupling element comprises a polarization selective turning element.

21. The system of any of the Examples above, wherein the at least one coupling element comprises a polarization grating.

22. The system of any of the Examples above, wherein the at least one coupling element is configured to turn light guided within the at least one waveguide out of the waveguide to the eye as collimated light directed to the eye of the user.

23. The system of any of the Examples above, wherein the at least one coupling element is configured to turn collimated light from the reflective surface into the at least one waveguide.

24. The system of any of the Examples above, wherein the at least one out-coupling element comprises an off-axis reflector.

25. The system of any of the Examples above, wherein the at least one out-coupling element comprises a polarization selective turning element.

26. The system of any of the Examples above, wherein the at least one out-coupling element comprises a polarization grating.

27. The system of any of the Examples above, further comprising a circular polarizer.

28. The system of any of the Examples above, wherein the in-coupling element comprises a polarization selective turning element.

29. The system of any of the Examples above, wherein the in-coupling element comprises a polarization grating.

30. The system of any of the Examples above, wherein the in-coupling element comprises an off-axis reflector.

31. The system of any of the Examples above, wherein the reflective surface comprises a liquid crystal reflector.

32. The system of any of the Examples above, wherein the reflective surface comprises a cholesteric liquid crystal reflective lens.

33. The system of any of the Examples above, wherein said image projector comprises a light source, a modulator, and projection optics.

34. The system of any of the Examples above, wherein the image projector comprises scanning optical fiber.

35. The system of any of the Examples above, wherein the modulator comprises a light modulator.

36. The system of Example 34, wherein the light modulator comprises a spatial light modulator.

37. The system of any of the Examples above, wherein said camera comprises a detector array and imaging optics.

38. The system of Example 36, wherein said imaging optics is configured to focus collimated light onto a detector array.

39. The system of any of the Examples above, wherein said at least one waveguide comprises material transparent to visible light having a refractive index sufficient to guide light in said waveguide by total internal reflection.

40. The system of any of the Examples above, wherein said at least one waveguide comprises a stack of waveguides.

41. The system of Example 40, wherein different waveguides of the stack of waveguides are configured to output light with different wavefront divergence as if projected from different distances from the user's eye.

42. The system of Example 40 or 41, wherein different waveguides of the stack of waveguides are configured to output light with different colors.

43. The system of any of Examples 40, 41, or 42, wherein different waveguides comprise first, second, and third waveguides, said system is configured such that said first is for red color light, the second for is green color light, and the third is for blue color light.

44. The system of any of the Examples above, wherein the in-coupling optical element comprises a diffractive optical element or reflector.

45. The system of any of the Examples above, wherein the coupling optical element comprises a diffractive optical element.

46. The system of any of the Examples above, wherein the out-coupling optical element comprises a diffractive optical element.

47. The system of any of the Examples above, wherein the coupling element is configured to increase dimensions of the eyebox along at least one axis.

48. The system of Example 47, further comprising an orthogonal pupil expander comprising at least one light redirecting element in or on said at least one waveguide that is configured to increase a dimension of an eyebox along an axis that is orthogonal to the at least one axis.

49. The system of Example 48, wherein said at least one light redirecting element comprises a diffractive optical element.

50. The system of any of the Examples above, wherein the same waveguide (a) guides light coupled from the user's eye into said at least one waveguide to be received by said camera so as to capture an image of at least a portion of the eye of the user, and (b) guides light coupled from said image projector such that light from said projector can be directed to said user's eye such that said image from said image projector is in the vision field of said the user 51. The system of any of the Examples above, wherein the same coupling element (a) couples light from said user's eye into said at least one waveguide to be received by said camera and (b) couples light from said image projector out from said at least one waveguide to said user's eye.

52. The system of any of the Examples above, further comprising electronics configured to cause the camera to capture a first image when light reflected from the reflective surface is blocked.

53. The system of Example 52, wherein said electronics is configured to cause the camera to capture a second image when light reflected from the reflective surface is not blocked.

54. The system of Example 53, wherein said electronics is configured to use the first image to modify the second image.

55. The system of Example 54, wherein said electronics is configured to subtract from the second image based on the first image.

56. The system of any of the Examples above, wherein said system is configured to perform eye tracking based on said image of said eye.

57. The system of Example 56, wherein performing eye tracking based on said image of said eye comprises storing an image of the retina of said eye.

58. The system of any of any of the Examples above, wherein said system is configured to:
store an image of the retina of said eye;
capture an image of a portion of said retina of said eye;
compare the stored image of said retina with the image of said portion of said retina; and
determine a gaze of the user based on the comparison of the stored image and image of the portion of the retina.

59. The system of Example 58, wherein determining a gaze of the user comprises determining to which portion of the retina corresponds to the image of said portion of the retina.

60. The system of any of Examples 58 to 59, wherein determining a gaze of the user comprises determining an orientation of the eye.

61. The system of any of the above Examples, wherein said coupling element is configured such that light from the environment in front of the user wearing the head mounted display is coupled into said waveguide and guided therein.

62. The system of any of the above Examples, wherein the camera is disposed in an optical path with respect to said at least one out-coupling optical element to receive at least a portion of the light from the environment in front of the user that is coupled into said waveguide via the coupling element and guided therein and that is coupled out from said waveguide by said outcoupling coupling element such that images of said environment may be captured by said camera.

63. The system of any of the above Examples, wherein the same waveguide (a) guides light coupled from said environment into said waveguide to be received by said camera so as to capture an image of at least a portion of the environment in front of the user, and (b) guides light coupled from said projector such that light from said projector can be directed to said user's eye so that said image from said projector is in the vision field of said the user.

64. The system of any of the above Examples, wherein the same coupling element (a) couples light from said environment into said at least one waveguide to be received by said camera and (b) couples light from said image projector out from said at least one waveguide to said user's eye.

65. A head mounted display system configured to project light to an eye of a user to display augmented reality image content in a vision field of said user and to image at least a portion of the eye of the user wearing the head mounted display system, said head-mounted display system comprising:
  a frame configured to be supported on a head of the user;
  an image projector configured to project an image;
  a camera;
  an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user, said eyepiece comprising:
    (a) at least one waveguide;
    (b) at least one in-coupling optical element configured to in-couple light from said image projector into said at least one waveguide so as to guide light from said image projector therein;
    (c) at least one coupling optical element configured to couple light from said image projector guided within said waveguide out of said waveguide and direct said light to the user's eye; and
    (d) at least one out-coupling element configured to couple said light guided within said waveguide out of said waveguide and direct said light to said camera; and
  a positive lens having positive optical power disposed in an optical path between the user's eye and said eyepiece such that light reflected from the user's eye is transmitted through said lens to said eyepiece; and
  a negative lens having negative optical power disposed on the other side of the eyepiece as the positive lens to offset the power of said positive lens for light from the environment in front of the user,
  wherein the image projector is disposed in an optical path with respect to said at least one in-coupling optical element to couple light from said image projector into said waveguide to be guided therein such that said light is coupled out from said waveguide by said at least one coupling element to said user's eye such that said image from said image projector is in the vision field of said the user,
  wherein said at least one coupling element is configured such that light from the user's eye that passes through the lens to the eyepiece is coupled into said waveguide and guided therein, and
  wherein the camera is disposed in an optical path with respect to said at least one out-coupling optical element to receive at least a portion of the light from the user's eye that is reflected from the reflective surface and coupled into said waveguide via the coupling element and guided therein and that is coupled out from said waveguide by said out-coupling coupling element.

66. The system of Example 65, wherein said positive lens comprises a Fresnel lens.

67. The system of Example 65 or 66, wherein said positive lens is configured to collimate light from an anterior region of said user's eye.

68. The system of any of Examples 65, 66, or 67 above, wherein said positive lens is configured to collimate light from the cornea of said user's eye.

69. The system of any of Examples 65 to 68, wherein said system is configured to perform eye tracking based on said image of said eye.

70. The system of any of Examples 65 to 69, further comprising a light source disposed so as to illuminate of the user's eye.

71. The system of Example 70, wherein said light source comprises one or more infrared light sources configured to direct infrared light to the user's eye.

72. The system of Examples 70 or 71, wherein said light source comprises one or more infrared light emitting diodes (LEDs).

73. The system of any of the Examples above, wherein said system is configured to identify the user via biometric sensing based on said image of said eye.

Example Section IV

1. A head mounted display system configured to project light to an eye of a user to display augmented reality image content in a vision field of said user, said head-mounted display system comprising:
  a frame configured to be supported on a head of the user;
  an image projector configured to project images into the user's eye to display image content in the vision field of the user;
  at least one camera;
  at least one waveguide;
  at least one coupling optical element configured such that light is coupled into said waveguide and guided therein, said at least one coupling optical element comprising a diffractive optical element having optical power; and at least one out-coupling element configured to couple light guided within said waveguide out of said waveguide and direct said light to said camera, wherein the camera is disposed in an optical path with respect to said at least one out-coupling optical element to receive at least a portion of the light that is coupled into said waveguide via the coupling optical element and guided therein and that is coupled out from said waveguide by said out-coupling coupling element such that images may be captured by said camera.

2. The system of any of the Examples above, wherein said at least one coupling optical element is configured such that light reflected from the eye of the user wearing the head mounted display system is coupled into said at least one waveguide and guided therein such that images of said eye may be captured by said at least one camera.

3. The system of any of the Examples above, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

4. The system of any of the Examples above, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

5. The system of any of the Examples above, wherein the optical power of said coupling optical element is configured to increase collimation of light reflected from the eye that is coupled into the waveguide to be guided to the camera.

6. The system of any of the Examples above, wherein the optical power of said coupling optical element is configured to increase collimation of light reflected from an anterior portion of the eye that is coupled into the waveguide to be guided to the camera.

7. The system of any of the Examples above, wherein the optical power of said coupling optical element is configured increase collimation of light reflected from the cornea of the eye that is coupled into the waveguide to be guided to the camera.

8. The system of any of Examples 1 or 7, wherein the optical power comprises positive optical power.

9. The system of any of the Examples above, wherein said at least one coupling optical element is configured such that light reflected from the retina of the eye of the user wearing the head mounted display system is coupled into said waveguide and guided therein such that images of said retina may be captured by said camera.

10. The system of any of the Examples above, further comprising an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user.

11. The system of Example 10, wherein said eyepiece is configured to receive light from said image projector and to direct said light into said user's eye to display augmented reality image content to the user's vision field.

12. The system of any of Examples 10-11, wherein said eyepiece comprises said at least one waveguide.

13. The system of any of Examples 10-12, wherein said image projector is configured to direct light into an edge of said eyepiece.

14. The system of Examples 12 or 13, wherein said image projector is configured to direct light into an edge of said at least one waveguide.

15. The system of any of the Examples above, further comprising at least one in-coupling optical element configured to in-couple light from said image projector into said at least one waveguide so as to guide light from said image projector for providing said image content to said user's eye.

16. The system of any of Examples 1 to 12, further comprising at least one image content out-coupling optical element configured to couple light from said image projector guided within said waveguide out of said at least one waveguide such that image content can be viewed by the user's eye.

17. The system of any of the Examples above, wherein said at least one coupling optical element faces the eye of the user wearing the head mounted imaging system to receive light from said eye.

18. The system of any of the Examples above, wherein said at least one coupling optical element is configured such that light from the environment in front of the user wearing the head mounted imaging system is coupled into said at least one waveguide and guided therein such that images of said environment may be captured by said camera.

19. The system of any of the Examples above, wherein said at least one coupling optical element faces the environment in front of the user wearing the head mounted imaging system to receive light from said environment.

20. The system of Example 16, wherein said at least one coupling optical element is configured such that light is coupled into a first waveguide and guided therein to said camera and said at least one image content out-coupling optical element is configured to couple light from said image projector guided within a second waveguide out of said second waveguide.

21. The system of any of the Examples above, wherein said at least one coupling optical element is configured such that light is coupled into a first waveguide and guided therein to said camera and said image projector is configured to couple light into a second waveguide to provide image content to said eye.

22. The system of any of the Examples above, wherein said image projector comprises a light source, a modulator, and projection optics.

23. The system of any of the Examples above, wherein the image projector comprises scanning optical fiber.

24. The system of any of Examples 22, wherein the modulator comprises a light modulator.

25. The system of Example 24, wherein the light modulator comprises a spatial light modulator.

26. The system of any of the Examples above, wherein said camera comprises a detector array and imaging optics.

27. The system of Example 26, wherein said imaging optics is configured to focus collimated light onto said detector array.

28. The system of any of the Examples above, wherein said at least one waveguide comprises material that is transparent to visible light having a refractive index sufficient to guide light in said waveguide by total internal reflection.

29. The system of any of the Examples above, wherein said at least one waveguide comprises material that is transparent to infrared light having a refractive index sufficient to guide light in said waveguide by total internal reflection.

30. The system of any of the Examples above, wherein said at least one waveguide comprises a stack of waveguides.

31. The system of Example 30, wherein different waveguides of the stack of waveguides are configured to output light with different wavefront divergence as if projected from different distances from the user's eye.

32. The system of Example 30 or 31, wherein different waveguides of the stack of waveguides are configured to output light with different colors.

33. The system of any of Examples 30, 31, or 32, wherein different waveguides comprise first, second, and third waveguides, said system is configured such that the first is for red color light, the second for is green color light, and the third is for blue color light.

34. The system of any of the Examples 15 to 33, wherein the at least one in-coupling optical element comprises a diffractive optical element.

35. The system of any of the Examples 15 to 33, wherein the at least one in-coupling optical element comprises a diffraction grating.

36. The system of any of the Examples above, wherein the in-coupling element comprises a polarization selective turning element.

37. The system of any of the Examples above, wherein the in-coupling element comprises a polarization grating.

38. The system of any of the Examples above, wherein the at least one coupling element comprises a polarization selective turning element.

39. The system of any of the Examples above, wherein the at least one coupling element comprises a polarization grating.

40. The system of any of the Examples above, wherein the coupling optical element comprises liquid crystal.

41. The system of any of the Examples above, wherein the coupling optical element comprises a liquid crystal polarization grating.

42. The system of any of the Examples above, wherein the out-coupling optical element comprises a diffractive optical element.

43. The system of any of the Examples above, wherein the at least one out-coupling element comprises a polarization selective turning element.

44. The system of any of the Examples above, wherein the at least one out-coupling element comprises a polarization grating.

45. The system of any of the Examples above, wherein the at least one out-coupling element comprises liquid crystal.

46. The system of any of the Examples above, wherein the at least one out-coupling element comprises a liquid crystal polarization grating.

47. The system of any of the Examples above, wherein the at least one out-coupling element comprises an off-axis reflector.

48. The system of any of the Examples above, wherein the same waveguide (a) guides light coupled from the user's eye into said at least one waveguide to be received by said camera so as to capture an image of at least a portion of the eye of the user, and (b) guides light coupled from said image projector such that light from said projector can be directed to said user's eye such that said image from said image projector is in the vision field of said the user.

49. The system of any of the Examples above, wherein said system is configured to perform eye tracking based images of said eye.

50. The system of Example 49, wherein performing eye tracking based on said images of said eye comprises storing an image of the retina of said eye.

51. The system of any of any of the Examples above, wherein said system is configured to:
obtain an image of a portion of said retina of said eye using said camera;
compare one or more stored images of said retina with the image of said portion of said retina; and
determine a gaze of the user based on the comparison of the one or more stored images and the image of the portion of the retina obtained from the camera.

52. The system of Example 51, wherein determining a gaze of the user comprises determining to which portion of the retina corresponds to the image of said portion of the retina.

53. The system of any of Examples 51 to 52, wherein determining a gaze of the user comprises determining an orientation of the eye.

54. The system of any of the Examples above, wherein said system is configured to obtain biometric data based on one or more images of the user's eye obtained with said camera.

55. The system of any of the Examples above, wherein said system is configured to identify the user via biometric sensing based on one or more images of said eye obtained with said camera.

56. The system of any of the above Examples, wherein said system is configured to provide illumination of a first polarization and to preferentially capture images with said camera using light of a second polarization different than said first polarization.

57. The system of any of the above Examples, wherein said system is configured to illuminate said user's eye with light of a first polarization and to preferentially capture images of said user's eye with said camera using light of a second polarization different than said first polarization.

58. The system of Examples 60 or 61, wherein said first and second polarizations are orthogonal.

59. The system of any of the above Examples, further comprising a light source disposed so as to provide illumination so as to capture images with said camera.

60. The system of any of the above Examples, further comprising a light source disposed so as to illuminate of the user's eye.

61. The system of Examples 59 or 60, wherein said light source comprises one or more infrared light sources.

62. The system of any of Examples 59 to 61, wherein said light source comprises one or more infrared light emitting diodes (LEDs).

63. The system of any of Examples 59 to 63, wherein said light source is pulsed.

64. The system of any of Examples 59 to 63, wherein said light source is configured to input light into a waveguide to provide said illumination.

65. The system of any of Examples 59 to 64, wherein said light source is configured to input light into a waveguide disposed with respect to said eye to provide illumination to said eye.

66. The system of Examples 64 or 65, further comprising an illumination in-coupling optical element configured to couple light from said light source into said waveguide.

67. The system of any of Examples 60 to 66, wherein said light source is configured to input light into said at least one waveguide to provide illumination.

68. The system of any of Examples 59 to 68, wherein said light source is configured to input light into the same waveguide as used to project image content to the user's eye.

69. The system of any of Examples 59 to 69, wherein said light source is configured, to provide illumination to the user's eye, to input light into the same waveguide as used to guide light to the camera.

70. The system of any of Examples 59 to 70, wherein said light source is configured to input light into the same waveguide as used to guide light from the user's eye to the camera.

71. The system of any of Examples 64 to 70, further comprising an illumination in-coupling optical element configured to couple light from said light source into said waveguide to provide illumination.

72. The system of Example 71, wherein said illumination in-coupling optical element is polarization selective, in-coupling light of a first polarization.

73. The system of Example 59 to 77, wherein said light source is a polarized light source configured to output polarized light having a first polarization.

74. The system of any of Examples 59 to 78, wherein said light source is configured to direct polarized light having a first polarization onto said eye.

75. The system of Example 59 to 79, further comprising an illumination polarizer having a first polarization disposed in the optical path between said light source and said eye to polarize light directed to said eye.

76. The system of Example 75, wherein the illumination polarizer is disposed in the optical path between said light source and said waveguide configured to provide illumination.

77. The system of any of Examples 59 to 76, further comprising an image acquisition polarizer in an optical path between said eye and said camera.

78. The system of Example 77, wherein said image acquisition polarizer is proximal said camera.

79. The system of Examples 77 or 78, wherein said image acquisition polarizer is disposed in an optical path between (a) said at least one waveguide configured guide light to said camera and (b) said camera.

80. The system of any of Examples 77 to 79, wherein said image acquisition polarizer reduces the amount of light of said first polarization that reaches said camera.

81. The system of Examples 77 to 80, wherein said image acquisition polarizer comprises a polarizer configured to selectively coupling light of a second polarization different than said first polarization to said camera.

82. The system of any of the Examples above, further comprising at least one light consolidating element disposed in an optical path between said at least one coupling element and said at least one out-coupling optical element to reduce lateral spatial extent of light from said at least one coupling element prior to reaching said at least one out-coupling optical element.

83. The system of any of the Examples above, wherein said at least one light consolidating element comprises a diffractive optical element.

84. The system of any of the Examples above, wherein said at least one light consolidating element comprises a hologram or diffraction grating.

85. The system of any of Examples 51, wherein the one or more stored images of the retina of the eye comprise a composite image of the retina of the eye generated using a plurality of images of different portions of the retina of the eye.

86. The system of any of Examples 51 to 85, wherein the composite image of the retina comprises a plurality of images of the retina stitched together.

87. The system of any of Examples 51 to 86, wherein the plurality of images of the retina stitched together comprises images obtained when a fixation target was displayed in the vision field of the user at various locations, respectively.

88. The system of any of Examples 51 to 87, wherein the one or more stored images of the retina comprises images obtained when a fixation target was displayed in the vision field of the user at various locations, respectively.

89. The system of any of Examples 51 to 88, wherein the system is further configured to use the obtained image of the portion of the retina of the eye to update the composite image.

90. The system of any of Examples 51 to 89, wherein using the obtained image of the portion of the retina to update the composite image of the retina comprises stitching the obtained image into a section of the composite image corresponding to the portion of the retina shown in the obtained image.

91. The system of any of Examples 51 to 90, wherein the system is further configured to apply a digital filter to the obtained image of the portion of the retina of the eye to obtain a filtered image of the portion of the retina.

92. The system of Examples 91, wherein the system is further configured to compare one or more stored images of the retina with the filtered image of the portion of the retina.

93. The system of any of Examples 91 to 92, wherein the digital filter comprises a Frangi Filter.

94. The system of any of Examples 51 to 93, wherein system is configured to apply edge enhance the obtained image of the portion of the retina.

95. The system of any of the Examples above, wherein said system is configured to perform user identification verification using images of the retina.

96. The system of any of the Examples above, wherein said system is configured to:
obtain an image of a portion of said retina of said eye using said camera;
compare one or more stored images of said retina with the image of said portion of said retina.

97. The system of Example 96, wherein the one or more stored images of the retina of the eye comprise a composite image of the retina of the eye generated using a plurality of images of different portions of the retina of the eye.

98. The system of any of Examples 96 to 97, wherein the composite image of the retina comprises a plurality of images of the retina stitched together.

99. The system of any of Examples 96 to 98, wherein the plurality of images of the retina stitched together comprises images obtained when a fixation target was displayed in the vision field of the user at various locations, respectively.

100. The system of any of Examples 96 to 99, wherein the one or more stored images of the retina comprises images obtained when a fixation target was displayed in the vision field of the user at various locations, respectively.

101. The system of any of Examples 96 to 100, wherein the system is further configured to use the obtained image of the portion of the retina of the eye to update the composite image.

102. The system of any of Examples 96 to 101, wherein using the obtained image of the portion of the retina to update the composite image of the retina comprises stitching the obtained image into a section of the composite image corresponding to the portion of the retina shown in the obtained image.

103. The system of any of Examples 96 to 102, wherein the system is further configured to apply a digital filter to the obtained image of the portion of the retina of the eye to obtain a filtered image of the portion of the retina.

104. The system of Examples 103, wherein the system is further configured to compare one or more stored images of the retina with the filtered image of the portion of the retina.

105. The system of any of Examples 96 to 104, wherein the digital filter comprises a Frangi Filter.

106. The system of any of Examples 96 to 105, wherein the system is configured to apply edge enhancement the obtained image of the portion of the retina.

107. The system of any of Examples above, wherein the optical power corresponds to a focal length about the distance of the eye to the coupling optical element.

108. The system of any of Examples above, wherein the optical power corresponds to a focal length of between 15 mm and 25 mm.

109. A head mounted display system configured to project light to an eye of a user to display augmented reality image content in a vision field of said user, said head-mounted display system comprising:
 a frame configured to be supported on a head of the user;
 at least one waveguide,
 an image projector for projecting images into the user's eye to display image content in the vision field of the user, said image projector configured to input light into at least one of said at least one waveguide to be guided therein;
 at least one image content out-coupling optical element configured to couple light from said image projector guided within said at least one of said at least one waveguide out thereof such that image content can be viewed by the user's eye.
 a camera;
 at least one coupling optical element configured such that light is coupled into at least one of said at least one waveguide and guided therein to said camera; and
 at least one out-coupling element configured to couple light guided within said at least one of said at least one waveguide out thereof and direct said light to said camera, said camera disposed in an optical path with respect to said at least one out-coupling optical element to receive at least a portion of the light that is coupled into said at least one of said at least one waveguide via the coupling optical element and guided therein and that is coupled out from said at least one of said at least one waveguide by said out-coupling coupling element such that images may be captured by said camera,
 wherein said at least one image content out-coupling optical element and said at least one coupling optical element are disposed laterally with respect to each other.

110. The system of any of Example 109, wherein said at least one image content out-coupling optical element is disposed more nasally than said at least one out-coupling element.

111. The system of any of Example 110, wherein said at least one image content out-coupling optical element is disposed more temporally than said at least one out-coupling element.

112. The system of any of the Examples above, further comprising at least one light consolidating element disposed in an optical path between said at least one coupling element and said at least one out-coupling optical element to reduce lateral spatial extent of light from said at least one coupling element prior to reaching said at least one out-coupling optical element.

113. The system of any of the Examples above, wherein said at least one light consolidating element comprises a diffractive optical element.

114. The system of any of the Examples above, wherein said at least one light consolidating element comprises a hologram or diffraction grating.

115. The system of any of the Examples above, wherein said coupling optical element comprises a diffractive optical element having optical power.

116. The system of any of the Examples above, further comprising a lens disposed with respect to said coupling optical element to provide optical power to light received by said coupling optical element.

117. The system of any of the Examples above, wherein the optical power is configured to increase collimation of light reflected from the eye that is coupled into the waveguide to be guided to the camera.

118. The system of any of the Examples above, wherein the optical power is configured to increase collimation of light reflected from an anterior portion of the eye that is coupled into the waveguide to be guided to the camera.

119. The system of any of the Examples above, wherein the optical power is configured increase collimation of light reflected from the cornea of the eye that is coupled into the waveguide to be guided to the camera.

120. The system of any of Examples above, wherein the optical power comprises positive optical power.

121. The system of any of Examples above, wherein the optical power corresponds to a focal length about the distance of the eye to the coupling optical element.

122. The system of any of Examples above, wherein the optical power corresponds to a focal length of between 15 mm and 25 mm.

123. The system of any of the Examples above, wherein said coupling optical element is configured such that light reflected from the eye of the user wearing the head mounted display system is coupled into said waveguide and guided therein such that images of said eye may be captured by said camera, said system configured to image an anterior portion of said eye.

124. The system of any of the Examples above, wherein said coupling optical element is configured such that light reflected from the eye of the user wearing the head mounted display system is coupled into said waveguide and guided therein such that images of said eye may be captured by said camera, said system configured to image a corneal surface of said eye.

125. The system of any of the Examples above, wherein said second coupling optical element is configured such that light reflected from the eye of the user wearing the head mounted display system is coupled into said waveguide and guided therein such that images of said eye may be captured by said camera, said system configured to image the retina of said user's eye.

126. The system of any of the above Examples, wherein said system is configured to provide illumination of a first polarization and to preferentially capture images with said camera using light of a second polarization different than said first polarization.

127. The system of any of the above Examples, wherein said system is configured to illuminate said user's eye with light of a first polarization and to preferentially capture images of said user's eye with said camera using light of a second polarization different than said first polarization.

128. The system of Examples 126 or 127, wherein said first and second polarizations are orthogonal.

129. The system of any of Examples 126 to 128, further comprising an illumination in-coupling optical element configured to couple light from a light source into said waveguide to provide illumination.

130. The system of Example 129, wherein said illumination in-coupling optical element is polarization selective, in-coupling light of a first polarization.

131. The system of any of the Examples above, further comprising a light source that is a polarized light source configured to output polarized light having a first polarization.

132. The system of any of Example above, wherein said light source is configured to direct polarized light having a first polarization onto said eye.

133. The system of any of the Examples above, further comprising an illumination polarizer having a first polarization disposed in the optical path between said light source and said eye to polarize light directed to said eye.

134. The system of Example 133, wherein the illumination polarizer is disposed in the optical path between said light source and said waveguide configured to provide illumination.

135. The system of any of the Example above, further comprising an image acquisition polarizer in an optical path between said eye and said camera.

136. The system of Example 135, wherein said image acquisition polarizer is proximal said camera.

137. The system of Examples 135 or 136, wherein said image acquisition polarizer is disposed in an optical path between (a) said at least one waveguide configured guide light to said camera and (b) said camera.

138. The system of any of Examples 135 to 137, wherein said image acquisition polarizer reduces the amount of light of said first polarization that reaches said camera.

139. The system of Examples 135 to 138, wherein said image acquisition polarizer comprises a polarizer configured to selectively coupling light of a second polarization different than said first polarization to said camera.

140. A head mounted display system configured to project light to an eye of a user to display augmented reality image content in a vision field of said user, said head-mounted display system comprising:
  a frame configured to be supported on a head of the user;
  an image projector configured to project images into the user's eye to display image content in the vision field of the user;
  at least one camera;
  at least one waveguide;
  a first coupling optical element configured such that light is coupled into said at least one waveguide and guided therein to at least one of said at least one cameras;
  a second coupling optical element configured such that light is coupled into said at least one waveguide and guided therein to at least one of said at least one cameras; and
  at least one out-coupling element configured to couple light coupled into said at least one waveguide by said first and second coupling optical elements and guided within said at least one waveguide out of said at least one waveguide and direct said light to said at least one said camera,
  wherein first coupling optical element and said second coupling optical element are disposed laterally with respect to each other.

141. The system of any of Example 140, wherein said first coupling optical element comprising a diffractive optical element having optical power.

142. The system of any of the Examples above, further comprising a lens disposed with respect to said first coupling optical element to provide optical power to light received by said first coupling optical element.

143. The system of any of the Examples above, wherein said optical power is configured to increase collimation of light reflected from the eye that is coupled into the waveguide to be guided to the camera.

144. The system of any of the Examples above, wherein said optical power is configured to increase collimation of light reflected from an anterior portion of the eye that is coupled into the waveguide to be guided to the camera.

145. The system of any of the Examples above, wherein said optical power is configured increase collimation of light reflected from the cornea of the eye that is coupled into the waveguide to be guided to the camera.

146. The system of any of the Examples above, wherein the optical power comprises positive optical power.

147. The system of any of the Examples above, wherein the optical power corresponds to a focal length about the distance of the eye to first coupling optical element.

148. The system of any of any the Examples above, wherein the optical power corresponds to a focal length of between 15 mm and 25 mm.

149. The system of any of the Examples above, wherein said first coupling optical element is configured such that light reflected from an anterior portion of the eye of the user wearing the head mounted display system is coupled into said waveguide and guided therein such that images of said anterior portion of said eye may be captured by said camera.

150. The system of any of the Examples above, wherein said first coupling optical element is configured such that light reflected from a corneal surface of the eye of the user wearing the head mounted display system is coupled into said waveguide and guided therein such that images of the corneal surface said eye may be captured by said camera.

151. The system of any of the Examples above, wherein said second coupling optical element is configured such that light reflected from the retina of the eye of the user wearing the head mounted display system is coupled into said waveguide and guided therein such that images of the retina of said eye may be captured by said camera.

152. The system of any of the Examples above, wherein said second coupling optical element does not include optical power.

153. The system of any of the Examples above, wherein said second coupling optical element does not include a lens in an optical path between the eye and said second coupling optical element.

154. The system of any of the Examples above, wherein said first and second coupling optical elements couple light into said waveguide that is guided therein to a single camera.

155. The system of any of the Examples above, wherein said at least one camera comprises first and second cameras, said first coupling optical element configured to couples light into said waveguide that is guided therein to said first camera and said second coupling optical element configured to couple light into said waveguide that is guided therein to the second camera.

156. The system of any of the Examples above, wherein said at least one camera comprises a single cameras, said first and second coupling optical element configured to couple light into said waveguide that is guided therein to said single camera.

157. The system of any of the Examples above, wherein at least one out-coupling element comprises a first out-coupling element for out-coupling light that is input into said at least one waveguide through said first coupling optical element and a second out-coupling element for out-coupling light guided that is input into said at least one waveguide through said second coupling optical element.

158. The system of any of the above Examples, wherein said system is configured to provide illumination of a first polarization.

159. The system of Example 158, said system is configured such that light received by said second coupling optical element is preferentially used to captures images with light having a second polarization different than said first polarization.

160. The system of any of the above Examples, wherein said system is configured to illuminate said user's eye with light of a first polarization.

161. The system of Example 160, wherein said system is configured such that light received by said second coupling optical element is preferentially used to captures images of said eye with light having a second polarization different than said first polarization.

162. The system of any of Examples 158 to 161, wherein said system is configured such that light received by said first coupling optical element enables capture of images of said eye with light having either said first or second polarizations.

163. The system of any of Examples 158 to 162, wherein said first and second polarizations are orthogonal.

164. The system of any of Examples 158 to 163, further comprising an illumination in-coupling optical element configured to couple light from a light source into said waveguide to provide illumination.

165. The system of Example 164, wherein said illumination in-coupling optical element is polarization selective, in-coupling light of a first polarization.

166. The system of any of Examples 158 to 165, further comprising a light source that is a polarized light source configured to output polarized light having a first polarization.

167. The system of any of Examples 158 to 166, wherein said light source is configured to direct polarized light having a first polarization onto said eye.

168. The system of any of Examples 158 to 167, further comprising an illumination polarizer having a first polarization disposed in the optical path between said light source and said eye to polarize light directed to said eye.

169. The system of Example 168, wherein the illumination polarizer is disposed in the optical path between said light source and said waveguide configured to provide illumination.

170. The system of any of Examples 158 to 169, further comprising an image acquisition polarizer in an optical path between said eye and said camera.

171. The system of any of Examples 158 to 169, wherein said image acquisition polarizer is disposed in an optical path between said second coupling optical element and said at least one camera that receives light from said second coupling optical element.

172. The system of any of the Examples above, wherein at least one out-coupling element comprises a first out-coupling element for out-coupling light that is input into said at least one waveguide through said first coupling optical element and a second out-coupling element for out-coupling light guided that is input into said at least one waveguide through said second coupling optical element.

173. The system of any of Examples 158 to 169, wherein said image acquisition polarizer is disposed in an optical path between a second out-coupling coupling optical element and said camera.

174. The system of Example 170, wherein said image acquisition polarizer is proximal said camera.

175. The system of Examples 170 or 171, wherein said image acquisition polarizer is disposed in an optical path between (a) said at least one waveguide configured guide light to said camera and (b) said camera.

176. The system of any of Examples 170 to 172, wherein said image acquisition polarizer reduces the amount of light of said first polarization that reaches said camera.

177. The system of Examples 170 to 173, wherein said image acquisition polarizer comprises a polarizer configured to selectively coupling light of a second polarization different than said first polarization to said camera.

178. The system of any of Examples 158 to 169, wherein said second out-coupling optical element is polarization selective, selectively outcoupling light of said second polarization from said at least one waveguide.

179. The system of any of the Examples above, wherein no polarization selective optical elements that selectively direct said second polarization in comparison to said first polarization to said at least one camera are not included in the path between the first coupling optical element and said at least one camera receiving light therefrom.

180. The system of any of the Examples above, wherein said first coupling optical element is not a polarization selective coupler that selectively couples said second polarization in comparison to said first polarization into said at least one waveguide.

181. The system of any of the Examples above, wherein the first out-coupling optical element polarization is not a selective coupling optical elements that selectively couples said second polarization in comparison to said first polarization to said at least one camera.

182. The system of any of the Examples above, wherein no polarization selective optical elements that selectively direct said second polarization in comparison to said first polarization to said at least one camera are included in the path between the first out-coupling optical element and said at least one camera receiving light therefrom.

183. The system of any of the Examples above, wherein no polarization selective optical elements that selectively direct said second polarization in comparison to said first polarization to said at least one camera are included in the path between the first coupling optical element and said first out-coupling optical element.

184. The system of any of the Examples above, wherein and an optical element having optical power is disposed with respect to said first coupling optical element such that propagation of light coupled into said first coupling optical element is altered by said optical power or said first coupling optical element has optical power.

185. The system of any of Examples above, wherein an optical element having optical power is disposed in an optical path to said first coupling optical element such that light coupled into said waveguide passes through said optical element having optical power or said first coupling optical element has optical power.

186. The system of any of Examples above, wherein an optical element having optical power is disposed in an optical path from said eye to said first coupling optical element such that light from said eye coupled into said waveguide passes through said optical element having optical power or said first coupling optical element has optical power.

187. The system of any of the Examples above, wherein an optical element having optical power is not disposed in an optical path from the eye to said second coupling optical element.

188. The system of any of the Examples above, wherein an optical element having optical power is not disposed with respect to said second coupling optical element such that the propagation of light to said second coupling optical element is not altered by an optical element having optical power.

189. The system of any of Examples above, wherein said second coupling optical element does not have optical power.

190. The system of any of the Examples above, wherein said system is configured such that said light from said first coupling element forms an image of an anterior surface of the eye on said at least one camera thereby enabling images of said anterior surface to be captured.

191. The system of any of the Examples above, wherein said system is configured such that said light from said first coupling optical element forms an image of glint on said at least one camera thereby enabling images of said glint to be captured.

192. The system of any of the Examples above, wherein said system is configured such that said light from said second coupling optical element forms an image of the retina on said at least one camera thereby enabling images of said retina to be captured.

193. The system of any of the Examples above, wherein said system is configured such that light from said first coupling optical element preferentially enabling images of glint to be captured by said at least one camera and light from said second coupling optical element preferentially enables images of the retina to be captured by said at least one camera.

194. The system of any of the Examples above, wherein said system is configured such that light from said first coupling optical element preferentially enabling images of an anterior surface of the eye to be captured by said at least one camera and light from said second coupling optical element preferentially enables images of the retina to be captured by said at least one camera.

195. The system of any of the Examples above, wherein said system is configured such that light from said first coupling optical element preferentially enabling images of a corneal surface to be captured by said at least one camera and light from said second coupling optical element preferentially enables images of the retina to be captured by said at least one camera.

196. The system of any of the Examples above, wherein said first and second coupling optical elements are in contact with each other.

197. The system of any of the Examples above, wherein said at least one coupling optical element comprises a diffractive optical element having a coupling area for coupling light into said waveguide, said coupling area having an average thickness in a range from 0.1 to 3 millimeters across, and wherein the light is coupled into said waveguide via the coupling area of the coupling element.

198. The system of any of the Examples above, wherein said average thickness of said coupling area is in a range from 0.5 to 2 millimeters.

199. The system of any of the Examples above, wherein said average thickness of said coupling area is in a range from 1 to 2 millimeters.

200. The system of any of the Examples above, wherein said coupling area is slit shaped.

201. The system of any of the Examples above, wherein said coupling area has a rectangular shape.

202. The system of any of the Examples above, wherein said coupling area has an arcuate shape.

203. The system of any of the Examples above, wherein said coupling area has an aspect ratio in a range from 5 to 100.

204. The system of any of the Examples above, wherein said coupling area has an aspect ratio in a range from 10 to 100.

205. The system of any of the Examples above, wherein said coupling area has an aspect ratio in a range from 15 to 100.

206. The system of any of the Examples above, wherein said coupling area has an aspect ratio in a range from 20 and 100.

207. The system of any of the Examples above, wherein said out-coupling optical element comprises a diffractive optical element.

208. The system of any of the Examples above, wherein said out-coupling optical element has a coupling area for coupling light out of said waveguide having an average thickness in a range from 0.5 mm to 3.0 millimeters.

209. The system of any of the Examples above, wherein said out-coupling optical element has a coupling area for coupling light out of said waveguide having an average thickness in a range from 1 mm to 2.5 millimeters.

210. The system of any of the Examples above, wherein said out-coupling optical element has a coupling area for coupling light out of said waveguide having a dimension in a range from 0.5 mm to 3.0 millimeters across in two orthogonal directions.

211. The system of any of the Examples above, wherein said out-coupling optical element has a coupling area for coupling light out of said waveguide having a dimension in a range from 1.0 mm to 2.5 millimeters across in two orthogonal directions.

212. The system of any of the Examples above, wherein said coupling area of said out-coupling optical element has an aspect ratio in a range from 1 to 2.

213. The system of any of the Examples above, wherein said coupling area of said out-coupling optical element has an aspect ratio in a range from 1 to 1.75.

214. The system of any of the Examples above, wherein said coupling area of said out-coupling optical element has an aspect ratio of in a range from 1 to 1.5.

215. The system of any of the Examples above, wherein said coupling area of said out-coupling optical element has an aspect ratio of in a range from 1 to 1.3.

216. The system of any of the Examples above, wherein said coupling area of said out-coupling optical element has an aspect ratio of in a range from 1 to 1.2.

217. The system of any of the Examples above, wherein said coupling area of said out-coupling optical element has an aspect ratio of in a range from 1 to 1.1.

218. The system of any of the Examples above, wherein said at least one coupling optical element is configured such that light reflected from the eye of the user wearing the head mounted display system is coupled into said at least one waveguide and guided therein such that images of said eye may be captured by said at least one camera.

219. The system of any of the Examples above, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

220. The system of any of the Examples above, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

221. The system of any of the Examples above, wherein the coupling optical element has optical power.

222. The system of any of the Examples above, wherein the optical power of the coupling optical element is configured to increase collimation of light reflected from the eye that is coupled into the waveguide to be guided to the camera.

223. The system of any of the Examples above, wherein the optical power of said coupling optical element is configured to increase collimation of light reflected from an anterior portion of the eye that is coupled into the waveguide to be guided to the camera.

224. The system of any of the Examples above, wherein the optical power of said coupling optical element is configured to increase collimation of light reflected from the cornea of the eye that is coupled into the waveguide to be guided to the camera.

225. The system of any of Examples above, wherein the optical power comprises positive optical power.

226. The system of any of Examples above, wherein the optical power corresponds to a focal length of in a range from 15 mm and 25 mm.

227. The system of any of Examples above, further comprising at least one image content out-coupling optical element configured to couple light from said image projector guided within said at least one of said at least one waveguide out thereof such that image content can be viewed by the user's eye.

228. The system of any of Examples above, wherein said at least one image content out-coupling optical element and said at least one coupling optical element are disposed laterally with respect to each other.

229. The system of any of Example 228, wherein said at least one image content out-coupling optical element is disposed more nasally than said at least one out-coupling element.

230. The system of any of Example 228, wherein said at least one image content out-coupling optical element is disposed more temporally than said at least one out-coupling element.

231. The system of any of Examples above, wherein said at least one coupling optical element comprises:
 a first coupling optical element configured such that light is coupled into said at least one waveguide and guided therein to at least one of said at least one cameras; and
 a second coupling optical element configured such that light is coupled into said at least one waveguide and guided therein to at least one of said at least one cameras,
 wherein first coupling optical element and said second coupling optical element are disposed laterally with respect to each other.

232. The system of any of Example 92, wherein said first coupling optical element comprising a diffractive optical element having optical power.

233. The system of any of the Examples above, further comprising a lens disposed with respect to said first coupling optical element to provide optical power to light received by said first coupling optical element.

234. The system of any of the Examples above, wherein said optical power is configured to increase collimation of light reflected from the eye that is coupled into the waveguide to be guided to the camera.

235. The system of any of the Examples above, wherein said optical power is configured to increase collimation of light reflected from an anterior portion of the eye that is coupled into the waveguide to be guided to the camera.

236. The system of any of the Examples above, wherein said optical power is configured increase collimation of light reflected from the cornea of the eye that is coupled into the waveguide to be guided to the camera.

237. The system of any of the Examples above, wherein the optical power comprises positive optical power.

238. The system of any of the Examples above, wherein the optical power corresponds to a focal length about the distance of the eye to first coupling optical element.

239. The system of any of any the Examples above, wherein the optical power corresponds to a focal length in a range from 15 mm to 25 mm.

240. The system of any of the Examples above, wherein said first coupling optical element is configured such that light reflected from an anterior portion of the eye of the user wearing the head mounted display system is coupled into said waveguide and guided therein such that images of said anterior portion of said eye may be captured by said camera.

241. The system of any of the Examples above, wherein said first coupling optical element is configured such that light reflected from a corneal surface of the eye of the user wearing the head mounted display system is coupled into said waveguide and guided therein such that images of the corneal surface said eye may be captured by said camera.

242. The system of any of the Examples above, wherein said second coupling optical element is configured such that light reflected from the retina of the eye of the user wearing the head mounted display system is coupled into said waveguide and guided therein such that images of the retina of said eye may be captured by said camera.

243. The system of any of the Examples above, wherein said second coupling optical element does not include optical power.

244. The system of any of the Examples above, wherein said second coupling optical element does not include a lens in an optical path between the eye and said second coupling optical element.

245. The system of any of the Examples above, wherein at least one coupling optical element is configured such that light is coupled into said waveguide and guided therein, said at least one coupling optical element comprising a diffractive optical element having a slit shaped coupling area for coupling light into said waveguide, and wherein the camera is disposed in an optical path with respect to said at least one out-coupling optical element to receive at least a portion of the light that is coupled into said waveguide via the coupling area of the coupling element.

246. The system of any of the Examples above, wherein said coupling area has an average thickness of in a range from 0.5 to 3 millimeters.

247. The system of any of the Examples above, wherein said coupling area has an average thickness in a range from 0.5 to 2 millimeters.

248. The system of any of the Examples above, wherein said coupling area has an average thickness in a range from 1 to 2 millimeters.

249. The system of any of the Examples above, wherein said coupling area has a rectangular shape.

250. The system of any of the Examples above, wherein said coupling area has an arcuate shape.

251. The system of any of the Examples above, wherein said coupling area has a non-arcuate shape.

252. The system of any of the Examples above, wherein said coupling area that has a length and a width, the length longer than the width and said coupling area is straight along said the length.

253. The system of any of the Examples above, wherein said coupling area has an aspect ratio in a range from 5 to 100.

254. The system of any of the Examples above, wherein said coupling area has an aspect ratio in a range from 10 to 100.

255. The system of any of the Examples above, wherein said coupling area has an aspect ratio in a range from 15 to 100.

256. The system of any of the Examples above, wherein said coupling area has an aspect ratio in a range from 20 to 100.

257. The system of any of the Examples above, wherein said out-coupling optical element has a coupling area for coupling light out of said waveguide having a thickness from 0.5 mm to 3.0 millimeters across.

258. The system of any of the Examples above, wherein said out-coupling optical element has a coupling area for coupling light out of said waveguide having an average thickness in a range from 1 mm to 2.5 millimeters across.

259. The system of any of the Examples above, wherein said out-coupling optical element has a coupling area for coupling light out of said waveguide having a dimension along one direction of in a range from 0.5 mm to 3.0 millimeters across in two orthogonal dimensions.

260. The system of any of the Examples above, wherein said out-coupling optical element has an coupling area having a dimension along one direction in a range from 1.0 mm to 2.5 millimeters across in two orthogonal dimensions.

261. The system of any of the Examples above, wherein said at least one out-coupling optical element has a coupling area for coupling light out of said waveguide having an aspect ratio in a range from 1 to 2.

262. The system of any of the Examples above, wherein said at least one out-coupling optical element has a coupling area for coupling light out of said waveguide having an aspect ratio in a range from 1 to 1.75.

263. The system of any of the Examples above, wherein said at least one out-coupling optical element has a coupling area for coupling light out of said waveguide having an aspect ratio in a range from 1 to 1.5.

264. The system of any of the Examples above, wherein said at least one out-coupling optical element has a coupling area for coupling light out of said waveguide having an aspect ratio in a range from 1 to 1.3.

265. The system of any of the Examples above, wherein said at least one out-coupling optical element has a coupling area for coupling light out of said waveguide having an aspect ratio in a range from 1 to 1.2.

266. The system of any of the Examples above, wherein said at least one out-coupling optical element has a coupling area for coupling light out of said waveguide having an aspect ratio in a range from 1 to 1.1.

267. The system of any of the Examples above, said at least one out-coupling element has a coupling area for coupling light out of said waveguide that is not a slit.

268. The system of any of the Examples above, wherein said average thickness of said coupling area is in a range from 0.1 to 0.3 millimeters.

269. The system of any of the Examples above, wherein said average thickness of said coupling area is in a range from 0.1 to 2 millimeters.

270. The system of any of the Examples above, wherein said average thickness of said coupling area is in a range from 0.1 to 1.5 millimeters.

271. The system of any of the Examples above, wherein said average thickness of said coupling area is in a range from 0.1 to 1 millimeters.

272. The system of any of the Examples above, wherein said average thickness of said coupling area is in a range from 0.2 to 2 millimeters.

273. The system of any of the Examples above, wherein said average thickness of said coupling area is in a range from 0.3 to 2 millimeters.

274. The system of any of the Examples above, wherein said average thickness of said coupling area is in a range from 0.2 to 1.5 millimeters.

275. The system of any of the Examples above, wherein said average thickness of said coupling area is in a range from 0.2 to 1 millimeters.

276. The system of any of the Examples above, wherein said average thickness of said coupling area is in a range from 0.3 to 1.5 millimeters.

277. The system of any of the Examples above, wherein said average thickness of said coupling area is in a range from 0.3 to 1 millimeters.

278. The system of any of the Examples above, wherein said average thickness of said coupling area is in a range from 0.1 to 0.5 millimeters.

279. The system of any of the Examples above, wherein said average thickness of said coupling area is in a range from 0.1 to 0.8 millimeters.

280. The system of any of the Examples above, wherein said average thickness of said coupling area is in a range from 0.2 to 0.5 millimeters.

281. The system of any of the Examples above, wherein said average thickness of said coupling area is in a range from 0.2 to 0.8 millimeters.

282. The system of any of the Examples above, wherein said average thickness of said coupling area is in a range from 0.1 to 0.2 millimeters.

283. The system of any of the Examples above, wherein said average thickness of said coupling area is in a range from 0.1 to 0.3 millimeters.

284. The system of any of the Examples above, wherein said average thickness of said coupling area is in a range from 0.2 to 0.3 millimeters.

285. The system of any of the Examples above, wherein said average thickness of said coupling area is in a range from 0.3 to 0.5 millimeters.

286. The system of any of the Examples above, wherein said average thickness of said coupling area is in a range from 0.3 to 0.8 millimeters.

287. The system of any of the Examples above, wherein said coupling area has a length of from 20 mm to 50 mm.

288. The system of any of the Examples above, wherein said coupling area has a length of from 10 mm to 40 mm.

289. The system of any of the Examples above, wherein said coupling area has a length of from 2 mm to 20 mm.

290. The system of any of the Examples above, wherein said coupling area has a length of from 5 mm to 20 mm.

291. The system of any of the Examples above, wherein said coupling area has a length of from 1 mm to 10 mm.

292. The system of any of the Examples above, wherein said coupling area has a length of from 0.5 mm to 2 mm.

293. The system of any of the Examples above, wherein said coupling area has a length of from 10 mm to 20 mm.

294. The system of any of the Examples above, wherein said coupling area has a length of from 10 mm to 30 mm.

295. The system of any of the Examples above, wherein said coupling area has a length of from 6 mm to 18 mm.

296. The system of any of Examples above, wherein the optical power corresponds to a focal length of between 10 mm and 30 mm.

297. The system of any of the Examples above, wherein said out-coupling optical element is polarization selective, preferentially filtering out light of said first polarization as compared to said second polarization.

298. The system of any of the Examples above, wherein said out-coupling optical element is polarization selective, preferentially coupling out light of said second polarization as compared to said first polarization.

299. The system of any of the Examples above, wherein said system is configured such that light coupled into said waveguide by said first coupling optical element is acted on by a first total optical power and light coupled into said waveguide by said second coupling optical element is acted on by a second total optical power and said first total optical power is larger than said second total optical power.

300. The system of any of the Examples above, wherein said first coupling optical element has a first optical power and said second coupling optical element has a second optical power, and said first optical power is larger than said second optical power.

301. The system of any of the Examples above, wherein said first coupling optical element has a first lens associated therewith having has a first optical power and said second coupling optical element has associated therewith a second lens having a second optical power, and said first optical power is larger than said second optical power.

Example Section V

1. A head mounted display system configured to project light to an eye of a user to display augmented reality image content in a vision field of said user, said head-mounted display system comprising:
a frame configured to be supported on a head of the user;
an image projector configured to project images into the user's eye to display image content in the vision field of the user;
at least one camera;
at least one waveguide;
at least one coupling optical element configured such that light is coupled into said waveguide and guided therein, said at least one coupling optical element comprising a diffractive optical element having an coupling area for coupling light into said waveguide, said coupling area having an average thickness in a range from 0.1 to 3 millimeters across; and
at least one out-coupling element configured to couple light guided within said waveguide out of said waveguide and direct said light to said camera,
wherein at least one camera is disposed in an optical path with respect to said at least one out-coupling optical element to receive at least a portion of the light that is coupled into said waveguide via the coupling area of the at least one coupling optical element and guided therein and that is coupled out from said waveguide by said at least one outcoupling element such that images may be captured by said camera.

2. The system of any of the Examples above, wherein said average thickness of said coupling area is in a range from 0.5 to 2 millimeters.

3. The system of any of the Examples above, wherein said average thickness of said coupling area is in a range from 1 to 2 millimeters.

4. The system of any of the Examples above, wherein said coupling area is slit shaped.

5. The system of any of the Examples above, wherein said coupling area has a rectangular shape.

6. The system of any of the Examples above, wherein said coupling area has an arcuate shape.

7. The system of any of the Examples above, wherein said coupling area has an aspect ratio in a range from 5 to 100.

8. The system of any of the Examples above, wherein said coupling area has an aspect ratio in a range from 10 to 100.

9. The system of any of the Examples above, wherein said coupling area has an aspect ratio in a range from 15 to 100.

10. The system of any of the Examples above, wherein said coupling area has an aspect ratio in a range from 20 and 100.

11. The system of any of the Examples above, wherein said out-coupling optical element comprises a diffractive optical element.

12. The system of any of the Examples above, wherein said out-coupling optical element has a coupling area for coupling light out of said waveguide having an average thickness in a range from 0.5 mm to 3.0 millimeters.

13. The system of any of the Examples above, wherein said out-coupling optical element has a coupling area for coupling light out of said waveguide having an average thickness in a range from 1 mm to 2.5 millimeters.

14. The system of any of the Examples above, wherein said out-coupling optical element has a coupling area for coupling light out of said waveguide having a dimension in a range from 0.5 mm to 3.0 millimeters across in two orthogonal directions.

15. The system of any of the Examples above, wherein said out-coupling optical element has a coupling area for coupling light out of said waveguide having a dimension in a range from 1.0 mm to 2.5 millimeters across in two orthogonal directions.

16. The system of any of the Examples above, wherein said coupling area of said out-coupling optical element has an aspect ratio in a range from 1 to 2.

17. The system of any of the Examples above, wherein said coupling area of said out-coupling optical element has an aspect ratio in a range from 1 to 1.75.

18. The system of any of the Examples above, wherein said coupling area of said out-coupling optical element has an aspect ratio of in a range from 1 to 1.5.

19. The system of any of the Examples above, wherein said coupling area of said out-coupling optical element has an aspect ratio of in a range from 1 to 1.3.

20. The system of any of the Examples above, wherein said coupling area of said out-coupling optical element has an aspect ratio of in a range from 1 to 1.2.

21. The system of any of the Examples above, wherein said coupling area of said out-coupling optical element has an aspect ratio of in a range from 1 to 1.1.

22. The system of any of the Examples above, wherein said at least one coupling optical element is configured such that light reflected from the eye of the user wearing the head mounted display system is coupled into said at least one waveguide and guided therein such that images of said eye may be captured by said at least one camera.

23. The system of any of the Examples above, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

24. The system of any of the Examples above, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

25. The system of any of the Examples above, wherein the coupling optical element has optical power.

26. The system of any of the Examples above, wherein the optical power of the coupling optical element is configured to increase collimation of light reflected from the eye that is coupled into the waveguide to be guided to the camera.

27. The system of any of the Examples above, wherein the optical power of said coupling optical element is configured to increase collimation of light reflected from an anterior portion of the eye that is coupled into the waveguide to be guided to the camera.

28. The system of any of the Examples above, wherein the optical power of said coupling optical element is configured to increase collimation of light reflected from the cornea of the eye that is coupled into the waveguide to be guided to the camera.

29. The system of any of Examples above, wherein the optical power comprises positive optical power.

30. The system of any of Examples above, wherein the optical power corresponds to a focal length of in a range from 15 mm and 25 mm.

31. The system of any of Examples above, further comprising at least one image content out-coupling optical element configured to couple light from said image projector guided within said at least one of said at least one waveguide out thereof such that image content can be viewed by the user's eye.

32. The system of any of Examples above, wherein said at least one image content out-coupling optical element and said at least one coupling optical element are disposed laterally with respect to each other.

33. The system of any of Example 32, wherein said at least one image content out-coupling optical element is disposed more nasally than said at least one out-coupling element.

34. The system of any of Example 32, wherein said at least one image content out-coupling optical element is disposed more temporally than said at least one out-coupling element.

35. The system of any of Examples above, wherein said at least one coupling optical element comprises:
 a first coupling optical element configured such that light is coupled into said at least one waveguide and guided therein to at least one of said at least one cameras; and
 a second coupling optical element configured such that light is coupled into said at least one waveguide and guided therein to at least one of said at least one cameras,
 wherein first coupling optical element and said second coupling optical element are disposed laterally with respect to each other.

36. The system of any of Example 35, wherein said first coupling optical element comprising a diffractive optical element having optical power.

37. The system of any of the Examples above, further comprising a lens disposed with respect to said first coupling optical element to provide optical power to light received by said first coupling optical element.

38. The system of any of the Examples above, wherein said optical power is configured to increase collimation of light reflected from the eye that is coupled into the waveguide to be guided to the camera.

39. The system of any of the Examples above, wherein said optical power is configured to increase collimation of light reflected from an anterior portion of the eye that is coupled into the waveguide to be guided to the camera.

40. The system of any of the Examples above, wherein said optical power is configured increase collimation of light reflected from the cornea of the eye that is coupled into the waveguide to be guided to the camera.

41. The system of any of the Examples above, wherein the optical power comprises positive optical power.

42. The system of any of the Examples above, wherein the optical power corresponds to a focal length about the distance of the eye to first coupling optical element.

43. The system of any of any the Examples above, wherein the optical power corresponds to a focal length in a range from 15 mm to 25 mm.

44. The system of any of the Examples above, wherein said first coupling optical element is configured such that light reflected from an anterior portion of the eye of the user wearing the head mounted display system is coupled into said waveguide and guided therein such that images of said anterior portion of said eye may be captured by said camera.

45. The system of any of the Examples above, wherein said first coupling optical element is configured such that light reflected from a corneal surface of the eye of the user wearing the head mounted display system is coupled into said waveguide and guided therein such that images of the corneal surface said eye may be captured by said camera.

46. The system of any of the Examples above, wherein said second coupling optical element is configured such that light reflected from the retina of the eye of the user wearing the head mounted display system is coupled into said waveguide and guided therein such that images of the retina of said eye may be captured by said camera.

47. The system of any of the Examples above, wherein said second coupling optical element does not include optical power.

48. The system of any of the Examples above, wherein said second coupling optical element does not include a lens in an optical path between the eye and said second coupling optical element.

49. A head mounted display system configured to project light to an eye of a user to display augmented reality image content in a vision field of said user, said head-mounted display system comprising:
- a frame configured to be supported on a head of the user;
- an image projector configured to project images into the user's eye to display image content in the vision field of the user;
- at least one camera;
- at least one waveguide;
- at least one coupling optical element configured such that light is coupled into said waveguide and guided therein, said at least one coupling optical element comprising a diffractive optical element having a slit shaped coupling area for coupling light into said waveguide; and
- at least one out-coupling element configured to couple light guided within said waveguide out of said waveguide and direct said light to said camera,
- wherein the camera is disposed in an optical path with respect to said at least one out-coupling optical element to receive at least a portion of the light that is coupled into said waveguide via the coupling area of the at least one coupling optical element and guided therein and that is coupled out from said waveguide by said at least one outcoupling element such that images may be captured by said camera.

50. The system of any of the Examples above, wherein said coupling area has an average thickness of in a range from 0.5 to 3 millimeters.

51. The system of any of the Examples above, wherein said coupling area has an average thickness in a range from 0.5 to 2 millimeters.

52. The system of any of the Examples above, wherein said coupling area has an average thickness in a range from 1 to 2 millimeters.

53. The system of any of the Examples above, wherein said coupling area has a rectangular shape.

54. The system of any of the Examples above, wherein said coupling area has an arcuate shape.

55. The system of any of the Examples above, wherein said coupling area has a non-arcuate shape.

56. The system of any of the Examples above, wherein said coupling area that has a length and a width, the length longer than the width and said coupling area is straight along said the length.

57. The system of any of the Examples above, wherein said coupling area has an aspect ratio in a range from 5 to 100.

58. The system of any of the Examples above, wherein said coupling area has an aspect ratio in a range from 10 to 100.

59. The system of any of the Examples above, wherein said coupling area has an aspect ratio in a range from 15 to 100.

60. The system of any of the Examples above, wherein said coupling area has an aspect ratio in a range from 20 to 100.

61. The system of any of the Examples above, wherein said out-coupling optical element has a coupling area for coupling light out of said waveguide having a thickness from 0.5 mm to 3.0 millimeters across.

62. The system of any of the Examples above, wherein said out-coupling optical element has a coupling area for coupling light out of said waveguide having an average thickness in a range from 1 mm to 2.5 millimeters across.

63. The system of any of the Examples above, wherein said out-coupling optical element has a coupling area for coupling light out of said waveguide having a dimension along one direction of in a range from 0.5 mm to 3.0 millimeters across in two orthogonal dimensions.

64. The system of any of the Examples above, wherein said out-coupling optical element has an coupling area having a dimension along one direction in a range from 1.0 mm to 2.5 millimeters across in two orthogonal dimensions.

65. The system of any of the Examples above, wherein said at least one out-coupling optical element has a coupling area for coupling light out of said waveguide having an aspect ratio in a range from 1 to 2.

66. The system of any of the Examples above, wherein said at least one out-coupling optical element has a coupling area for coupling light out of said waveguide having an aspect ratio in a range from 1 to 1.75.

67. The system of any of the Examples above, wherein said at least one out-coupling optical element has a coupling area for coupling light out of said waveguide having an aspect ratio in a range from 1 to 1.5.

68. The system of any of the Examples above, wherein said at least one out-coupling optical element has a coupling area for coupling light out of said waveguide having an aspect ratio in a range from 1 to 1.3.

69. The system of any of the Examples above, wherein said at least one out-coupling optical element has a coupling area for coupling light out of said waveguide having an aspect ratio in a range from 1 to 1.2.

70. The system of any of the Examples above, wherein said at least one out-coupling optical element has a coupling area for coupling light out of said waveguide having an aspect ratio in a range from 1 to 1.1.

71. The system of any of the Examples above, said at least one out-coupling element has a coupling area for coupling light out of said waveguide that is not a slit.

72. The system of any of the Examples above, wherein said average thickness of said coupling area is in a range from 0.1 to 0.3 millimeters.

73. The system of any of the Examples above, wherein said average thickness of said coupling area is in a range from 0.1 to 2 millimeters.

74. The system of any of the Examples above, wherein said average thickness of said coupling area is in a range from 0.1 to 1.5 millimeters.

75. The system of any of the Examples above, wherein said average thickness of said coupling area is in a range from 0.1 to 1 millimeters.

76. The system of any of the Examples above, wherein said average thickness of said coupling area is in a range from 0.2 to 2 millimeters.

77. The system of any of the Examples above, wherein said average thickness of said coupling area is in a range from 0.3 to 2 millimeters.

78. The system of any of the Examples above, wherein said average thickness of said coupling area is in a range from 0.2 to 1.5 millimeters.

79. The system of any of the Examples above, wherein said average thickness of said coupling area is in a range from 0.2 to 1 millimeters.

80. The system of any of the Examples above, wherein said average thickness of said coupling area is in a range from 0.3 to 1.5 millimeters.

81. The system of any of the Examples above, wherein said average thickness of said coupling area is in a range from 0.3 to 1 millimeters.

82. The system of any of the Examples above, wherein said average thickness of said coupling area is in a range from 0.1 to 0.5 millimeters.

83. The system of any of the Examples above, wherein said average thickness of said coupling area is in a range from 0.1 to 0.8 millimeters.

84. The system of any of the Examples above, wherein said average thickness of said coupling area is in a range from 0.2 to 0.5 millimeters.

85. The system of any of the Examples above, wherein said average thickness of said coupling area is in a range from 0.2 to 0.8 millimeters.

86. The system of any of the Examples above, wherein said average thickness of said coupling area is in a range from 0.1 to 0.2 millimeters.

87. The system of any of the Examples above, wherein said average thickness of said coupling area is in a range from 0.1 to 0.3 millimeters.

88. The system of any of the Examples above, wherein said average thickness of said coupling area is in a range from 0.2 to 0.3 millimeters.

89. The system of any of the Examples above, wherein said average thickness of said coupling area is in a range from 0.3 to 0.5 millimeters.

90. The system of any of the Examples above, wherein said average thickness of said coupling area is in a range from 0.3 to 0.8 millimeters.

91. The system of any of the Examples above, wherein said coupling area has a length of from 20 mm to 50 mm.

92. The system of any of the Examples above, wherein said coupling area has a length of from 10 mm to 40 mm.

93. The system of any of the Examples above, wherein said coupling area has a length of from 2 mm to 20 mm.

94. The system of any of the Examples above, wherein said coupling area has a length of from 5 mm to 20 mm.

95. The system of any of the Examples above, wherein said coupling area has a length of from 1 mm to 10 mm.

96. The system of any of the Examples above, wherein said coupling area has a length of from 0.5 mm to 2 mm.

97. The system of any of the Examples above, wherein said coupling area has a length of from 10 mm to 20 mm.

98. The system of any of the Examples above, wherein said coupling area has a length of from 10 mm to 30 mm.

99. The system of any of the Examples above, wherein said coupling area has a length of from 6 mm to 18 mm.

100. The system of any of the Examples above, wherein at least one coupling optical element is configured such that light is coupled into said waveguide and guided therein, said at least one coupling optical element comprising a diffractive optical element having optical power, and wherein the camera is disposed in an optical path with respect to said at least one out-coupling optical element to receive at least a portion of the light that is coupled into said waveguide via the coupling optical element.

101. The system of any of the Examples above, wherein said at least one coupling optical element is configured such that light reflected from the eye of the user wearing the head mounted display system is coupled into said at least one waveguide and guided therein such that images of said eye may be captured by said at least one camera.

102. The system of any of the Examples above, wherein said at least one coupling optical element is configured such that light reflected from an anterior portion of the eye of the user wearing the head mounted display system is coupled into said waveguide and guided therein such that images of said eye may be captured by said camera such that said at least one camera can capture images of said anterior portion of said eye.

103. The system of any of the Examples above, wherein said at least one coupling optical element is configured such that light reflected from a corneal surface of said eye of the user wearing the head mounted display system is coupled into said waveguide and guided therein such that images of said eye may be captured by said camera such that said at least one camera can capture images of said corneal surface of said eye.

104. The system of any of the Examples above, wherein the optical power of said coupling optical element is configured to increase collimation of light reflected from the eye that is coupled into the waveguide to be guided to the camera.

105. The system of any of the Examples above, wherein the optical power of said coupling optical element is configured to increase collimation of light reflected from an anterior portion of the eye that is coupled into the waveguide to be guided to the camera.

106. The system of any of the Examples above, wherein the optical power of said coupling optical element is configured increase collimation of light reflected from the cornea of the eye that is coupled into the waveguide to be guided to the camera.

107. The system of any of Examples above, wherein the optical power comprises positive optical power.

108. The system of any of the Examples above, wherein said at least one coupling optical element is configured such that light reflected from the retina of the eye of the user wearing the head mounted display system is coupled into said waveguide and guided therein such that images of said retina may be captured by said camera.

109. The system of any of the Examples above, further comprising an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user.

110. The system of Example 109, wherein said eyepiece is configured to receive light from said image projector and to direct said light into said user's eye to display augmented reality image content to the user's vision field.

111. The system of any of Examples 109-110, wherein said eyepiece comprises said at least one waveguide.

112. The system of any of Examples 109-111, wherein said image projector is configured to direct light into an edge of said eyepiece.

113. The system of Examples 111 or 112, wherein said image projector is configured to direct light into an edge of said at least one waveguide.

114. The system of any of the Examples above, further comprising at least one in-coupling optical element configured to in-couple light from said image projector into said at least one waveguide so as to guide light from said image projector for providing said image content to said user's eye.

115. The system of any of Examples above, further comprising at least one image content out-coupling optical element configured to couple light from said image projector guided within said waveguide out of said at least one waveguide such that image content can be viewed by the user's eye.

116. The system of any of the Examples above, wherein said at least one coupling optical element faces the eye of the user wearing the head mounted imaging system to receive light from said eye.

117. The system of any of the Examples above, wherein said at least one coupling optical element is configured such that light from the environment in front of the user wearing the head mounted imaging system is coupled into said at least one waveguide and guided therein such that images of said environment may be captured by said camera.

118. The system of any of the Examples above, wherein said at least one coupling optical element faces the environment in front of the user wearing the head mounted imaging system to receive light from said environment.

119. The system of Example 118, wherein said at least one coupling optical element is configured such that light is coupled into a first waveguide and guided therein to said camera and said at least one image content out-coupling optical element is configured to couple light from said image projector guided within a second waveguide out of said second waveguide.

120. The system of any of the Examples above, wherein said at least one coupling optical element is configured such that light is coupled into a first waveguide and guided therein to said camera and said image projector is configured to couple light into a second waveguide to provide image content to said eye.

121. The system of any of the Examples above, wherein said image projector comprises a light source, a modulator, and projection optics.

122. The system of any of the Examples above, wherein the image projector comprises scanning optical fiber.

123. The system of any of Examples 122, wherein the modulator comprises a light modulator.

124. The system of Example 123, wherein the light modulator comprises a spatial light modulator.

125. The system of any of the Examples above, wherein said camera comprises a detector array and imaging optics.

126. The system of Example 125, wherein said imaging optics is configured to focus collimated light onto said detector array.

127. The system of any of the Examples above, wherein said at least one waveguide comprises material that is transparent to visible light having a refractive index sufficient to guide light in said waveguide by total internal reflection.

128. The system of any of the Examples above, wherein said at least one waveguide comprises material that is transparent to infrared light having a refractive index sufficient to guide light in said waveguide by total internal reflection.

129. The system of any of the Examples above, wherein said at least one waveguide comprises a stack of waveguides.

130. The system of any of the Examples above, wherein different waveguides of the stack of waveguides are configured to output light with different wavefront divergence as if projected from different distances from the user's eye.

131. The system of any of the Examples above, wherein different waveguides of the stack of waveguides are configured to output light with different colors.

132. The system of any of the Examples above, wherein different waveguides comprise first, second, and third waveguides, said system is configured such that the first is for red color light, the second for is green color light, and the third is for blue color light.

133. The system of any of the Examples above, wherein the at least one in-coupling optical element comprises a diffractive optical element.

134. The system of any of the Examples above, wherein the at least one in-coupling optical element comprises a diffraction grating.

135. The system of any of the Examples above, wherein the in-coupling element comprises a polarization selective turning element.

136. The system of any of the Examples above, wherein the in-coupling element comprises a polarization grating.

137. The system of any of the Examples above, wherein the at least one coupling element comprises a polarization selective turning element.

138. The system of any of the Examples above, wherein the at least one coupling element comprises a polarization grating.

139. The system of any of the Examples above, wherein the coupling optical element comprises liquid crystal.

140. The system of any of the Examples above, wherein the coupling optical element comprises a liquid crystal polarization grating.

141. The system of any of the Examples above, wherein the out-coupling optical element comprises a diffractive optical element.

142. The system of any of the Examples above, wherein the at least one out-coupling element comprises a polarization selective turning element.

143. The system of any of the Examples above, wherein the at least one out-coupling element comprises a polarization grating.

144. The system of any of the Examples above, wherein the at least one out-coupling element comprises liquid crystal.

145. The system of any of the Examples above, wherein the at least one out-coupling element comprises a liquid crystal polarization grating.

146. The system of any of the Examples above, wherein the at least one out-coupling element comprises an off-axis reflector.

147. The system of any of the Examples above, wherein the same waveguide (a) guides light coupled from the user's eye into said at least one waveguide to be received by said camera so as to capture an image of at least a portion of the eye of the user, and (b) guides light coupled from said image projector such that light from said projector can be directed to said user's eye such that said image from said image projector is in the vision field of said the user.

148. The system of any of the Examples above, wherein said system is configured to perform eye tracking based images of said eye.

149. The system of Example 148, wherein performing eye tracking based on said images of said eye comprises storing an image of the retina of said eye.

150. The system of any of any of the Examples above, wherein said system is configured to:
obtain an image of a portion of said retina of said eye using said camera;
compare one or more stored images of said retina with the image of said portion of said retina; and
determine a gaze of the user based on the comparison of the one or more stored images and the image of the portion of the retina obtained from the camera.

151. The system of Example 150, wherein determining a gaze of the user comprises determining to which portion of the retina corresponds to the image of said portion of the retina.

152. The system of any of the Examples above, wherein determining a gaze of the user comprises determining an orientation of the eye.

153. The system of any of the Examples above, wherein said system is configured to obtain biometric data based on one or more images of the user's eye obtained with said camera.

154. The system of any of the Examples above, wherein said system is configured to identify the user via biometric sensing based on one or more images of said eye obtained with said camera.

155. The system of any of the above Examples, wherein said system is configured to provide illumination of a first polarization and to preferentially capture images with said camera using light of a second polarization different than said first polarization.

156. The system of any of the above Examples, wherein said system is configured to illuminate said user's eye with light of a first polarization and to preferentially capture images of said user's eye with said camera using light of a second polarization different than said first polarization.

157. The system of any of the Examples above, wherein said first and second polarizations are orthogonal.

158. The system of any of the above Examples, further comprising a light source disposed so as to provide illumination so as to capture images with said camera.

159. The system of any of the above Examples, further comprising a light source disposed so as to illuminate of the user's eye.

160. The system of any of the Examples above, wherein said light source comprises one or more infrared light sources.

161. The system of any of the Examples above, wherein said light source comprises one or more infrared light emitting diodes (LEDs).

162. The system of any of the Examples above, wherein said light source is pulsed.

163. The system of any of the Examples above, wherein said light source is configured to input light into a waveguide to provide said illumination.

164. The system of any of the Examples above, wherein said light source is configured to input light into a waveguide disposed with respect to said eye to provide illumination to said eye.

165. The system of any of the Examples above, further comprising an illumination in-coupling optical element configured to couple light from said light source into said waveguide.

166. The system of any of the Examples above, wherein said light source is configured to input light into said at least one waveguide to provide illumination.

167. The system of any of the Examples above, wherein said light source is configured to input light into the same waveguide as used to project image content to the user's eye.

168. The system of any of the Examples above, wherein said light source is configured, to provide illumination to the user's eye, to input light into the same waveguide as used to guide light to the camera.

169. The system of any of the Examples above, wherein said light source is configured to input light into the same waveguide as used to guide light from the user's eye to the camera.

170. The system of any of the Examples above, further comprising an illumination in-coupling optical element configured to couple light from said light source into said waveguide to provide illumination.

171. The system of any of the Examples above, wherein said illumination in-coupling optical element is polarization selective, in-coupling light of a first polarization.

172. The system of any of the Examples above, wherein said light source is a polarized light source configured to output polarized light having a first polarization.

173. The system of any of the Examples above, wherein said light source is configured to direct polarized light having a first polarization onto said eye.

174. The system of any of the Examples above, further comprising an illumination polarizer having a first polarization disposed in the optical path between said light source and said eye to polarize light directed to said eye.

175. The system of any of the Examples above, wherein the illumination polarizer is disposed in the optical path between said light source and said waveguide configured to provide illumination.

176. The system of any of the Examples above, further comprising an image acquisition polarizer in an optical path between said eye and said camera.

177. The system of any of the Examples above, wherein said image acquisition polarizer is proximal said camera.

178. The system of any of the Examples above, wherein said image acquisition polarizer is disposed in an optical path between (a) said at least one waveguide configured guide light to said camera and (b) said camera.

179. The system of any of the Examples above, wherein said image acquisition polarizer reduces the amount of light of said first polarization that reaches said camera.

180. The system of any of the Examples above, wherein said image acquisition polarizer comprises a polarizer configured to selectively coupling light of a second polarization different than said first polarization to said camera.

181. The system of any of the Examples above, further comprising at least one light consolidating element disposed in an optical path between said at least one coupling element and said at least one out-coupling optical element to reduce lateral spatial extent of light from said at least one coupling element prior to reaching said at least one out-coupling optical element.

182. The system of any of the Examples above, wherein said at least one light consolidating element comprises a diffractive optical element.

183. The system of any of the Examples above, wherein said at least one light consolidating element comprises a hologram or diffraction grating.

184. The system of any of Examples 183, wherein the one or more stored images of the retina of the eye comprise a composite image of the retina of the eye generated using a plurality of images of different portions of the retina of the eye.

185. The system of any of the Examples above, wherein the composite image of the retina comprises a plurality of images of the retina stitched together.

186. The system of any of the Examples above, wherein the plurality of images of the retina stitched together comprises images obtained when a fixation target was displayed in the vision field of the user at various locations, respectively.

187. The system of any of the Examples above, wherein the one or more stored images of the retina comprises images obtained when a fixation target was displayed in the vision field of the user at various locations, respectively.

188. The system of any of the Examples above, wherein the system is further configured to use the obtained image of the portion of the retina of the eye to update the composite image.

189. The system of any of the Examples above, wherein using the obtained image of the portion of the retina to update the composite image of the retina comprises stitching the obtained image into a section of the composite image corresponding to the portion of the retina shown in the obtained image.

190. The system of any of the Examples above, wherein the system is further configured to apply a digital filter to the obtained image of the portion of the retina of the eye to obtain a filtered image of the portion of the retina.

191. The system of any of the Examples above, wherein the system is further configured to compare one or more stored images of the retina with the filtered image of the portion of the retina.

192. The system of any of the Examples above, wherein the digital filter comprises a Frangi Filter.

193. The system of any of the Examples above, wherein the system is configured to apply edge enhance the obtained image of the portion of the retina.

194. The system of any of the Examples above, wherein said system is configured to perform user identification verification using images of the retina.

195. The system of any of the Examples above, wherein said system is configured to:
    obtain an image of a portion of said retina of said eye using said camera;
    compare one or more stored images of said retina with the image of said portion of said retina.

196. The system of any of the Examples above, wherein the one or more stored images of the retina of the eye comprise a composite image of the retina of the eye generated using a plurality of images of different portions of the retina of the eye.

197. The system of any of the Examples above, wherein the composite image of the retina comprises a plurality of images of the retina stitched together.

198. The system of any of the Examples above, wherein the plurality of images of the retina stitched together comprises images obtained when a fixation target was displayed in the vision field of the user at various locations, respectively.

199. The system of any of the Examples above, wherein the one or more stored images of the retina comprises images obtained when a fixation target was displayed in the vision field of the user at various locations, respectively.

200. The system of any of the Examples above, wherein the system is further configured to use the obtained image of the portion of the retina of the eye to update the composite image.

201. The system of any of the Examples above, wherein using the obtained image of the portion of the retina to update the composite image of the retina comprises stitching the obtained image into a section of the composite image corresponding to the portion of the retina shown in the obtained image.

202. The system of any of the Examples above, wherein the system is further configured to apply a digital filter to the obtained image of the portion of the retina of the eye to obtain a filtered image of the portion of the retina.

203. The system of any of the Examples above, wherein the system is further configured to compare one or more stored images of the retina with the filtered image of the portion of the retina.

204. The system of any of the Examples above, wherein the digital filter comprises a Frangi Filter.

205. The system of any of the Examples above, wherein the system is configured to apply edge enhancement the obtained image of the portion of the retina.

206. The system of any of the Examples above, wherein the optical power corresponds to a focal length about the distance of the eye to the coupling optical element.

207. The system of any of the Examples above, wherein the optical power corresponds to a focal length of between 15 mm and 25 mm.

208. The system of any of the Examples above, wherein the optical power corresponds to a focal length of between 10 mm and 30 mm.

209. The system of any of the Examples above, wherein said out-coupling optical element is polarization selective, preferentially filtering out light of said first polarization as compared to said second polarization.

210. The system of any of the Examples above, wherein said out-coupling optical element is polarization selective, preferentially coupling out light of said second polarization as compared to said first polarization.

211. The system of any of the Examples above, wherein said system is configured such that light coupled into said waveguide by said first coupling optical element is acted on by a first total optical power and light coupled into said waveguide by said second coupling optical element is acted on by a second total optical power and said first total optical power is larger than said second total optical power.

212. The system of any of the Examples above, wherein said first coupling optical element has a first optical power and said second coupling optical element has a second optical power, and said first optical power is larger than said second optical power.

213. The system of any of the Examples above, wherein said first coupling optical element has a first lens associated therewith having has a first optical power and said second coupling optical element has associated therewith a second lens having a second optical power, and said first optical power is larger than said second optical power.

Example Section VI

1. A head-mounted system configured to image at least a portion of an eye of a user wearing the head-mounted system, said head-mounted system comprising:
    a frame configured to be supported on a head of the user;
    at least one camera; and
    an eyepiece disposed on the frame, at least a portion of said eyepiece being transparent and disposed at a location in front of the user's eye when the user wears said head-mounted system such that said transparent portion transmits light from the environment in front of the user to the user's eye to provide a view of the environment in front of the user, said eyepiece comprising:
        at least one waveguide;
        at least two optical elements spaced a particular distance apart, said at least two optical elements comprising:
            at least one coupling optical element configured such that light from the eye of the user wearing the head-mounted system is coupled into said waveguide and guided therein, said at least one coupling optical element comprising a coupling area for coupling light into said waveguide, said coupling area having at least one dimension measuring less than or equal to 2.5% of the particular distance; and at least one out-coupling element configured to couple light guided within said waveguide out of said waveguide and direct said light to said camera, wherein said at least one camera is disposed in an optical path with respect to said at least one out-coupling optical element to receive at least a portion of the light that is coupled into said waveguide via the coupling area of the coupling optical element and guided therein and that is coupled out from said waveguide by said out-coupling coupling element such that images may be captured by said camera.

2. The system of any of the Examples above, wherein said at least one dimension of said coupling area of said at least one coupling optical element is less than or equal to 2% of the particular distance.

3. The system of any of the Examples above, wherein said at least one dimension of said coupling area of said at least one coupling optical element is less than or equal to 1.5% of the particular distance.

4. The system of any of the Examples above, wherein said at least one dimension of said coupling area of said at least one coupling optical element is less than or equal to 1% of the particular distance.

5. The system of any of the Examples above, wherein said at least one out-coupling element comprises a coupling area for coupling light into said waveguide, said coupling area having at least one dimension measuring less than or equal to 2.5% of the particular distance.

6. The system of any of the Examples above, wherein said at least one dimension of said coupling area of said at least one out-coupling optical element is less than or equal to 2% of the particular distance.

7. The system of any of the Examples above, wherein said at least one dimension of said coupling area of said at least one out-coupling optical element is less than or equal to 1.5% of the particular distance.

8. The system of any of the Examples above, wherein said at least one dimension of said coupling area of said at least one out-coupling optical element is less than or equal to 1% of the particular distance.

9. The system of any of the Examples above, wherein said particular distance is substantially equal to the distance of the eye to the coupling optical element.

10. The system of any of the Examples above, wherein said particular distance is between 10 and 30 millimeters.

11. The system of any of the Examples above, wherein said particular distance is between 10 and 25 millimeters.

12. The system of any of the Examples above, wherein said at least one coupling optical element comprises a diffractive optical element.

13. The system of any of the Examples above, further comprising:
an image projector for projecting images into the user's eye to display image content in the vision field of the user, said image projector configured to input light into at least one of said at least one waveguide to be guided therein;
at least one image content in-coupling optical element configured to in-couple light from said image projector into said at least one waveguide so as to guide light from said image projector therein; and
at least one image content out-coupling optical element configured to couple light from said image projector guided within said at least one of said at least one waveguide out thereof such that image content can be viewed by the user's eye.

Example Section VII

1. A head-mounted system configured to image at least a portion of an eye of a user wearing the head-mounted system, said head-mounted system comprising:
a frame configured to be supported on a head of the user;
at least one camera; and
an eyepiece disposed on the frame, at least a portion of said eyepiece being transparent and disposed at a particular distance in front of the user's eye when the user wears said head-mounted system such that said transparent portion transmits light from the environment in front of the user to the user's eye to provide a view of the environment in front of the user, said eyepiece comprising:
at least one waveguide;
at least one coupling optical element configured such that light from the eye of the user wearing the head-mounted system is coupled into said waveguide and guided therein, said at least one coupling optical element comprising a coupling area for coupling light into said waveguide, said coupling area having at least one dimension measuring less than or equal to 2.5% of the particular distance; and
at least one out-coupling element configured to couple light guided within said waveguide out of said waveguide and direct said light to said camera,
wherein said at least one camera is disposed in an optical path with respect to said at least one out-coupling optical element to receive at least a portion of the light that is coupled into said waveguide via the coupling area of the coupling optical element and guided therein and that is coupled out from said waveguide by said out-coupling coupling element such that images may be captured by said camera.

2. The system of any of the Examples above, wherein said at least one dimension of said coupling area of said at least one coupling optical element is less than or equal to 2% of the particular distance.

3. The system of any of the Examples above, wherein said at least one dimension of said coupling area of said at least one coupling optical element is less than or equal to 1.5% of the particular distance.

4. The system of any of the Examples above, wherein said at least one dimension of said coupling area of said at least one coupling optical element is less than or equal to 1% of the particular distance.

5. The system of any of the Examples above, wherein said at least one out-coupling element comprises a coupling area for coupling light into said waveguide, said coupling area having at least one dimension measuring less than or equal to 2.5% of the particular distance.

6. The system of any of the Examples above, wherein said at least one dimension of said coupling area of said at least one out-coupling optical element is less than or equal to 2% of the particular distance.

7. The system of any of the Examples above, wherein said at least one dimension of said coupling area of said at least one out-coupling optical element is less than or equal to 1.5% of the particular distance.

8. The system of any of the Examples above, wherein said at least one dimension of said coupling area of said at least one out-coupling optical element is less than or equal to 1% of the particular distance.

9. The system of any of the Examples above, wherein said at least one coupling optical element and said at least one out-coupling optical element are spaced apart by a distance substantially equal to the particular distance is substantially equal to the distance of the eye to the coupling optical element.

10. The system of any of the Examples above, wherein said particular distance is between 10 and 30 millimeters.

11. The system of any of the Examples above, wherein said particular distance is between 10 and 25 millimeters.

12. The system of any of the Examples above, wherein said at least one coupling optical element comprises a diffractive optical element.

13. The system of any of the Examples above, further comprising:
- an image projector for projecting images into the user's eye to display image content in the vision field of the user, said image projector configured to input light into at least one of said at least one waveguide to be guided therein;
- at least one image content in-coupling optical element configured to in-couple light from said image projector into said at least one waveguide so as to guide light from said image projector therein; and
- at least one image content out-coupling optical element configured to couple light from said image projector guided within said at least one of said at least one waveguide out thereof such that image content can be viewed by the user's eye.

Example Section VIII

1. A head mounted display system configured to project light to an eye of a user to display augmented reality image content in a vision field of said user, said head-mounted display system comprising:
- a frame configured to be supported on a head of the user;
- an image projector configured to project images into the user's eye to display image content in the vision field of the user;
- a transparent layer supported on said frame and disposed at a location in front of the user's eye when the user wears said head-mounted display such that said transparent layer transmits light from an environment in front of the user to the user's eye to provide a view of the environment in front of the user;
- at least one elongate light guide having a first end and a second end, said first end disposed within said transparent layer, said first end of said elongate light guide having an output for emitting light such that said light is directed to said eye;
- at least one camera disposed to receive at least a portion of the light reflected from the eye to capture images using light reflected from the user's eye.

2. The system of Example, 1, wherein said first end of said elongate light guide includes an angled reflector configured to couple light through said output of said elongate light guide.

3. The system of Example 2, wherein said angled reflector comprises a beveled surface at said first end of said elongate light guide.

4. The system of any of Examples 2 or 3, wherein said angled reflector comprises a cleaved surface at said first end of said elongate light guide.

5. The system of any of Examples 2 to 4, wherein said angled reflector comprises metallization.

6. The system of any of Examples 2 to 5, wherein said angled reflector comprises IR reflective coating.

7. The system of any of Examples 2 to 6, wherein said elongate light guide extends along a length within said transparent layer and said angle reflector is oriented at an angle of from 35° and 55° with respect to said length of said elongate light guide.

8. The system of any of Examples 2 to 7, wherein said transparent layer has oppositely facing front and rear major surfaces and said angle reflector is oriented at an angle of from 35° and 55° with respect to said front and rear major surfaces.

9. The system of any of the above Examples, wherein said transparent layer comprises an index matching material disposed between front and rear glass covers.

10. The system of any of the above Examples, wherein the transparent layer comprises a channel configured to accept the elongate light guide.

11. The system of any of the above Examples, wherein said elongate light guide is disposed within a channel of the transparent layer.

12. The system of any of the above Examples, wherein said second end of said elongate light guide has an input for receiving light, said elongate light guide configured such that light received by said input of said elongate light guide at said second end is guided within said elongate light guide to said output at said first end of said elongate light guide.

13. The system of any of the above Examples, wherein said at least one elongate light guide comprises an optical fiber comprising a core and a cladding and said core is between 8 μm and 110 μm across.

14. The system of any of the above Examples, wherein said at least one elongate waveguide comprises an optical fiber comprises a core and a cladding and said cladding is between 100 μm and 150 μm across.

15. The system of Example 14, wherein the cladding comprises 125 μm across.

16. The system of any of the above Examples, wherein said second end of said elongate light guide extends outside of said transparent layer such that said input for receiving light is outside said transparent layer.

17. The system of any of the above Examples, wherein said at least one elongate light guide comprises a plurality of elongate light guides.

18. The system of any of the above Examples, wherein said transparent layer has first and second sides and said at least one elongate light guide comprises a first elongate light guide embedded in said first side of said transparent layer and a second elongate light guides embedded in said second side of said transparent layer.

19. The system of any of the above Examples, wherein said transparent layer has first and second sides and said at least one elongate light guide comprises a first pair of elongate light guides embedded in said first side of said transparent layer and a second pair of elongate light guides embedded in said second side of said transparent layer.

20. The system of Examples 18 or 19, wherein first and second sides are nasal and temporal sides of said transparent layer.

21. The system of any of Examples 18 to 20, wherein first and second sides are superior and inferior sides of said transparent layer.

22. The system of any of the above Examples, wherein said output of said elongate light guide creates a point source illuminating said eye of the user.

23. The system of Examples 17-22, wherein said plurality of elongate light guides each have outputs that create point sources illuminating said eye of the user.

24. The system of Examples 17-23, wherein said first and second pairs of elongate light guides each have outputs that create point sources illuminating said eye of the user.

25. The system of any of the above Examples, further comprising at least one light source, said at least one light source optically coupled to said elongate light guides to inject light therein such that light is output from said first end of said elongate light guide.

26. The system of Example 25, wherein said at least one light source comprises one or more infrared light sources.

27. The system of any of Examples 25 or 26, wherein said at least one light source comprises one or more light emitting diodes (LEDs) or lasers.

28. The system of any of the Examples above, further comprising an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user.

29. The system of Example 28, wherein said eyepiece is configured to receive light from said image projector and to direct said light into said user's eye to display augmented reality image content to the user's vision field.

30. The system of Examples 28 or 29, wherein said eyepiece comprises at least one waveguide.

31. The system of Example 30, wherein said image projector is configured to direct light into said at least one waveguide.

32. The system of Examples 30 or 31 above, wherein said at least one waveguide comprises a stack of waveguides.

33. The system of Example 32, wherein different waveguides of the stack of waveguides are configured to output light with different wavefront divergence as if projected from different distances from the user's eye.

34. The system of Example 32 or 33, wherein different waveguides of the stack of waveguides are configured to output light with different colors.

35. The system of any of the Examples 28 to 34, wherein said transparent layer comprises a layer in said eyepiece.

36. The system of any of the Examples 28 to 34, wherein said transparent layer comprises a protective layer for said eyepiece.

37. The system of any of the above Examples, further comprising:
  at least one waveguide;
  at least one coupling optical element configured such that light from said output of said elongate light guide that is reflected from said eye is coupled into said waveguide and guided therein; and
  at least one out-coupling element configured to couple light guided within said waveguide out of said waveguide and direct said light to said at least one camera to capture images of said eye.

38. The system of any of the Examples above, wherein said system is configured to perform eye tracking based on images of said eye captured by said camera.

39. The system of any of the Examples above, further comprising a diffuser at said output of said elongate light guide at said first end of said elongate light guide.

40. The system of any of the Examples above, wherein said angled reflector is polished.

41. The system of any of the Examples above, wherein said at least one light source comprises a UV or visible light source.

42. The system of any of the Examples above, wherein said at least one elongate light guide has a length to thickness ratio of at least 10.

43. The system of any of the Examples above, wherein said at least one elongate light guide has a length to thickness ratio of at least 20.

44. The system of any of the Examples above, wherein said at least one elongate light guide comprises an optical fiber.

45. The system of any of the Examples above, wherein said at least one elongate light guide comprises an optical rod comprising optically transmissive material.

46. The system of any of the above Examples, wherein said at least one elongate light guide comprises a plurality of optical fibers.

47. The system of any of the above Examples, wherein said at least one elongate light guide comprises a plurality of an optical rods.

48. A head mounted display system configured to project light to an eye of a user to display augmented reality image content in a vision field of said user, said head-mounted display system comprising:
  a frame configured to be supported on a head of the user;
  an image projector configured to project images into the user's eye to display image content in the vision field of the user;
  a transparent layer supported on said frame and disposed at a location in front of the user's eye when the user wears said head-mounted display such that said transparent layer transmits light from an environment in front of the user to the user's eye to provide a view of the environment in front of the user, said transparent layer comprising front and rear major surfaces surrounded by a plurality of edges, said transparent layer further comprising and at least one tilted surface, said tilted surface angled such that light guided within said transparent layer is reflected from said tilted surface and directed through said rear major surface out of said transparent layer to said eye; and
  at least one camera disposed to receive at least a portion of the light reflected from the user's eye to capture images using light reflected from the user's eye.

49. The system of any of the above Examples, wherein said tilted surface comprises metallization.

50. The system of any of any of the above Examples, wherein said tilted surface comprises IR reflective coating.

51. The system of any of the above Examples, wherein said tilted surface is angled from 35° to 55° with respect to front and/or rear major surface of said transparent layer.

52. The system of any of the above Examples, further comprising at least one light source disposed with respect to said at least one transparent layer such that light from said at least one light source is injected into said at least one transparent layer, is incident on said tilted surface, and reflected therefrom toward the eye of the user.

53. The system of any of the above Examples, further comprising at least one light source disposed with respect to at least one edge of said transparent layer such that light from said at least one light source is injected into said at least one transparent layer, is incident on said tilted surface and reflected therefrom toward said eye of said user.

54. The system of Examples 52 or 53, wherein said at least one light source comprises a plurality of spaced apart light sources.

55. The system of any of Examples 52 to 54, wherein said light source comprises one or more infrared light sources.

56. The system of Examples 54 or 55, wherein said plurality of light sources comprises three light sources.

57. The system of any of Examples 54 to 56, wherein said plurality of light sources comprises four light sources.

58. The system of any of Examples 52 to 57, wherein said light source creates a point source illuminating said eye of the user.

59. The system of any of Examples 54 to 58, wherein said plurality of light sources creates a plurality of point sources illuminating said eye of the user.

60. The system of any of the above Examples, wherein four light sources create four point sources illuminating said eye of the user.

61. The system of any of Examples 54 to 60, wherein said light source comprises one or more light emitting diodes (LEDs) or lasers.

62. The system of any of Examples 54 to 61, wherein said light from said light source is guided within said transparent layer by total internal reflection off said front and rear surfaces of said transparent layer.

63. The system of any of the above Examples, wherein said transparent layer comprises plastic.

64. The system of any of the above Examples, wherein said tilted surface is planar.

65. The system of any of the Examples above, further comprising an eyepiece disposed on the frame, said eyepiece configured to direct light into said user's eye to display augmented reality image content to the user's vision field, at least a portion of said eyepiece being transparent and disposed at a location in front of the user's eye when the user wears said head-mounted display such that said transparent portion transmits light from an environment in front of the user to the user's eye to provide a view of the environment in front of the user.

66. The system of Example 65, wherein said eyepiece is configured to receive light from said image projector and to direct said light into said user's eye to display augmented reality image content to the user's vision field.

67. The system of Examples 65 or 66, wherein said eyepiece comprises at least one waveguide.

68. The system of Example 67, wherein said image projector is configured to direct light into said at least one waveguide.

69. The system of Examples 67 or 68 above, wherein said at least one waveguide comprises a stack of waveguides.

70. The system of Example 69, wherein different waveguides of the stack of waveguides are configured to output light with different wavefront divergence as if projected from different distances from the user's eye.

71. The system of Example 69 or 70, wherein different waveguides of the stack of waveguides are configured to output light with different colors.

72. The system of any of the above Examples 65 to 71, wherein said transparent layer comprises a layer in said eyepiece.

73. The system of any of the above Examples 65 to 71, wherein said transparent layer comprises a protective layer for said eyepiece.

74. The system of any of the above Examples, further comprising:
at least one waveguide;
at least one coupling optical element configured such that light output from said transparent layer that is reflected from said eye is coupled into said waveguide and guided therein; and
at least one out-coupling element configured to couple light guided within said waveguide out of said waveguide and direct said light to said camera to capture images of said eye.

75. The system of any of the Examples above, wherein said system is configured to perform eye tracking based on images of said eye captured by said camera.

76. The system of any of the Examples above, wherein said at least one light source comprises a UV or visible light source.

Terminology

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially exampled as such, one or more features from an exampled combination may in some cases be excised from the combination, and the exampled combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended examples are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following examples. In some cases, the actions recited in the examples may be performed in a different order and still achieve desirable results.

Accordingly, the disclosure are not intended to be limited to the embodiments shown herein, but are to be accorded the widest scope consistent with this disclosure, the principles and the novel features disclosed herein. A variety of example systems and methods are provided below.

What is claimed:

1. A head-mounted display system configured to project light to an eye of a user to display augmented reality image content in a vision field of said user, said head-mounted display system comprising:
   a frame configured to be supported on a head of the user;
   an image projector configured to project images into the user's eye to display image content in the vision field of the user;
   a transparent layer supported on said frame and disposed at a location in front of the user's eye when the user wears said head-mounted display system such that said transparent layer transmits light from an environment in front of the user to the user's eye to provide a view of the environment in front of the user;
   an elongate light guide having a first end and a second end, said first end disposed within said transparent layer, said first end of said elongate light guide having an output for emitting light such that said light is directed to said eye, wherein the transparent layer comprises a channel configured to accept the elongate light guide; and
   at least one camera disposed to receive at least a portion of the light reflected from the eye to capture images using light reflected from the user's eye.

2. The system of claim 1, wherein said first end of said elongate light guide includes an angled reflector configured to couple light through said output of said elongate light guide.

3. The system of claim 2, wherein said angled reflector comprises a beveled surface at said first end of said elongate light guide.

4. The system of claim 2, wherein said angled reflector comprises a cleaved surface at said first end of said elongate light guide.

5. The system of claim 2, wherein said angled reflector comprises metallization.

6. The system of claim 2, wherein said angled reflector comprises IR reflective coating.

7. The system of claim 2, wherein said angled reflector is polished.

8. The system of claim 1, wherein said elongate light guide is disposed within a channel of the transparent layer.

9. The system of claim 1, wherein said second end of said elongate light guide has an input for receiving light, said elongate light guide configured such that light received by said input of said elongate light guide at said second end is guided within said elongate light guide to said output at said first end of said elongate light guide.

10. The system of claim 1, wherein said elongate light guide comprises an optical fiber comprising a core and a cladding and said core is between 8 µm and 110 µm across.

11. The system of claim 1, wherein said elongate light guide comprises an optical fiber comprising a core and a cladding and said cladding is between 100 µm and 150 µm across.

12. The system of claim 1, wherein said second end of said elongate light guide has an input for receiving light, wherein said second end of said elongate light guide extends outside of said transparent layer such that said input for receiving light is outside said transparent layer.

13. The system of claim 1, further comprising:
   at least one waveguide;
   at least one coupling optical element configured such that light from said output of said elongate light guide that is reflected from said eye is coupled into said waveguide and guided therein; and
   at least one out-coupling element configured to couple light guided within said waveguide out of said waveguide and direct said light to said at least one camera to capture images of said eye.

14. The system of claim 1, wherein said system is configured to perform eye tracking based on images of said eye captured by said camera.

15. The system of claim 1, further comprising a diffuser at said output of said elongate light guide at said first end of said elongate light guide.

16. The system of claim 1, wherein said elongate light guide has a length to thickness ratio of at least 10.

17. The system of claim 1, wherein said elongate light guide comprises at least one optical fiber.

18. The system of claim 1, wherein said elongate light guide comprises at least one optical rod.

* * * * *